(12) United States Patent
Corcoran et al.

(10) Patent No.: US 9,447,028 B2
(45) Date of Patent: Sep. 20, 2016

(54) THERAPEUTIC ARYL-AMIDO-ARYL COMPOUNDS AND THEIR USE

(71) Applicant: King's College London, London (GB)

(72) Inventors: Jonathan Patrick Thomas Corcoran, London (GB); Sarkis Barret Kalindjian, London (GB); Alan David Borthwick, London (GB); David Reginald Adams, High Wycombe (GB); Jane Theresa Brown, Nottingham (GB); David Michel Adrien Taddei, Nottingham (GB); Jason John Shiers, Nottingham (GB)

(73) Assignee: King's College London, London (GB)

( * ) Notice: Subject to any disclaimer, the term of this patent is extended or adjusted under 35 U.S.C. 154(b) by 0 days.

(21) Appl. No.: 14/879,340

(22) Filed: Oct. 9, 2015

(65) Prior Publication Data

US 2016/0039747 A1    Feb. 11, 2016

Related U.S. Application Data

(63) Continuation of application No. 13/391,207, filed as application No. PCT/GB2010/001650 on Sep. 1, 2010, now abandoned.

(30) Foreign Application Priority Data

Sep. 1, 2009 (GB) .................. 0915196.0

(51) Int. Cl.

| A61K 31/16 | (2006.01) |
|---|---|
| C07C 235/84 | (2006.01) |
| C07C 233/75 | (2006.01) |
| C07C 235/56 | (2006.01) |
| C07C 237/42 | (2006.01) |
| C07D 213/30 | (2006.01) |
| C07D 213/80 | (2006.01) |
| C07D 213/81 | (2006.01) |
| C07D 237/24 | (2006.01) |

(52) U.S. Cl.
CPC ........... *C07C 235/84* (2013.01); *C07C 233/75* (2013.01); *C07C 235/56* (2013.01); *C07C 237/42* (2013.01); *C07D 213/30* (2013.01); *C07D 213/80* (2013.01); *C07D 213/81* (2013.01); *C07D 237/24* (2013.01); *C07C 2101/02* (2013.01); *C07C 2101/04* (2013.01); *C07C 2101/08* (2013.01); *C07C 2101/14* (2013.01)

(58) Field of Classification Search
CPC . C07C 235/84; C07C 235/56; C07C 233/75; C07C 237/42; C07C 2101/08; C07C 2101/14; C07C 2101/02; C07C 2101/04; C07D 237/24; C07D 213/80; C07D 213/81; C07D 213/30

USPC ............................. 514/563; 562/455
See application file for complete search history.

(56) References Cited

U.S. PATENT DOCUMENTS

| 4,703,110 A | 10/1987 | Shudo |
|---|---|---|
| 4,808,631 A | 2/1989 | Klaus |
| 4,925,979 A | 5/1990 | Shudo |
| 4,992,468 A | 2/1991 | Chandraratna |
| 5,525,618 A | 6/1996 | Shudo |
| 5,559,248 A | 9/1996 | Starrett, Jr. |
| 5,587,367 A | 12/1996 | Reichert et al. |

(Continued)

FOREIGN PATENT DOCUMENTS

| EP | 0515684 | 12/1992 |
|---|---|---|
| EP | 0768084 | 4/1997 |

(Continued)

OTHER PUBLICATIONS

RN1050118-03-0(available Sep. 18, 2008), corresponding to 4-(3-bromo-5-ethoxy-4-methoxybenzamido)-3-methylbenzoic acid.*

(Continued)

*Primary Examiner* — Jason Sims
*Assistant Examiner* — Ibrahim D Bori
(74) *Attorney, Agent, or Firm* — Swanson & Bratschun, L.L.C.

(57) ABSTRACT

The present invention pertains generally to the field of therapeutic compounds, and more specifically to certain aryl-amido-aryl compounds of the following formula (for convenience, collectively referred to herein as "AAA compounds"), which, inter alia, are (selective) retinoic acid receptor α (RARα) agonists. The present invention also pertains to pharmaceutical compositions comprising such compounds, and the use of such compounds and compositions, both in vitro and in vivo, to (selectively) activate RARα, and in the treatment of diseases and conditions that are mediated by RARα, that are ameliorated by the activation of RARα, etc., including cognitive disorders, memory impairment, memory deficit, senile dementia, Alzheimer's disease, early stage Alzheimer's disease, intermediate stage Alzheimer's disease, late stage Alzheimer's disease, cognitive impairment, and mild cognitive impairment.

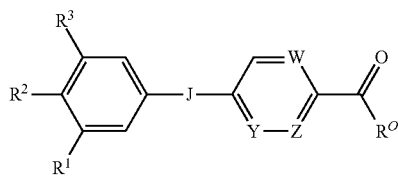

20 Claims, No Drawings

(56) References Cited

U.S. PATENT DOCUMENTS

| | | |
|---|---|---|
| 5,618,839 A | 4/1997 | Starrett |
| 5,663,357 A | 9/1997 | Teng et al. |
| 5,750,515 A | 5/1998 | Shibata |
| 5,849,735 A | 12/1998 | Albright et al. |
| 5,917,048 A | 6/1999 | Teng |
| 6,051,713 A | 4/2000 | Teng |
| 6,063,797 A | 5/2000 | Fesus et al. |
| 6,232,202 B1 | 5/2001 | Hong |
| 6,245,786 B1 | 6/2001 | Teng |
| 6,320,047 B1 | 11/2001 | Teng |
| 6,437,129 B1 | 8/2002 | Teng |
| 6,541,474 B2 | 4/2003 | Kikuchi |
| 6,545,009 B1 | 4/2003 | Sugiyama et al. |
| 2002/0072050 A1 | 6/2002 | Hook |
| 2012/0022080 A1 | 1/2012 | Miyata |
| 2012/0149737 A1 | 6/2012 | Corcoran et al. |

FOREIGN PATENT DOCUMENTS

| | | |
|---|---|---|
| EP | 1092711 | 4/2001 |
| GB | 1409689 | 10/1975 |
| JP | 61-233678 | 10/1986 |
| KR | 10-2009-0049898 A1 | 5/2009 |
| KR | 10-0921173 | 10/2009 |
| WO | WO 96/32101 | 10/1996 |
| WO | WO 97/19062 | 5/1997 |
| WO | WO 00/24707 | 5/2000 |
| WO | WO 02/47679 | 6/2002 |
| WO | WO 02/066068 | 8/2002 |
| WO | WO 2009/035430 | 3/2009 |
| WO | WO 2010/113022 | 10/2010 |
| WO | WO 2011/027106 A1 | 3/2011 |
| WO | WO 2012/058378 | 5/2012 |

OTHER PUBLICATIONS

Annaert et al., 2000, "Neuronal models to study amyloid precursor protein expression and processing in vitro", Biochim. Biophys. Acta, vol. 1502, pp. 53-62.
Bastien et al., 2004, "Nuclear retinoid receptors and the transcription of retinoid-target genes", Gene, vol. 328, pp. 1-16.
Bejanin et al., 1994, "A unique gene organization for two cholinergic markers, choline acetyltransferase and a putative vesicular transporter of acetylcholine", J. Biol. Chem., vol. 269, pp. 21944-21947.
Berrard et al., 1995, "Coregulation of two embedded gene products, choline acetyltransferase and the vesicular acetylcholine transporter", J. Neurochem., vol. 65, pp. 939-942.
Bierer et al., 1995, "Neurochemical correlates of dementia severity in Alzheimer's disease: relative importance of the cholinergic deficits", J. Neurochem., vol. 64, pp. 749-760.
Cervini, et al., 1994, "Regulation by CDF/LIF and retinoic acid of multiple ChAT mRNAs produced from distinct promoters", Neuroreport, vol. 5, pp. 1346-1348.
Cocco et al., 2002, "Vitamin A deficiency produces spatial learning and memory impairment in rats", Neuroscience, vol. 115, pp. 475-482.
Collerton et al., 1986, "Cholinergic function and intellectual decline in Alzheimer's disease", Neuroscience, vol. 19, pp. 1-28.
Coppola et al., 2005, "Perhydroquinolylbenzamides as novel inhibitors of 11β-hydroxysteroid dehydrogenase type 1", J. Med. Chem., vol. 48, pp. 6696-6712.
Corcoran, et al., 2004, "Disruption of the retinoid signaling pathway causes a deposition of amyloid beta in the adult rat brain", Eur. J. Neurosci., vol. 20, pp. 896-902.
Coyle et al., 1983, "Alzheimer's disease: a disorder of cortical cholinergic innervation", Science, vol. 219, pp. 1184-1190.
DeKosky et al., 1992, "Cortical biopsy in Alzheimer's disease: diagnostic accuracy and neurochemical, neuropathological, and cognitive correlations", Intraventricular Bethanecol Study Group, Ann. Neurol., vol. 32, pp. 625-632.

Ding et al., 2008, "Retinoic Acid Attenuates β-Amyloid Deposition and Rescues Memory Deficits in an Alzheimer's Disease Transgenic Mouse Model", J. Neuroscience, vol. 28, No. 45, pp. 11622-11634.
Endres et al., 2005, "Shedding of the amyloid precursor protein-like protein APLP2 by disintegrin-metalloproteinases", FEBS J., vol. 272, pp. 5808-5820.
Etchamendy et al., 2001, "Alleviation of a selective age-related relational memory deficit in mice by pharmacologically induced normalization of brain retinoid signalling", J. Neurosci., vol. 21, pp. 6423-6429.
Fahrenholz et al., 2006, "α-Secretase Activation—An Approach to Alzheimer's Disease Therapy", Neurodegenerative Dis., vol. 3, pp. 255-261.
Fischer et al., 1989, "Degenerative Changes in Forebrain Cholinergic Nuclei Correlate with Cognitive Impairments in Aged Rats", Eur. J. Neurosci., vol. 1, pp. 34-45.
Geula et al., 1998, "Relationship between plaques, tangles, and loss of cortical cholinergic fibers in Alzheimer disease", J. Neuropathol. Exp. Neurol., vol. 57, pp. 63-75.
Goodman et al., 2003, "Evidence for defective retinoid transport and function in late onset Alzheimer's disease", Proc. Natl. Acad. Sci. USA, vol. 100, pp. 2901-2905.
International Preliminary Report on Patentability (IPRP/Chapter II) for PCT/GB2010/001650 published Mar. 1, 2012.
International Search Report (ISR) and Written Opinion of the International Search Authority (WOISA) for PCT/GB2010/001650 published Mar. 1, 2012.
Ladner et al., 1998, "Pharmacological drug treatment of Alzheimer disease: the cholinergic hypothesis revisited", J. Neuropathol. Exp. Neurol., vol. 57, pp. 719-731.
Lammich et al., 1999, "Constitutive and regulated alphasecretase cleavage of Alzheimer's amyloid precursor protein by a disintegrin metalloprotease", Proc. Natl. Acad. Sci. USA, vol. 96, pp. 3922-3927.
Misner et al., 2001, "Vitamin A deprivation results in reversible loss of hippocampal long-term synaptic plasticity", Proc. Natl. Acad. Sci. USA, vol. 98, pp. 11714-11719.
Moffett, 1964, "Central nervous system depressants. VI. Polymethoxyphenyl esters and amides", J. Med. Chem., vol. 7, pp. 319-325.
Pan et al., 1993, "Altered levels and splicing of the amyloid precursor protein in the adult rat hippocampus after treatment with DMSO or retinoic acid", Brain Res. Mol. Brain Res., vol. 18, pp. 259-266.
Perry et al., 1992, "Convergent cholinergic activities in aging and Alzheimer's disease", Neurobiol. Aging, vol. 13, pp. 393-400.
Prinzen et al., 2005, "Genomic structure and functional characterization of the human ADAM10 promoter", FASEB J., vol. 19, pp. 1522-1524.
Search report for GB0915196.0, issued Dec. 24, 2009, published Mar. 19, 2011.
Selkoe et al., 2001, "Alzheimer's disease: genes, proteins, and therapy", Physiol. Rev., vol. 81, pp. 741-766.
Shudo et al., 2009, "Towards retinoid therapy for Alzheimer's disease", Curr. Alzheimer Res., vol. 6, p. 302-311.
Sogani et al., 1965, "Central nervous system depressant. X. Structure-activity relation of some 3,4,5-trimethoxybenzamides", Indian J. Pharm., vol. 27, pp. 173-176.
Splies et al., "3,4,5-Triiodobenzamides as Derivatives of Amines", Journal of Chemical Engineering Data, 1964, vol. 9, No. 3, p. 382.
Talesa, 2001, "Acetylcholinesterase in Alzheimer's disease", Mech. Ageing Dev., vol. 122, pp. 1961-1969.
Toldy et al., 1966, "Piperazinderivative, I. 3,4,5-Trimethoxybenzoylderviative, eine neue Verbindungsgruppe mit antizerogener Wirkung", Acta Chim. Hung., vol. 49, pp. 265-286 (in German with English abstract and partial translation).
Tucker et al., 1992, "Novel inhibitors of prolyl 4-hydroxylase. 2. 5-Amide substituted pyridine-2-carboxylic acids", J. Med. Chem., vol. 35, pp. 804-807.
Vinters, 1987, "Cerebral amyloid angiopathy: A critical review", Stroke, vol. 18, pp. 311-324.
Yoo et al., "Cosmetics containing benzamidobenzoate derivatives for promoting biosynthesis of hyaluronic acid in the skin", Database

(56) References Cited

OTHER PUBLICATIONS

CA [Online], Chemical Abstracts Service, Columbus, OH, USA., XP002608079 retrieved from STN, database accession No. 2009. 626681 (corresponding to KR 10-2009-0049898 A1).
CAS Registry No. 690982-75-3.
CAS Registry No. 1003421-96-2.
CAS Registry No. 885546-20-3.
CAS Registry No. 1030651-77-4.
CAS Registry No. 1053999-86-2.
CAS Registry No. 1272527-28-2.

* cited by examiner

THERAPEUTIC ARYL-AMIDO-ARYL COMPOUNDS AND THEIR USE

RELATED APPLICATION

This application is a continuation of U.S. application Ser. No. 13/391,207, filed Feb. 17, 2012. U.S. application Ser. No. 13/391,207 is a 35 U.S.C. §371 national phase application of PCT/GB2010/001650, filed Sep. 1, 2010 (WO 2011/027106), entitled "Therapeutic Aryl-Amido-Aryl Compounds and Their Use." PCT/GB2010/001650 is a non-provisional application of United Kingdom patent application number 0915196.0 filed Sep. 1, 2009, the contents of which are incorporated herein by reference in their entirety.

TECHNICAL FIELD

The present invention pertains generally to the field of therapeutic compounds, and more specifically to certain aryl-amido-aryl compounds (for convenience, collectively referred to herein as "AAA compounds"), which, inter alia, are (selective) retinoic acid receptor α (RARα) agonists. The present invention also pertains to pharmaceutical compositions comprising such compounds, and the use of such compounds and compositions, both in vitro and in vivo, to (selectively) activate RARα, and in the treatment of diseases and conditions that are mediated by RARα, that are ameliorated by the activation of RARα, etc., including cognitive disorders, memory impairment, memory deficit, senile dementia, Alzheimer's disease, early stage Alzheimer's disease, intermediate stage Alzheimer's disease, late stage Alzheimer's disease, cognitive impairment, and mild cognitive impairment.

BACKGROUND

A number of patents and publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

Alzheimer's Disease

The current licensed treatments for Alzheimer's disease (AD) improve the symptoms that people experience but do not alter the progression of the underlying disease changes in the brain. Most of the attempts to develop new treatments have focused on altering deposits of the amyloid protein in the brain, but despite more than a decade of intensive research this has still not yielded any new therapies in the clinic.

The only currently approved medications for the treatment of AD are two groups of drugs, acetylcholinesterase inhibitors (e.g., Aricept™) and non-competitive NMDA receptor blockers (e.g., Memantine'), which give significant symptomatic improvement but do not fundamentally prevent or alter disease progression.

Recent research has concentrated on the mis-processing of the amyloid precursor protein (APP) and overproduction amyloid β(Aβ), as the central causative substrates in the disease process and the main treatment target. However, despite considerable effort and research over more than a decade, these treatments have not yet translated into treatments in the clinic.

The inventors have now determined the importance of RARα signalling in processing the APP into the non-amyloidic pathway, and a key role of this pathway in modulating neuronal survival.

Retinoic Acid Receptors

The retinoic acid receptor (RAR) is a type of nuclear receptor which is activated by both all-trans retinoic acid and 9-cis retinoic acid. There are three retinoic acid receptors, known as RARα, RARβ, and RARγ.

The inventors' studies have highlighted a specific retinoic acid receptor, (RAR)α, as a novel and exciting target for the development of new treatments. This receptor has two potential mechanisms of action; it regulates amyloid deposits in the brain and also plays a key role in the survival of neurons.

The pathological hallmarks of Alzheimer's disease (AD) are the presence of senile plaques containing amyloid β(Aβ) peptide and the formation of neuronal tangles in the cerebral cortex. In addition, 90% of AD patients have amyloid β deposits in their cerebral blood vessels (see, e.g., Vinters, 1987). Recently it has been shown that in AD there are genetic linkages to the disease which are close to genes involved in the retinoid signalling pathway (see, e.g., Goodman and Pardee, 2003). This is mediated by retinoic acid receptors (RARs) and retinoid X receptors (RXRs), both of which have three types α, β, and γ and various isoforms (see, e.g., Bastien and Rochette-Egly, 2004). Transcription occurs when the small lipophilic molecule, retinoic acid (RA) binds to an RAR/RXR heterodimer which then binds to retinoic acid response elements (RAREs) located in the regulatory regions of target genes (see, e.g., Bastien and Rochette-Egly, 2004).

Vitamin A deficiency in rats leads to Aβ deposits in the brain vasculature and a down-regulation of RARα in their cortical neurons; the same receptor deficit is found in the cortices in pathology samples of AD (see, e.g., Corcoran et al., 2004). In addition, vitamin A deficiency produces spatial learning and memory impairments and this cognitive decline, which is a symptom of AD, can be reversed by normalization of brain retinoid signalling (see, e.g., Fischer et al., 1989; Cocco et al., 2002). Similarly, in aged mice, there is a loss of retinoid signalling in the brain and cognitive decline and this can also be reversed by supplementing their diet with retinoids (see, e.g., Etchamendy et al., 2001). Also, vitamin A deficiency in mice can lead to a loss in hippocampal synaptic plasticity, which can be reversed by the addition of retinoids to the diet (see, e.g., Misner et al., 2001).

It has also been shown that the amyloid precursor protein (APP), which gives rise to amyloid β protein, can be differentially spliced depending on the concentration of RA (see, e.g., Pan et al., 1993). The APP can be cleaved into Aβ40 and Aβ42 by β and γ secretases (see, e.g., Selkoe, 2001). Alternatively, APP can be cleaved by a secretases into a soluble neuroprotective fragment (see, e.g., Annaert and De, 2000). Disintegrin-metalloproteinases (ADAMS) have been shown to act as α secretases (see, e.g., Lammich et al., 1999; Endres et al., 2005), and one of these (ADAM10) has been shown to be regulated by RA (see, e.g., Endres et al., 2005) and this appears to be direct as the promoter of this gene contains an RARE (see, e.g., Prinzen et al., 2005).

Other consistent aspects of AD are defects in the levels of the neurotransmitter, acetylcholine, which is produced by cholinergic neurons. In AD, there is a loss of the cholinergic markers choline acetyltransferase (chAT), which synthesises acetylcholine and acetylcholinesterase (Ache); Ache breaks down acetylcholine, and subsequently causes the loss of cholinergic neurons themselves (see, e.g., Coyle et al., 1983; Perry et al., 1992; Geula et al., 1998; Ladner and Lee, 1998; Talesa, 2001). It is the loss in cholinergic function that leads to the memory deficits in AD (see, e.g., Collerton, 1986; DeKosky et al., 1992; Bierer et al., 1995; Fischer et al., 1989). RA can also increase chAT expression (see, e.g., Cervini et al., 1994; Berrard et al., 1995; Bejanin et al., 1994).

The inventors' have now shown that RARα agonists are likely to be useful in the treatment of AD. They prevent neuronal cell death in the presence of Aβ42; in culture, they up-regulate chAT, down-regulate APP and increase the expression of ADAM10. In vivo, the inventors' have shown that feeding RARα agonists to Tg2576 mice (which overexpresses the Swedish mutation of the human APP leading to amyloid β deposits and cognitive decline) results in a significant reduction in the levels of both Aβ40 and Aβ42. Studies demonstrating these findings are described in more detail in the Examples below.

Certain aryl-amido-aryl compounds are known in the art.

Teng et al., 1997 (U.S. Pat. No. 5,663,357) describes certain compounds which apparently have retinoid-like biological activity. All of the compounds exemplified therein (see Table 1, spanning column 6 and 7 therein) have the following formula, in which the ring that is opposite the ring bearing the carboxylic acid group has two tert-butyl substituents.

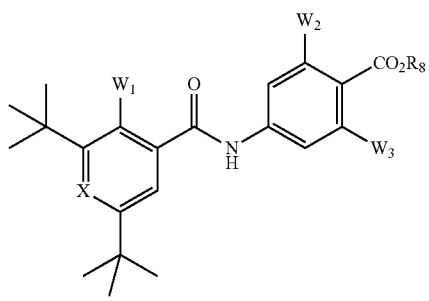

U.S. Pat. No. 5,663,357

Shudo, 1987 (U.S. Pat. No. 4,703,110) describes certain compounds which apparently are useful for diagnosis of leukemia types, the treatment of dermatological disorders, and as differentiation-inducing agents for neoplastic cells. Among the compounds exemplified therein (see Tables 1 and 2 spanning columns 8 to 12 therein) are compounds of the following formula, wherein —X— is an amide linkage (see, e.g., the last few compounds in Table 1, and compounds 15-40, 64, 65, 67, and 68 in Table 2). However, in each case, the substituents $R_1$, $R_2$, $R_3$, $R_4$, and $R_5$, when not hydrogen, are alkyl (e.g., -Et, -iPr, -tBu), cycloalkyl (e.g., cyclohexyl), or together form a ring fused to the parent phenyl ring.

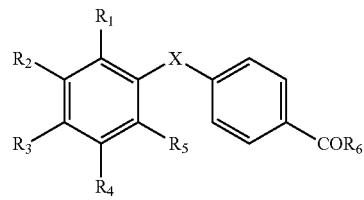

U.S. Pat. No. 4,703,110

Shudo et al., 1996, (U.S. Pat. No. 5,525,618) describes certain compounds which apparently are useful in osteopathic treatment. The following compounds are shown in Table 1 (see columns 8 to 9 therein).

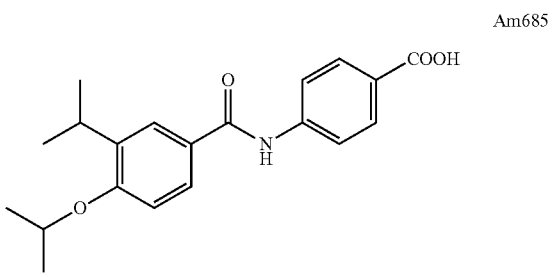

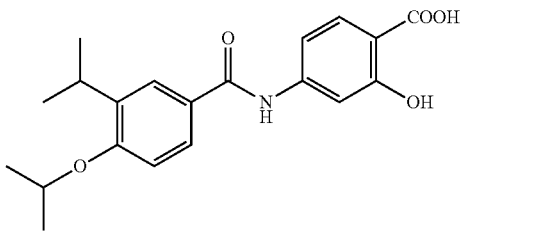

U.S. Pat. No. 5,525,618

Kato et al., 1992 (EP 0 515 684 A1) describes compounds according to the following general formula. These compounds are said to be useful in treating arteriosclerosis, peptic ulcer, cancer, ischemic organ disease, inflammation and pulmonary silicosis.

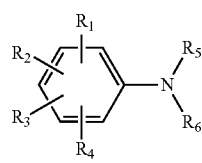

Of the numerous compounds described therein, Compound 132 on page 59 has the structure given below.

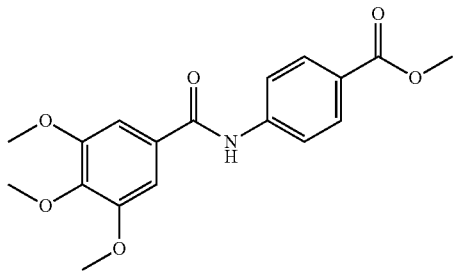

Mizukoshi et al., 1986 (JP 61-233678 A) describes compounds useful as anti-ulcer agents. Compound 1849-89-4 therein has the structure shown below.

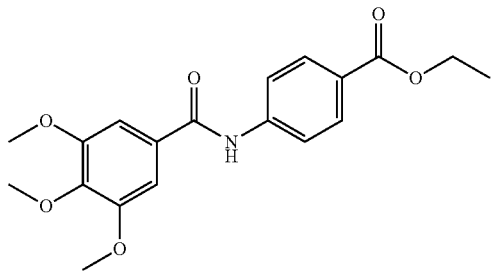 [SMILES: CCOC(=O)c1ccc(NC(=O)c2cc(OC)c(OC)c(OC)c2)cc1]

Albright et al., 1998 (U.S. Pat. No. 5,849,735) describes tricyclic compounds of the following general formula. These compounds are said to exhibit in vivo vasopressin antagonist activity and antagonist activity at oxytocin receptors, and to be useful in treating conditions where decreased vasopressin levels are desired, such as in congestive heart failure, in disease conditions with excess renal water reabsorption and in conditions with increased vascular resistance and coronary vasoconstriction.

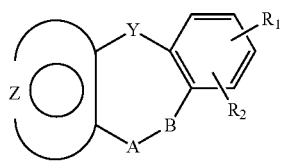

Additionally, the document includes, as reference example 65 (see column 53 therein), a compound having the structure shown below, without attributing any particular activity to the compound.

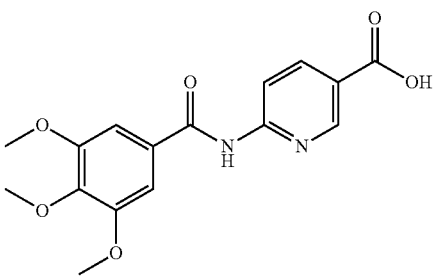 [SMILES: COc1cc(C(=O)Nc2ccc(C(=O)O)cn2)cc(OC)c1OC]

Schmidt et al., 1975 (GB 1 409 689) describes compounds referred to as "new penicillin compounds", which are said to be suitable for treating bacterial infections. Additionally, 4-(3,4,5-trimethoxybenzoylamino)-benzoic acid is mentioned as a precursor compound (for compound 22; see page 35 therein). This precursor compound has the structure shown below.

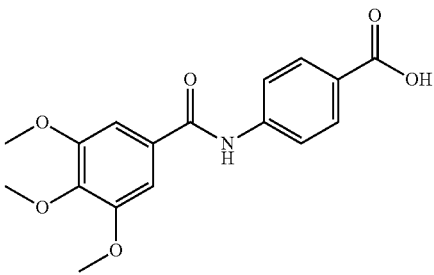 [SMILES: COc1cc(C(=O)Nc2ccc(C(=O)O)cc2)cc(OC)c1OC]

Coppola et al., 2005 describes compounds said to have activity as inhibitors of 11β-HSD1, and suggests that the compounds may "serve as useful tools to study the effect of 11β-HSD1 inhibition in animal models of diabetes, dyslipidemia and obesity". Of the compounds described in the document, compound 9a has the structure shown below.

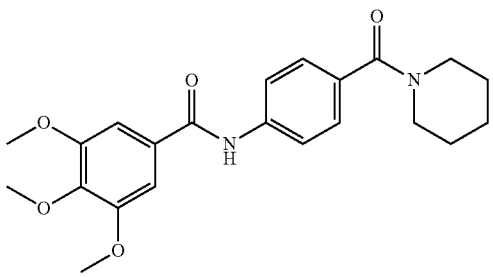 [SMILES: COc1cc(C(=O)Nc2ccc(C(=O)N3CCCCC3)cc2)cc(OC)c1OC]

SUMMARY OF THE INVENTION

One aspect of the invention pertains to certain aryl-amido-aryl compounds (for convenience, collectively referred to herein as "AAA compounds"), as described herein.

Another aspect of the invention pertains to a composition (e.g., a pharmaceutical composition) comprising an AAA compound, as described herein, and a pharmaceutically acceptable carrier or diluent.

Another aspect of the invention pertains to method of preparing a composition (e.g., a pharmaceutical composition) comprising the step of admixing an AAA compound, as described herein, and a pharmaceutically acceptable carrier or diluent.

Another aspect of the present invention pertains to a method of activating retinoic acid receptor α (RARα), in vitro or in vivo, comprising contacting RARα with an effective amount of an AAA compound, as described herein.

Another aspect of the present invention pertains to a method of selectively activating retinoic acid receptor α (RARα) (e.g., with respect to RARβ and/or RARγ), in vitro or in vivo, comprising contacting RARα with an effective amount of an AAA compound, as described herein.

Another aspect of the present invention pertains to a method of activating retinoic acid receptor α (RARα) in a neuronal cell, in vitro or in vivo, comprising contacting the cell with an effective amount of an AAA compound, as described herein.

Another aspect of the present invention pertains to a method of selectively activating retinoic acid receptor α (RARα) (e.g., with respect to RARβ and/or RARγ) in a neuronal cell, in vitro or in vivo, comprising contacting the cell with an effective amount of an AAA compound, as described herein.

Another aspect of the present invention pertains to a method of up-regulating chAT expression in a cortical neuron, comprising contacting the cortical neuron, in vitro or in vivo, with an effective amount of an AAA compound, as described herein.

Another aspect of the present invention pertains to a method of down-regulating APP expression in a cortical neuron, comprising contacting the cortical neuron, in vitro or in vivo, with an effective amount of an AAA compound, as described herein.

Another aspect of the present invention pertains to a method of up-regulating ADAM10 expression in a cortical neuron, comprising contacting the cortical neuron, in vitro or in vivo, with an effective amount of an AAA compound, as described herein.

Another aspect of the present invention pertains to a method of down-regulating Aβ40 and Aβ42 expression in a cortical neuron, comprising contacting the cortical neuron, in vitro or in vivo, with an effective amount of an AAA compound, as described herein.

Another aspect of the present invention pertains to a method of up-regulating chAT expression in a cortical neuron in a patient, comprising administering to the patient a therapeutically effective amount of an AAA compound, as described herein.

Another aspect of the present invention pertains to a method of down-regulating APP expression in a cortical neuron in a patient, comprising administering to the patient a therapeutically effective amount of an AAA compound, as described herein.

Another aspect of the present invention pertains to a method of up-regulating ADAM10 expression in a cortical neuron in a patient, comprising administering to the patient a therapeutically effective amount of an AAA compound, as described herein.

Another aspect of the present invention pertains to a method of down-regulating Aβ40 and Aβ42 expression in a cortical neuron in a patient, comprising administering to the patient a therapeutically effective amount of an AAA compound, as described herein.

Another aspect of the present invention pertains to a method of preventing, reducing, or slowing cortical neuronal death in a patient, comprising administering to the patient a therapeutically effective amount of an AAA compound, as described herein.

Another aspect of the present invention pertains to a method of treatment comprising administering to a subject in need of treatment a therapeutically-effective amount of an AAA compound, as described herein, preferably in the form of a pharmaceutical composition.

Another aspect of the present invention pertains to an AAA compound as described herein for use treatment of the human or animal body by therapy.

Another aspect of the present invention pertains to use of an AAA compound, as described herein, in the manufacture of a medicament for use in treatment.

In one embodiment, the treatment is treatment of a disease or condition that is mediated by RARα.

In one embodiment, the treatment is treatment of a disease or condition that is ameliorated by the activation of RARα.

In one embodiment, the treatment is treatment of a disease or condition that is ameliorated by the selective activation of RARα(e.g., with respect to RARβ and/or RARγ).

In one embodiment, the treatment is treatment of a cognitive disorder, memory impairment, memory deficit, senile dementia, Alzheimer's disease, early stage Alzheimer's disease, intermediate stage Alzheimer's disease, late stage Alzheimer's disease, cognitive impairment, or mild cognitive impairment.

In one embodiment, the treatment is treatment of Alzheimer's disease.

In one embodiment, the treatment is treatment of early stage Alzheimer's disease.

In one embodiment, the treatment is treatment of intermediate stage Alzheimer's disease.

In one embodiment, the treatment is treatment of late stage Alzheimer's disease.

In one embodiment, the treatment is treatment of cognitive impairment.

In one embodiment, the treatment is treatment of mild cognitive impairment.

Another aspect of the present invention pertains to a kit comprising (a) an AAA compound, as described herein, preferably provided as a pharmaceutical composition and in a suitable container and/or with suitable packaging; and (b) instructions for use, for example, written instructions on how to administer the compound.

Another aspect of the present invention pertains to an AAA compound obtainable by a method of synthesis as described herein, or a method comprising a method of synthesis as described herein.

Another aspect of the present invention pertains to an AAA compound obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspect of the invention.

DETAILED DESCRIPTION OF THE INVENTION

Compounds

One aspect of the present invention relates to certain compounds which are structurally related to the following compounds:

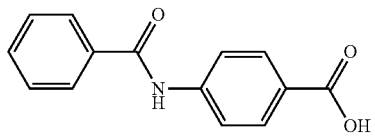

4-Benzoylamino-benzoic acid

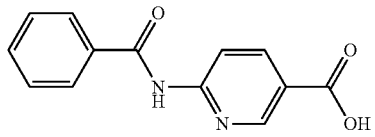

6-Benzoylamino-nicotinic acid

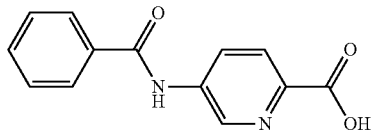

5-Benzoylamino-pyridine-2-carboxylic acid

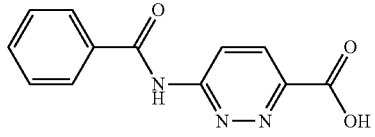

6-Benzoylamino-pyridine-3-carboxylic acid

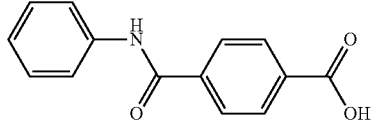

N-Phenyl-terephthalamic acid

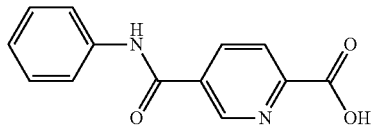

5-Phenylcarbamoyl-pyridine-2-carboxylic acid

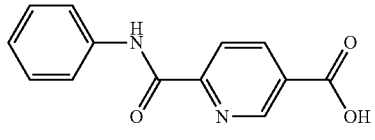

6-Phenylcarbamoyl-nicotinic acid

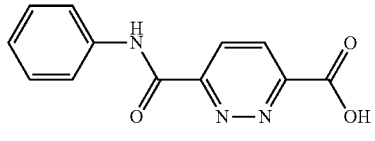

6-Phenylcarbamoyl-pyridazine-3-carboxylic acid

Thus, one aspect of the present invention pertains to compounds selected from compounds of the following formula, and pharmaceutically acceptable salts, hydrates, and solvates thereof, wherein —$R^1$, —$R^2$, —$R^3$, -J-, =W=, =Y=, =Z=, and —$R^O$ are as defined herein (for convenience, collectively referred to herein as "aryl-amido-aryl compounds" or "AAA compounds"):

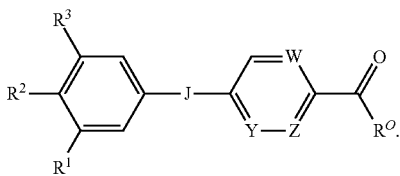

Some embodiments of the invention include the following:

(1) A compound selected from compounds of the following formula, and pharmaceutically acceptable salts, hydrates, and solvates thereof:

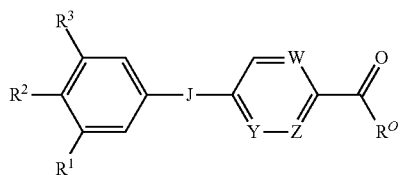

wherein:
—$R^1$ is independently —X, —$R^X$, —O—$R^X$, —O—$R^A$, —O—$R^C$, —O-L-$R^C$, —O—$R^{AR}$, or —O-L-$R^{AR}$;
—$R^2$ is independently —X, —$R^X$, —O—$R^X$, —O—$R^A$, —O—$R^C$, —O-L-$R^C$, —O—$R^{AR}$, or —O-L-$R^{AR}$;
—$R^3$ is independently —X, —$R^X$, —O—$R^X$, —O—$R^A$, —O—$R^C$, —O-L-$R^C$, —O—$R^{AR}$, or —O-L-$R^{AR}$;
wherein:
each —X is independently —F, —Cl, —Br, or —I;
each —$R^A$ is independently saturated aliphatic $C_{1-6}$alkyl;
each —$R^X$ is independently saturated aliphatic $C_{1-6}$haloalkyl;
each —$R^C$ is independently saturated $C_{3-7}$cycloalkyl;
each —$R^{AR}$ is independently phenyl or $C_{5-6}$heteroaryl;
each -L- is independently saturated aliphatic $C_{1-3}$alkylene;
and wherein:
-J- is independently —C(=O)—$NR^N$— or —$NR^N$—C(=O)—;
—$R^N$ is independently —H or —$R^{NN}$;
—$R^{NN}$ is independently saturated aliphatic $C_{1-4}$alkyl;
=Y— is =$CR^Y$— and —Z= is —$CR^Z$=; or
=Y— is =N— and —Z= is —$CR^Z$=; or
=Y— is =$CR^Y$— and —Z= is —N=; or
=Y— is =N— and —Z= is —N=;
—$R^Y$ is independently —H or —$R^{YY}$;
—$R^{YY}$ is independently —F, —Cl, —Br, —I, or saturated aliphatic $C_{1-4}$alkyl;
—$R^Z$ is independently —H or —$R^{ZZ}$;
—$R^{ZZ}$ is independently —F, —Cl, —Br, —I, —OH, saturated aliphatic $C_{1-4}$alkoxy, saturated aliphatic $C_{1-4}$alkyl, or saturated aliphatic $C_{1-4}$haloalkyl;
=W— is =$CR^W$—;
—$R^W$ is independently —H or —$R^{WW}$;
—$R^{WW}$ is independently —F, —Cl, —Br, —I, —OH, saturated aliphatic $C_{1-4}$alkoxy, saturated aliphatic $C_{1-4}$alkyl, or saturated aliphatic $C_{1-4}$haloalkyl;
—$R^O$ is independently —OH, —$OR^E$, —$NH_2$, —$NHR^{T1}$, —$NR^{T1}R^{T1}$, or —$NR^{T2}R^{T3}$;
—$R^E$ is independently saturated aliphatic $C_{1-6}$alkyl;
each —$R^{T1}$ is independently saturated aliphatic $C_{1-6}$alkyl;

—NR$^{72}$R$^{73}$ is independently azetidino, pyrrolidino, piperidino, piperizino, N—(C$_{1-3}$alkyl) piperizino, or morpholino.

For the avoidance of doubt, it is not intended that —R$^1$ and —R$^2$ and —R$^3$ are attached to one another other than as shown in the above formula. For example, it is not intended that —R$^1$ and —R$^2$ together form a ring fused to the benzene ring to which they are attached. Similarly, it is not intended that —R$^2$ and —R$^3$ together form a ring fused to the benzene ring to which they are attached. Similarly, it is not intended that —R$^1$ and —R$^3$ together form a ring fused to the benzene ring to which they are attached.

For the avoidance of doubt, the term "C$_{1-6}$haloalkyl" refers to a C$_{1-6}$alkyl group that has one or more (e.g., 1, 2, 3, etc.) halo substituents, and includes, for example, —CF$_3$, —CH$_2$CF$_3$, —CH$_2$CH$_2$F, etc.

For the avoidance of doubt, the term "agonist" is intended to encompass compounds which are partial agonists.

Optional Provisos

In one or more aspects of the present invention (e.g., compounds, compositions, compounds for use in therapy, use of compounds in the manufacture of a medicament, methods, methods of treatment, etc.), the compounds are optionally as defined herein, but with one or more optional provisos, as defined herein.

(2) A compound according to (1), with the proviso that the compound is not a compound selected from: compounds (PP-01), (PP-02), and (PP-03), and salts, hydrates, and solvates thereof.

(3) A compound according to (1), with the proviso that the compound is not a compound selected from: compounds (PP-01), (PP-02), (PP-03), (PP-04), (PP-05), (PP-06), (PP-07), and (PP-08), and salts, hydrates, and solvates thereof.

| # | Structure | Name | Registry No. |
|---|---|---|---|
| PP-01 | 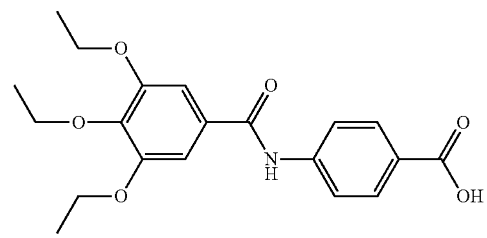 [SMILES: CCOc1cc(C(=O)Nc2ccc(C(=O)O)cc2)cc(OCC)c1OCC] | 4-(3,4,5-triethoxy-benzoylamino)-benzoic acid | 926257-87-6 |
| PP-02 | 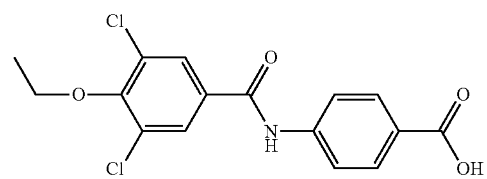 | 4-(3,5-Dichloro-4-ethoxy-benzoylamino)-benzoic acid | 690982-75-3 |
| PP-03 | 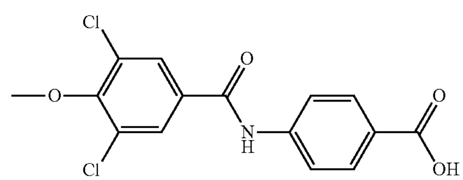 [SMILES: COc1c(Cl)cc(C(=O)Nc2ccc(C(=O)O)cc2)cc1Cl] | 4-(3,5-Dichloro-4-methoxy-benzoylamino)-benzoic acid | 832094-08-3 |
| PP-04 | 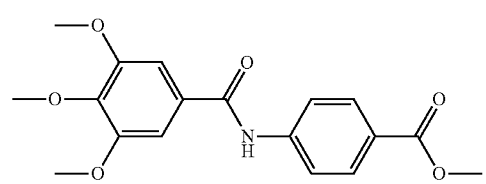 | 4-(3,4,5-Trimethoxy-benzoylamino)-benzoic acid methyl ester | 303796-30-7 |
| PP-05 | 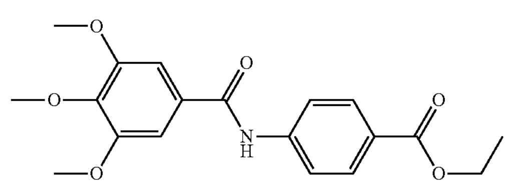 [SMILES: CCOC(=O)c1ccc(NC(=O)c2cc(OC)c(OC)c(OC)c2)cc1] | 4-(3,4,5-Trimethoxy-benzoylamino)-benzoic acid ethyl ester | 1849-89-4 |
| PP-06 | 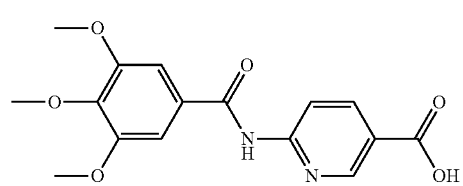 [SMILES: COc1cc(C(=O)Nc2ccc(C(=O)O)cn2)cc(OC)c1OC] | 6-(3,4,5-Trimethoxy-benzoylamino)-nicotinic acid | 180339-52-0 |

| # | Structure | Name | Registry No. |
|---|---|---|---|
| PP-07 | 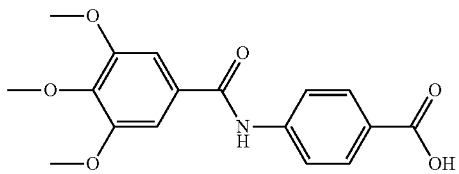 [SMILES: COc1cc(C(=O)Nc2ccc(C(=O)O)cc2)cc(OC)c1OC] | 4-(3,4,5-Trimethoxy-benzoylamino)-benzoic acid | 54057-51-1 |
| PP-08 | 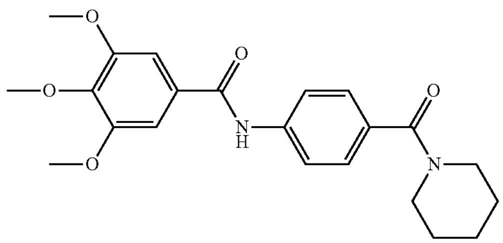 [SMILES: COc1cc(C(=O)Nc2ccc(C(=O)N3CCCCC3)cc2)cc(OC)c1OC] | 3,4,5-Trimethoxy-N-[4-(piperidine-1-carbonyl)-phenyl]-benzamide | 901062-25-7 |

It appears that compounds (PP-01), (PP-02), and (PP-03) are commercially available. However, their usefulness (e.g., as RARα agonists, in method of therapy, etc., as described herein) has not yet been published.

In one or more aspects of the present invention (e.g., compounds for use in therapy, use of compounds in the manufacture of a medicament, methods of treatment, etc.), the compounds are optionally as defined herein, but without the proviso regarding compounds (PP-01), (PP-02), and (PP-03).

In one or more aspects of the present invention (e.g., compounds for use in therapy, use of compounds in the manufacture of a medicament, methods of treatment, etc.), the compounds are optionally as defined herein, but without the proviso regarding compounds (PP-01), (PP-02), (PP-03), (PP-04), (PP-05), (PP-06), (PP-07), and (PP-08).

For example, a reference to a particular group of compounds "without the recited proviso regarding compounds (PP-01), (PP-02), and (PP-03)" (e.g., for use in therapy) is intended to be a reference to the compounds as defined, but wherein the definition no longer includes the indicated proviso. In such cases, it is as if the indicated proviso has been deleted from the definition of compounds, and the definition has been expanded to encompass those compounds which otherwise would have been excluded by the indicated proviso.

In one or more aspects of the present invention (e.g., compounds for use in therapy, use of compounds in the manufacture of a medicament, methods of treatment, etc.), the compounds are optionally as defined herein, with the proviso regarding compounds (PP-01), (PP-02), and (PP-03).

In one or more aspects of the present invention (e.g., compounds for use in therapy, use of compounds in the manufacture of a medicament, methods of treatment, etc.), the compounds are optionally as defined herein, with the proviso regarding compounds (PP-01), (PP-02), (PP-03), (PP-04), (PP-05), (PP-06), (PP-07), and (PP-08).

The Group —$R^1$ (4) A compound according to any one of (1) to (3), wherein:
—$R^1$ is independently —X, —$R^X$, —O—$R^X$, —O—$R^A$, —O—$R^C$, —O-L-$R^C$, or —O-L-$R^{AR}$.

(5) A compound according to any one of (1) to (3), wherein:
—$R^1$ is independently —X, —$R^X$, —O—$R^X$, —O—$R^A$, —O—$R^C$, —O-L-$R^C$.

(6) A compound according to any one of (1) to (3), wherein:
—$R^1$ is independently —X, —$R^X$, —O—$R^X$, —O—$R^A$, or —O—$R^C$.

(7) A compound according to any one of (1) to (3), wherein:
—$R^1$ is independently —X, —$R^X$, —O—$R^A$, or —O—$R^C$.

(8) A compound according to any one of (1) to (3), wherein:
—$R^1$ is independently —X, —$R^X$, or —O—$R^A$.

(9) A compound according to any one of (1) to (3), wherein:
—$R^1$ is independently —X or —$R^X$.

(10) A compound according to any one of (1) to (3), wherein:
—$R^1$ is independently —X.

(11) A compound according to any one of (1) to (3), wherein:
—$R^1$ is independently —$R^X$.

(12) A compound according to any one of (1) to (3), wherein:
—$R^1$ is independently —O—$R^X$.

(13) A compound according to any one of (1) to (3), wherein:
—$R^1$ is independently —O—$R^A$.

(14) A compound according to any one of (1) to (3), wherein:
—$R^1$ is independently —O—$R^C$.

(15) A compound according to any one of (1) to (3), wherein:
—$R^1$ is independently —O-L-$R^C$.

(16) A compound according to any one of (1) to (3), wherein:
—$R^1$ is independently —O—$R^{AR}$.

(17) A compound according to any one of (1) to (3), wherein:
—$R^1$ is independently —O-L-$R^{AR}$.

The Group —$R^2$

(18) A compound according to any one of (1) to (17), wherein:
—$R^2$ is independently —O—$R^X$, —O—$R^A$, —O—$R^C$, —O-L-$R^C$, —O—$R^{AR}$, or —O-L-$R^{AR}$.

(19) A compound according to any one of (1) to (17), wherein:
—$R^2$ is independently —O—$R^X$, —O—$R^A$, —O—$R^C$, —O-L-$R^C$, or —O-L-$R^{AR}$.

(20) A compound according to any one of (1) to (17), wherein:
—$R^2$ is independently —O—$R^A$, —O—$R^C$, —O-L-$R^C$, or —O-L-$R^{AR}$.

(21) A compound according to any one of (1) to (17), wherein:

—$R^2$ is independently —O—$R^A$, —O—$R^C$, or —O-L-$R^C$.

(22) A compound according to any one of (1) to (17), wherein:
—$R^2$ is independently —O—$R^A$ or —O—$R^C$.

(23) A compound according to any one of (1) to (17), wherein:
—$R^2$ is independently —X or —$R^X$.

(24) A compound according to any one of (1) to (17), wherein:
—$R^2$ is independently —X.

(25) A compound according to any one of (1) to (17), wherein:
—$R^2$ is independently —$R^X$.

(26) A compound according to any one of (1) to (17), wherein:
—$R^2$ is independently —O—$R^X$.

(27) A compound according to any one of (1) to (17), wherein:
—$R^2$ is independently —O—$R^A$.

(28) A compound according to any one of (1) to (17), wherein:
—$R^2$ is independently —O—$R^C$.

(29) A compound according to any one of (1) to (17), wherein:
—$R^2$ is independently —O-L-$R^C$.

(30) A compound according to any one of (1) to (17), wherein:
—$R^2$ is independently —O—$R^{AR}$.

(31) A compound according to any one of (1) to (17), wherein:
—$R^2$ is independently —O-L-$R^{AR}$.

The Group —$R^3$

(32) A compound according to any one of (1) to (31), wherein:
—$R^3$ is independently —X, —$R^X$, —O—$R^X$, —O—$R^A$, —O—$R^C$, —O-L-$R^C$, or —O-L-$R^{AR}$.

(33) A compound according to any one of (1) to (31), wherein:
—$R^3$ is independently —X, —$R^X$, —O—$R^X$, —O—$R^A$, —O—$R^C$, —O-L-$R^C$.

(34) A compound according to any one of (1) to (31), wherein:
—$R^3$ is independently —X, —$R^X$, —O—$R^X$, —O—$R^A$, or —O—$R^C$.

(35) A compound according to any one of (1) to (31), wherein:
—$R^3$ is independently —X, —$R^X$, —O—$R^A$, or —O—$R^C$.

(36) A compound according to any one of (1) to (31), wherein:
—$R^3$ is independently —X, —$R^X$, or —O—$R^A$.

(37) A compound according to any one of (1) to (31), wherein:
—$R^3$ is independently —X or —$R^X$.

(38) A compound according to any one of (1) to (31), wherein:
—$R^3$ is independently —X.

(39) A compound according to any one of (1) to (31), wherein:
—$R^3$ is independently —$R^X$.

(40) A compound according to any one of (1) to (31), wherein:
—$R^3$ is independently —O—$R^X$.

(41) A compound according to any one of (1) to (31), wherein:
—$R^3$ is independently —O—$R^A$.

(42) A compound according to any one of (1) to (31), wherein:
—$R^3$ is independently —O—$R^C$.

(43) A compound according to any one of (1) to (31), wherein:
—$R^3$ is independently —O-L-$R^C$.

(44) A compound according to any one of (1) to (31), wherein:
—$R^3$ is independently —O—$R^{AR}$.

(45) A compound according to any one of (1) to (31), wherein:
—$R^3$ is independently —O-L-$R^{AR}$.

Examples of Some Particular Combinations of —$R^1$, —$R^2$, and —$R^3$

(46) A compound according to any one of (1) to (3), wherein:
—$R^1$ is independently —X, —$R^X$, —O—$R^X$, —O—$R^A$, —O—$R^C$, —O-L-$R^C$, —O—$R^{AR}$, or —O-L-$R^{AR}$;
—$R^2$ is independently —X, —$R^X$, —O—$R^X$, —O—$R^A$, —O—$R^C$, —O-L-$R^C$, —O—$R^{AR}$, or —O-L-$R^{AR}$;
—$R^3$ is independently —X, —$R^X$, —O—$R^X$, —O—$R^A$, —O—$R^C$, —O-L-$R^C$, —O—$R^{AR}$, or —O-L-$R^{AR}$;
with the proviso that —$R^1$, —$R^2$, and —$R^3$ are not all —O-Me; and
with the proviso that —$R^1$, —$R^2$, and —$R^3$ are not all —O-Et.

(47) A compound according to any one of (1) to (3), wherein:
—$R^1$ is independently —X, —$R^X$, —O—$R^X$, —O—$R^A$, —O—$R^C$, —O-L-$R^C$, —O—$R^{AR}$, or —O-L-$R^{AR}$;
—$R^2$ is independently —X, —$R^X$, —O—$R^X$, —O—$R^A$, —O—$R^C$, —O-L-$R^C$, —O—$R^{AR}$, or —O-L-$R^{AR}$;
—$R^3$ is independently —X, —$R^X$, —O—$R^X$, —O—$R^A$, —O—$R^C$, —O-L-$R^C$, —O—$R^{AR}$, or —O-L-$R^{AR}$;
with the proviso that if: —$R^1$, —$R^2$, and —$R^3$ are all —O—$R^A$,
then: —$R^1$, —$R^2$, and —$R^3$ are not all the same.

(48) A compound according to any one of (1) to (3), wherein:
—$R^1$ is independently —X, —$R^X$, —O—$R^X$, —O—$R^A$, —O—$R^C$, —O-L-$R^C$, —O—$R^{AR}$, or —O-L-$R^{AR}$;
—$R^2$ is independently —X, —$R^X$, —O—$R^X$, —O—$R^A$, —O—$R^C$, —O-L-$R^C$, —O—$R^{AR}$, or —O-L-$R^{AR}$;
—$R^3$ is independently —X, —$R^X$, —O—$R^X$, —O—$R^A$, —O—$R^C$, —O-L-$R^C$, —O—$R^{AR}$, or —O-L-$R^{AR}$;
with the proviso that —$R^1$, —$R^2$, and —$R^3$ are not all —O—$R^A$.

(49) A compound according to any one of (1) to (3), wherein:
—$R^1$ is independently —X, —$R^X$, —O—$R^X$, —O—$R^A$, —O—$R^C$, or —O-L-$R^C$;
—$R^2$ is independently —O—$R^A$, —O—$R^C$, or —O-L-$R^C$; and
—$R^3$ is independently —X, —$R^X$, —O—$R^X$, —O—$R^A$, —O—$R^C$, or —O-L-$R^C$.

(50) A compound according to any one of (1) to (3), wherein:
—$R^1$ is independently —X, —$R^X$, —O—$R^X$, —O—$R^A$, —O—$R^C$, or —O-L-$R^C$; —$R^2$ is independently —O—$R^A$, —O—$R^C$, or —O-L-$R^C$; and
—$R^3$ is independently —X, —$R^X$, —O—$R^X$, —O—$R^A$, —O—$R^C$, or —O-L-$R^C$;
with the proviso that —$R^1$, —$R^2$, and —$R^3$ are not all —O-Me; and
with the proviso that —$R^1$, —$R^2$, and —$R^3$ are not all —O-Et.

(51) A compound according to any one of (1) to (3), wherein:
—$R^1$ is independently —X, —$R^X$, —O—$R^X$, —O—$R^A$, —O—$R^C$, or —O-L-$R^C$;

—$R^2$ is independently —O—$R^A$, —O—$R^C$, or —O-L-$R^C$; and
—$R^3$ is independently —X, —$R^X$, —O—$R^X$, —O—$R^A$, —O—$R^C$, or —O-L-$R^C$;
with the proviso that if: —$R^1$, —$R^2$, and —$R^3$ are all —O—$R^A$,
then: —$R^1$, —$R^2$, and —$R^3$ are not all the same.

(52) A compound according to any one of (1) to (3), wherein:
—$R^1$ is independently —X, —$R^X$, —O—$R^X$, —O—$R^A$, —O—$R^C$, or —O-L-$R^C$;
—$R^2$ is independently —O—$R^A$, —O—$R^C$, or —O-L-$R^C$; and
—$R^3$ is independently —X, —$R^X$, —O—$R^X$, —O—$R^A$, —O—$R^C$, or —O-L-$R^C$;
with the proviso that —$R^1$, —$R^2$, and —$R^3$ are not all —O—$R^A$.

(53) A compound according to any one of (1) to (3), wherein:
—$R^1$ is independently —X, —$R^X$, —O—$R^A$, —O—$R^C$, or —O-L-$R^C$;
—$R^2$ is independently —O—$R^A$, —O—$R^C$, or —O-L-$R^C$; and
—$R^3$ is independently —X, —$R^X$, —O—$R^A$, —O—$R^C$, or —O-L-$R^C$.

(54) A compound according to any one of (1) to (3), wherein:
—$R^1$ is independently —X, —$R^X$, —O—$R^A$, —O—$R^C$, or —O-L-$R^C$;
—$R^2$ is independently —O—$R^A$, —O—$R^C$, or —O-L-$R^C$; and
—$R^3$ is independently —X, —$R^X$, —O—$R^A$, —O—$R^C$, or —O-L-$R^C$;
with the proviso that —$R^1$, —$R^2$, and —$R^3$ are not all —O-Me; and
with the proviso that —$R^1$, —$R^2$, and —$R^3$ are not all —O-Et.

(55) A compound according to any one of (1) to (3), wherein:
—$R^1$ is independently —X, —$R^X$, —O—$R^A$, —O—$R^C$, or —O-L-$R^C$;
—$R^2$ is independently —O—$R^A$, —O—$R^C$, or —O-L-$R^C$; and
—$R^3$ is independently —X, —$R^X$, —O—$R^A$, —O—$R^C$, or —O-L-$R^C$;
with the proviso that if: —$R^1$, —$R^2$, and —$R^3$ are all —O—$R^A$,
then: —$R^1$, —$R^2$, and —$R^3$ are not all the same.

(56) A compound according to any one of (1) to (3), wherein:
—$R^1$ is independently —X, —$R^X$, —O—$R^A$, —O—$R^C$, or —O-L-$R^C$;
—$R^2$ is independently —O—$R^A$, —O—$R^C$, or —O-L-$R^C$; and
—$R^3$ is independently —X, —$R^X$, —O—$R^A$, —O—$R^C$, or —O-L-$R^C$;
with the proviso that —$R^1$, —$R^2$, and —$R^3$ are not all —O—$R^A$.

(57) A compound according to any one of (1) to (3), wherein:
—$R^1$ is independently —X or —$R^X$;
—$R^2$ is independently —O—$R^A$, —O—$R^C$, or —O-L-$R^C$; and
—$R^3$ is independently —X or —$R^X$.

(58) A compound according to any one of (1) to (3), wherein:
—$R^1$ is independently —X;
—$R^2$ is independently —O—$R^A$, —O—$R^C$, or —O-L-$R^C$; and
—$R^3$ is independently —X.

(59) A compound according to any one of (1) to (3), wherein:
—$R^1$ is independently —X;
—$R^2$ is independently —O—$R^A$ or —O—$R^C$; and
—$R^3$ is independently —X.

(60) A compound according to any one of (1) to (3), wherein:
—$R^1$ is independently —O—$R^A$, —O—$R^C$, or —O-L-$R^C$;
—$R^2$ is independently —O—$R^A$, —O—$R^C$, or —O-L-$R^C$; and
—$R^3$ is independently —X or —$R^X$;
or:
—$R^1$ is independently —X or —$R^X$;
—$R^2$ is independently —O—$R^A$, —O—$R^C$, or —O-L-$R^C$; and
—$R^3$ is independently —O—$R^A$, —O—$R^C$, or —O-L-$R^C$.

(61) A compound according to any one of (1) to (3), wherein:
—$R^1$ is independently —O—$R^A$ or —O—$R^C$;
—$R^2$ is independently —O—$R^A$ or —O—$R^C$; and
—$R^3$ is independently —X or —$R^X$;
or:
—$R^1$ is independently —X or —$R^X$;
—$R^2$ is independently —O—$R^A$ or —O—$R^C$; and
—$R^3$ is independently —O—$R^A$ or —O—$R^C$.

(62) A compound according to any one of (1) to (3), wherein:
—$R^1$ is independently —O—$R^A$;
—$R^2$ is independently —O—$R^A$; and
—$R^3$ is independently —X or —$R^X$;
or:
—$R^1$ is independently —X or —$R^X$;
—$R^2$ is independently —O—$R^A$; and
—$R^3$ is independently —O—$R^A$.

(63) A compound according to any one of (1) to (3), wherein:
—$R^1$ is independently —O—$R^A$, —O—$R^C$, or —O-L-$R^C$;
—$R^2$ is independently —O—$R^A$, —O—$R^C$, or —O-L-$R^C$; and
—$R^3$ is independently —X;
or:
—$R^1$ is independently —X;
—$R^2$ is independently —O—$R^A$, —O—$R^C$, or —O-L-$R^C$; and
—$R^3$ is independently —O—$R^A$, —O—$R^C$, or —O-L-$R^C$.

(64) A compound according to any one of (1) to (3), wherein:
—$R^1$ is independently —O—$R^A$ or —O—$R^C$;
—$R^2$ is independently —O—$R^A$ or —O—$R^C$; and
—$R^3$ is independently —X;
or:
—$R^1$ is independently —X;
—$R^2$ is independently —O—$R^A$ or —O—$R^C$; and
—$R^3$ is independently —O—$R^A$ or —O—$R^C$.

(65) A compound according to any one of (1) to (3), wherein:
—$R^1$ is independently —O—$R^A$;
—$R^2$ is independently —O—$R^A$; and
—$R^3$ is independently —X;
or:
—$R^1$ is independently —X;
—$R^2$ is independently —O—$R^A$; and
—$R^3$ is independently —O—$R^A$.

(66) A compound according to any one of (1) to (3), wherein:
—$R^1$ is independently —O—$R^A$, —O—$R^C$, or —O-L-$R^C$;
—$R^2$ is independently —O—$R^A$, —O—$R^C$, or —O-L-$R^C$; and
—$R^3$ is independently —O—$R^A$, —O—$R^C$, or —O-L-$R^C$.

(67) A compound according to any one of (1) to (3), wherein:
—$R^1$ is independently —O—$R^A$, —O—$R^C$, or —O-L-$R^C$;

—R² is independently —O—R^A, —O—R^C, or —O-L-R^C; and

—R³ is independently —O—R^A, —O—R^C, or —O-L-R^C;

with the proviso that —R¹, —R², and —R³ are not all —O-Me; and with the proviso that —R¹, —R², and —R³ are not all —O-Et.

(68) A compound according to any one of (1) to (3), wherein:
—R¹ is independently —O—R^A, —O—R^C, or —O-L-R^C;
—R² is independently —O—R^A, —O—R^C, or —O-L-R^C; and
—R³ is independently —O—R^A, —O—R^C, or —O-L-R^C;
with the proviso that if: —R¹, —R², and —R³ are all —O—R^A,
then: —R¹, —R², and —R³ are not all the same.

(69) A compound according to any one of (1) to (3), wherein:
—R¹ is independently —O—R^A, —O—R^C, or —O-L-R^C;
—R² is independently —O—R^A, —O—R^C, or —O-L-R^C; and
—R³ is independently —O—R^A, —O—R^C, or —O-L-R^C;
with the proviso that —R¹, —R², and —R³ are not all —O—R^A.

(70) A compound according to any one of (1) to (3), wherein:
—R¹ is independently —O—R^A or —O—R^C;
—R² is independently —O—R^A or —O—R^C; and
—R³ is independently —O—R^A or —O—R^C.

(71) A compound according to any one of (1) to (3), wherein:
—R¹ is independently —O—R^A or —O—R^C;
—R² is independently —O—R^A or —O—R^C; and
—R³ is independently —O—R^A or —O—R^C;
with the proviso that —R¹, —R², and —R³ are not all —O-Me; and
with the proviso that —R¹, —R², and —R³ are not all —O-Et.

(72) A compound according to any one of (1) to (3), wherein:
—R¹ is independently —O—R^A or —O—R^C;
—R² is independently —O—R^A or —O—R^C; and
—R³ is independently —O—R^A or —O—R^C;
with the proviso that if: —R¹, —R², and —R³ are all —O—R^A,
then: —R¹, —R², and —R³ are not all the same.

(73) A compound according to any one of (1) to (3), wherein:
—R¹ is independently —O—R^A or —O—R^C;
—R² is independently —O—R^A or —O—R^C; and
—R³ is independently —O—R^A or —O—R^C;
with the proviso that —R¹, —R², and —R³ are not all —O—R^A.

The Group —X
(74) A compound according to any one of (1) to (73), wherein:
each —X, if present, is independently —F, —Cl, or —Br.
(75) A compound according to any one of (1) to (73), wherein:
each —X, if present, is independently —F or —Cl.
(76) A compound according to any one of (1) to (73), wherein:
each —X, if present, is independently —Cl or —Br.
(77) A compound according to any one of (1) to (73), wherein:
each —X, if present, is independently —F.
(78) A compound according to any one of (1) to (73), wherein:
each —X, if present, is independently —Cl.
(79) A compound according to any one of (1) to (73), wherein:
each —X, if present, is independently —Br.

The Group —R^A
(80) A compound according to any one of (1) to (79), wherein:
each —R^A, if present, is independently saturated aliphatic $C_{1-4}$alkyl.
(81) A compound according to any one of (1) to (79), wherein:
each —R^A, if present, is independently -Me, -Et, -nPr, or -iPr.
(82) A compound according to any one of (1) to (79), wherein:
each —R^A, if present, is independently -Me.
(83) A compound according to any one of (1) to (79), wherein:
each —R^A, if present, is independently -Et.
(84) A compound according to any one of (1) to (79), wherein:
each —R^A, if present, is independently -iPr.

The Group —R^X
(85) A compound according to any one of (1) to (84), wherein:
each —R^X, if present, is independently saturated aliphatic $C_{1-4}$haloalkyl.
(86) A compound according to any one of (1) to (84), wherein:
each —R^X, if present, is independently —CF₃, —CH₂CF₃, or —CH₂CH₂F.
(87) A compound according to any one of (1) to (84), wherein:
each —R^X, if present, is independently —CF₃.

The Group —R^C
(88) A compound according to any one of (1) to (87), wherein:
each —R^C, if present, is independently cyclopropyl, cyclobutyl, cyclopentyl, or cyclohexyl.
(89) A compound according to any one of (1) to (87), wherein:
each —R^C, if present, is independently cyclopropyl, cyclobutyl, or cyclopentyl.
(90) A compound according to any one of (1) to (87), wherein:
each —R^C, if present, is independently cyclopropyl.
(91) A compound according to any one of (1) to (87), wherein:
each —R^C, if present, is independently cyclobutyl.
(92) A compound according to any one of (1) to (87), wherein:
each —R^C, if present, is independently cyclopentyl.

The Group —R^AR
(93) A compound according to any one of (1) to (92), wherein:
each —R^AR, if present, is independently phenyl or $C_6$heteroaryl.
(94) A compound according to any one of (1) to (92), wherein:
each —R^AR, if present, is independently phenyl, pyridinyl, pyrimidinyl, or pyridizinyl.
(95) A compound according to any one of (1) to (92), wherein:
each —R^AR, if present, is independently phenyl or pyridinyl.

(96) A compound according to any one of (1) to (92), wherein:
each —$R^{AR}$, if present, is independently phenyl.
(97) A compound according to any one of (1) to (92), wherein:
each —$R^{AR}$, if present, is independently pyridinyl.

The Group -L-
(98) A compound according to any one of (1) to (97), wherein:
each -L-, if present, is independently —$CH_2$— or —$CH_2CH_2$—.
(99) A compound according to any one of (1) to (97), wherein:
each -L-, if present, is independently —$CH_2$—.

The Groups Y and Z
(100) A compound according to any one of (1) to (99), wherein:
=Y— is =$CR^Y$— and —Z= is —$CR^Z$.

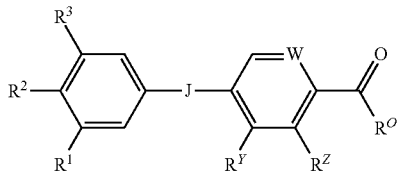

(101) A compound according to any one of (1) to (99), wherein:
=Y— is =N— and —Z= is —$CR^Z$.

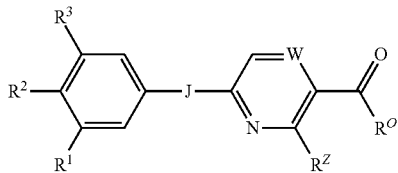

(102) A compound according to any one of (1) to (99), wherein:
=Y— is =$CR^Y$— and —Z= is —N=.

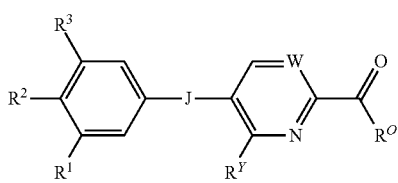

(103) A compound according to any one of (1) to (99), wherein:
=Y— is =N— and —Z= is —N=.

The Groups —$R^Y$ and —$R^{YY}$

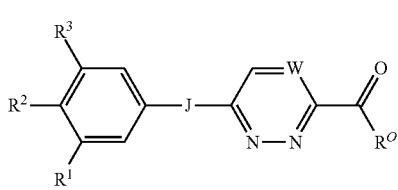

(104) A compound according to any one of (1) to (103), wherein:
—$R^Y$, if present, is independently —H.
(105) A compound according to any one of (1) to (103), wherein:
—$R^Y$, if present, is independently —$R^{YY}$.
(106) A compound according to any one of (1) to (105), wherein:
—$R^{YY}$, if present, is independently —F, —Cl, —Br, —I, -Me, or -Et.
(107) A compound according to any one of (1) to (105), wherein:
—$R^{YY}$, if present, is independently —F, —Cl, or -Me.
(108) A compound according to any one of (1) to (105), wherein:
—$R^{YY}$, if present, is independently —F or —Cl.
(109) A compound according to any one of (1) to (105), wherein:
—$R^{YY}$, if present, is independently —F.
(110) A compound according to any one of (1) to (105), wherein:
—$R^{YY}$, if present, is independently —Cl.
(111) A compound according to any one of (1) to (105), wherein:
—$R^{YY}$, if present, is independently -Me.

The Groups —$R^Z$ and —$R^{ZZ}$
(112) A compound according to any one of (1) to (111), wherein:
—$R^Z$, if present, is independently —H.
(113) A compound according to any one of (1) to (111), wherein:
—$R^Z$, if present, is independently —$R^{ZZ}$.
(114) A compound according to any one of (1) to (113), wherein:
—$R^{ZZ}$, if present, is independently —F, —Cl, —Br, —I, —OH, —OMe, —OEt, -Me, -Et, or —$CF_3$.
(115) A compound according to any one of (1) to (113), wherein:
—$R^{ZZ}$, if present, is independently —F, —Cl, —Br, —I, —OH, saturated aliphatic $C_{1-4}$alkyl.
(116) A compound according to any one of (1) to (113), wherein:
—$R^{ZZ}$, if present, is independently —F, —Cl, —Br, —I, —OH, -Me or -Et.
(117) A compound according to any one of (1) to (113), wherein:
—$R^{ZZ}$, if present, is independently —F, —Cl, —Br, —I, or saturated aliphatic $C_{1-4}$alkyl.
(118) A compound according to any one of (1) to (113), wherein:
—$R^{ZZ}$, if present, is independently —F, —Cl, —Br, —I, -Me, or -Et.
(119) A compound according to any one of (1) to (113), wherein:
—$R^{ZZ}$, if present, is independently —F, —Cl, -Me, or —OH.
(120) A compound according to any one of (1) to (113), wherein:
—$R^{ZZ}$, if present, is independently —F, -Me, or —OH.
(121) A compound according to any one of (1) to (113), wherein:
—$R^{ZZ}$, if present, is independently —F, —Cl, or -Me.
(122) A compound according to any one of (1) to (113), wherein:
—$R^{ZZ}$, if present, is independently -Me.

(123) A compound according to any one of (1) to (113), wherein:
—$R^{ZZ}$, if present, is independently —F.
(124) A compound according to any one of (1) to (113), wherein:
—$R^{ZZ}$, if present, is independently —OH.
(125) A compound according to any one of (1) to (113), wherein:
—$R^{ZZ}$, if present, is independently —Cl.

The Groups —$R^W$ and —$R^{WW}$
(126) A compound according to any one of (1) to (125), wherein:
—$R^W$, if present, is independently —H.
(127) A compound according to any one of (1) to (125), wherein:
—$R^W$, if present, is independently —$R^{WW}$.
(128) A compound according to any one of (1) to (127), wherein:
—$R^{WW}$, if present, is independently —F, —Cl, —Br, —I, —OH, —OMe, —OEt, -Me, -Et, or —$CF_3$.
(129) A compound according to any one of (1) to (127), wherein:
—$R^{WW}$, if present, is independently —F, —Cl, —Br, —I, or saturated aliphatic $C_{1-4}$alkyl.
(130) A compound according to any one of (1) to (127), wherein:
—$R^{WW}$, if present, is independently —F, —Cl, —Br, —I, -Me, or -Et.
(131) A compound according to any one of (1) to (127), wherein:
—$R^{WW}$, if present, is independently —F, —Cl, or -Me.
(132) A compound according to any one of (1) to (127), wherein:
—$R^{WW}$, if present, is independently —F.
(133) A compound according to any one of (1) to (127), wherein:
—$R^{WW}$, if present, is independently —Cl.
(134) A compound according to any one of (1) to (127), wherein:
—$R^{WW}$, if present, is independently -Me.

The Group -J-
(135) A compound according to any one of (1) to (134), wherein:
-J- is independently —C(=O)—$NR^N$—.

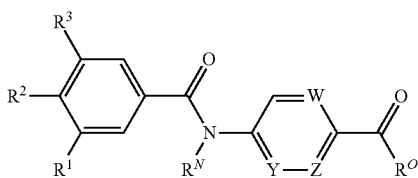

(136) A compound according to any one of (1) to (134), wherein:
-J- is independently —$NR^N$—C(=O)—.

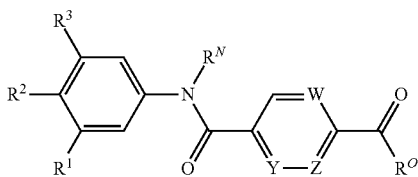

The Groups —$R^N$ and —$R^{NN}$
(137) A compound according to any one of (1) to (136), wherein:
—$R^N$ is independently —H.
(138) A compound according to any one of (1) to (136), wherein:
—$R^N$ is independently —$R^{NN}$.
(139) A compound according to any one of (1) to (138), wherein:
—$R^{NN}$, if present, is independently -Me or -Et.
(140) A compound according to any one of (1) to (138), wherein:
—$R^{NN}$, if present, is independently -Me.

The Group —$R^O$
(141) A compound according to any one of (1) to (140), wherein:
—$R^O$ is independently —OH, —$OR^E$, —$NH_2$, or —$NHR^{T1}$.
(142) A compound according to any one of (1) to (140), wherein:
—$R^O$ is independently —OH or —$OR^E$.
(143) A compound according to any one of (1) to (140), wherein:
—$R^O$ is independently —OH.

The Group —$R^E$
(144) A compound according to any one of (1) to (143), wherein:
—$R^E$, if present, is independently saturated aliphatic $C_{1-4}$alkyl.
(145) A compound according to any one of (1) to (143), wherein:
—$R^E$, if present, is independently -Me or -Et.
(146) A compound according to any one of (1) to (143), wherein:
—$R^E$, if present, is independently -Me.

The Group —$R^{T1}$
(147) A compound according to any one of (1) to (146), wherein:
each —$R^{T1}$, if present, is independently saturated aliphatic $C_{1-4}$alkyl.
(148) A compound according to any one of (1) to (146), wherein:
each —$R^{T1}$, if present, is independently -Me or -Et.
(149) A compound according to any one of (1) to (146), wherein:
each —$R^{T1}$, if present, is independently -Me.

The Group —$NR^{T2}R^{T3}$
(150) A compound according to any one of (1) to (149), wherein:
—$NR^{T2}R^{T3}$ is independently piperidino, piperizino, N—($C_{1-3}$alkyl) piperizino, or morpholino.

Molecular Weight
(151) A compound according to any one of (1) to (150), wherein the compound has a molecular weight of from 295 to 1200.
(152) A compound according to (151), wherein the bottom of range is 300, 325, 350, or 400.
(153) A compound according to (151) or (152), wherein the top of range is 1100, 1000, 900, 800, 700, or 600.
(154) A compound according to any one of (1) to (150), wherein the compound has a molecular weight of range from 325 to 600.

Activity and Selectivity
(155) A compound according to any one of (1) to (154), wherein the compound has a RARα activity ratio (with respect to atRA) of less than about 200; or less than about 70; or less than about 30; or less than about 10; or less than about 5.

(156) A compound according to any one of (1) to (155), wherein the compound is selective for RARα, as compared to RARβ.

(157) A compound according to any one of (1) to (155), wherein the compound is selective for RARα, as compared to RARγ.

(158) A compound according to any one of (1) to (155), wherein the compound is selective for RARα, as compared to both RARβ and RARγ.

(159) A compound according to any one of (1) to (158), wherein the compound has a ratio of RARα activity ratio (with respect to atRA) to RARβ activity ratio (with respect to atRA) of at least 10; or at least 20; or at least 50; or at least 100; or at least 200.

Specific Compounds (160) A compound according to (1), selected from compounds of the following formulae and pharmaceutically acceptable salts, hydrates, and solvates thereof:

| Code No. | Synthesis | Structure |
|---|---|---|
| AAA-001 | 1 | 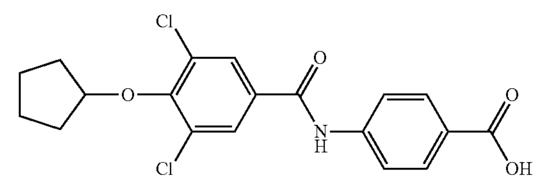 [SMILES: O=C(O)c1ccc(NC(=O)c2cc(Cl)c(OC3CCCC3)c(Cl)c2)cc1] |
| AAA-002 | 1 | 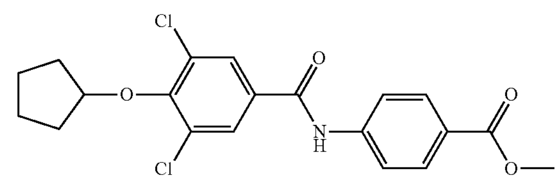 [SMILES: COC(=O)c1ccc(NC(=O)c2cc(Cl)c(OC3CCCC3)c(Cl)c2)cc1] |
| AAA-003 | 2 | 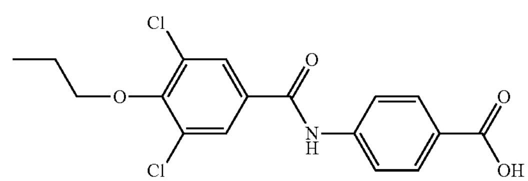 [SMILES: CCCOc1c(Cl)cc(C(=O)Nc2ccc(C(=O)O)cc2)cc1Cl] |
| AAA-004 | 3 | 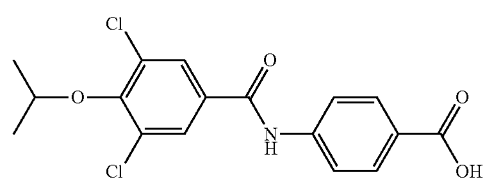 [SMILES: CC(C)Oc1c(Cl)cc(C(=O)Nc2ccc(C(=O)O)cc2)cc1Cl] |
| AAA-005 | 4 | 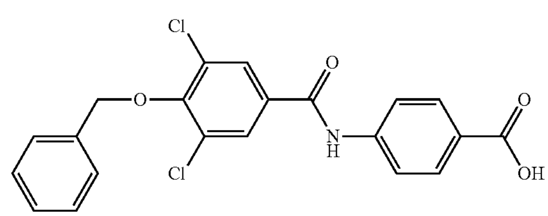 [SMILES: O=C(O)c1ccc(NC(=O)c2cc(Cl)c(OCc3ccccc3)c(Cl)c2)cc1] |
| AAA-006 | 5 | 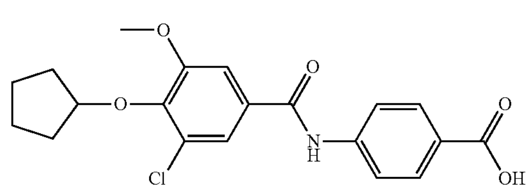 [SMILES: COc1cc(C(=O)Nc2ccc(C(=O)O)cc2)cc(Cl)c1OC1CCCC1] |

-continued

| Code No. | Synthesis | Structure |
|---|---|---|
| AAA-007 | 6 | 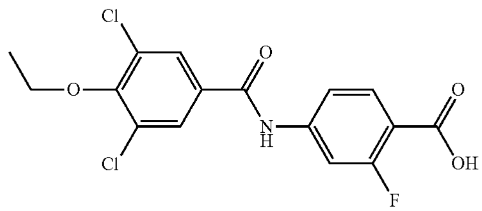 [SMILES: CCOc1c(Cl)cc(C(=O)Nc2ccc(C(=O)O)c(F)c2)cc1Cl] |
| AAA-008 | 7 | 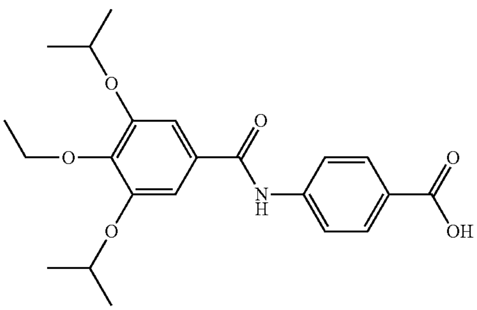 [SMILES: CCOc1c(OC(C)C)cc(C(=O)Nc2ccc(C(=O)O)cc2)cc1OC(C)C] |
| AAA-009 | 8 | 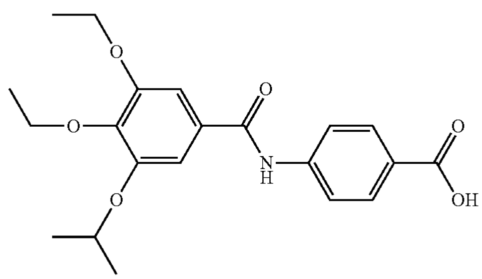 [SMILES: CCOc1cc(C(=O)Nc2ccc(C(=O)O)cc2)cc(OC(C)C)c1OCC] |
| AAA-010 | 9 | 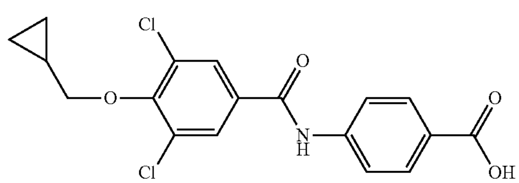 [SMILES: O=C(O)c1ccc(NC(=O)c2cc(Cl)c(OCC3CC3)c(Cl)c2)cc1] |
| AAA-011 | 10 | 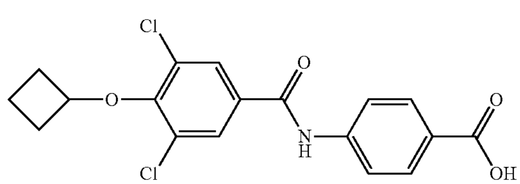 [SMILES: O=C(O)c1ccc(NC(=O)c2cc(Cl)c(OC3CCC3)c(Cl)c2)cc1] |
| AAA-012 | 11 | 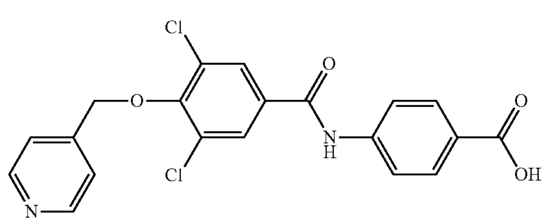 [SMILES: O=C(O)c1ccc(NC(=O)c2cc(Cl)c(OCc3ccncc3)c(Cl)c2)cc1] |
| AAA-013 | 12 | 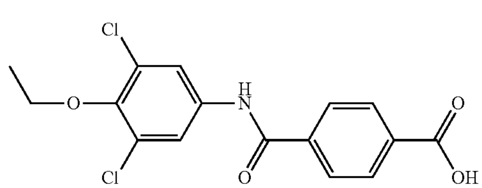 [SMILES: CCOc1c(Cl)cc(NC(=O)c2ccc(C(=O)O)cc2)cc1Cl] |

-continued

| Code No. | Synthesis | Structure |
|---|---|---|
| AAA-014 | 13 | 3,5-dibromo-4-ethoxyphenyl / terephthalamic acid derivative |
| AAA-015 | 14 | 4-ethoxy-3,5-bis(trifluoromethyl)phenyl / terephthalamic acid derivative |
| AAA-016 | 15 | 3,5-dichloro-4-ethoxybenzoyl / 4-carbamoylaniline derivative |
| AAA-017 | 16 | 3,5-dichloro-4-ethoxybenzoyl / methyl 4-aminobenzoate derivative |
| AAA-018 | 17 | 3,5-dichloro-4-ethoxybenzoyl / 4-amino-2-chlorobenzoic acid derivative |
| AAA-019 | 18 | 3,5-dichloro-4-ethoxybenzoyl / 4-amino-2-methylbenzoic acid derivative |
| AAA-020 | 19 | 4-ethoxy-3,5-bis(trifluoromethyl)phenyl / pyridine-2,5-dicarboxamide derivative |
| AAA-021 | 20 | 3,5-difluoro-4-ethoxyphenyl / terephthalamic acid derivative |

-continued

| Code No. | Synthesis | Structure |
|---|---|---|
| AAA-022 | 21 | 3-chloro-5-(trifluoromethyl)-4-ethoxy-N-(4-carboxy-3,5-difluorophenyl)benzamide |
| AAA-023 | 22 | 3,5-dibromo-4-ethoxy-N-(4-carboxyphenyl)benzamide |
| AAA-024 | 23 | 3-chloro-4-ethoxy-5-methoxy-N-(4-carboxyphenyl)benzamide |
| AAA-025 | 24 | 3-chloro-4-ethoxy-5-(trifluoromethyl)-N-(4-carboxyphenyl)benzamide |
| AAA-026 | 25 | 3,5-dichloro-4-ethoxy-N-(6-carboxypyridin-3-yl)benzamide |
| AAA-027 | 26 | 3,5-dichloro-4-ethoxy-N-(5-carboxypyridin-2-yl)benzamide |
| AAA-028 (PP-01) | 27 | 3,4,5-triethoxy-N-(4-carboxyphenyl)benzamide |
| AAA-029 (PP-02) | 28 | 3,5-dichloro-4-ethoxy-N-(4-carboxyphenyl)benzamide |

-continued

| Code No. | Synthesis | Structure |
|---|---|---|
| AAA-030 (PP-03) | 29 | 3,5-dichloro-4-methoxy-N-(4-carboxyphenyl)benzamide |

(161) A compound according to (1), selected from compounds of the following formulae and pharmaceutically acceptable salts, hydrates, and solvates thereof: AAA-001 to AA-027.

(162) A compound according to (1), selected from compounds of the following formulae and pharmaceutically acceptable salts, hydrates, and solvates thereof:

| Code No. | Synthesis | Structure |
|---|---|---|
| AAA-031 | 33 | 3,5-dichloro-4-tert-butoxy-N-(4-carboxyphenyl)benzamide |
| AAA-032 | 34 | 3,5-dichloro-4-isopropoxy-N-(4-carboxy-2-methylphenyl)benzamide |
| AAA-033 | 35 | 3,5-dichloro-4-ethoxy-N-(4-carboxy-2-trifluoromethylphenyl)benzamide |
| AAA-034 | 36 | 3-trifluoromethyl-4-isopropoxy-5-chloro-N-(4-carboxyphenyl)benzamide |
| AAA-035 | 37 | 3-trifluoromethyl-4-methoxy-5-chloro-N-(4-carboxyphenyl)benzamide |
| AAA-036 | 38 | 3-trifluoromethyl-4-cyclobutoxy-5-chloro-N-(4-carboxyphenyl)benzamide |

-continued

| Code No. | Synthesis | Structure |
|---|---|---|
| AAA-037 | 39 | 4-tert-butoxy-3-chloro-5-(trifluoromethyl)-N-(4-carboxyphenyl)benzamide |
| AAA-038 | 40 | 4-tert-butoxy-3-chloro-5-(trifluoromethyl)-N-(4-carboxy-3-methylphenyl)benzamide |
| AAA-039 | 41 | 3-chloro-4-ethoxy-5-(trifluoromethyl)-N-(4-carboxy-3-methylphenyl)benzamide |
| AAA-040 | 42 | 3-chloro-4-isopropoxy-5-(trifluoromethyl)-N-(4-carboxy-3-methylphenyl)benzamide |
| AAA-041 | 43 | 3-chloro-4-methoxy-5-(trifluoromethyl)-N-(4-carboxy-3-methylphenyl)benzamide |
| AAA-042 | 44 | 3-bromo-4-ethoxy-5-(trifluoromethyl)-N-(4-carboxyphenyl)benzamide |
| AAA-043 | 45 | 3-chloro-4-cyclopentyloxy-5-(trifluoromethyl)-N-(4-carboxyphenyl)benzamide |

-continued

| Code No. | Synthesis | Structure |
|---|---|---|
| AAA-044 | 46 | 3-cyclopentyloxy-4-cyclopentyloxy-5-chloro-N-(4-carboxyphenyl)benzamide |
| AAA-045 | 47 | 3-benzyloxy-4-benzyloxy-5-chloro-N-(4-carboxyphenyl)benzamide |
| AAA-046 | 48 | 3-cyclopentyloxy-4-cyclopentyloxy-5-chloro-N-(4-carboxy-3-methylphenyl)benzamide |
| AAA-047 | 49 | 3-cyclohexyloxy-4-cyclohexyloxy-5-chloro-N-(4-carboxyphenyl)benzamide |
| AAA-048 | 50 | 3-neopentyl-4-tert-butoxy-5-chloro-N-(4-carboxyphenyl)benzamide |
| AAA-049 | 51 | 3-tert-butoxy-4-tert-butoxy-5-chloro-N-(4-carboxy-3-methylphenyl)benzamide |
| AAA-050 | 52 | 3-isopropoxy-4-isopropoxy-5-chloro-N-(4-carboxyphenyl)benzamide |

-continued

| Code No. | Synthesis | Structure |
|---|---|---|
| AAA-051 | 53 | 3-chloro-4,5-diisopropoxy-N-(4-carboxy-3-methylphenyl)benzamide |
| AAA-052 | 54 | 3,5-dibromo-4-isopropoxy-N-(4-carboxy-3-methylphenyl)benzamide |
| AAA-053 | 55 | 3,5-dibromo-4-ethoxy-N-(4-carboxy-3-methylphenyl)benzamide |
| AAA-054 | 56 | 3,5-dichloro-4-cyclopentyloxy-N-(4-carboxy-3-methylphenyl)benzamide |
| AAA-055 | 57 | 3,5-dichloro-4-methoxy-N-(4-carboxy-3-methylphenyl)benzamide |
| AAA-056 | 58 | 3,5-dichloro-4-tert-butoxy-N-(4-carboxy-3-methylphenyl)benzamide |
| AAA-057 | 59 | 3,5-dichloro-4-ethoxy-N-(4-carboxy-3-hydroxyphenyl)benzamide |

-continued

| Code No. | Synthesis | Structure |
|---|---|---|
| AAA-058 | 60 | 3,5-bis(cyclopentyloxy)-4-ethoxy-N-(4-carboxyphenyl)benzamide |
| AAA-059 | 61 | 3,4,5-triisopropoxy-N-(4-carboxyphenyl)benzamide |
| AAA-060 | 62 | 3,4,5-tri-tert-butoxy-N-(4-carboxyphenyl)benzamide |
| AAA-061 | 63 | 4-ethoxy-3,5-diisopropoxy-N-(4-carboxy-3-methylphenyl)benzamide |
| AAA-062 | 64 | 3,5-diisopropoxy-4-methoxy-N-(4-carboxyphenyl)benzamide |
| AAA-063 | 65 | 3,5-diisopropoxy-4-methoxy-N-(4-carboxy-3-methylphenyl)benzamide |

-continued

| Code No. | Synthesis | Structure |
|---|---|---|
| AAA-064 | 66 | 3,5-diisopropoxy-4-ethoxy-N-(4-carboxy-3-fluorophenyl)benzamide |
| AAA-065 | 67 | 3-chloro-4-methoxy-5-(trifluoromethyl)-N-(5-carboxypyridin-2-yl)benzamide |
| AAA-066 | 68 | 3-chloro-4-methoxy-5-(trifluoromethyl)-N-(4-carboxy-3-fluorophenyl)benzamide |
| AAA-067 | 69 | 3-chloro-4-methoxy-5-(trifluoromethyl)-N-(4-carboxy-2-fluorophenyl)benzamide |
| AAA-068 | 70 | 3-chloro-4-ethoxy-5-(trifluoromethyl)-N-(4-carboxy-3-fluorophenyl)benzamide |
| AAA-069 | 71 | 3-chloro-4-isopropoxy-5-(trifluoromethyl)-N-(4-carboxy-3-fluorophenyl)benzamide |
| AAA-070 | 72 | 3-chloro-4-methoxy-5-(trifluoromethyl)-N-(4-carboxy-5-hydroxypyridin-2-yl)benzamide |

| Code No. | Synthesis | Structure |
|---|---|---|
| AAA-071 | 73 | 3-(trifluoromethyl)-4-ethoxy-5-bromo-N-(4-carboxy-3-methylphenyl)benzamide |
| AAA-072 | 74 | 3-(trifluoromethyl)-4-ethoxy-5-bromo-N-(4-carboxy-3-fluorophenyl)benzamide |
| AAA-073 | 75 | 3,5-difluoro-4-ethoxy-N-(4-carboxyphenyl)benzamide |
| AAA-074 | 76 | 3-chloro-4-isopropoxy-5-fluoro-N-(4-carboxy-3-methylphenyl)benzamide |
| AAA-075 | 77 | 3-isopropoxy-4-methoxy-5-chloro-N-(4-carboxy-3-methylphenyl)benzamide |
| AAA-076 | 78 | 3-isopropoxy-4-methoxy-5-chloro-N-(4-carboxyphenyl)benzamide |
| AAA-077 | 79 | 3-isopropoxy-4-methoxy-5-chloro-N-(4-carboxy-3-fluorophenyl)benzamide |

-continued

| Code No. | Synthesis | Structure |
|---|---|---|
| AAA-078 | 80 | 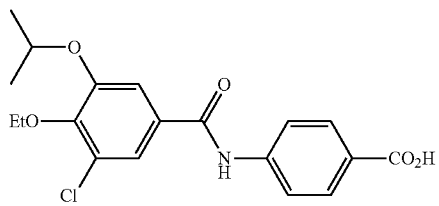 [SMILES: CCOc1c(Cl)cc(C(=O)Nc2ccc(C(=O)O)cc2)cc1OC(C)C] |
| AAA-079 | 81 | 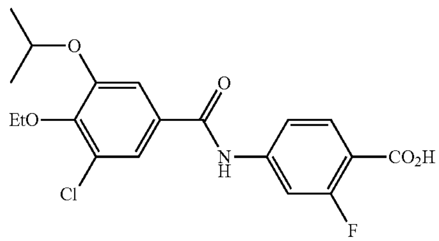 [SMILES: CCOc1c(Cl)cc(C(=O)Nc2ccc(C(=O)O)c(F)c2)cc1OC(C)C] |
| AAA-080 | 82 | 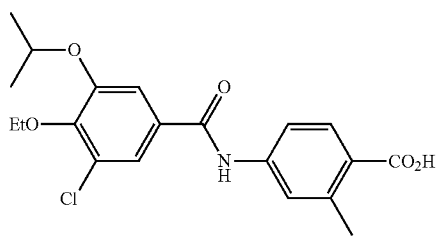 |
| AAA-081 | 83 | 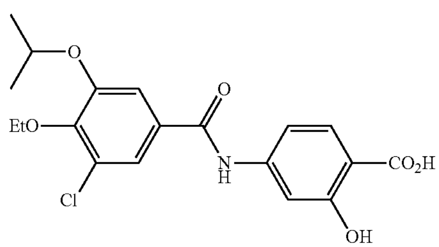 |
| AAA-082 | 84 | 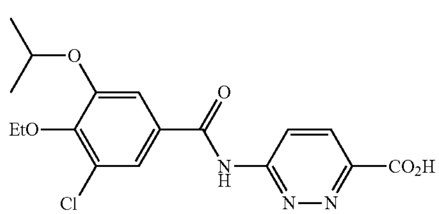 [SMILES: CCOc1c(Cl)cc(C(=O)Nc2ccc(C(=O)O)nn2)cc1OC(C)C] |
| AAA-083 | 85 | 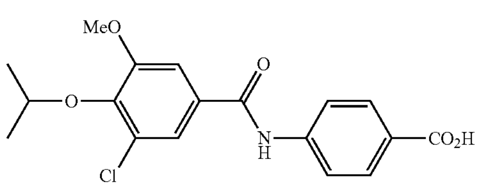 [SMILES: COc1cc(C(=O)Nc2ccc(C(=O)O)cc2)cc(Cl)c1OC(C)C] |
| AAA-084 | 86 | 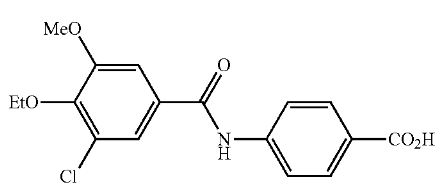 [SMILES: CCOc1c(Cl)cc(C(=O)Nc2ccc(C(=O)O)cc2)cc1OC] |

-continued

| Code No. | Synthesis | Structure |
|---|---|---|
| AAA-085 | 87 | 3-chloro-4-ethoxy-5-methoxy-N-(4-carboxy-3-methylphenyl)benzamide |
| AAA-086 | 88 | 3-chloro-5-ethoxy-4-isopropoxy-N-(4-carboxyphenyl)benzamide |
| AAA-087 | 89 | 3-chloro-5-ethoxy-4-isopropoxy-N-(4-carboxy-3-methylphenyl)benzamide |
| AAA-088 | 90 | 3-chloro-5-cyclobutoxy-4-ethoxy-N-(4-carboxyphenyl)benzamide |
| AAA-089 | 91 | 3-chloro-5-(cyclopropylmethoxy)-4-ethoxy-N-(4-carboxyphenyl)benzamide |
| AAA-090 | 92 | 3-chloro-5-(cyclopropylmethoxy)-4-ethoxy-N-(4-carboxy-3-hydroxyphenyl)benzamide |
| AAA-091 | 93 | 3-chloro-4,5-diisopropoxy-N-(4-carboxy-3-hydroxyphenyl)benzamide |

-continued

| Code No. | Synthesis | Structure |
|---|---|---|
| AAA-092 | 94 | 3-cyclobutoxy-4-cyclobutoxy-5-chloro-N-(4-carboxyphenyl)benzamide |
| AAA-093 | 95 | 3-cyclobutoxy-4-cyclobutoxy-5-chloro-N-(4-carboxy-3-methylphenyl)benzamide |
| AAA-094 | 96 | 3-cyclobutoxy-4-cyclobutoxy-5-chloro-N-(4-carboxy-3-hydroxyphenyl)benzamide |
| AAA-095 | 97 | 3-isopropoxy-4-isopropoxy-5-chloro-N-(4-carboxy-3-fluorophenyl)benzamide |
| AAA-096 | 98 | 3-cyclobutoxy-4-ethoxy-5-chloro-N-(4-carboxy-3-methylphenyl)benzamide |
| AAA-097 | 99 | 3-(cyclopropylmethoxy)-4-ethoxy-5-chloro-N-(4-carboxy-3-methylphenyl)benzamide |
| AAA-098 | 100 | 3-cyclobutoxy-4-methoxy-5-chloro-N-(4-carboxyphenyl)benzamide |

-continued
| Code No. | Synthesis | Structure |
|---|---|---|
| AAA-099 | 101 | 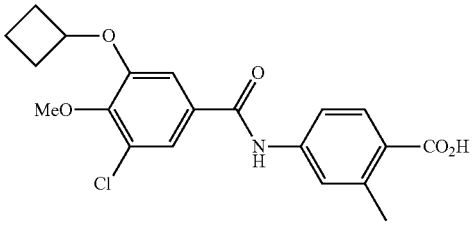 [SMILES: COc1c(Cl)cc(C(=O)Nc2ccc(C(=O)O)c(C)c2)cc1OC1CCC1] |
| AAA-100 | 102 | 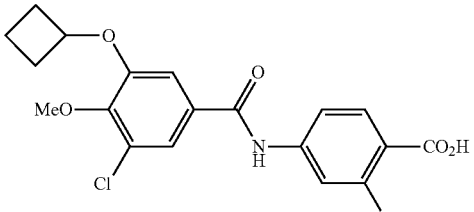 |
| AAA-101 | 103 | 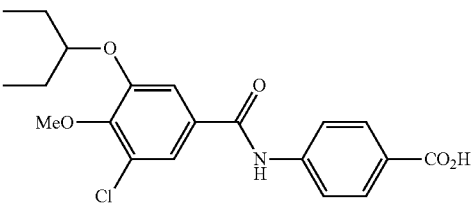 |
| AAA-102 | 104 | 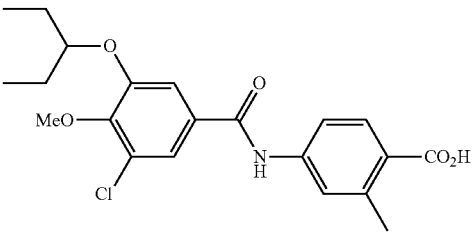 [SMILES: CCC(CC)Oc1cc(C(=O)Nc2ccc(C(=O)O)c(C)c2)cc(Cl)c1OC] |
| AAA-103 | 105 | 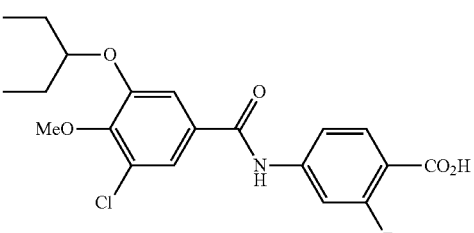 |
| AAA-104 | 106 | 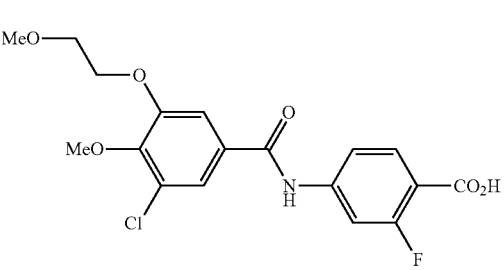 [SMILES: COCCOc1cc(C(=O)Nc2ccc(C(=O)O)c(F)c2)cc(Cl)c1OC] |

-continued

| Code No. | Synthesis | Structure |
|---|---|---|
| AAA-105 | 107 | 3-chloro-5-(neopentyloxy)-4-ethoxy-N-(4-carboxyphenyl)benzamide |
| AAA-106 | 108 | 4-bromo-3,5-diethoxy-N-(4-carboxyphenyl)benzamide |
| AAA-107 | 109 | 4-bromo-3,5-diisopropoxy-N-(4-carboxyphenyl)benzamide |
| AAA-108 | 110 | 4-bromo-3,5-diisopropoxy-N-(4-carboxy-3-fluorophenyl)benzamide |
| AAA-109 | 111 | 4-bromo-3,5-diisopropoxy-N-(4-carboxy-3-hydroxyphenyl)benzamide |
| AAA-110 | 112 | 4-bromo-3,5-diethoxy-N-(4-carboxy-3-methylphenyl)benzamide |
| AAA-111 | 113 | 4-bromo-3,5-diisopropoxy-N-(4-carboxy-3-methylphenyl)benzamide |

-continued

| Code No. | Synthesis | Structure |
|---|---|---|
| AAA-112 | 114 | 4-chloro-3,5-diisopropoxy-N-(4-carboxyphenyl)benzamide |
| AAA-113 | 115 | 3,5-dichloro-4-isopropoxy... |

| Code No. | Synthesis |
|---|---|
| AAA-112 | 114 |
| AAA-113 | 115 |
| AAA-114 | 116 |
| AAA-115 | 117 |
| AAA-116 | 118 |
| AAA-117 | 119 |

| Code No. | Synthesis | Structure |
|---|---|---|
| AAA-118 | 120 | 4-chloro-3-methoxy-5-isopropoxy-N-(4-carboxyphenyl)benzamide |
| AAA-119 | 121 | 4-fluoro-3,5-diisopropoxy-N-(4-carboxyphenyl)benzamide |
| AAA-120 | 122 | 3,4-diisopropoxy-5-(trifluoromethyl)-N-(4-carboxyphenyl)benzamide |

(163) A compound according to (1), selected from compounds of the following formulae and pharmaceutically acceptable salts, hydrates, and solvates thereof: AAA-01 to AA-027 and AA-031 to AA-120.

Combinations

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the chemical groups represented by the variables (e.g., —$R^1$, —$R^2$, —$R^3$, -J-, —W═, —Y═, —Z═, —$R^O$, —X, —$R^X$, —$R^A$, —$R^C$, -L-, —$R^N$, —$R^{NN}$, —$R^W$, —$R^{WW}$, —$R^Y$, —$R^{YY}$, —$R^Z$, —$R^{ZZ}$, —$R^E$, —$R^{T1}$, —$NR^{T2}R^{T3}$, etc.) are specifically embraced by the present invention and are disclosed herein just as if each and every combination was individually and explicitly disclosed, to the extent that such combinations embrace compounds that are stable compounds (i.e., compounds that can be isolated, characterised, and tested for biological activity). In addition, all sub-combinations of the chemical groups listed in the embodiments describing such variables are also specifically embraced by the present invention and are disclosed herein just as if each and every such sub-combination of chemical groups was individually and explicitly disclosed herein.

Substantially Purified Forms

One aspect of the present invention pertains to AAA compounds, as described herein, in substantially purified form and/or in a form substantially free from contaminants.

In one embodiment, the compound is in substantially purified form and/or in a form substantially free from contaminants.

In one embodiment, the compound is in a substantially purified form with a purity of least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless specified, the substantially purified form refers to the compound in any stereoisomeric or enantiomeric form. For example, in one embodiment, the substantially purified form refers to a mixture of stereoisomers, i.e., purified with respect to other compounds. In one embodiment, the substantially purified form refers to one stereoisomer, e.g., optically pure stereoisomer. In one embodiment, the substantially purified form refers to a mixture of enantiomers. In one embodiment, the substantially purified form refers to an equimolar mixture of enantiomers (i.e., a racemic mixture, a racemate). In one embodiment, the substantially purified form refers to one enantiomer, e.g., optically pure enantiomer.

In one embodiment, the compound is in a form substantially free from contaminants wherein the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Unless specified, the contaminants refer to other compounds, that is, other than stereoisomers or enantiomers. In one embodiment, the contaminants refer to other compounds and other stereoisomers. In one embodiment, the contaminants refer to other compounds and the other enantiomer.

In one embodiment, the compound is in a substantially purified form with an optical purity of at least 60% (i.e., 60% of the compound, on a molar basis, is the desired stereoisomer or enantiomer, and 40% is undesired stereoisomer(s) or enantiomer), e.g., at least 70%, e.g., at least 80%, e.g., at least 90%, e.g., at least 95%, e.g., at least 97%, e.g., at least 98%, e.g., at least 99%.

Isomers

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., C$_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

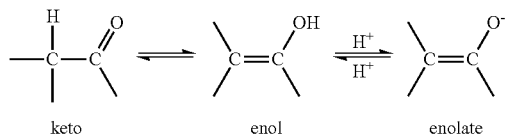

keto    enol    enolate

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including mixtures (e.g., racemic mixtures) thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts

It may be convenient or desirable to prepare, purify, and/or handle a corresponding salt of the compound, for example, a pharmaceutically-acceptable salt. Examples of pharmaceutically acceptable salts are discussed in Berge et al., 1977, "Pharmaceutically Acceptable Salts," J. Pharm. Sci., Vol. 66, pp. 1-19.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{3+}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Hydrates and Solvates

It may be convenient or desirable to prepare, purify, and/or handle a corresponding solvate of the compound. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes solvate and hydrate forms thereof.

Chemically Protected Forms

It may be convenient or desirable to prepare, purify, and/or handle the compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Greene and P. Wuts; 4th Edition; John Wiley and Sons, 2006).

A wide variety of such "protecting," "blocking," or "masking" methods are widely used and well known in organic synthesis. For example, a compound which has two nonequivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)CH$_3$, —OAc).

For example, an aldehyde or ketone group may be protected as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulfonyl)ethyloxy amide (—NH-Psec); or, in suitable cases (e.g., cyclic amines), as a nitroxide radical (>N—O●).

For example, a carboxylic acid group may be protected as an ester for example, as: an C$_{1-7}$alkyl ester (e.g., a methyl ester; a t-butyl ester); a C$_{1-7}$haloalkyl ester (e.g., a C$_{1-7}$trihaloalkyl ester); a triC$_{1-7}$alkylsilyl-C$_{1-7}$alkyl ester; or a C$_{5-20}$aryl-C$_{1-7}$alkyl ester (e.g., a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

Prodruqs

It may be convenient or desirable to prepare, purify, and/or handle the compound in the form of a prodrug. The term "prodrug," as used herein, pertains to a compound which, when metabolised (e.g., in vivo), yields the desired active compound. Typically, the prodrug is inactive, or less active than the desired active compound, but may provide advantageous handling, administration, or metabolic properties.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Chemical Synthesis

Several methods for the chemical synthesis of compounds of the present invention are described herein. These and/or other well known methods may be modified and/or adapted in known ways in order to facilitate the synthesis of additional compounds within the scope of the present invention.

In one approach, certain compounds of the invention (where -J- is —C(=O)—NR$^N$—) may conveniently be prepared by coupling a suitably substituted benzoic acid with a suitably protected para-amino benzoic acid compound. Deprotection gives the corresponding carboxylic acid compound, which can be converted to the corresponding amide.

For example, coupling a suitably substituted benzoic acid (e.g., (1)(i)) with a suitably protected para-amino benzoic acid compound (e.g., (1)(ii), wherein —R$^P$ denotes a protecting group, such as -Me), gives the corresponding amide (e.g., (1)(iii)). Coupling may be carried out using a variety of agents, for example oxalyl chloride in the presence of diisopropylethylamine, triethylamine or catalytic quantities of dimethylformamide in a solvent such as dichloromethane where coupling proceeds via the acid chloride, or by using agents such as HATU, EEDQ, PyBOP, PyBrOP, EDC, or CDI under usual conditions.

If necessary or desired, the protecting group can be removed using conventional methods to give the carboxylic acid compound (e.g., (1)(iv)). For example, if the protecting group (e.g., —R$^P$) is alkyl, then hydrolysis can be achieved using lithium hydroxide in a mixture of THF or dioxane and water. If the protecting group (e.g., —R$^P$) is benzyl, it may be removed by hydrogenation, for example by using hydrogen over a metal catalyst.

If necessary or desired, the carboxylic acid compound (e.g., (1)(iv)) can be converted to a corresponding amide compound (e.g., (1)(v)), for example, by reaction with a suitable amine.

An example of such a method is illustrated in the following scheme.

Scheme 1

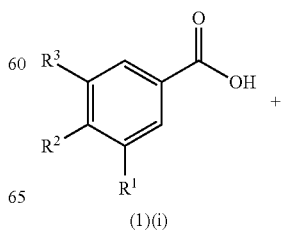

(1)(i)

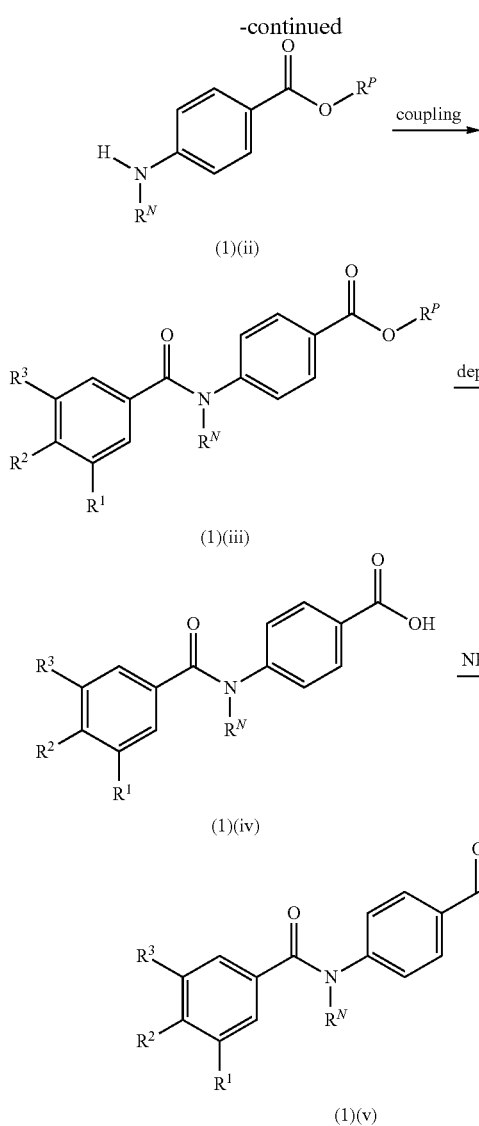

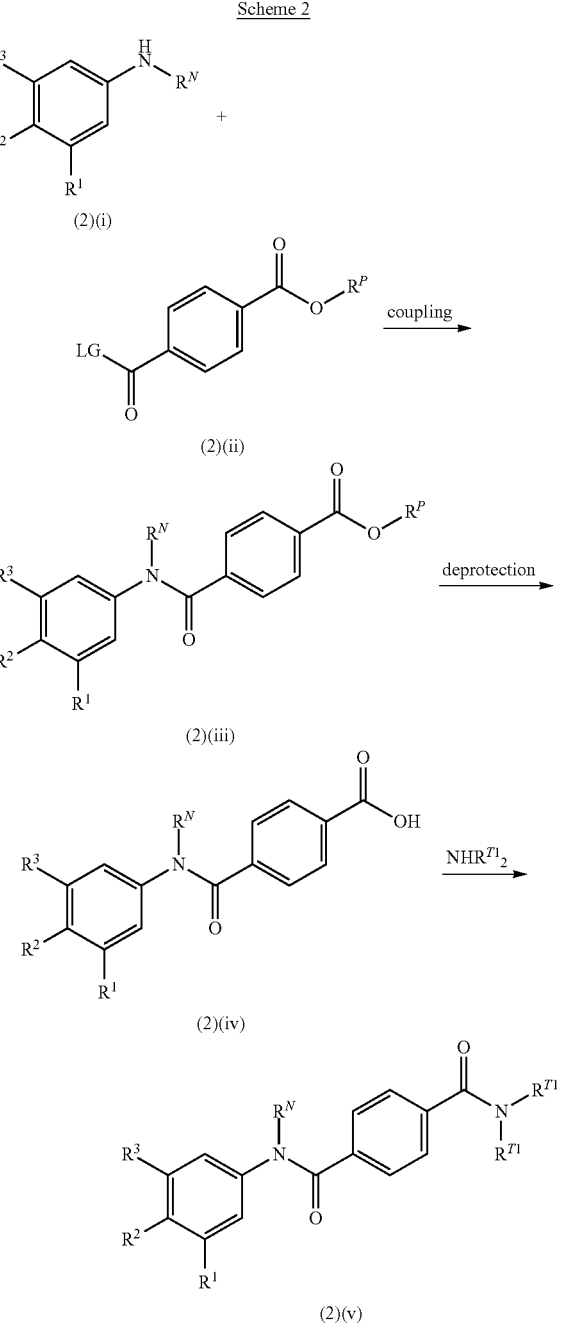

acid compound (e.g., (2)(iv)). For example, if the protecting group (e.g., —$R^P$) is alkyl, then hydrolysis can be achieved using lithium hydroxide in a mixture of THF or dioxane and water. If the protecting group (e.g., —$R^P$) is benzyl, it may be removed by hydrogenation, for example by using hydrogen over a metal catalyst.

If necessary or desired, the carboxylic acid compound (e.g., (2)(iv)) can be converted to a corresponding amide compound (e.g., (2)(v)), for example, by reaction with a suitable amine.

An example of such a method is illustrated in the following scheme.

In another approach, certain compounds of the invention (where -J- is —$NR^N$—C(=O)—) may conveniently be prepared by coupling a suitably substituted aniline with a suitably protected and activated terephthalic acid compound. Deprotection gives the corresponding carboxylic acid compound, which can be converted to the corresponding amide.

For example, coupling a suitably substituted aniline (e.g., (2)(i)) with a suitably protected terephthalic acid compound (e.g., (2)(ii), wherein —$R^P$ denotes a protecting group and -LG denotes a leaving group), gives the corresponding amide (e.g., (2)(iii)). An example of a suitable leaving group is halogen (e.g., Cl), and the corresponding compound may be prepared, for example, from the corresponding benzoic acid by treatment with a variety of reagents including thionyl chloride and oxalyl chloride. In this case, coupling may be achieved, for example, by mixing the two components in a suitable solvent such as dichloromethane in the presence of a base such as triethylamine or diisopropylethylamine. Another example of a suitable leaving group is —OH. In this case, coupling may be achieved, for example, using oxalyl chloride, HATU, EEDQ, PyBOP, PyBrOP, CDI or EDC under usual conditions.

If necessary or desired, the protecting group can be removed using conventional methods to give the carboxylic The benzoic acids (e.g., (1)(i)) are often commercially available, but if not, the requisite material can be prepared from commercially available starting materials in a few steps using conventional methods. For example, suitably protected hydroxyl-benzoic acids may be alkylated. Deprotection gives the corresponding substituted benzoic acid.

For example, suitably protected hydroxyl-benzoic acid (e.g., (3)(i)) may be alkylated using a base such as potassium carbonate or sodium hydride in a suitable solvent to form the phenolate anion, which is then quenched with the requisite halide, to give the corresponding substituted protected benzoic acid compound (e.g., (3)(ii)). The carboxylic acid protecting group may be removed using conventional methods to give the desired substituted benzoic acid compound (e.g., (3)(iii)). For example, if the protecting group (e.g., —$R^P$) is alkyl, then hydrolysis can be achieved using lithium hydroxide in a mixture of THF or dioxane and water. If the protecting group (e.g., —$R^P$) is benzyl, it may be removed by hydrogenation, for example by using hydrogen over a metal catalyst.

An example of such a method is illustrated in the following scheme.

trichloride) converts this —OCH$_2$Ph group to —OH (e.g., (4)(iv)). This —OH group may be then be alkylated, for example, using a base such as potassium carbonate or sodium hydride in a suitable solvent to form the phenolate anion, which is then quenched with the requisite halide, to give the corresponding alkylated compound (e.g., (4)(v)).

Again, if necessary or desired, the protecting group can be removed using conventional methods to give the carboxylic acid compound (e.g., (4)(iv)). For example, if the protecting group (e.g., —$R^P$) is alkyl, then hydrolysis can be achieved using lithium hydroxide in a mixture of THF or dioxane and water. If the protecting group (e.g., —$R^P$) is benzyl, it may be removed by hydrogenation, for example by using hydrogen over a metal catalyst.

Again, if necessary or desired, the carboxylic acid compound (e.g., (4)(vi)) can be converted to a corresponding amide compound (e.g., (4)(vii)), for example, by reaction with a suitable amine.

An example of such a method is illustrated in the following scheme.

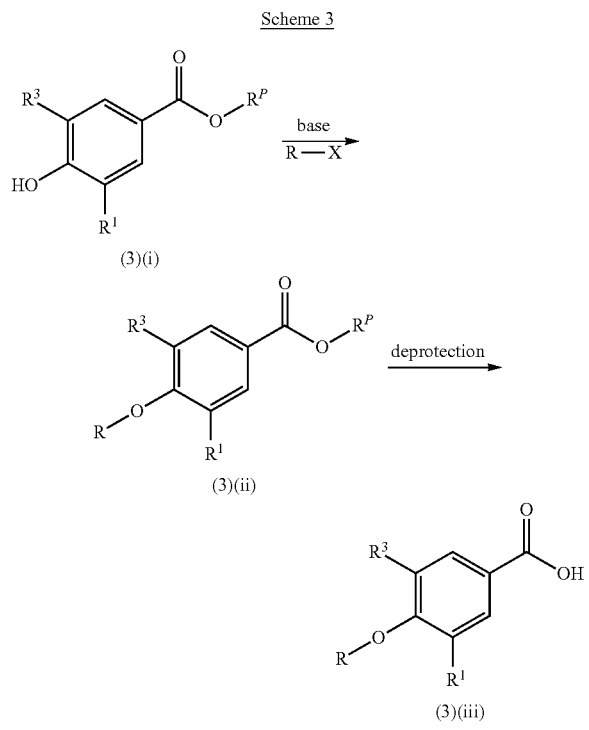

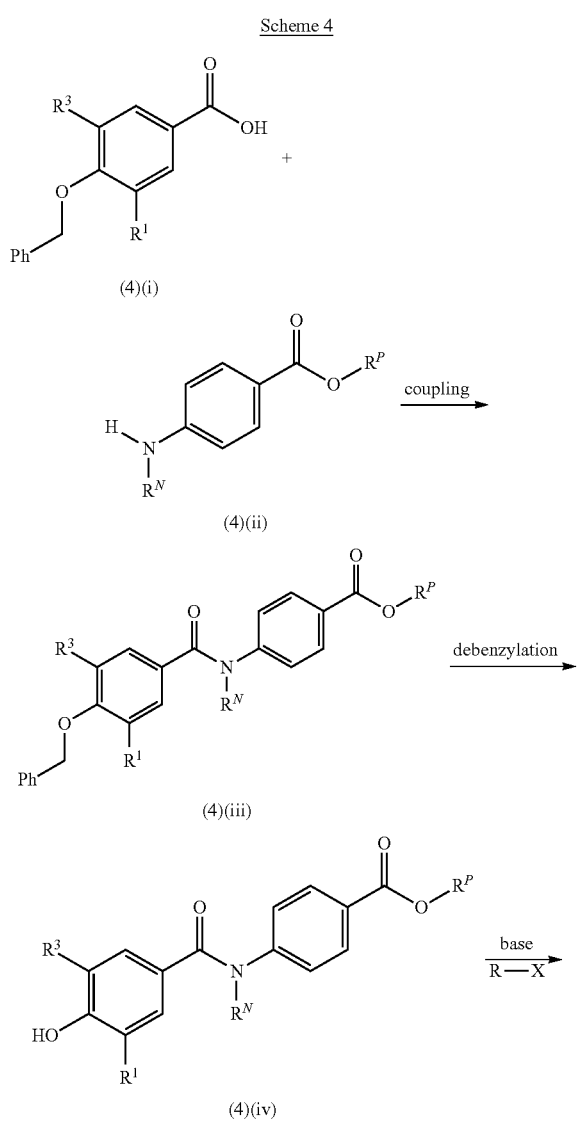

The amines (e.g., (1)(ii)) are often commercially available, but if not, the requisite material can be prepared from commercially available starting materials in a few steps using conventional methods. For example, compounds where —$R^N$ is other than —H can be prepared by reductive amination of a suitably protected 4-aminobenzoic acid derivative.

In another approach, one or more of the groups —$R^1$, —$R^2$, and —$R^3$ may be changed after coupling. For example, debenzylation of a pendant —OCH$_2$Ph group gives a corresponding —OH group, which can then be alkylated.

For example, in a method similar to Scheme 1 above, when one of —$R^1$, —$R^2$, and —$R^3$ in the starting material (e.g., (4)(i)) is —OCH$_2$Ph, then, following coupling (e.g., to give (4)(iii)), debenzylation (for example, using boron

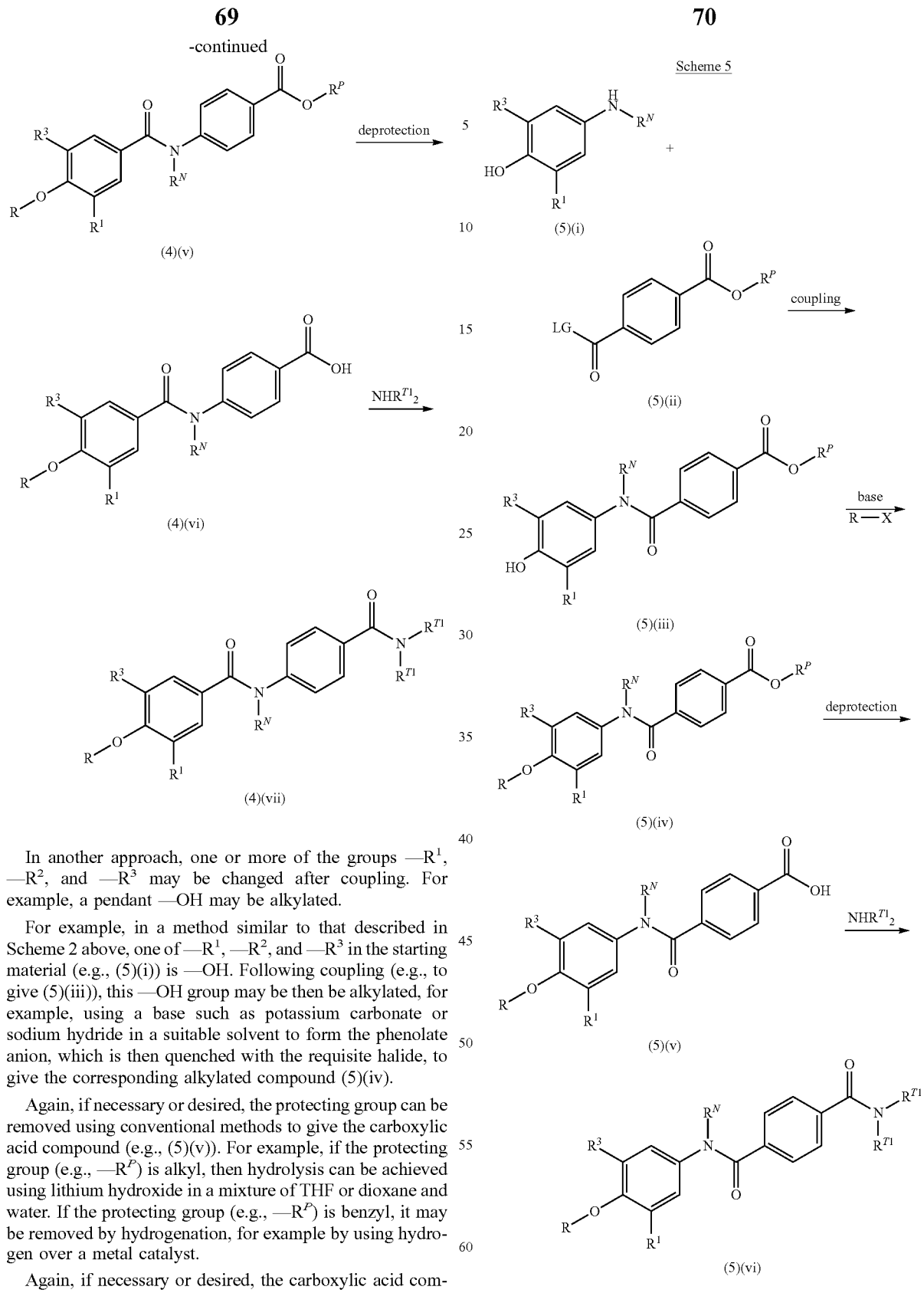

In another approach, one or more of the groups —R¹, —R², and —R³ may be changed after coupling. For example, a pendant —OH may be alkylated.

For example, in a method similar to that described in Scheme 2 above, one of —R¹, —R², and —R³ in the starting material (e.g., (5)(i)) is —OH. Following coupling (e.g., to give (5)(iii)), this —OH group may be then be alkylated, for example, using a base such as potassium carbonate or sodium hydride in a suitable solvent to form the phenolate anion, which is then quenched with the requisite halide, to give the corresponding alkylated compound (5)(iv).

Again, if necessary or desired, the protecting group can be removed using conventional methods to give the carboxylic acid compound (e.g., (5)(v)). For example, if the protecting group (e.g., —$R^P$) is alkyl, then hydrolysis can be achieved using lithium hydroxide in a mixture of THF or dioxane and water. If the protecting group (e.g., —$R^P$) is benzyl, it may be removed by hydrogenation, for example by using hydrogen over a metal catalyst.

Again, if necessary or desired, the carboxylic acid compound (e.g., (5)(v)) can be converted to a corresponding amide compound (e.g., (5)(vi)), for example, by reaction with a suitable amine.

An example of such a method is illustrated in the following scheme.

In the above methods, the core 1,4-phenylene group of the protected para-amino benzoic acid compound (e.g., (1)(ii) and (4)(ii)) and of the activated terephthalic acid compound (e.g., (2)(ii) and (5)(ii)) may bear additional substituents (e.g., —R$^{YY}$, —R$^{ZZ}$, —R$^{WW}$), or may be replaced with a pyridine-diyl group (e.g., =Y— is =N— or —Z= is —N=), which may itself bear additional substituents (e.g., —R$^{YY}$, —R$^{ZZ}$, —R$^{WW}$).

Compositions

One aspect of the present invention pertains to a composition (e.g., a pharmaceutical composition) comprising an AAA compound, as described herein, and a pharmaceutically acceptable carrier, diluent, or excipient.

Another aspect of the present invention pertains to a method of preparing a composition (e.g., a pharmaceutical composition) comprising admixing an AAA compound, as described herein, and a pharmaceutically acceptable carrier, diluent, or excipient.

Uses

The compounds described herein are useful, for example, in the treatment of diseases and conditions that are ameliorated by the (selective) activation of RARα, such as, for example, Alzheimer's disease.

Use in Methods of Activating Retinoic Acid Receptor α (RARα)

One aspect of the present invention pertains to a method of activating retinoic acid receptor α (RARα), in vitro or in vivo, comprising contacting RARα with an effective amount of an AAA compound, as described herein.

One aspect of the present invention pertains to a method of selectively activating retinoic acid receptor α (RARα) (e.g., with respect to RARβ and/or RARγ), in vitro or in vivo, comprising contacting RARα with an effective amount of an AAA compound, as described herein.

In one embodiment, the method is performed in vitro.
In one embodiment, the method is performed in vivo.

One aspect of the present invention pertains to a method of activating retinoic acid receptor α (RARα) in a neuronal cell, in vitro or in vivo, comprising contacting the cell with an effective amount of an AAA compound, as described herein.

One aspect of the present invention pertains to a method of selectively activating retinoic acid receptor α (RARα) (e.g., with respect to RARβ and/or RARγ) in a neuronal cell, in vitro or in vivo, comprising contacting the cell with an effective amount of an AAA compound, as described herein.

In one embodiment, the AAA compound is provided in the form of a pharmaceutically acceptable composition.

Suitable assays for determining RARα activation are described herein and/or are known in the art.

Use in Methods of Up-Requlatinq chAT, Etc.

The AAA compounds described herein are useful in the up-regulation of chAT expression in cortical neurons; the down-regulation of APP expression in cortical neurons, the up-regulation of ADAM10 expression in cortical neurons; and the down-regulation of Aβ40 and Aβ42 expression in cortical neurons.

One aspect of the present invention pertains to a method of up-regulating chAT expression in a cortical neuron, comprising contacting the cortical neuron, in vitro or in vivo, with an effective amount of an AAA compound, as described herein.

One aspect of the present invention pertains to a method of down-regulating APP expression in a cortical neuron, comprising contacting the cortical neuron, in vitro or in vivo, with an effective amount of an AAA compound, as described herein.

One aspect of the present invention pertains to a method of up-regulating ADAM10 expression in a cortical neuron, comprising contacting the cortical neuron, in vitro or in vivo, with an effective amount of an AAA compound, as described herein.

One aspect of the present invention pertains to a method of down-regulating Aβ40 and Aβ42 expression in a cortical neuron, comprising contacting the cortical neuron, in vitro or in vivo, with an effective amount of an AAA compound, as described herein.

In one embodiment, the method is performed in vitro.
In one embodiment, the method is performed in vivo.

One aspect of the present invention pertains to a method of up-regulating chAT expression in a cortical neuron in a patient, comprising administering to the patient a therapeutically effective amount of an AAA compound, as described herein.

One aspect of the present invention pertains to a method of down-regulating APP expression in a cortical neuron in a patient, comprising administering to the patient a therapeutically effective amount of an AAA compound, as described herein.

One aspect of the present invention pertains to a method of up-regulating ADAM10 expression in a cortical neuron in a patient, comprising administering to the patient a therapeutically effective amount of an AAA compound, as described herein.

One aspect of the present invention pertains to a method of down-regulating Aβ40 and Aβ42 expression in a cortical neuron in a patient, comprising administering to the patient a therapeutically effective amount of an AAA compound, as described herein.

In one embodiment, the AAA compound is provided in the form of a pharmaceutically acceptable composition.

Suitable assays for determining up-regulation of chAT expression; down-regulation of APP expression; up-regulation of ADAM10 expression; and down-regulation of Aβ40 and Aβ42 expression; are described herein and/or are known in the art.

Use in Methods of Preventing Cortical Neuronal Death

The AAA compounds described herein are useful in preventing, reducing, or slowing cortical neuronal death.

One aspect of the present invention pertains to a method of preventing, reducing, or slowing cortical neuronal death in a patient, comprising administering to the patient a therapeutically effective amount of an AAA compound, as described herein.

Use in Methods of Therapy

Another aspect of the present invention pertains to an AAA compound, as described herein, for treatment of the human or animal body by therapy.

Use in the Manufacture of Medicaments

Another aspect of the present invention pertains to use of an AAA compound, as described herein, in the manufacture of a medicament for use in treatment.

In one embodiment, the medicament comprises the AAA compound.

Methods of Treatment

Another aspect of the present invention pertains to a method of treatment comprising administering to a patient in need of treatment a therapeutically effective amount of an AAA compound, as described herein, preferably in the form of a pharmaceutical composition.

Conditions Treated—Conditions Mediated by RARα

In one embodiment (e.g., of use in methods of therapy, of use in the manufacture of medicaments, of methods of treatment), the treatment is treatment of a disease or condition that is mediated by RARα.

Conditions Treated—Conditions Ameliorated by the Activation of RARα

In one embodiment (e.g., of use in methods of therapy, of use in the manufacture of medicaments, of methods of treatment), the treatment is treatment of: a disease or condition that is ameliorated by the activation of RARα.

In one embodiment (e.g., of use in methods of therapy, of use in the manufacture of medicaments, of methods of treatment), the treatment is treatment of: a disease or condition that is ameliorated by the selective activation of RARα (e.g., with respect to RARβ and/or RARγ).

Conditions Treated

In one embodiment (e.g., of use in methods of therapy, of use in the manufacture of medicaments, of methods of treatment), the treatment is treatment of a cognitive disorder, memory impairment, memory deficit, senile dementia, Alzheimer's disease, early stage Alzheimer's disease, intermediate stage Alzheimer's disease, late stage Alzheimer's disease, cognitive impairment, or mild cognitive impairment.

In one embodiment, the treatment is treatment of Alzheimer's disease.

In one embodiment, the treatment is treatment of early stage Alzheimer's disease.

In one embodiment, the treatment is treatment of intermediate stage Alzheimer's disease.

In one embodiment, the treatment is treatment of late stage Alzheimer's disease.

In one embodiment, the treatment is treatment of cognitive impairment.

In one embodiment, the treatment is treatment of mild cognitive impairment.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, alleviation of symptoms of the condition, amelioration of the condition, and cure of the condition. Treatment as a prophylactic measure (i.e., prophylaxis) is also included. For example, use with patients who have not yet developed the condition, but who are at risk of developing the condition, is encompassed by the term "treatment" (that is, treatment of condition encompasses reducing the risk of that condition).

For example, treatment includes the prophylaxis of Alzheimer's disease, reducing the risk of Alzheimer's disease, alleviating the symptoms of Alzheimer's disease, etc.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Combination Therapies

The term "treatment" includes combination treatments and therapies, in which two or more treatments or therapies are combined, for example, sequentially or simultaneously. For example, the compounds described herein may also be used in combination therapies, e.g., in conjunction with other agents. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; photodynamic therapy; gene therapy; and controlled diets.

For example, it may be beneficial to combine treatment with a compound as described herein with one or more other (e.g., 1, 2, 3, 4) agents or therapies, e.g., that treat Alzheimer's disease.

One aspect of the present invention pertains to a compound as described herein, in combination with one or more additional therapeutic agents, as described below.

The particular combination would be at the discretion of the physician who would select dosages using his common general knowledge and dosing regimens known to a skilled practitioner.

The agents (i.e., the compound described herein, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

The agents (i.e., the compound described here, plus one or more other agents) may be formulated together in a single dosage form, or alternatively, the individual agents may be formulated separately and presented together in the form of a kit, optionally with instructions for their use.

Other Uses

The AAA compounds described herein may also be used as cell culture additives to activate RARα, e.g., to up-regulate chAT expression; to down-regulate APP expression; to up-regulate ADAM10 expression; to down-regulate Aβ40 and Aβ42 expression; to prevent, reduce, or slow cortical neuronal death.

The AAA compounds described herein may also be used, for example, as part of an in vitro assay, for example, in order to determine whether a candidate host is likely to benefit from treatment with the compound in question.

The AAA compounds described herein may also be used as a standard, for example, in an assay, in order to identify other compounds, other RARα agonists, etc.

Kits

One aspect of the invention pertains to a kit comprising (a) an AAA compound as described herein, or a composition comprising an AAA compound as described herein, e.g., preferably provided in a suitable container and/or with suitable packaging; and (b) instructions for use, e.g., written instructions on how to administer the compound or composition.

The written instructions may also include a list of indications for which the active ingredient is a suitable treatment.

Routes of Administration

The AAA compound or pharmaceutical composition comprising the AAA compound may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject/Patient

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus.

In one preferred embodiment, the subject/patient is a human.

Formulations

While it is possible for the AAA compound to be administered alone, it is preferable to present it as a pharmaceutical formulation (e.g., composition, preparation, medicament) comprising at least one AAA compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising admixing at least one AAA compound, as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Reminqton's Pharmaceutical Sciences*, 18th edition, Mack Publishing Company, Easton, Pa., 1990; and *Handbook of Pharmaceutical Excipients*, 5th edition, 2005.

The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

The compound may be dissolved in, suspended in, or admixed with one or more other pharmaceutically acceptable ingredients. The compound may be presented in a liposome or other microparticulate which is designed to target the compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the compound in a flavored basis, usually sucrose and acacia or tragacanth. Pastilles typically comprise the compound in an inert matrix, such as gelatin and glycerin, or sucrose and acacia. Mouthwashes typically comprise the compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the compound and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from the compound and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for ocular administration include eye drops wherein the compound is dissolved or suspended in a suitable carrier, especially an aqueous solvent for the compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/mL to about 10 µg/mL, for example from about 10 ng/ml to about 1 µg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosaqe

It will be appreciated by one of skill in the art that appropriate dosages of the AAA compounds, and compositions comprising the AAA compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular AAA compound, the route of administration, the time of administration, the rate of excretion of the AAA compound, the duration of the treatment, other drugs, compounds, and/or materials used in combination, the severity of the condition, and the species, sex, age, weight, condition, general health, and prior medical history of the patient. The amount of AAA compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the AAA compound is in the range of about 10 μg to about 250 mg (more typically about 100 μg to about 25 mg) per kilogram body weight of the subject per day. Where the compound is a salt, an ester, an amide, a prodrug, or the like, the amount administered is calculated on the basis of the parent compound and so the actual weight to be used is increased proportionately.

EXAMPLES

The following examples are provided solely to illustrate the present invention and are not intended to limit the scope of the invention, as described herein.

ABBREVIATIONS

AcOH=glacial acetic acid
aq.=aqueous
Boc=tert-butoxycarbonyl
br=broad
CDI=1,1-carbonyldiimidazole
d=doublet
DCM=dichloromethane
DIPEA=N,N-diisopropylethylamine
DMA=N,N-dimethylacetamide
DMAP=4-dimethylaminopyridine
DMF=N,N-dimethylformamide
DMSO=dimethylsulfoxide
EDC=1-Ethyl-3-(3-dimethylaminopropyl)carbodiimide hydrochloride
eq.=no. of molar equivalents
EtOAc=ethyl acetate
h=hour(s)
HATU=2-(7-aza-1H-benzotriazole-1-yl)-1,1,3,3-tetramethyluronium hexafluorophosphate
HOBt=N-hydroxybenzotriazole
HPLC=high performance liquid chromatography
IPA=isopropanol
m=multiplet
MeOH=methanol
min=minute(s)
NMR=nuclear magnetic resonance
PTSA=toluene-4-sulfonic acid
quin=quintet
RT=room temperature
s=singlet
sat.=saturated
SAX=solid supported strong anion exchange resin
SCX=solid supported strong cation exchange resin
sep=septet
t=triplet
T3P=2-propanephosphonic acid anhydride
TBAF=tetrabutylammonium fluoride
TEA=triethylamine
TFA=trifluoroacetic acid
THF=tetrahydrofuran
TMSCI=trimethylchlorosilane General Procedures All starting materials and solvents were either obtained from commercial sources or prepared according to literature conditions.

Hydrogenations were performed either on a Thales H-cube flow reactor or with a suspension of the catalyst under a balloon of hydrogen.

Microwave reactions were carried out on a Personal Chemistry SmithSynthesizer Workstation with a 300 W single mode microwave cavity.

SCX was purchased from Sigma Aldrich and washed with methanol prior to use. The reaction mixture to be purified was first dissolved in methanol and then loaded directly onto the SCX and washed with methanol. The desired material was then eluted by washing with 1% $NH_3$ in methanol.

Column chromatography was performed on Silicycle pre-packed silica (230-400 mesh, 40-63 μM) cartridges.

Analytical Methods

Preparative HPLC:

The system consisted of a Gilson HPLC and an Agilent 5 μm Prep-C18 21.2×50 mm column. Detection was achieved using a UV detector at 254 nm. Mobile phase A: 0.1% aqueous formic acid, Mobile phase B: 0.1% formic acid in methanol.

Method 1: Flow rate 40 mL/min. Gradient: 0.0-0.8 min 5% B; 0.8-7.3 min 5-95% B; 7.3-8.3 min 95% B; 8.3-8.4 min 95-5% B.

$^1$H NMR Spectroscopy:

NMR spectra were recorded using a Bruker Avance III™ 400 MHz instrument, using either residual non-deuterated solvent or tetra-methylsilane as reference.

Chemical Synthesis

Synthesis 1

4-(3,5-dichloro-4-(cyclopentyloxy)benzamido)benzoic acid (AAA-001) and Methyl 4-(3,5-dichloro-4-(cyclopentyloxy)benzamido)benzoate (AAA-002)

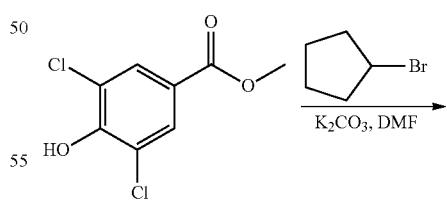

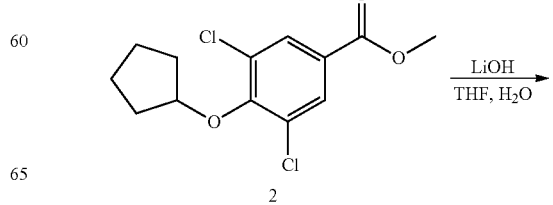

81

Step (i): Methyl 3,5-dichloro-4-(cyclopentyloxy)benzoate (2)

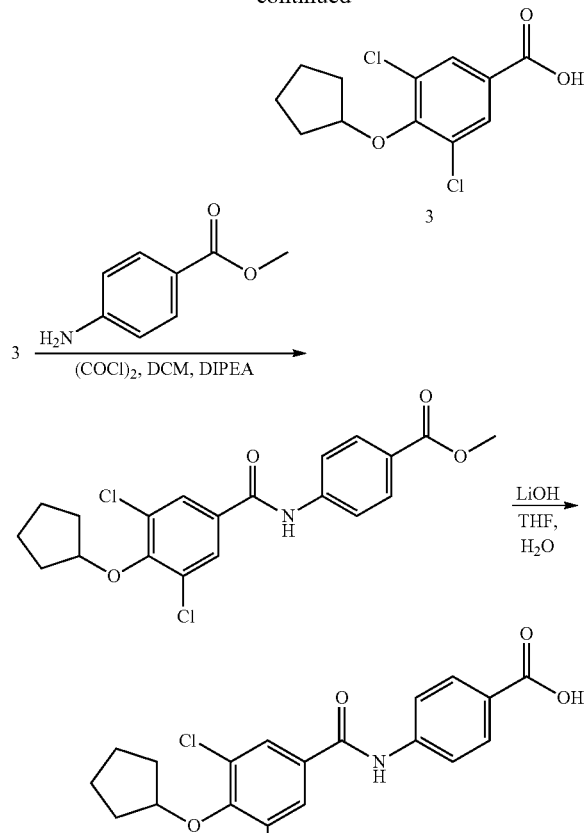

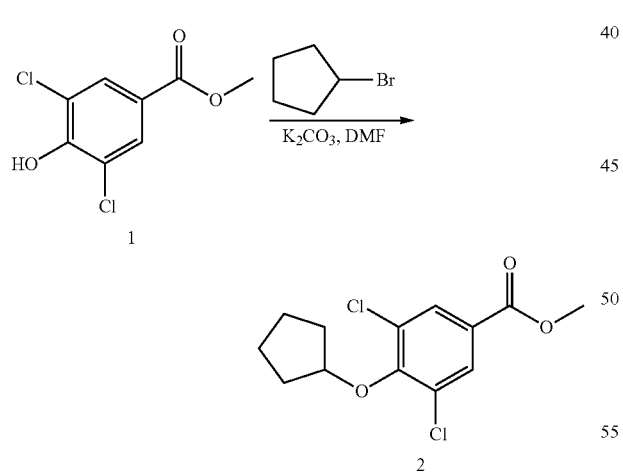

Methyl 3,5-dichloro-4-hydroxybenzoate (1) (1.00 g, 4.52 mmol) was dissolved in DMF (8 mL) and treated with bromocyclopentane (534 µL, 4.98 mmol), followed by potassium carbonate (937 mg, 6.79 mmol). The mixture was stirred at 80° C. for 3 h and then partitioned between EtOAc (100 mL) and H₂O (100 mL). The aqueous phase was extracted with EtOAc (50 mL) and the combined organic phases washed successively with water (5×50 mL) and brine (50 mL), then dried over MgSO₄ and filtered. The solvent was removed in vacuo to afford methyl 3,5-dichloro-4-

82

(cyclopentyloxy)benzoate (2) (1.10 g, 84%): ¹H NMR (400 MHz, CDCl₃) δ: 7.97 (2H, s), 5.04 (1H, m), 3.90 (3H, s), 2.04-1.91 (4H, m), 1.82-1.75 (2H, m), 1.69-1.60 (2H, m).

Step (ii): 3,5-Dichloro-4-(cyclopentyloxy)benzoic acid (3)

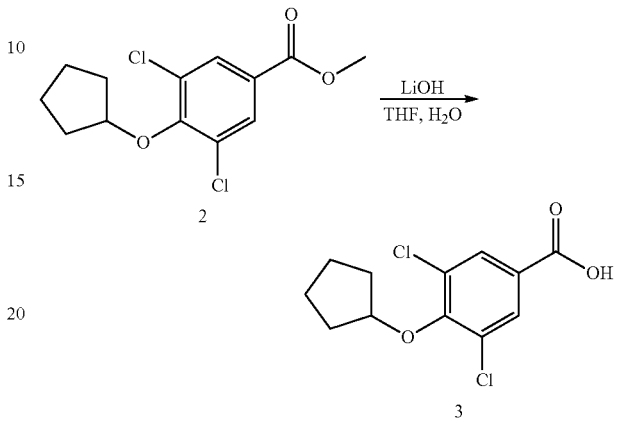

Methyl 3,5-dichloro-4-(cyclopentyloxy)benzoate (2) (1.05 g, 3.63 mmol) and lithium hydroxide (174 mg, 7.26 mmol) were combined in THF (10 mL) and water (ca. 1.5 mL) was added dropwise until a solution formed. The resultant mixture was stirred at RT for 12 h. The THF was removed in vacuo and the residue acidified using aqueous HCl (1 M). The resultant precipitate was filtered to afford 3,5-dichloro-4-(cyclopentyloxy)benzoic acid (3) (820 mg, 82%): m/z 273 (M–H)⁻ (ES⁻).

Step (iii): Methyl 4-(3,5-dichloro-4-(cyclopentyloxy)benzamido)benzoate (AAA-002)

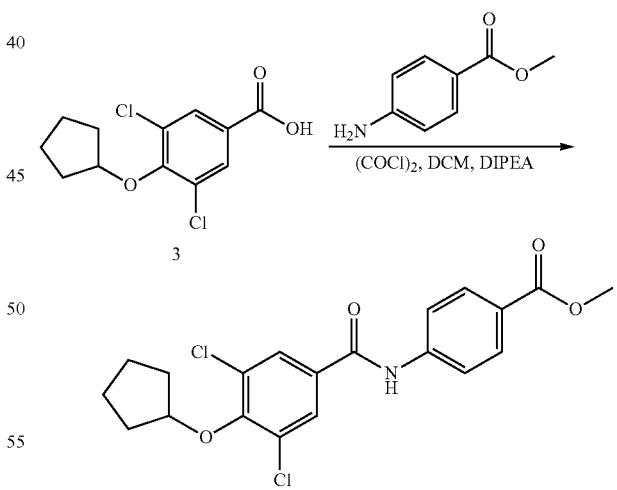

A solution of 3,5-dichloro-4-(cyclopentyloxy)benzoic acid (3) (100 mg, 363 µmol) in DCM (5 mL), cooled to 0° C., was treated with oxalyl chloride (63.6 µL, 727 µmol), followed by a drop of DMF. The resultant mixture was stirred for 1 h at RT. The solvent was evaporated in vacuo and the residue dissolved in DCM (5 mL), and then treated with a solution of methyl 4-aminobenzoate (54.9 mg, 363 µmol) and DIPEA (190 µL, 1.09 mmol) in DCM (5 mL). The reaction mixture was stirred for 12 h at RT and then partitioned between DCM (20 mL) and aqueous HCl (20 mL, 1 M). The phases were separated and the organic phase was washed successively with water (2×20 mL), and brine (20 mL), dried over MgSO$_4$, filtered and then the solvent was removed in vacuo. The residue was purified by silica gel chromatography (12 g, 0-100% EtOAc in isohexane) to afford methyl 4-(3,5-dichloro-4-(cyclopentyloxy)benzamido)benzoate (AAA-002) (30 mg, 20%): m/z 406 (M−H)$^−$ (ES$^−$). NMR (400 MHz, CDCl$_3$) δ: 8.06 (2H, d), 7.85 (1H, br s), 7.82 (2H, s), 7.71 (2H, d), 5.05 (1H, m), 3.92 (3H, s), 2.10-1.90 (4H, m), 1.85-1.70 (2H, m), 1.70-1.60 (2H, m).

Step (iv): 4-(3,5-Dichloro-4-(cyclopentyloxy)benzamido)benzoic acid (AAA-001)

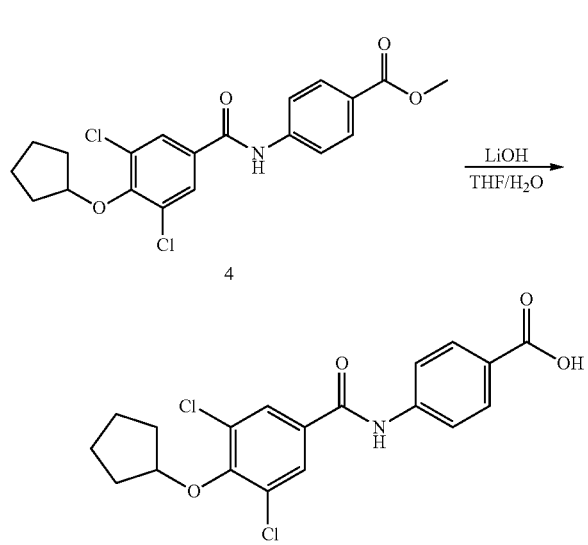

4-(3,5-Dichloro-4-(cyclopentyloxy)benzamido)benzoic acid (AAA-001) (15.0 mg, 51%) was prepared from methyl 4-(3,5-dichloro-4-(cyclopentyloxy)benzamido)benzoate (AAA-002) (30.0 mg, 74 μmol) using a procedure essentially the same as in Step (ii): m/z 392 (M−H)$^−$ (ES$^−$). $^1$H NMR (400 MHz, DMSO-d$_6$) δ: 12.77 (1H, s), 10.58 (1H, s), 8.07 (2H, s), 7.93 (2H, d), 7.88 (2H, d), 5.02 (1H, m), 1.90-1.60 (8H, m).

Synthesis 2

4-(3,5-Dichloro-4-propoxybenzamido)benzoic acid (AAA-003)

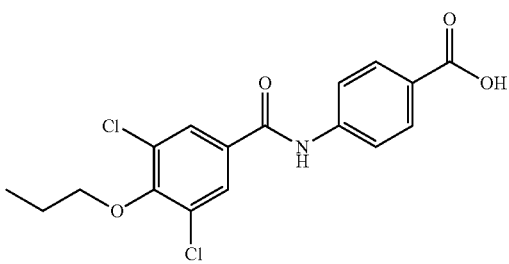 [SMILES: CCCOc1c(Cl)cc(C(=O)Nc2ccc(C(=O)O)cc2)cc1Cl]

4-(3,5-Dichloro-4-propoxybenzamido)benzoic acid (AAA-003) (34 mg, 71% for final step) was prepared in essentially the same manner as in Steps (iii) and (iv) for AAA-001 except that 3,5-dichloro-4-propoxybenzoic acid was used instead of 3,5-dichloro-4-(cyclopentyloxy)-benzoic acid in step (iii): m/z 366 (M−H)$^−$ (ES$^−$). $^1$H NMR (400 MHz, MeOH-d$_4$) δ: 7.99 (4H, s), 7.85 (2H, d), 4.07 (2H, s), 3.89 (3H, s), 1.89 (2H, s), 1.12 (3H, s).

Synthesis 3

4-(3,5-Dichloro-4-isopropoxybenzamido)benzoic acid (AAA-004)

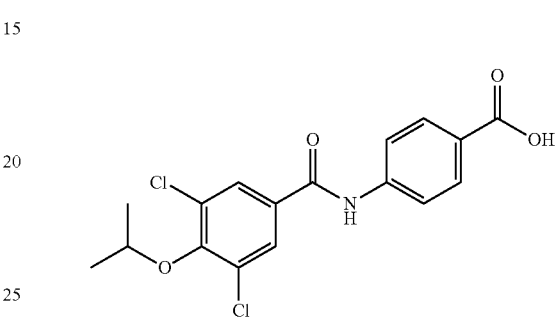

4-(3,5-Dichloro-4-isopropoxybenzamido)benzoic acid (AAA-004) (48.5 mg, 53% for final step) was prepared in essentially the same manner as AAA-001 except that isopropyl bromide was used instead of cyclopentyl bromide in step (i): m/z 366 (M−H)$^−$ (ES$^−$), 368 (M+H)$^+$ (ES$^+$). $^1$H NMR (400 MHz, MeOH-d$_4$) δ: 8.03 (4H, m), 7.83 (2H, d), 4.77 (1H, m), 1.38 (6H, s).

Synthesis 4

4-(4-(Benzyloxy)-3,5-dichlorobenzamido)benzoic acid (AAA-005)

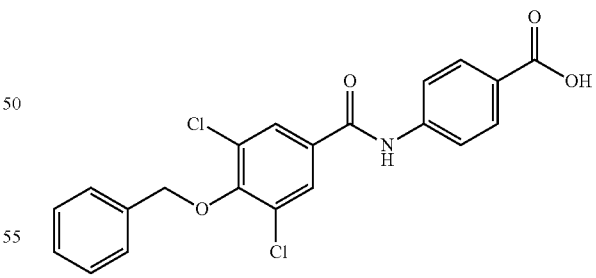

4-(4-Benzyloxy-3,5-dichlorobenzamido)benzoic acid (AAA-005) (21 mg, 46% for final step) was prepared in essentially the same manner as for AAA-001 except that benzyl bromide was used instead of cyclopentyl bromide in step (i): m/z 414 (M−H)$^−$ (ES$^−$). $^1$H NMR (400 MHz, MeOH-d$_4$) δ: 8.03 (4H, d), 7.83 (2H, d), 7.53 (2H, d), 7.38 (3H, m), 5.15 (2H, s).

Synthesis 5

4-(3-Chloro-4-(cyclopentyloxy)-5-methoxybenzamido)benzoic acid (AAA-006)

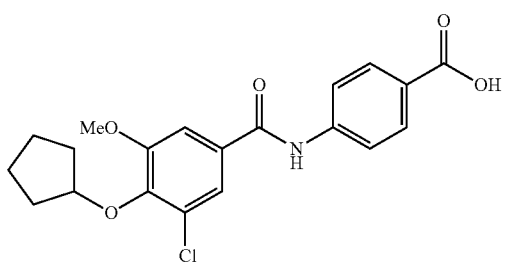 [SMILES: COc1cc(C(=O)Nc2ccc(C(=O)O)cc2)cc(Cl)c1OC1CCCC1]

4-(3-Chloro-4-(cyclopentyloxy)-5-methoxybenzamido)benzoic acid (AAA-006) (56 mg, 57% for final step) was prepared in essentially the same manner as in Steps (iii) and (iv) for AAA-001 except that 3-chloro-4-(cyclopentyloxy)-5-methoxybenzoic acid was used instead of 3,5-dichloro-4-(cyclopentyloxy)benzoic acid in step (iii): m/z 388 (M–H)⁻ (ES⁻), 390 (M+H)⁺ (ES⁺). $^1$H NMR (400 MHz, CDCl$_3$) δ: 12.68 (1H, s), 10.41 (1H, s), 7.86 (2H, d), 7.82 (2H, d), 7.63 (1H, d), 7.49 (1H, d), 4.95 (1H, m), 3.85 (3H, s), 1.80-1.47 (8H, m).

Synthesis 6

4-(3,5-Dichloro-4-ethoxybenzamido)-2-fluorobenzoic acid (AAA-007)

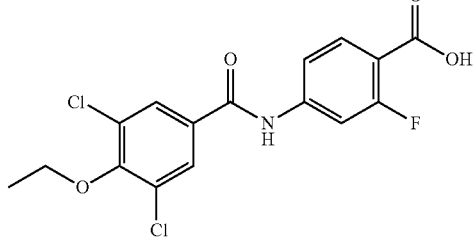

4-(3,5-Dichloro-4-ethoxybenzamido)-2-fluorobenzoic acid (AAA-007) (380 mg, 48% for final step) was prepared in essentially the same manner as for AAA-001 except that ethyl iodide was used instead of cyclopentyl bromide in step (i) and methyl 4-amino-2-fluorobenzoate (prepared by the action of hydrogen and 10% Pd/C on methyl 2-fluoro-4-nitrobenzoate) was used instead of methyl 4-aminobenzoate in step (iii): m/z 370 (M–H)⁻ (ES⁻), 372 (M+H)⁺ (ES⁺). $^1$H NMR (400 MHz, MeOH-d$_4$) δ: 8.01 (2H, s), 7.92 (1H, t), 7.79 (1H, d), 7.53 (1H, d), 4.18 (2H, q), 1.46 (3H, t).

Synthesis 7

4-(4-Ethoxy-3,5-diisopropoxybenzamido)benzoic acid (AAA-008)

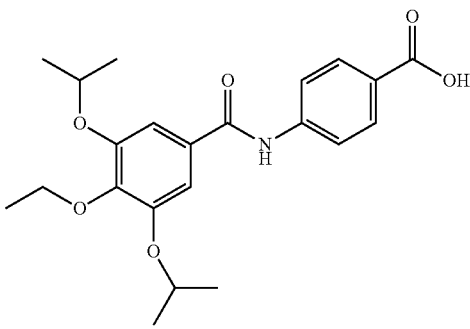 [SMILES: CCOc1c(OC(C)C)cc(C(=O)Nc2ccc(C(=O)O)cc2)cc1OC(C)C]

4-(4-Ethoxy-3,5-diisopropoxybenzamido)benzoic acid (AAA-008) (288 mg, 57% for final step) was prepared in essentially the same manner as in Steps (iii) and (iv) for AAA-001 except that 4-ethoxy-3,5-diisopropoxybenzoic acid (prepared in 3 steps from methyl 3,4,5-trihydroxybenzoate by sequential treatment with ethyl iodide and base, isopropyl bromide and base and then lithium hydroxide) was used instead of 3,5-dichloro-4-(cyclopentyloxy)benzoic acid in step (iii): m/z 400 (M–H)⁻ (ES⁻), 402 (M+H)⁺ (ES⁺). $^1$H NMR (400 MHz, MeOH-d$_4$) δ: 8.02 (2H, d), 7.85 (2H, d), 7.28 (2H, s), 4.70 (2H, m), 4.10 (2H, q), 1.37 (15H, m).

Synthesis 8

4-(3,4-Diethoxy-5-isopropoxybenzamido)benzoic acid (AAA-009)

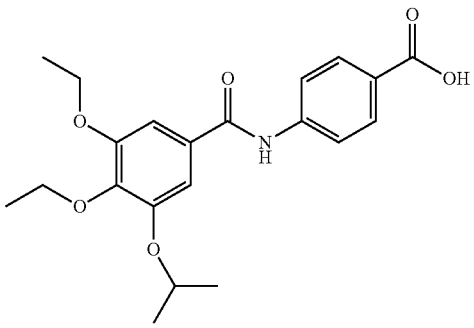 [SMILES: CCOc1cc(C(=O)Nc2ccc(C(=O)O)cc2)cc(OC(C)C)c1OCC]

4-(3,4-Diethoxy-5-isopropoxybenzamido)benzoic acid (AAA-009) (5 mg, 15% for final step) was prepared in essentially the same manner as in Steps (iii) and (iv) for AAA-001 except that 3,4-diethoxy-5-diisopropoxybenzoic acid (prepared in 3 steps from methyl 3,4,5-trihydroxybenzoate by sequential treatment with ethyl iodide and base, isopropyl bromide and base and then lithium hydroxide, the product being a by-product of the preparation of 4-ethoxy-3,5-diisopropoxybenzoic acid shown in the synthesis of AAA-008) was used instead of 3,5-dichloro-4-(cyclopentyloxy)benzoic acid in step (iii): m/z 386 (M–H)⁻ (ES⁻), 388 (M+H)⁺ (ES⁺). $^1$H NMR (400 MHz, CDCl$_3$) δ: 8.12 (2H, d), 7.75 (2H, d), 7.08 (2H, d), 4.63 (1H, m), 4.13 (4H, m), 1.47 (3H, t), 1.40-1.36 (9H, m).

Synthesis 9

4-(3,5-Dichloro-4-(cyclopropylmethoxy)benzamido)benzoic acid (AAA-010)

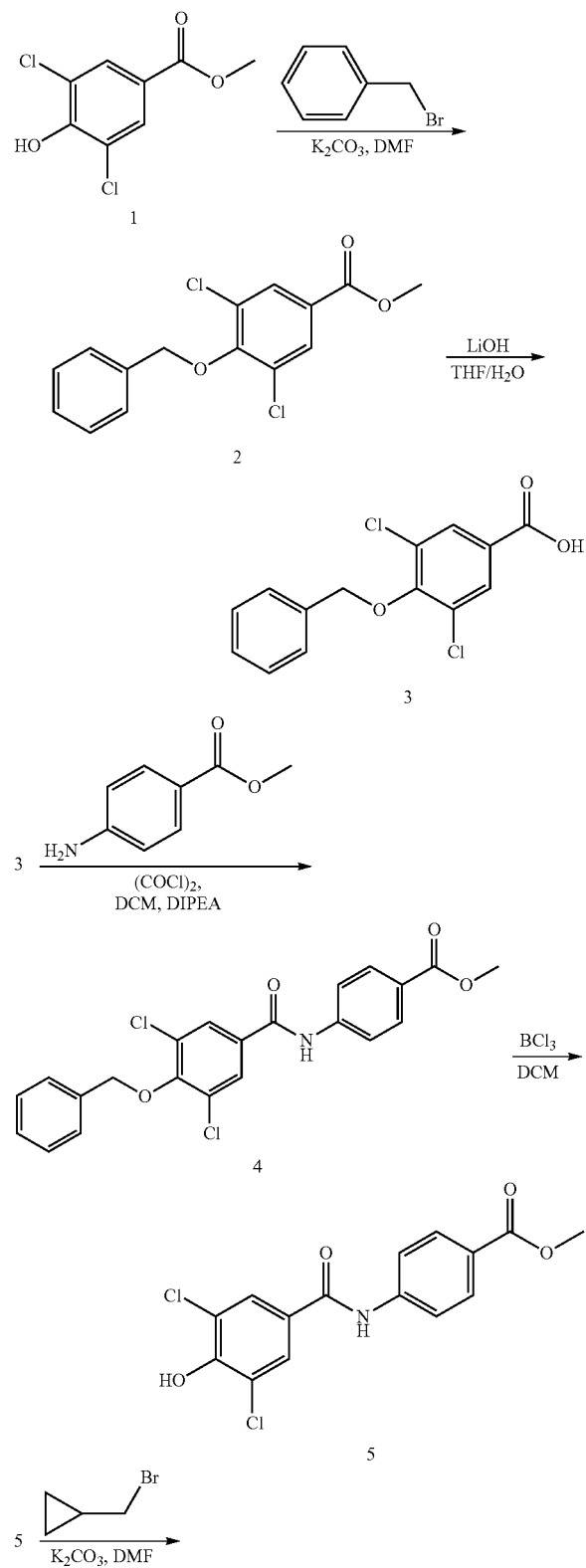

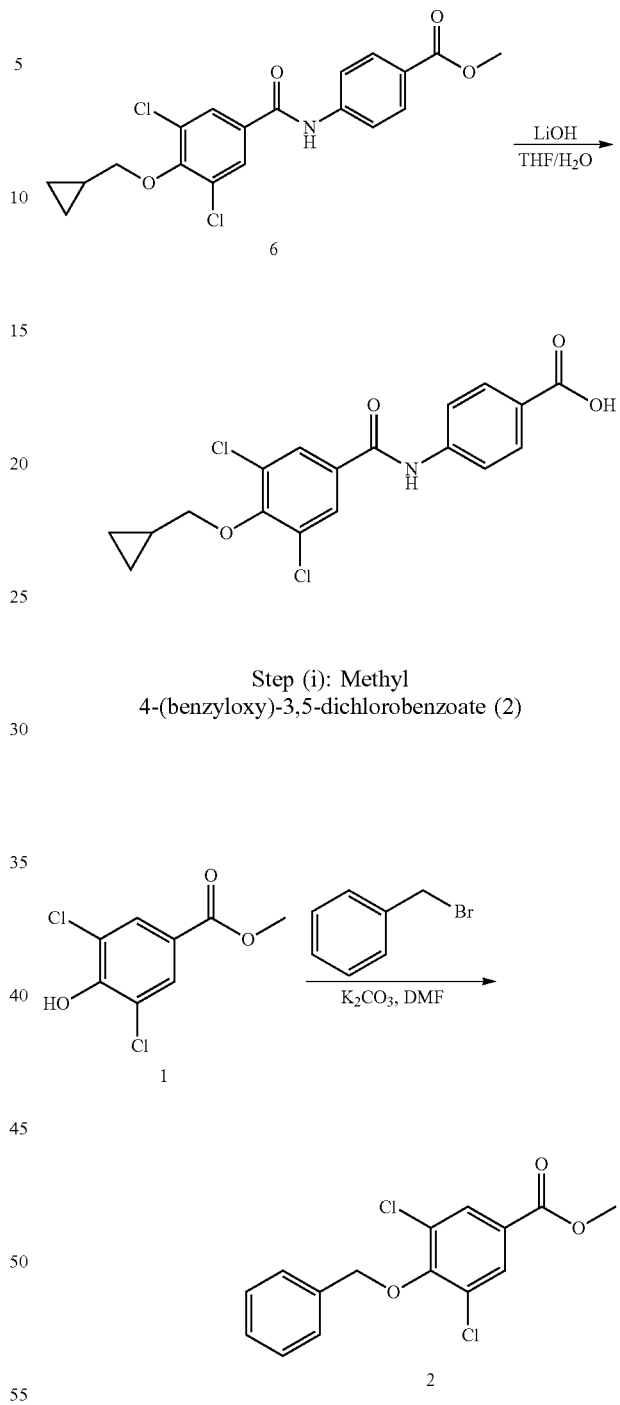

Step (i): Methyl 4-(benzyloxy)-3,5-dichlorobenzoate (2)

Crude methyl 4-(benzyloxy)-3,5-dichlorobenzoate (2) (16.9 g) was prepared from methyl 3,5-dichloro-4-hydroxybenzoate (1) (10 g, 45.2 mmol) and benzyl bromide (15.5 g, 90 mmol) using a procedure essentially the same as in Step (i) for AAA-001, except that the mixture was stirred at RT for 18 h. The crude product was partially purified by silica gel chromatography (330 g, 0-10% EtOAc/isohexane) to afford a white solid. The material was used in the next step without further purification.

Step (ii): 4-(Benzyloxy)-3,5-dichlorobenzoic acid (3)

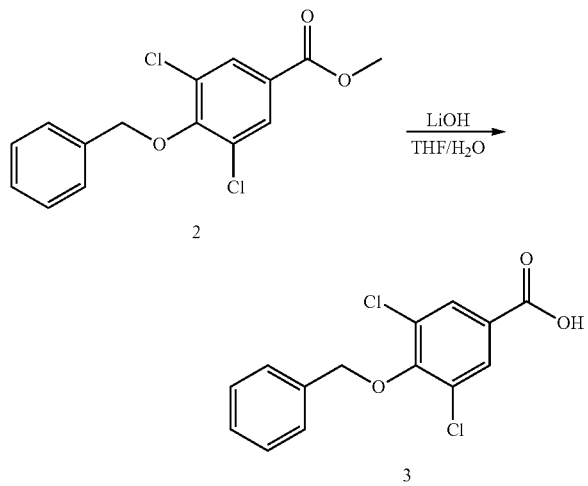

4-(Benzyloxy)-3,5-dichlorobenzoic acid (3) (12.8 g, 96% over 2 steps) was prepared from crude 4-(benzyloxy)-3,5-dichlorobenzoate (2) (16.9 g) using a procedure essentially the same as in Step (iv) for AAA-001: m/z 295 (M−H)⁻ (ES⁻). ¹H NMR (400 MHz, DMSO-$d_6$) δ: 7.88 (2H, s), 7.51 (2H, d), 7.44-7.37 (3H, m), 5.05 (2H, s).

Step (iii): Methyl 4-(4-(benzyloxy)-3,5-dichlorobenzamido)benzoate (4)

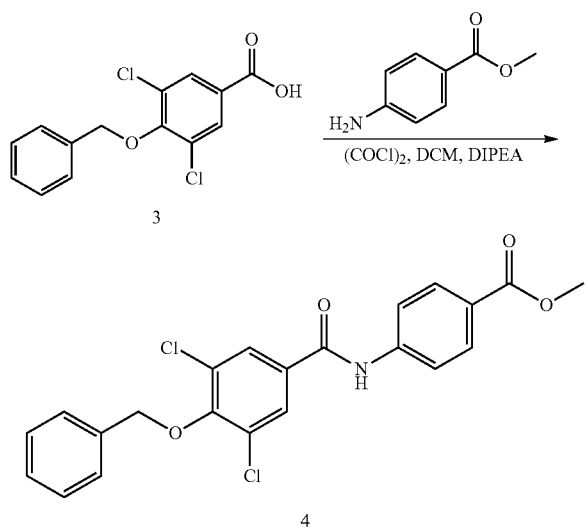

Methyl 4-(4-(benzyloxy)-3,5-dichlorobenzamido)benzoate (4) (9.81 g, 51%) was prepared from 4-(benzyloxy)-3,5-dichlorobenzoic acid (3) (12.8 g, 43.2 mmol) using a procedure essentially the same as in Step (iii) for AAA-001, except the crude product was crystallised from isohexane/EtOAc to afford the product as a white solid. m/z 428 (M−H)⁻ (ES⁻). ¹H NMR (400 MHz, CDCl₃) δ: 8.07 (2H, d), 7.84 (2H, s), 7.73 (2H, d), 7.54 (2H, d), 7.44-7.36 (3H, m), 5.13 (2H, s), 3.92 (3H, s).

Step (iv): Methyl 4-(3,5-dichloro-4-hydroxybenzamido)benzoate (5)

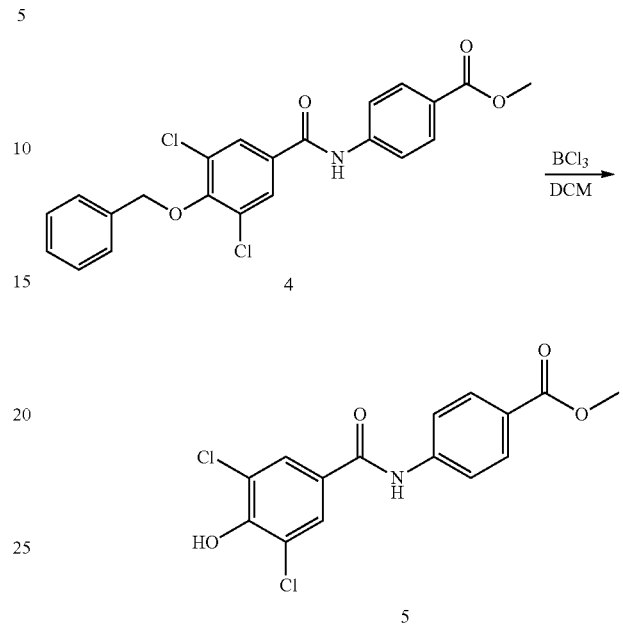

A solution of methyl 4-(4-(benzyloxy)-3,5-dichlorobenzamido)benzoate (4) (8.8 g, 20.5 mmol) in DCM (500 mL) was cooled to 0° C. and treated dropwise with boron trichloride (20.5 mL, 20.5 mmol, 1 M in DCM). The mixture was then allowed to stir at RT for 12 h. The mixture was cooled in an ice bath then quenched by addition of water (150 mL). The resultant mixture was partitioned between EtOAc (200 mL) and H₂O (100 mL). The aqueous phase was extracted with EtOAc (2×75 mL) and the combined organic phases washed successively with water (50 mL) and brine (50 mL), then dried over MgSO₄ and filtered. The solvent was removed in vacuo. The residue was crystallised from isohexane/EtOAc to afford methyl 4-(3,5-dichloro-4-hydroxybenzamido)benzoate (5) (5.81 g, 84%): m/z 338 (M−H)⁻ (ES⁻). ¹H NMR (400 MHz, DMSO-$d_6$) δ: 11.06 (1H, s), 10.52 (1H, s), 8.06 (2H, s), 8.00 (2H, d), 7.95 (2H, d), 3.88 (3H, s).

Step (v): Methyl 4-(3,5-dichloro-4-(cyclopropylmethoxy)benzamido)benzoate (6)

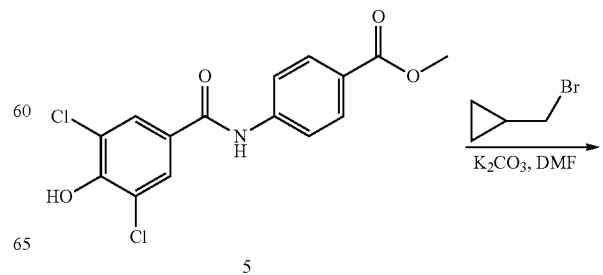

-continued

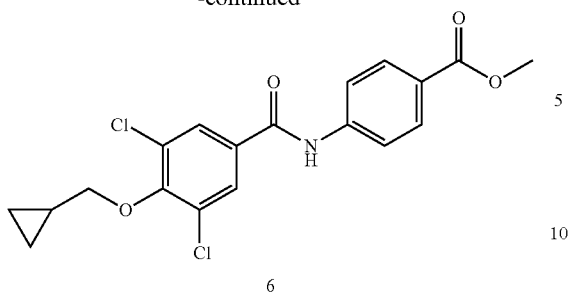

6

Methyl 4-(3,5-dichloro-4-(cyclopropylmethoxy)benzamido)benzoate (6) (120 mg, 100%) was prepared from methyl 4-(3,5-dichloro-4-hydroxybenzamido)benzoate (5) (100 mg, 294 μmol) and (bromomethyl)cyclopropane (57 μL, 588 μmol) using a procedure essentially the same as in Step (i) for AAA-001 except the mixture was stirred at 50° C. for 18 h: m/z 392 (M−H)⁻ (ES⁻). $^1$H NMR (400 MHz, DMSO-$d_6$) δ: 7.99 (4H, d), 7.85 (2H, d), 3.99 (2H, d), 3.90 (3H, s), 1.49-1.29 (1H, m), 0.65-0.60 (2H, m), 0.37-0.34 (2H, m).

Step (vi): 4-(3,5-Dichloro-4-(cyclopropylmethoxy)benzamido)benzoic acid (AAA-010)

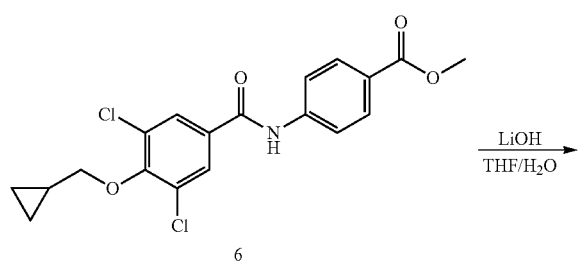

6

4-(3,5-Dichloro-4-(cyclopropylmethoxy)benzamido)benzoic acid (AAA-010) (82 mg, 71%) was prepared from methyl 4-(3,5-dichloro-4-(cyclopropylmethoxy)benzamido)-benzoate (6) (120 mg, 304 μmol) using a procedure essentially the same as in Step (iv) for AAA-001: m/z 378 (M−H)⁻ (ES⁻). $^1$H NMR (400 MHz, MeOH-$d_4$) δ: 8.01 (4H, d), 7.83 (2H, d), 3.98 (2H, d), 1.40-1.30 (1H, m), 0.64-0.60 (2H, m), 0.37-0.33 (2H, m).

Synthesis 10

4-(3,5-Dichloro-4-cyclobutoxybenzamido)benzoic acid (AAA-011)

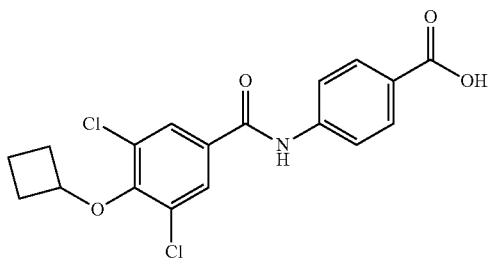 [SMILES: O=C(O)c1ccc(NC(=O)c2cc(Cl)c(OC3CCC3)c(Cl)c2)cc1]

4-(3,5-Dichloro-4-cyclobutoxybenzamido)benzoic acid (AAA-011) (23 mg, 31% for final step) was prepared in essentially the same manner as in Steps (v) and (vi) for AAA-010 except that bromocyclobutane was used instead of (bromomethyl)cyclopropane in step (v): m/z 378 (M−H)⁻ (ES⁻). $^1$H NMR (400 MHz, MeOH-$d_4$) δ: 8.01 (4H, d), 7.85 (2H, s), 4.78-4.71 (1H, m), 2.4-2.35 (4H, m) 1.8-1.75 (1H, m), 1.64-1.49 (1H, m).

Synthesis 11

4-(3,5-Dichloro-4-(pyridin-4-ylmethoxy)benzamido)benzoic acid (AAA-012)

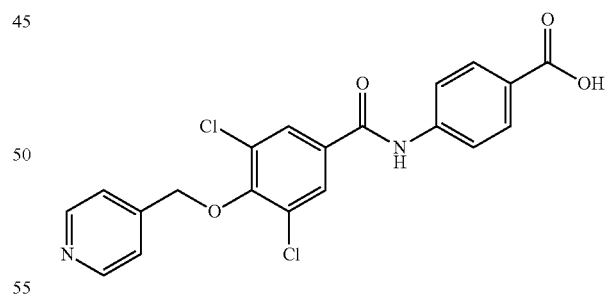

4-(3,5-Dichloro-4-(pyridin-4-ylmethoxy)benzamido)benzoic acid (AAA-012) (47 mg, 63% for final step) was prepared in essentially the same manner as in Steps (v) and (vi) for AAA-010 except that 4-(chloromethyl)pyridine was used instead of (bromomethyl)cyclopropane in step (v): m/z 415 [M−H]⁻ (ES⁻), 417 [M+H]⁺ (ES⁺), 1H NMR (400 MHz, MeOH-$d_4$) δ: 10.43 (1H, s), 8.92 (2H, d), 8.30 (2H, d), 8.13 (2H, s), 8.04 (2H, d), 7.86 (2H, d), 5.54 (2H, s).

Synthesis 12
4-(3,5-Dichloro-4-ethoxyphenylcarbamoyl)benzoic acid (AAA-013)

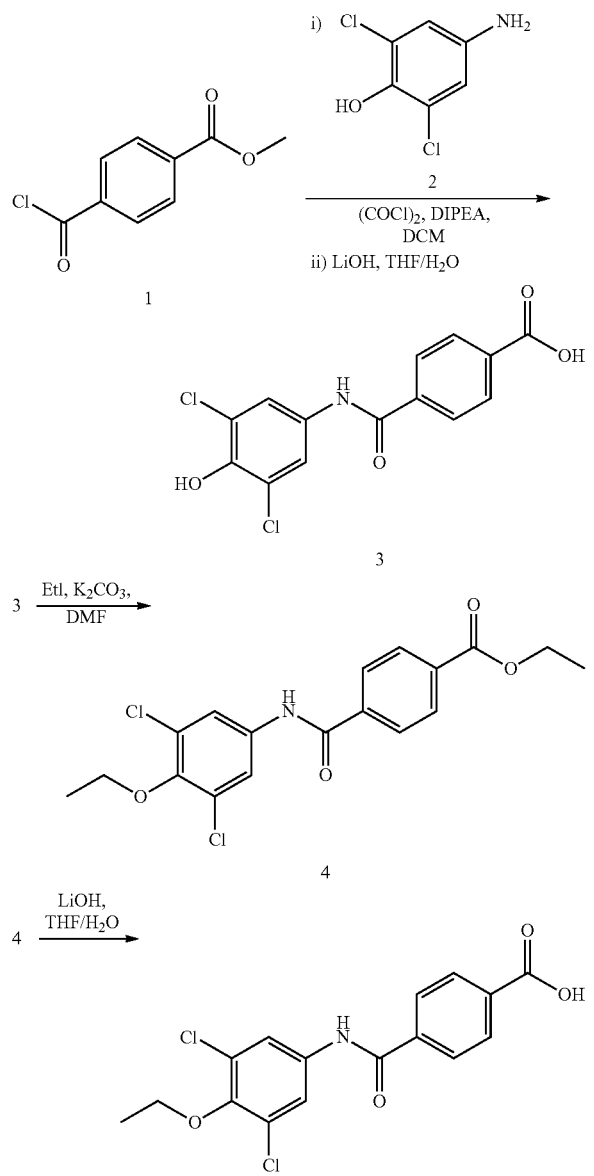

Step (i): 4-(3,5-Dichloro-4-hydroxyphenylcarbamoyl)benzoic acid (4)

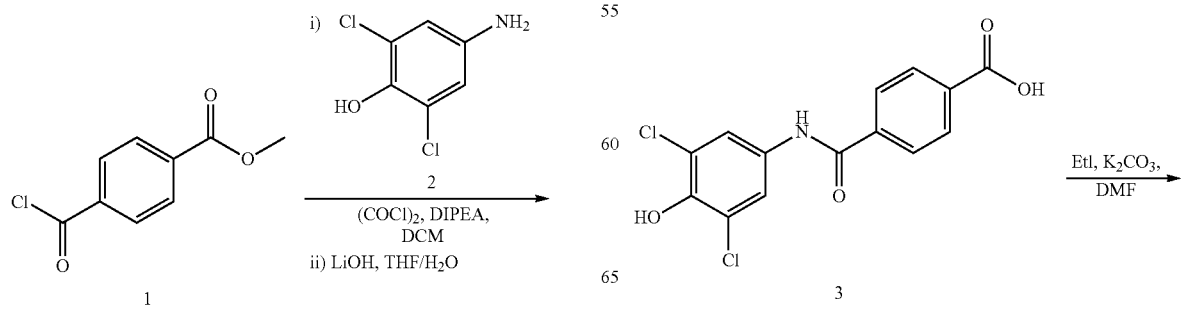

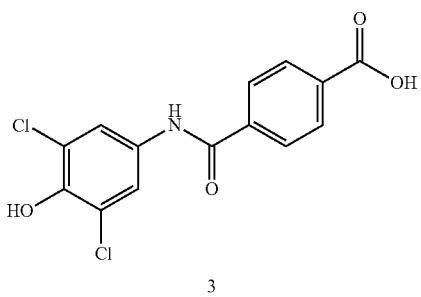

A mixture of 4-(chlorocarbonyl)benzoic acid methyl ester (1) (600 mg, ca. 3.02 mmol) contaminated with 4-(methoxycarbonyl)benzoic acid was suspended in DCM (5 mL) and cooled to 0° C. The mixture was treated with oxalyl chloride (529 µL, 6.04 mmol) and DMF (1 drop). The resultant mixture was warmed to RT, stirred for 2 h, and then concentrated in vacuo. The residue was dissolved in DCM (3 mL) and a suspension of 4-amino-2,6-dichlorophenol (2) (511 mg, 2.9 mmol) in DCM (18 mL) was added. The resultant suspension was treated with DIPEA (1.58 mL, 9.06 mmol) and was stirred at RT overnight. The solvent was removed in vacuo and the residue partitioned between EtOAc/DCM and aqueous HCl (1 M). The layers were separated and the organic layer was washed with water and brine. The organic layer was dried over MgSO$_4$, filtered and then the solvent evaporated in vacuo to afford a pale brown solid (930 mg), which was triturated in hot acetonitrile/methanol (9:1) and filtered. The precipitate and filtrate were recombined, the solvent was evaporated in vacuo and then the residue was dissolved in THF (40 mL). Water (10 mL) was added and the mixture treated with lithium hydroxide (340 mg, 14.2 mmol). The mixture was stirred overnight and then partitioned between EtOAc and aqueous HCl (1 M). The organic layer was washed successively with water (2×50 mL), brine, dried over MgSO$_4$, filtered and then concentrated in vacuo to afford crude 4-(3,5-dichloro-4-hydroxyphenylcarbamoyl)benzoic acid (3) as a pale brown solid. This material was used in the subsequent reaction step without purification.

Step (ii): Ethyl 4-(3,5-dichloro-4-ethoxyphenylcarbamoyl)benzoate (4)

-continued

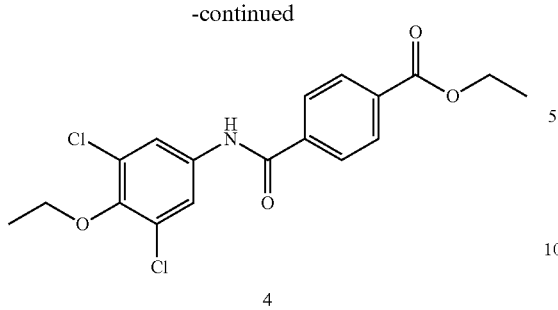

Crude 4-(3,5-dichloro-4-hydroxyphenylcarbamoyl)benzoic acid (3) (450 mg) was dissolved in DMF (15 mL) and treated with potassium carbonate (829 mg, 6.00 mmol) and iodoethane (436 μL, 5.4 mmol). The mixture was stirred at 65° C. overnight. Iodoethane (200 μL, 2.48 mmol) was added and the reaction mixture stirred at 70° C. for 3 h. The mixture was partitioned between EtOAc (150 mL) and aqueous HCl (100 mL, 1 M). The layers were separated and the organic layer was washed successively with saturated aqueous NaHCO₃ and water. The organic layer was dried over MgSO₄, filtered and the solvent evaporated in vacuo. The residue was purified by silica gel chromatography (10-25% EtOAc/isohexane) to afford Ethyl 4-(3,5-dichloro-4-ethoxyphenylcarbamoyl)benzoate (4) (500 mg, 75% over 2 steps) as a pale pink solid: m/z 380 (M−H)⁺ (ES⁻).

Step (iii): 4-(3,5-Dichloro-4-ethoxyphenylcarbamoyl)benzoic acid (AAA-013)

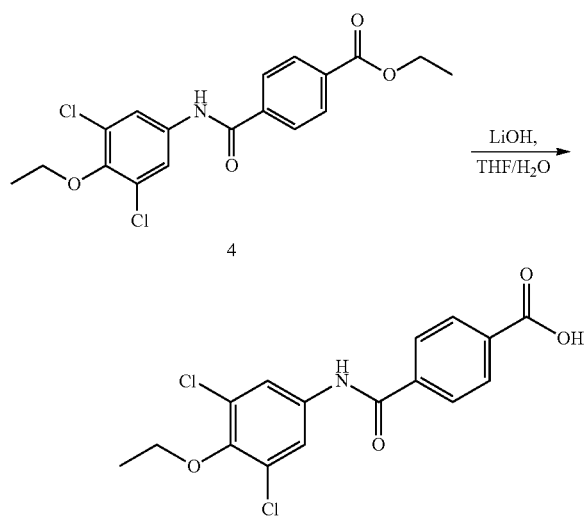

Ethyl 4-(3,5-dichloro-4-ethoxyphenylcarbamoyl)benzoate (6) (109 mg, 285 μmol) in THF (5 mL) was treated with aqueous lithium hydroxide (1.43 mL, 1 M, 1.43 mmol) and the mixture was stirred at RT for 5 h. The reaction mixture was partitioned between EtOAc and aqueous HCl (1 M). The organic layer was separated and washed successively with water and brine. The organic layer was dried over MgSO₄, filtered and then concentrated in vacuo to afford 4-(3,5-dichloro-4-ethoxyphenylcarbamoyl)benzoic acid (AAA-013) (89 mg, 88%) as a pale lilac solid: m/z 352 [M−H]⁻ (ES⁻). ¹H NMR (400 MHz, DMSO-d₆) δ: 13.30 (1H, s), 10.58 (1H, s), 8.08 (2H, d), 8.03 (2H, d), 7.94 (2H, d), 4.04 (2H, q), 1.37 (3H, t).

Synthesis 13

4-(3,5-Dibromo-4-ethoxyphenylcarbamoyl)benzoic acid (AAA-014)

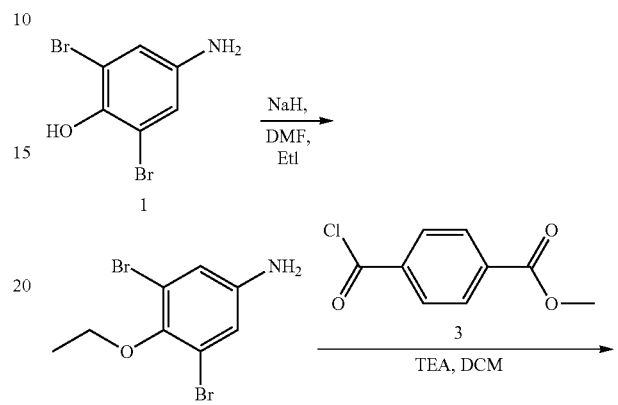

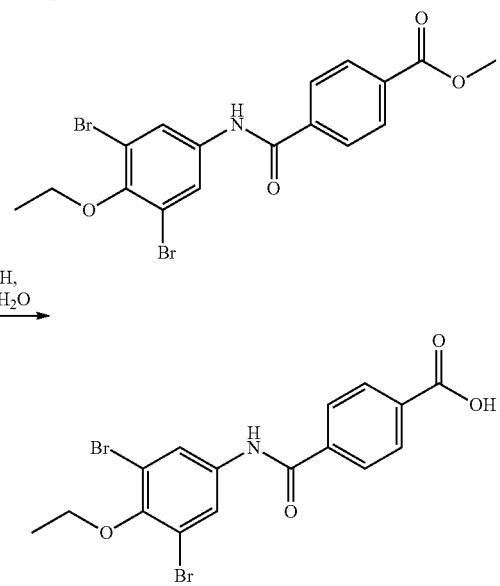

Step (i): 3,5-Dibromo-4-ethoxyaniline (2)

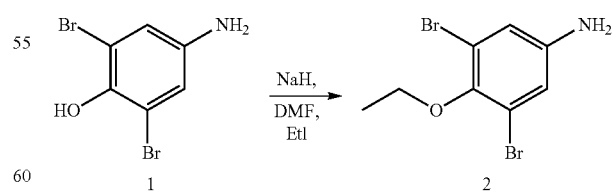

4-Amino-2,6-dibromophenol (1) (1.00 g, 3.75 mmol) was dissolved in anhydrous DMF (10 mL) and cooled to 0° C. Sodium hydride (165 mg, 4.12 mmol) was added portionwise. The dark blue solution was stirred for 1 h at RT before iodoethane (318 μL, 3.93 mmol) was added. The mixture was stirred at RT for 3 days and then partitioned between EtOAc and aqueous NaOH (1 M). The organic layer was washed successively with water and brine, then dried over MgSO$_4$ and filtered. The solvent was evaporated in vacuo and the residue purified by silica gel chromatography (10% EtOAc/isohexane) to afford 3,5-dibromo-4-ethoxyaniline (2) (790 mg, 72%) as a dark orange solid: m/z 296 [M+H]$^+$ (ES$^+$). $^1$H NMR (400 MHz, CDCl$_3$) δ: 6.82 (2H, s), 3.99 (2H, q), 3.58 (2H, s), 1.54 (3H, s), 1.44 (3H, t).

Step (ii): Methyl 4-(3,5-dibromo-4-ethoxyphenylcarbamoyl)benzoate (4)

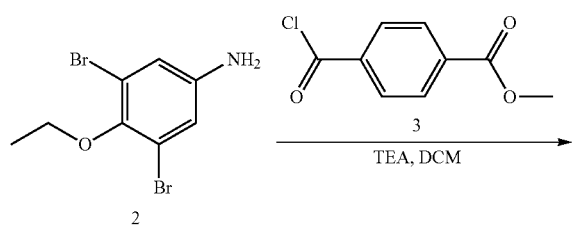

3,5-Dibromo-4-ethoxyaniline (2) (100 mg, 339 μmol) was dissolved in DCM (2.5 mL) and treated with triethylamine (143 μL, 1.02 mmol). 4-(Chlorocarbonyl)benzoic acid methyl ester (3) (135 mg, 678 μmol) was added in one portion and the resultant dark orange mixture was stirred at RT for 3 h then partitioned between EtOAc and aqueous 1M HCl. The organic layer was washed successively with saturated aqueous NaHCO$_3$, water and brine. The organic layer was then dried over MgSO$_4$, filtered and the solvent evaporated in vacuo. The residue was triturated from Et$_2$O and filtered. The filtered solid was washed with methanol and the washings were concentrated in vacuo to provide methyl 4-(3,5-dibromo-4-ethoxyphenylcarbamoyl)benzoate (4) (141 mg, 73%) as a pale brown solid: m/z 456 [M–H]$^-$ (ES$^-$).

Step (iii): 4-(3,5-Dibromo-4-ethoxyphenylcarbam-oyl)benzoic acid (AAA-014)

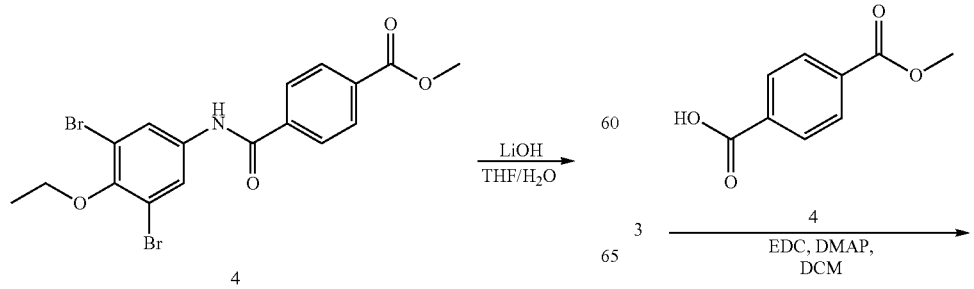

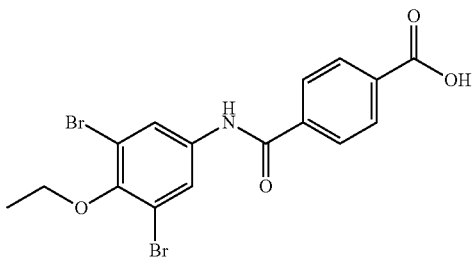

4-(3,5-Dibromo-4-ethoxyphenylcarbamoyl)benzoic acid (AAA-014) (31 mg, 71%) was prepared from methyl 4-(3,5-dibromo-4-ethoxyphenylcarbamoyl)benzoate (4) (45 mg, 98 μmol) using a procedure essentially the same as in Step (iii) for AAA-013, except the mixture was stirred overnight: m/z 442 [M–H]$^-$ (ES$^-$). $^1$H NMR (400 MHz, DMSO-d$_6$) δ: 13.31 (1H, s), 10.59 (1H, s), 8.15 (2H, s), 8.05 (2H, d), 8.03 (2H, d), 4.01 (2H, q), 1.40 (3H, t).

Synthesis 14

4-(4-Ethoxy-3,5-bis(trifluoromethyl)phenylcarbam-oyl)benzoic acid (AAA-015)

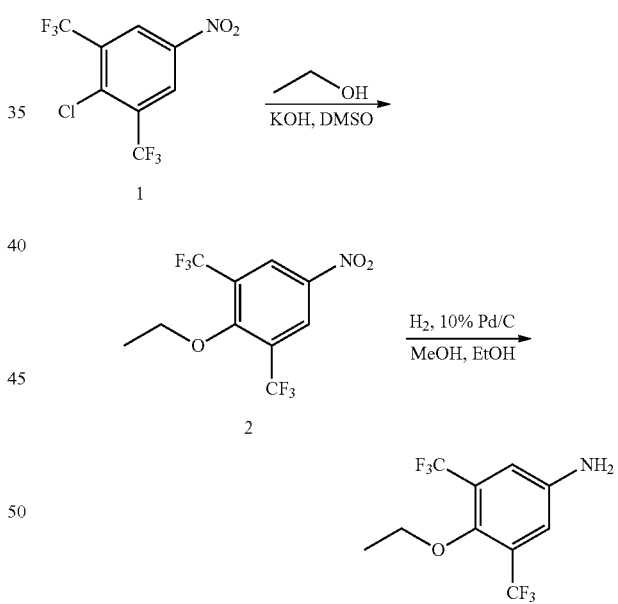

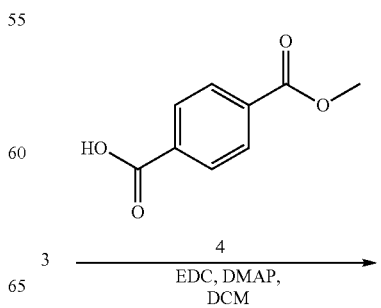

Step (ii): 4-Ethoxy-3,5-bis(trifluoromethyl)aniline (3)

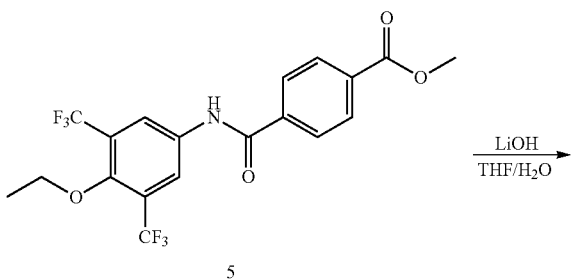

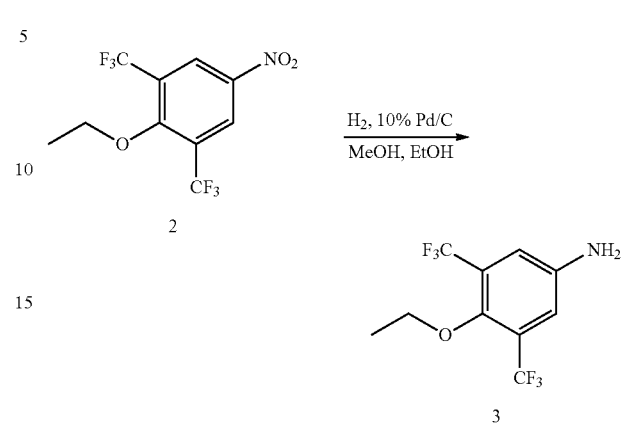

2-Ethoxy-5-nitro-1,3-bis(trifluoromethyl)benzene (2) (1.00 g, 3.30 mmol) was dissolved in MeOH (150 mL) and passed through a Thales 'H-cube' cartridge (10% Pd/C) at a flow rate of 1 mL/min at 30° C. under $H_2$ (full $H_2$ mode). The solvent was removed in vacuo and the residue was dissolved in EtOH (20 mL) and then treated with 10% Pd/C (182 mg, 171 µmol). Hydrogen gas was bubbled through the mixture, with stirring at RT for 2 h. The mixture was then filtered through Celite and concentrated in vacuo. The residue was purified by silica gel chromatography (15% EtOAc in iso-hexane) to afford 4-ethoxy-3,5-bis(trifluoromethyl)aniline (3) (460 mg, 56%) as a white solid: m/z 273 [M+H]$^+$ (ES$^+$). $^1$H NMR (400 MHz, DMSO-d$_6$) δ: 7.09 (2H, s), 5.76 (2H, s), 3.87 (2H, q), 1.29 (3H, t).

Step (iii): Methyl 4-(4-ethoxy-3,5-bis(trifluoromethyl)phenylcarbamoyl)benzoate (5)

Step (i): 2-Ethoxy-5-nitro-1,3-bis(trifluoromethyl) benzene (2)

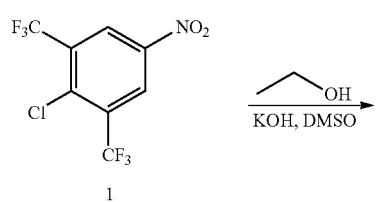

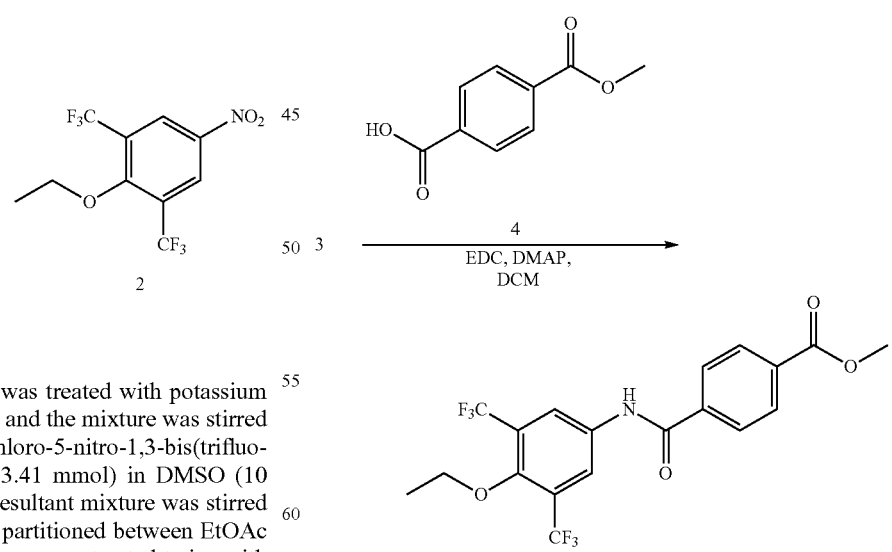

Ethanol (20 mL, 343 mmol) was treated with potassium hydroxide (956 mg, 17.0 mmol) and the mixture was stirred at RT for 1 h. A solution of 2-chloro-5-nitro-1,3-bis(trifluoromethyl)benzene (1) (1.00 g, 3.41 mmol) in DMSO (10 mL) was added dropwise. The resultant mixture was stirred at RT for 1 h. The mixture was partitioned between EtOAc and water and the aqueous phase was extracted twice with EtOAc. The combined organic phases were washed with brine, dried over MgSO$_4$, filtered and the solvent removed in vacuo to afford 2-ethoxy-5-nitro-1,3-bis(trifluoromethyl) benzene (2) (1.00 g, 93%) as a yellow solid. $^1$H NMR (400 MHz, DMSO-d$_6$) δ: 8.72 (2H, s), 4.21 (2H, q), 1.41 (3H, t).

4-(Methoxycarbonyl)benzoic acid (4) (246 mg, 1.37 mmol) was dissolved in DCM (15 mL) and treated with EDC (654 mg, 3.41 mmol) and DMAP (33 mg, 273 µmol).

The resultant mixture was stirred at RT for 15 min. 4-Ethoxy-3,5-bis(trifluoromethyl)aniline (3) (360 mg, 1.32 mmol) was added and the resultant mixture was stirred at RT for 20 h. The mixture was diluted with EtOAc and washed three times with 1 M HCl and then three times with NaHCO$_3$ solution. The organic phase was washed with brine, dried over MgSO$_4$, filtered and the solvent removed in vacuo. The residue was purified by silica gel chromatography (10% EtAOc in isohexane) to afford methyl 4-(4-ethoxy-3,5-bis(trifluoromethyl)phenylcarbamoyl)benzoate (5) (150 mg, 28%): m/z 436 [M+H]$^+$ (ES$^+$).

$^1$H NMR (400 MHz, DMSO-d$_6$) δ: 10.88 (1H, s), 8.48 (2H, s), 8.11 (4H, m), 4.04 (2H, q), 3.90 (3H, s), 1.37 (3H, t).

Step (iv): 4-(4-Ethoxy-3,5-bis(trifluoromethyl)phenylcarbamoyl)benzoic acid (AAA-015)

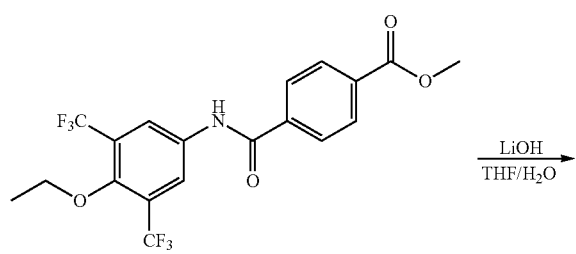

4-(4-Ethoxy-3,5-bis(trifluoromethyl)phenylcarbamoyl) benzoic acid (AAA-015) (107 mg, 70%) was prepared from methyl 4-(4-ethoxy-3,5-bis(trifluoromethyl)phenyl carbamoyl)benzoate (5) (150 mg, 345 μmol) using a procedure essentially the same as in Step (vi) for AAA-010: m/z 422 [M+H]$^+$ (ES$^+$). $^1$H NMR (400 MHz, DMSO-d$_6$) δ: 13.39 (1H, bs), 10.92 (1H, s), 8.55 (2H, s), 8.15 (4H, m), 4.11 (2H, q), 1.44 (3H, t).

Synthesis 15

N-(4-Carbamoylphenyl)-3,5-dichloro-4-ethoxybenzamide (AAA-016)

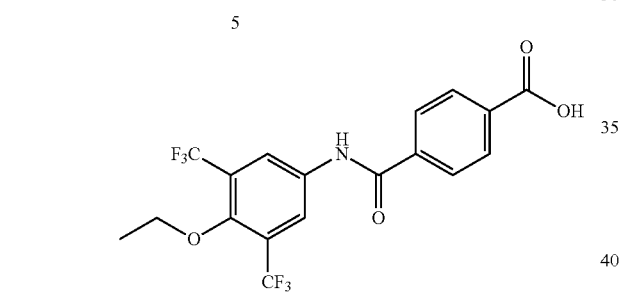

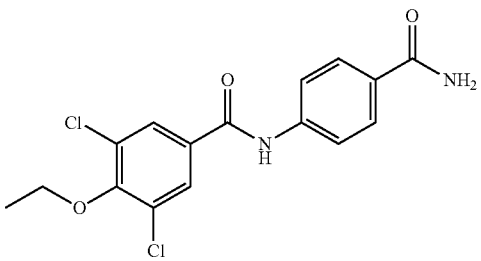

3,5-Dichloro-4-ethoxybenzoic acid (1) (100 mg, 425 μmol) was dissolved in DCM (2 mL) and treated with EDC (204 mg, 1.06 mmol) and DMAP (10 mg, 85 μmol). The resultant mixture was stirred at RT for 30 min. 4-Aminobenzamide (2) (58 mg, 425 μmol) was added and the resultant mixture was stirred at RT for 4 h. The mixture was filtered and the solid washed with DCM to afford N-(4-carbamoylphenyl)-3,5-dichloro-4-ethoxybenzamide (AAA-016) (98 mg, 64%) as a white solid: m/z 355 [M+H]$^+$ (ES$^+$). $^1$H NMR (400 MHz, DMSO-d$_6$) δ: 10.51 (1H, bs), 8.08 (2H, s), 7.84 (5H, m), 7.27 (1H, bs), 4.14 (2H, q), 1.40 (3H, t).

Synthesis 16

Methyl 4-(3,5-dichloro-4-ethoxybenzamido)-2-chlorobenzoate (AAA-017)

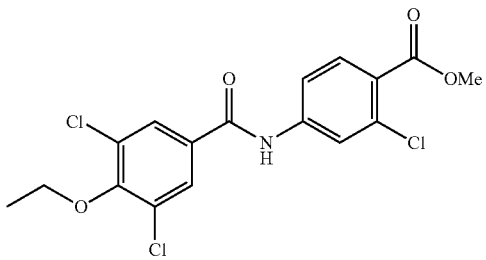 [SMILES: CCOc1c(Cl)cc(C(=O)Nc2ccc(C(=O)OC)c(Cl)c2)cc1Cl]

Methyl 4-(3,5-dichloro-4-ethoxybenzamido)-2-chlorobenzoate (AAA-017) (175 mg, 39%) was prepared in essentially the same manner as in Step (iii) for AAA-001, except that 3,5-dichloro-4-ethoxybenzoic acid was used instead of 3,5-dichloro-4-(cyclopentyloxy)benzoic acid and methyl 4-amino-2-chlorobenzoate was used instead of methyl 4-aminobenzoate: m/z 402 (M−H)$^-$ (ES$^-$). $^1$H NMR (400 MHz, CDCl$_3$) δ: 7.93 (2H, d), 7.85 (1H, s), 7.83 (1H, d), 7.80 (2H, s), 4.18 (2H, q), 3.93 (3H, s), 1.49 (3H, t).

Synthesis 17

2-Chloro-4-(3,5-dichloro-4-ethoxybenzamido)benzoic acid (AAA-018)

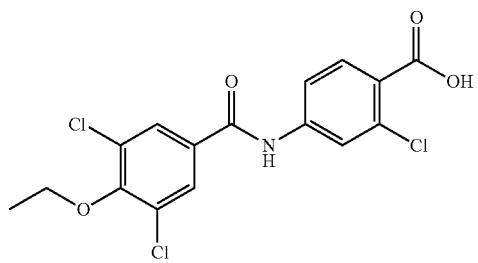 [SMILES: CCOc1c(Cl)cc(C(=O)Nc2ccc(C(=O)O)c(Cl)c2)cc1Cl]

2-Chloro-4-(3,5-dichloro-4-ethoxybenzamido)benzoic acid (AAA-018) (39 mg, 39% for the final step) was prepared in essentially the same manner as in Steps (iii) and (iv) for AAA-001, except that 3,5-dichloro-4-ethoxybenzoic acid was used instead of 3,5-dichloro-4-(cyclopentyloxy) benzoic acid and methyl 4-amino-2-chlorobenzoate was used instead of methyl 4-aminobenzoate in Step (iii): m/z 386 (M–H)⁻ (ES⁻). ¹H NMR (400 MHz, DMSO-$d_6$) δ: 13.18 (1H, s), 10.65 (1H, s), 8.07 (2H, s), 8.00 (1H, d), 7.88 (1H, d), 7.78 (1H, dd), 4.13 (2H, q), 1.39 (3H, t).

Synthesis 18

4-(3,5-Dichloro-4-ethoxybenzamido)-2-methylbenzoic acid (AAA-019)

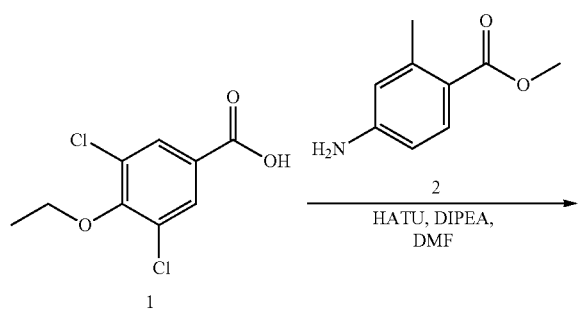

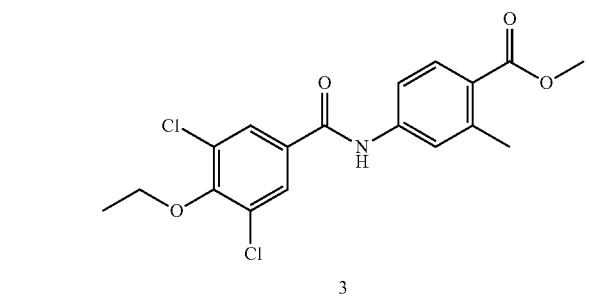

Step (i): Methyl 4-(3,5-dichloro-4-ethoxybenzamido)-2-methylbenzoate (3)

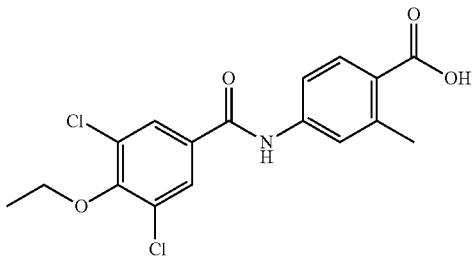

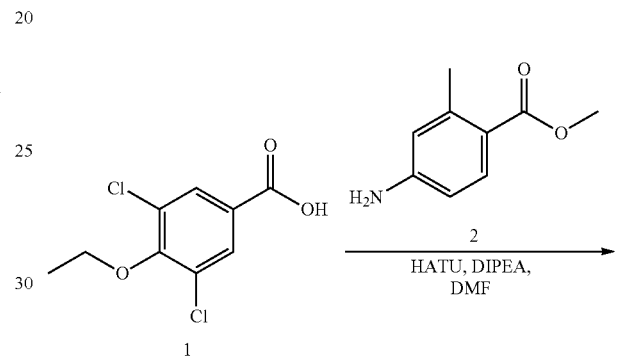

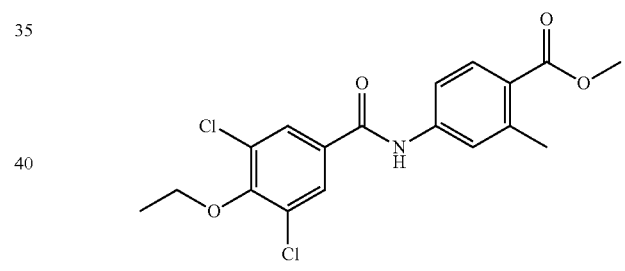

A solution of 3,5-dichloro-4-ethoxybenzoic acid (1) (285 mg, 1.21 mmol) and DIPEA (1.05 mL, 6.05 mmol) in DMF (2.5 mL) was added to HATU (690 mg, 1.82 mmol) and the orange mixture was stirred for 5 min prior to the addition of methyl 4-amino-2-methylbenzoate (2) (200 mg, 1.21 mmol) in DMF (1 mL). The resulting dark orange solution was stirred overnight for 18 h. 2 M HCl (10 mL) was added and stirring continued for 10 min, and then the mixture was extracted with diethyl ether. The organic layer was washed with water (3×15 mL), dried over MgSO₄, filtered and the solvent was evaporated in vacuo. The yellow residue was purified by silica gel chromatography (40 g, 0-100% EtOAc in isohexane) to afford methyl 4-(3,5-dichloro-4-ethoxybenzamido)-2-methylbenzoate (3) (267 mg, 56%): m/z 380 (M–H)⁻ (ES⁻). ¹H NMR (400 MHz, CDCl₃) δ: 7.97 (1H, s), 7.80 (3H, m), 7.54 (1H, dd), 7.51 (1H, d), 4.18 (2H, q), 3.89 (3H, s), 2.63 (3H, s), 1.49 (3H, t).

Step (ii): 4-(3,5-Dichloro-4-ethoxybenzamido)-2-methylbenzoic acid (AAA-019)

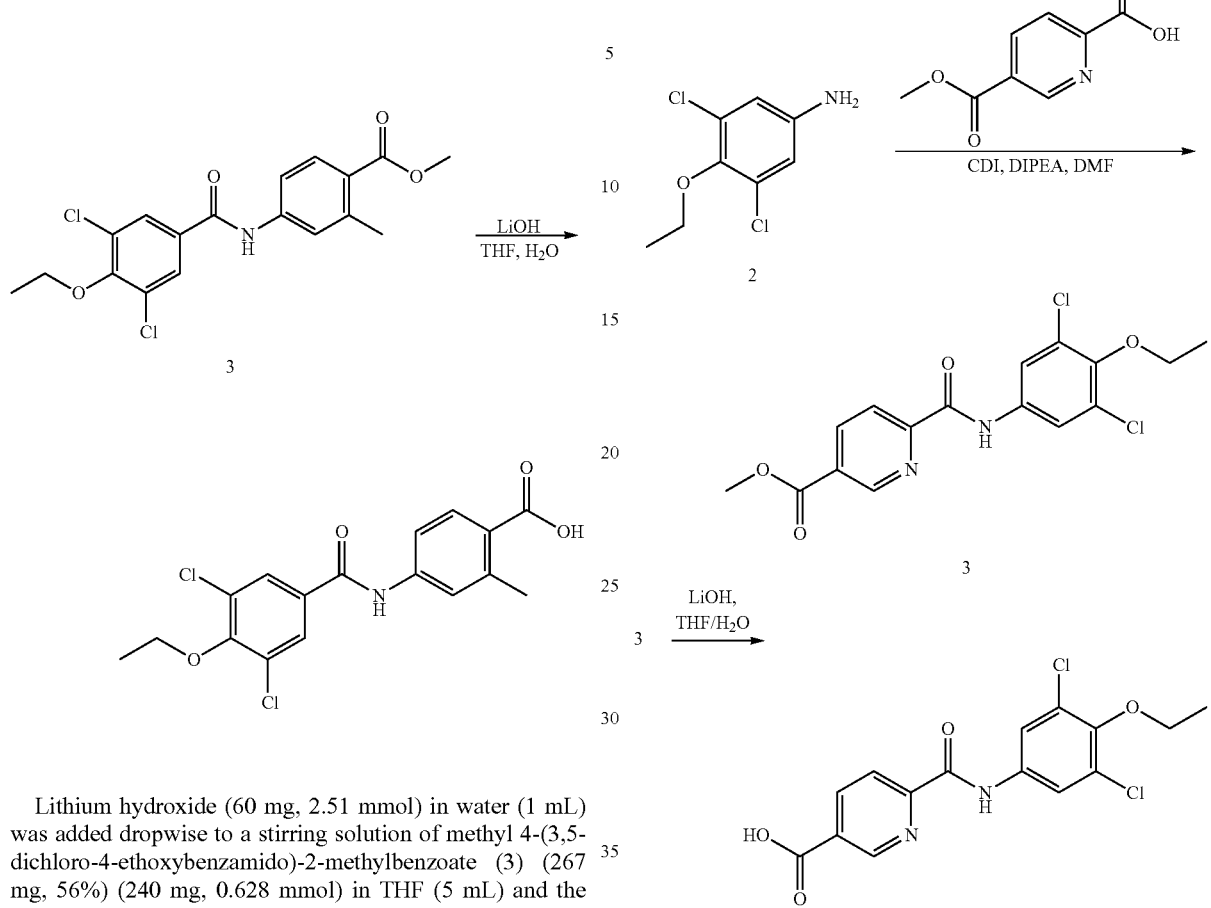

Lithium hydroxide (60 mg, 2.51 mmol) in water (1 mL) was added dropwise to a stirring solution of methyl 4-(3,5-dichloro-4-ethoxybenzamido)-2-methylbenzoate (3) (267 mg, 56%) (240 mg, 0.628 mmol) in THF (5 mL) and the resulting yellow solution was stirred for 5 days at RT. The solvent was evaporated in vacuo and dissolved in water (5 mL), then acidified with 2 M HCl. The resultant mixture was extracted with EtOAc. The organic layer was washed with water, dried over $MgSO_4$ and filtered and pre-adsorbed on silica. Silica gel chromatography (40 g, 0-10% IPA in DCM) provided 4-(3,5-dichloro-4-ethoxybenzamido)-2-methylbenzoic acid (AAA-019) (52 mg, 22%): m/z 366 (M−H)⁻ (ES⁻). $^1$H NMR (400 MHz, DMSO-$d_6$) δ: 12.66 (1H, s), 10.49 (1H, s), 8.08 (2H, s), 7.87 (1H, d), 7.71 (1H, dd), 7.68 (1H, d), 4.14 (2H, q), 2.54 (3H, s), 1.40 (2H, t).

Synthesis 19

6-(3,5-dichloro-4-ethoxyphenylcarbamoyl) nicotinic acid (AAA-020

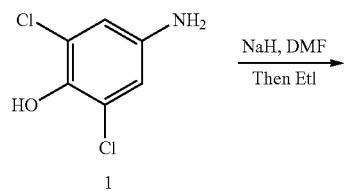

Step (i): 3,5-Dichloro-4-ethoxyaniline (2)

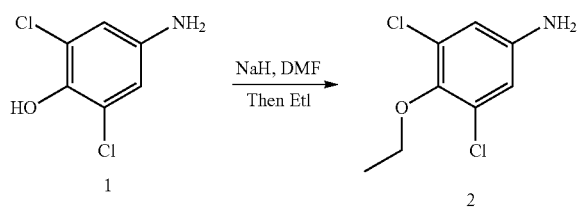

4-Amino-2,6-dichlorophenol (1) (1.00 g, 5.62 mmol) was dissolved in dry DMF (9 mL) and cooled to 0° C. Sodium hydride (142 mg, 5.90 mmol) was added to the mixture portionwise. The dark purple solution was stirred for 1 h at RT, then iodoethane (468 μL, 5.79 mmol) was added. The reaction mixture was stirred for 3 h and partitioned between EtOAc and aqueous NaOH (1 M). The organic layer was washed successively with water and brine, and then dried over $MgSO_4$, filtered and the solvent evaporated in vacuo. The residue was purified by silica gel chromatography (5% EtOAc/isohexane) to afford 3,5-dichloro-4-ethoxyaniline (2) (460 mg, 40%): m/z 206 [M+H]⁺ (ES⁺). $^1$H NMR (400 MHz, CDCl$_3$) δ: 6.60 (2H, s), 4.01 (2H, q), 3.60 (2H, s), 1.42 (3H, t).

Step (ii): Methyl 6-(3,5-dichloro-4-ethoxyphenylcarbamoyl)nicotinate (3)

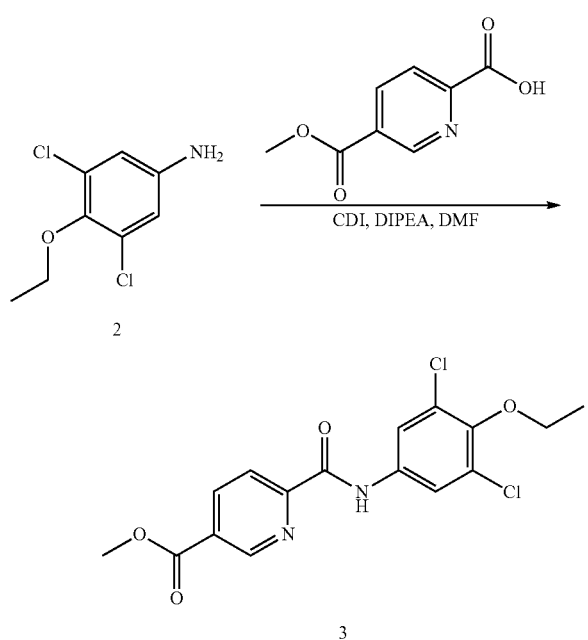

5-(Methoxycarbonyl)-2-pyridine carboxylic acid (50 mg, 276 µmol) was dissolved in DMF (2 mL) and treated with CDI (60 mg, 370 µmol). The reaction mixture was stirred at RT for 2 h. 3,5-Dichloro-4-ethoxyaniline (2) (57 mg, 276 µmol) and DIPEA (96 µL, 552 µmol) were added sequentially and the reaction mixture was stirred at RT overnight, then at 70° C. for 19 h. The reaction mixture was partitioned between EtOAc and aqueous HCl (1 M). The organic layer was washed successively with water and brine, and then dried over MgSO$_4$, filtered and concentrated in vacuo. The residue was crystallised from methanol to afford methyl 6-(3,5-dichloro-4-ethoxyphenylcarbamoyl)nicotinate (3) (46 mg, 45%) as a white solid: m/z 369 [M+H]$^+$ (ES$^+$). $^1$H NMR (400 MHz, DMSO-d$_6$) δ: 11.12 (1H, s), 9.18 (1H, dd), 8.55 (1H, dd), 8.29 (1H, dd), 8.13 (2H, s), 4.06 (2H, q), 3.94 (3H, s), 1.37 (3H, t).

Step (iii): 6-(3,5-Dichloro-4-ethoxyphenylcarbamoyl)nicotinic acid (AAA-020)

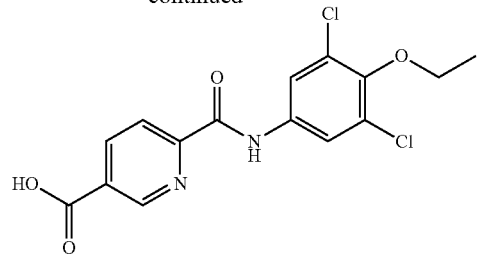

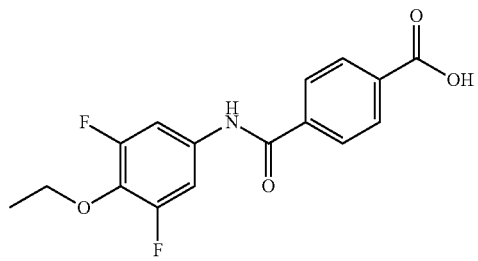 [SMILES: CCOc1c(F)cc(NC(=O)c2ccc(C(=O)O)cc2)cc1F]

6-(3,5-Dichloro-4-ethoxyphenylcarbamoyl)nicotinic acid (AAA-020) (19 mg, 109%) was prepared from methyl 6-(3,5-dichloro-4-ethoxyphenylcarbamoyl)nicotinate (3) (18 mg, 49 µmol) using a procedure essentially the same as in Step (iii) for AAA-013, except methanol (0.5 mL) was also added and the reaction mixture was stirred at RT overnight: m/z 353 [M−H]$^−$ (ES$^−$). $^1$H NMR (400 MHz, DMSO-d$_6$) δ: 11.12 (1H, s), 9.18 (1H, dd), 8.55 (1H, dd), 8.29 (1H, dd), 8.13 (2H, s), 4.06 (2H, q), 1.37 (3H, t).

Synthesis 20

4-(4-Ethoxy-3,5-difluorophenylcarbamoyl)benzoic acid (AAA-021)

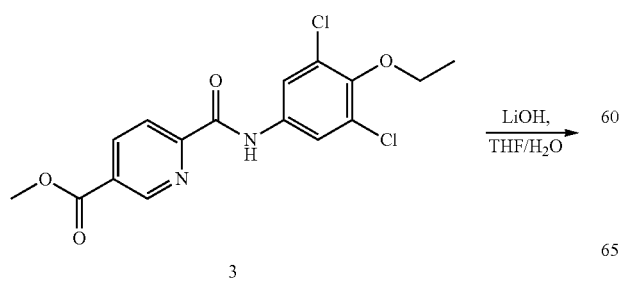

4-(4-Ethoxy-3,5-difluorophenylcarbamoyl)benzoic acid (AAA-021) (7 mg, 17%) was prepared was prepared in essentially the same manner as in Steps (ii) and (iii) for AAA-014, except that 3,5-difluoro-4-ethoxyaniline was used instead of 3,5-dibromo-4-ethoxyaniline in step (ii) and purification was effected by trituration with Et$_2$O/EtOAc 8:1 and purification by preparative HPLC (Method 1): m/z 320 [M−H]$^−$ (ES$^−$). $^1$H NMR (400 MHz, MeOD-d$_4$) δ: 8.42 (1H, s), 8.10 (2H, d), 7.94 (2H, d), 7.45 (2H, d), 4.14 (2H, q), 1.35 (3H, t).

Synthesis 21

4-(3-Chloro-4-ethoxy-5-(trifluoromethyl)benzamido)-2,6-difluorobenzoic acid (AAA-022)

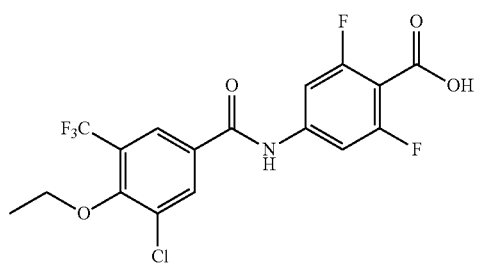 [SMILES: CCOc1c(Cl)cc(C(=O)Nc2cc(F)c(C(=O)O)c(F)c2)cc1C(F)(F)F]

4-(3-Chloro-4-ethoxy-5-(trifluoromethyl)benzamido)-2,6-difluorobenzoic acid (AAA-022) (5 mg, 7% for final step) was prepared in essentially the same manner as in Steps (iii) and (iv) for AAA-001, except that 3-chloro-4-ethoxy-5-trifluoromethylbenzoic acid (prepared in 3 steps from 4-hydroxy-3-(trifluoromethyl)benzoic acid by sequential treatment with sulfuryl chloride, ethyl iodide and base and then lithium hydroxide) and ethyl 2,6-difluoro-4-aminobenzoate were used instead of 3,5-dichloro-4-(cyclopentyloxy)benzoic acid and methyl 4-aminobenzoate respectively in step (iii): m/z 422 (M–H)⁻ (ES⁻). ¹H NMR (400 MHz, MeOD) δ: 8.32 (d, 1H), 8.21 (d, 1H), 7.49 (d, 2H), 4.24 (q, 2H), 1.48 (t, 3H).

Synthesis 22

4-(3,5-Dibromo-4-ethoxybenzamido)benzoic acid (AAA-023)

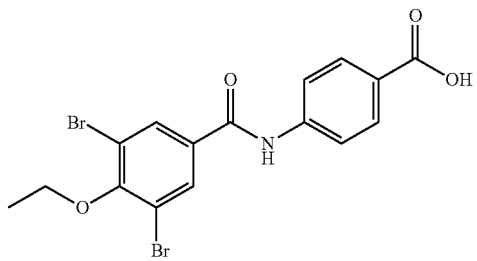 [SMILES: CCOc1c(Br)cc(C(=O)Nc2ccc(C(=O)O)cc2)cc1Br]

4-(3,5-Dibromo-4-ethoxybenzamido)benzoic acid (AAA-023) (42 mg, 87% for final step) was prepared in essentially the same manner as in Steps (iii) and (iv) for AAA-001, except that 3,5-dibromo-4-ethoxybenzoic acid (prepared in 2 steps from methyl 3,5-dibromo-4-hydroxybenzoate by sequential treatment with ethyl iodide and base and then lithium hydroxide) was used instead of 3,5-dichloro-4-(cyclopentyloxy)benzoic acid in step (iii): m/z 442 (M–H)⁻ (ES⁻). ¹H NMR (400 MHz, CDCl₃) 10.59 (1H, s), 8.24 (2H, s), 7.94 (2H, d), 7.87 (2H, d), 4.10 (2H, q), 1.43 (3H, t).

Synthesis 23

4-(3-Chloro-4-ethoxy-5-methoxybenzamido)benzoic acid (AAA-024)

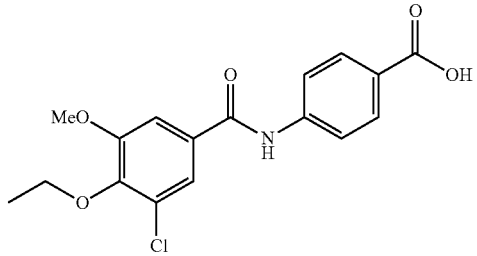 [SMILES: CCOc1c(Cl)cc(C(=O)Nc2ccc(C(=O)O)cc2)cc1OC]

4-(3-Chloro-4-ethoxy-5-methoxybenzamido)benzoic acid (AAA-024) (80 mg, 79% for final step) was prepared in essentially the same manner as in Steps (iii) and (iv) for AAA-001, except that 3-chloro-4-ethoxy-5-methoxybenzoic acid was used instead of 3,5-dichloro-4-(cyclopentyloxy)-benzoic acid in step (iii): m/z 348 (M–H)⁻ (ES⁻). ¹H NMR (400 MHz, DMSO) 12.76 (1H, br s), 10.46 (1H, br s), 7.93 (2H, d), 7.87 (2H, d), 7.69 (1H, d), 7.56 (1H, d), 4.19 (2H, q), 3.85 (3H, s), 1.39 (3H, t).

Synthesis 24

4-(3-Chloro-4-ethoxy-5-(trifluoromethyl)benzamido)benzoic acid (AAA-025)

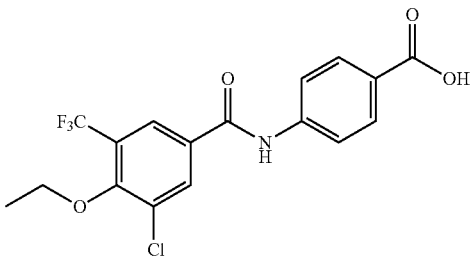

4-(3-Chloro-4-ethoxy-5-(trifluoromethyl)benzamido)benzoic acid (AAA-025) (17 mg, 34% for final step) was prepared in essentially the same manner as in Steps (iii) and (iv) for AAA-001, except that 3-chloro-4-ethoxy-5-(trifluoromethyl)benzoic acid was used instead of 3,5-dichloro-4-(cyclopentyloxy)benzoic acid in step (iii): m/z 386 (M–H)⁻ ES⁻. ¹H NMR (400 MHz, DMSO) 12.78 (1H, br s), 10.69 (1H, br s), 8.42 (1H, d), 8.22 (1H, d), 7.95 (2H, d), 7.87 (2H, d), 3.37 (2H, q), 1.41 (3H, t).

Synthesis 25

5-(3,5-Dichloro-4-ethoxybenzamido)picolinic acid (AAA-026)

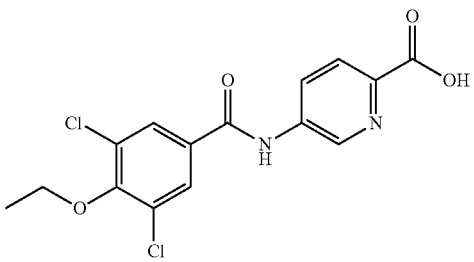 [SMILES: CCOc1c(Cl)cc(C(=O)Nc2ccc(C(=O)O)nc2)cc1Cl]

5-(3,5-Dichloro-4-ethoxybenzamido)picolinic acid (AAA-026) (20 mg, quant. for final step) was prepared in essentially the same manner as in Steps (iii) and (iv) for AAA-001, except that 3,5-dichloro-4-ethoxybenzoic acid and methyl 5-aminopicolinate (prepared by treating 5-aminopyridine-2-carboxylic acid with acetyl chloride and methanol) were used instead of 3,5-dichloro-4-(cyclopentyloxy) benzoic acid and methyl 4-aminobenzoate respectively in step (iii): m/z 355 (M+H)⁺ (ES⁺). ¹H NMR 400 MHz, DMSO-d₆) δ: 10.9 (1H, s), 9.0 (1H, d), 8.4 (1H, dd), 8.2 (2H, s), 8.1 (1H, d), 4.1 (2H, q), 1.4 (3H, t). (The final compound was isolated as a hydrochloride salt.

Synthesis 26

6-(3,5-Dichloro-4-ethoxybenzamido)nicotinic acid (AAA-027)

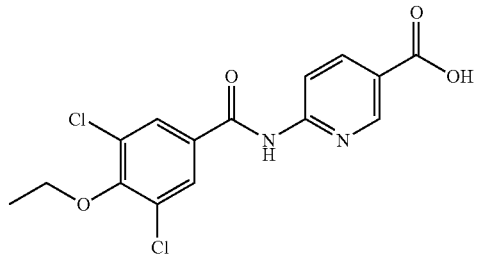 [SMILES: CCOc1c(Cl)cc(C(=O)Nc2ccc(C(=O)O)cn2)cc1Cl]

6-(3,5-Dichloro-4-ethoxybenzamido)nicotinic acid (AAA-027) (28 mg, 29% for final step) was prepared in essentially the same manner as in Steps (iii) and (iv) for AAA-001, except that 3,5-dichloro-4-ethoxybenzoic acid and methyl 6-aminonicotinate were used instead of 3,5-dichloro-4-(cyclopentyloxy)benzoic acid and methyl 4-aminobenzoate respectively in step (iii): m/z 353 (M−H)⁻ (ES⁻). ¹H NMR (400 MHz, DMSO-$d_6$) δ: 11.3 (1H, s), 8.9 (1H, d), 8.3 (1H, dd), 8.2 (1H, d), 8.1 (2H, s), 4.1 (2H, q), 1.4 (3H, t).

Synthesis 27

4-(3,4,5-Triethoxybenzamido)benzoic acid (AAA-028) (PP-01)

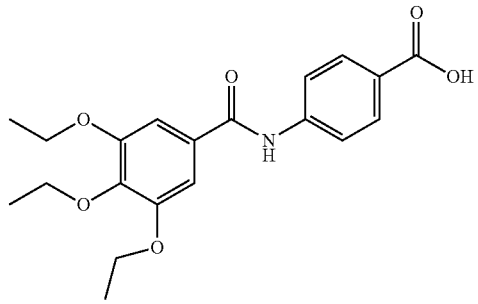 [SMILES: CCOc1cc(C(=O)Nc2ccc(C(=O)O)cc2)cc(OCC)c1OCC]

4-(3,4,5-Triethoxybenzamido)benzoic acid (AAA-028) (42 mg, 68% for final step) was prepared in essentially the same manner as in Steps (iii) and (iv) for AAA-001, except that 3,4,5-triethoxybenzoic acid was used instead of 3,5-dichloro-4-(cyclopentyloxy)benzoic acid in step (iii): m/z 374 (M+H)⁺ (ES⁺). ¹H NMR (400 MHz, DMSO-$d_6$) δ: 10.3 (1H, s), 7.9 (2H, d), 7.8 (2H, d), 7.2 (2H, s), 4.1 (4H, q), 4.0 (2H, q), 1.4 (6H, t), 1.2 (3H, t).

Synthesis 28

4-(3,5-Dichloro-4-ethoxybenzamido)benzoic acid (AAA-029) (PP-02)

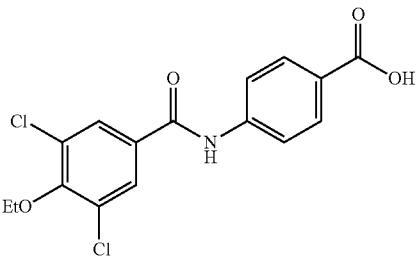 [SMILES: CCOc1c(Cl)cc(C(=O)Nc2ccc(C(=O)O)cc2)cc1Cl]

The title compound was obtained from commercial sources.

Synthesis 29

4-(3,5-Dichloro-4-methoxybenzamido)benzoic acid (AAA-030) (PP-03)

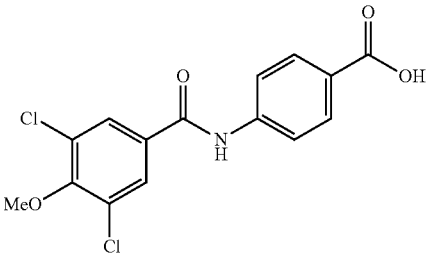 [SMILES: COc1c(Cl)cc(C(=O)Nc2ccc(C(=O)O)cc2)cc1Cl]

The title compound was obtained from commercial sources.

Synthesis 30 (Comparison Compound)

4-(4-Ethoxy-3-(trifluoromethyl)benzamido)benzoic acid (XXX-01)

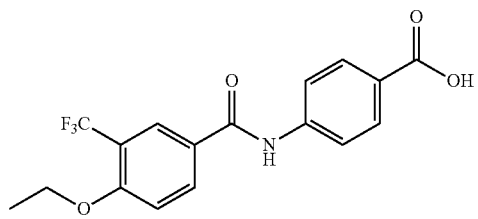 [SMILES: CCOc1ccc(C(=O)Nc2ccc(C(=O)O)cc2)cc1C(F)(F)F]

4-(4-Ethoxy-3-(trifluoromethyl)benzamido)benzoic acid (XXX-01) (14 mg, 49% for final step) was prepared in essentially the same manner as in Steps (iii) and (iv) for AAA-001, except that 4-ethoxy-3-(trifluoromethyl)benzoic acid (prepared in 2 steps from 4-hydroxy-3-(trifluoromethyl)benzoic acid by sequential treatment with ethyl iodide and base and then lithium hydroxide) was used instead of 3,5-dichloro-4-(cyclopentyloxy)benzoic acid in step (iii):

m/z 352 (M−H)⁻ (ES⁻). ¹H NMR (400 MHz, DMSO) 12.75 (1H, br s) 10.54 (1H, br s), 8.26 (1H, d), 8.24 (1H, d), 7.94 (2H, d), 7.88 (2H, d), 7.41 (1H, d), 4.27 (2H, q), 1.36 (3H, t).

Synthesis 31 (Comparison Compound)

4-(4-Ethoxy-3-(trifluoromethyl)benzamido)-2,6-difluorobenzoic acid (XXX-02)

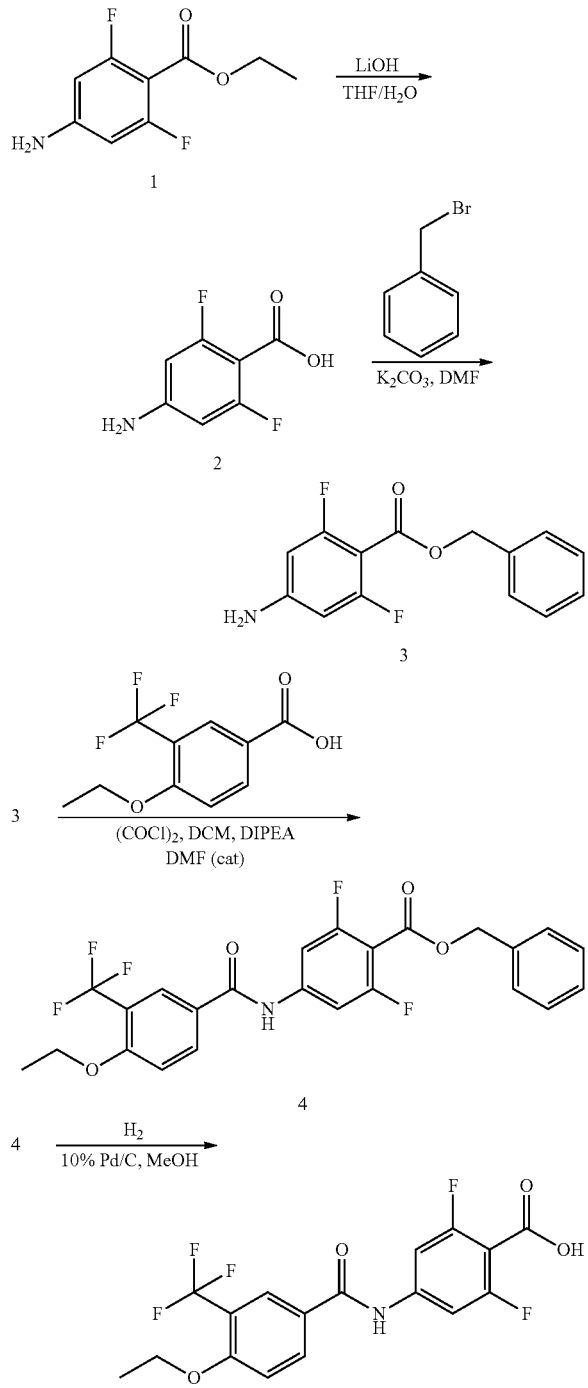

Step (i): 4-Amino-2,6-difluorobenzoic acid (2)

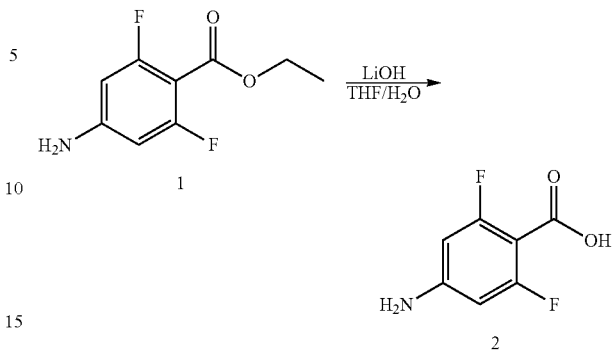

Ethyl 4-amino-2,6-difluorobenzoate (1) (3.26 g, 16.2 mmol) was dissolved in THF (40 mL) and treated with lithium hydroxide (1.94 g, 81 mmol), followed by water (10 mL). The resultant mixture was stirred at RT for 20 h. Methanol (4 mL) was added and the resultant mixture was stirred at RT for 20 h. The solvent was removed in vacuo. The residue was twice dissolved in toluene and the solvent removed in vacuo. The material was divided into three equal portions and each was dissolved in AcOH (5 mL) and then partitioned between EtOAc and water. The phases were separated and the organic phase was washed successively with water and brine, then dried over MgSO₄, filtered and the solvent removed in vacuo. The residues were combined to afford 4-amino-2,6-difluorobenzoic acid (2) (2.46 g, 88%) as a pale yellow solid: m/z 173 (M−H)⁻ (ES⁻). ¹H NMR (400 MHz, DMSO-d₆) δ: 12.59 (1H, br s), 6.31 (1H, s), 6.16 (2H, dt).

Step (iv): Benzyl 4-amino-2,6-difluorobenzoate (3)

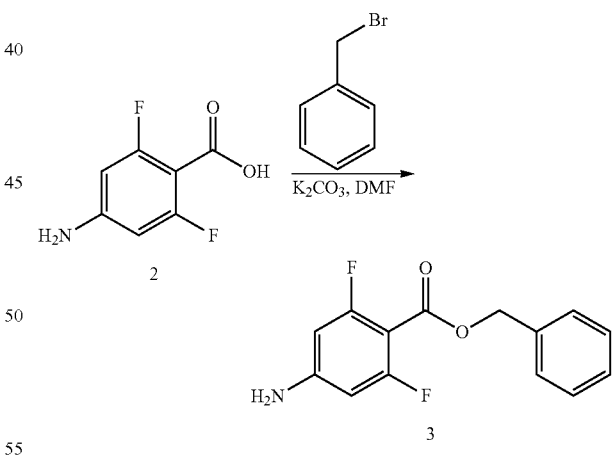

4-Amino-2,6-difluorobenzoic acid (5) (900 mg, 5.20 mmol) was dissolved in DMF (15 mL) and treated with potassium carbonate (790 mg, 5.72 mmol). Benzyl bromide (617 μL, 5.20 mmol) was added over 5 min. The resultant mixture was stirred at RT for 2 h. The mixture was then partitioned between EtOAc (150 mL) and water. The phases were separated and the aqueous phase extracted with EtOAc. The combined organic phases were washed successively with water (4 times) and then brine. The organic phase was then dried over MgSO₄, filtered and the solvent removed in vacuo. The residue was purified by silica gel chromatography (100% DCM). The resultant material was dissolved in the minimum volume of EtOAc and added dropwise to isohexane (150 mL). The resultant white precipitate was collected by filtration to afford benzyl 4-amino-2,6-difluorobenzoate (6) (910 mg, 64%) as a white solid: m/z 264 $(M+H)^+$ $(ES^+)$. $^1H$ NMR (400 MHz, $CDCl_3$) δ: 7.44 (2H, dd), 7.39-7.29 (3H, m), 6.16 (2H, dt), 5.34 (2H, s), 4.18 (2H, br s).

Step (v): Benzyl 4-(4-ethoxy-3-(trifluoromethyl) benzamido)-2,6-difluorobenzoate (4)

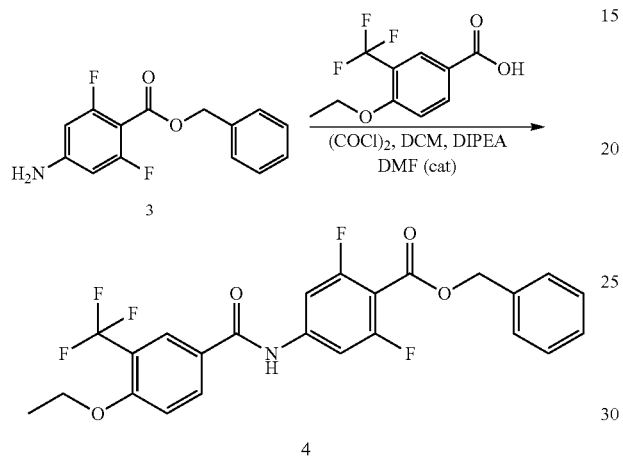

Benzyl 4-(4-ethoxy-3-(trifluoromethyl)benzamido)-2,6-difluorobenzoate (4) (172 mg, 37%) was prepared from 4-ethoxy-3-(trifluoromethyl)benzoic acid (250 mg, 1.07 mmol) and benzyl 4-amino-2,6-difluorobenzoate (4) (255 mg, 970 µmol) using a procedure essentially the same as in Step (iii) for AAA-001, except the reaction mixture was stirred at RT for 16 h and then heated at 35° C. for 1 h. The crude product was partially purified by silica gel chromatography (15-20% EtOAc/isohexane) followed by trituration successively with 10% EtOAc/isohexane and then diethyl ether. The filtered solid was dissolved in EtOAc and washed twice with $NaHCO_3$, then successively with water and brine. The organic phase was dried over $MgSO_4$, filtered and the solvent removed in vacuo. The residue was further purified by silica gel chromatography (50% DCM/isohexane): m/z 477.8 $(M-H)^-$ $(ES^-)$. $^1H$ NMR (400 MHz, MeOD) δ: 8.22 (1H, d), 8.18 (1H, dd), 7.55 (2H, dt), 7.46-7.44 (2H, m), 7.41-7.36 (3H, m), 7.29 (1H, d), 5.37 (2H, s), 4.25 (2H, q), 1.46 (3H, t).

Step (vi): 4-(4-Ethoxy-3-(trifluoromethyl)benzamido)-2,6-difluorobenzoic acid (XXX-02)

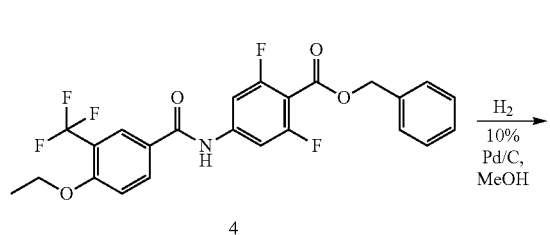

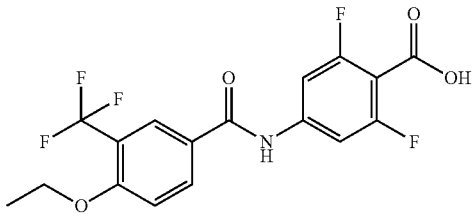

Benzyl 4-(4-ethoxy-3-(trifluoromethyl)benzamido)-2,6-difluorobenzoate (4) (25 mg, 52 µmol) was dissolved in methanol (10 mL) and was passed through a Thales 'H-cube' cartridge (10% Pd/C) at a flow rate of 1 mL/min at 25° C. under $H_2$ (10 bar). The solvent was removed in vacuo to afford 4-(4-ethoxy-3-(trifluoromethyl)benzamido)-2,6-difluorobenzoic acid (XXX-02) (20 mg, 97%) as a white solid: m/z 388.1 $(M-H)^-$ $(ES^-)$. $^1H$ NMR (400 MHz, MeOD) δ: 8.23 (1H, d), 8.19 (1H, dd), 7.53 (2H, dt), 7.30 (1H, d), 4.26 (2H, q), 1.46 (3H, t).

Synthesis 32 (Comparison Compound)

4-(3,5-Dichlorobenzamido)benzoic acid (XXX-03)

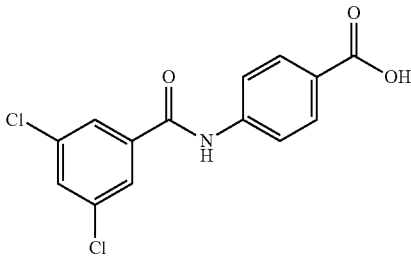 [SMILES: O=C(O)c1ccc(NC(=O)c2cc(Cl)cc(Cl)c2)cc1]

The title compound was obtained from commercial sources.

Synthesis 33

4-(4-(tert-Butoxy)-3,5-dichlorobenzamido)benzoic acid (AAA-031)

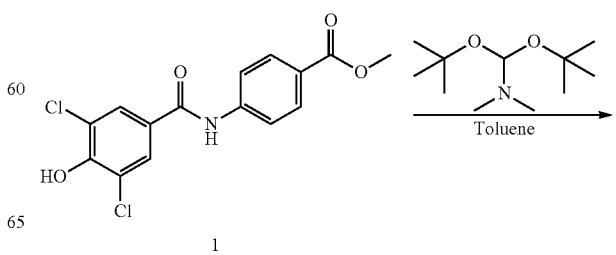

0-50% EtOAc in isohexane) to afford methyl 4-(4-(tert-butoxy)-3,5-dichlorobenzamido)benzoate (2) (82 mg, 71%). The material was used in the next step without further purification.

Step (ii): 4-(4-(tert-Butoxy)-3,5-dichlorobenzamido) benzoic acid (AAA-031)

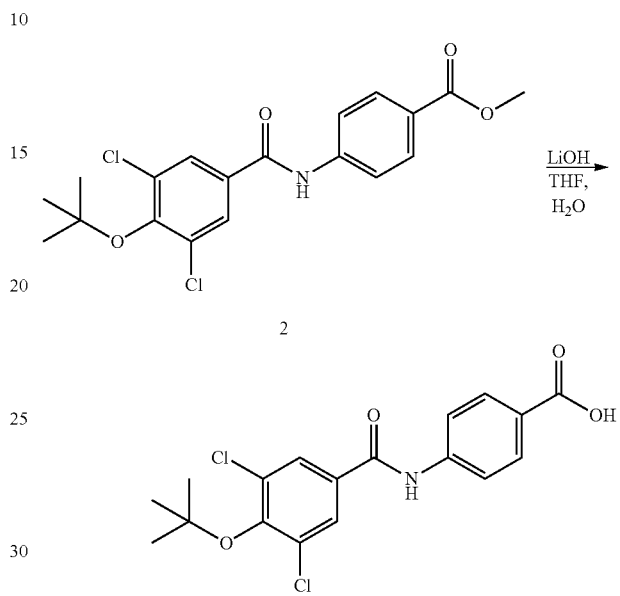

4-(4-(tert-Butoxy)-3,5-dichlorobenzamido)benzoic acid (AAA-031) (39 mg, 51%) was prepared from methyl 4-(4-(tert-butoxy)-3,5-dichlorobenzamido)benzoate (2) (82 mg, 294 µmol) using a procedure essentially the same as in step (ii) for AAA-001: m/z 380 [M–H]⁻ (ES⁻); ¹H NMR (400 MHz, DMSO-d$_6$) δ: 12.79 (1H, s), 10.60 (1H, s), 8.06 (2H, s), 7.94 (2H, d), 7.87 (2H, d), 1.49 (9H, s).

Synthesis 34

4-(3,5-Dichloro-4-isopropoxybenzamido-2-methyl-benzoic acid (AAA-032)

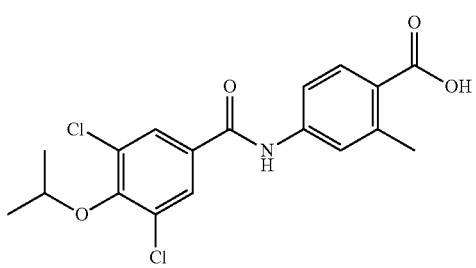

4-(3,5-Dichloro-4-isopropoxybenzamido-2-methylbenzoic acid (AAA-032) (30 mg, 41% for final step) was prepared in essentially the same manner as for (AAA-001) except that isopropyl bromide was used instead of cyclopentyl bromide in step (i) and methyl 4-amino-2-methylbenzoate was used instead of methyl 4-aminobenzoate in step (iii): m/z 383 (M+H)⁺ (ES⁺); ¹H NMR (400 MHz,

---

117

-continued

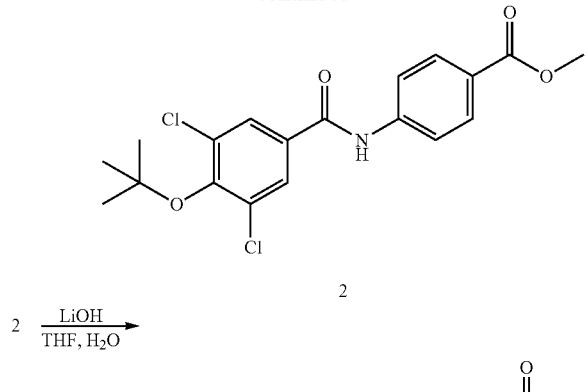

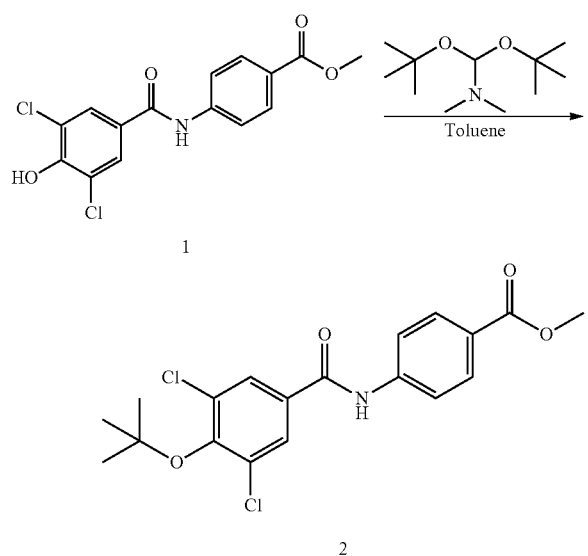

Step (i): Methyl 4-(4-(tert-butoxy)-3,5-dichloroben-zamido)benzoate (2)

A stirred suspension of methyl 4-(3,5-dichloro-4-hydroxybenzamido)benzoate (1) (Synthesis 9) (100 mg, 294 µmol) in toluene (2 mL) was heated at 80° C. until homogenous. The resultant solution was treated with 1,1-di-tert-butoxy-N,N-dimethylmethanamine (141 µL, 588 µmol) and the mixture heated at 80° C. for 3 h, and then at RT for 18 h. Additional 1,1-di-tert-butoxy-N,N-dimethylmethanamine (141 µL, 588 µmol) was added and mixture was heated at 80° C. for 5 h. The reaction mixture was cooled to RT and solvent was removed in vacuo. The residue was diluted with water and extracted with Et$_2$O. The organic layer was dried over MgSO$_4$, filtered and concentrated in vacuo. The residue was partially purified by silica gel chromatography (12 g, DMSO) 12.61 (1H, bs), 10.46 (1H, s), 8.07 (2H, s), 7.86 (1H, m), 7.69 (2H, m), 4.66 (1H, m), 2.53 (3H, s), 1.33 (6H, d).

Synthesis 35

4-(3,5-Dichloro-4-ethoxybenzamido)-2-(trifluoromethyl)benzoic acid (AAA-033)

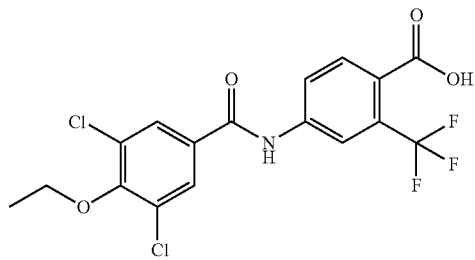 [SMILES: CCOc1c(Cl)cc(C(=O)Nc2ccc(C(=O)O)c(C(F)(F)F)c2)cc1Cl]

4-(3,5-Dichloro-4-ethoxybenzamido)-2-(trifluoromethyl)benzoic acid (AAA-033) (12 mg, 10% for final step) was prepared in essentially the same manner as for AAA-001 except that ethyl iodide was used instead of cyclopentyl bromide in step (i) and methyl 4-amino-2-(trifluoromethyl)benzoate (prepared from 4-amino-2-(trifluoromethyl)benzoic acid by reaction with MeOH and TMSCI) was used instead of methyl 4-aminobenzoate in step (iii): m/z 422 [M+H]$^+$ (ES$^+$); 420 [M–H]$^-$ (ES$^-$); $^1$H NMR (400 MHz, DMSO-d$_6$) δ: 10.77 (1H, s), 8.26 (1H, s), 8.14 (1H, d), 8.10 (2H, s), 7.88 (1H, d), 7.15 (1H, br s), 4.14 (2H, q), 1.40 (3H, t).

Synthesis 36

4-(3-Chloro-4-isopropoxy-5-(trifluoromethyl)benzamido)benzoic acid (AAA-034)

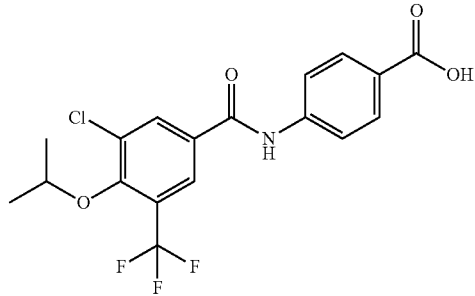 [SMILES: CC(C)Oc1c(Cl)cc(C(=O)Nc2ccc(C(=O)O)cc2)cc1C(F)(F)F]

4-(3-Chloro-4-isopropoxy-5-(trifluoromethyl)benzamido)benzoic acid (AAA-034) (35 mg, 38% for final step) was prepared in essentially the same manner as in steps (iii) and (iv) for AAA-001 except that 3-chloro-4-isopropoxy-5-(trifluoromethyl)benzoic acid (prepared in 3 steps from 4-hydroxy-3-(trifluoromethyl)benzoic acid by sequential treatment with sulfuryl chloride, isopropyl bromide and base and then lithium hydroxide) was used instead of 3,5-dichloro-4-(cyclopentyloxy)benzoic acid in step (iii): m/z 400 [M–H]$^-$ (ES$^-$); $^1$H NMR (400 MHz, DMSO-d$_6$) δ: 12.80 (1H, br s), 10.69 (1H, s), 8.39 (1H, d), 8.22 (1H, d), 7.94 (2H, m), 7.87 (2H, m), 5.06 (1H, m), 1.28 (6H, d).

Synthesis 37

4-(3-Chloro-4-methoxy-5-(trifluoromethyl)benzamido)benzoic acid (AAA-035)

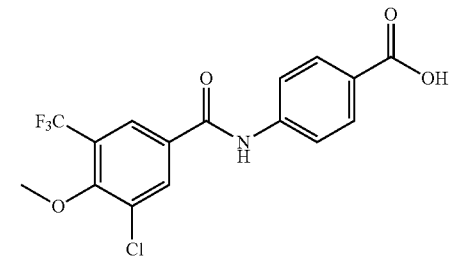 [SMILES: COc1c(Cl)cc(C(=O)Nc2ccc(C(=O)O)cc2)cc1C(F)(F)F]

4-(3-Chloro-4-methoxy-5-(trifluoromethyl)benzamido)benzoic acid (AAA-035) (5 mg, 73% for final step) was prepared in essentially the same manner as in steps (iii) and (iv) for AAA-001 except that 3-chloro-4-methoxy-5-trifluoromethylbenzoic acid (prepared in 3 steps from 4-hydroxy-3-(trifluoromethyl)benzoic acid by sequential treatment with sulfuryl chloride, methyl iodide and base and then lithium hydroxide) was used instead of 3,5-dichloro-4-(cyclopentyloxy)benzoic acid in step (iii): m/z 374 [M+H]$^+$ (ES$^+$), 372 [M–H]$^-$ (ES$^-$); $^1$H-NMR (400 MHz, DMSO-d$_6$) δ: 12.79 (1H, bs), 10.70 (1H, s), 8.44 (1H, d), 8.23 (1H, d), 7.96 (2H, d), 7.88 (2H, d), 3.98 (3H, s).

Synthesis 38

4-(3-Chloro-4-cyclobutoxy-5-(trifluoromethyl)benzamido)benzoic acid (AAA-036)

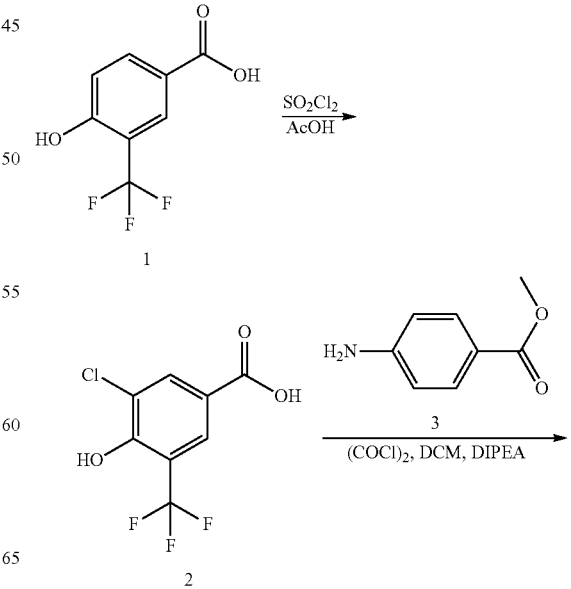

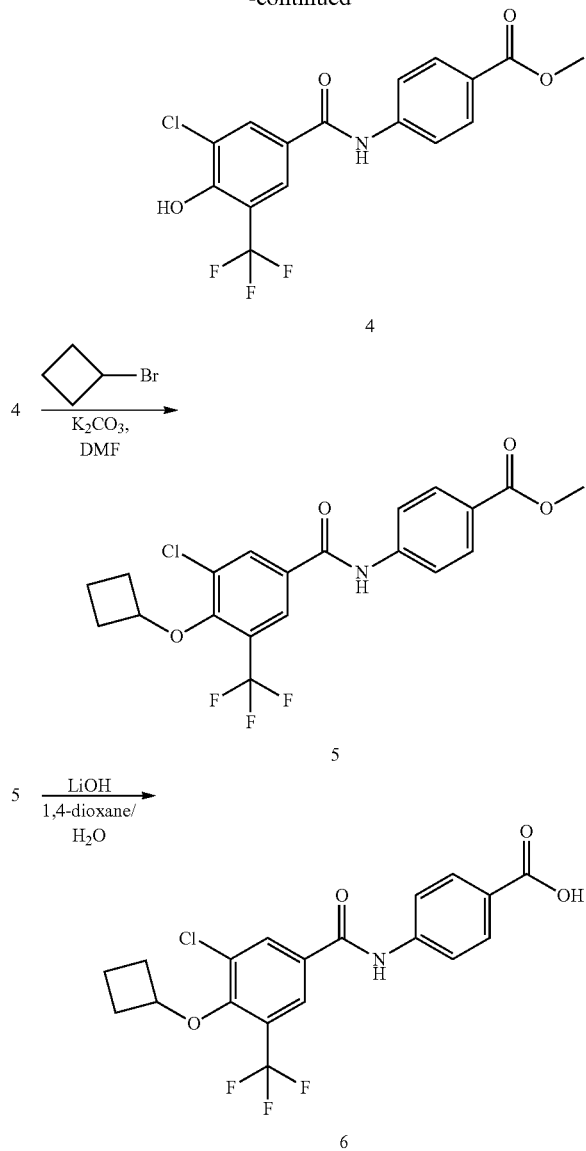
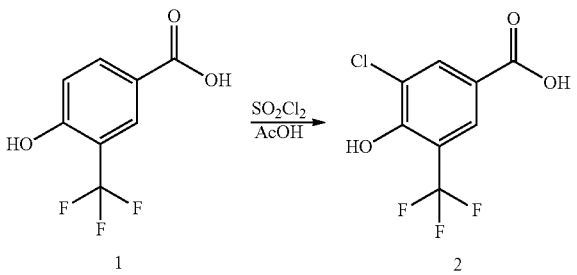

Step (i) 3-Chloro-4-hydroxy-5-(trifluoromethyl)benzoic acid (2)

4-Hydroxy-3-(trifluoromethyl)benzoic acid (1) (2.00 g, 9.70 mmol) was dissolved in AcOH (40 mL) and treated with sulfuryl chloride (2.37 mL, 29.1 mmol). The mixture was stirred at 60° C. for 20 h. The reaction mixture was allowed to cool to RT and then poured into water (100 mL). The product was extracted with EtOAc (75 mL) and the organic solution was washed with water (2×75 mL) and brine (75 mL), then dried over MgSO$_4$ and filtered. The solvent was removed in vacuo and the residue was purified by silica gel chromatography (120 g, 0-100% EtOAc/isohexane) to afford 3-chloro-4-hydroxy-5-(trifluoromethyl) benzoic acid (2) (1.87 g, 80%) as a white solid: m/z 241 [M+H]$^+$ (ES$^+$), 239 [M−H]$^−$ (ES$^−$).

Step (ii): Methyl 4-(3-chloro-4-hydroxy-5-(trifluoromethyl)benzamido)benzoate (4)

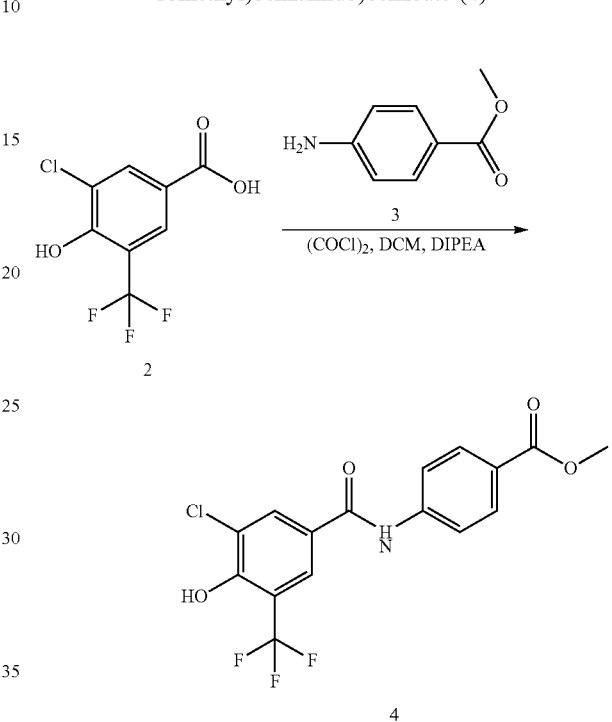

Methyl 4-(3-chloro-4-hydroxy-5-(trifluoromethyl)benzamido)benzoate (4) (178 mg, 22%) was prepared in essentially the same manner as in step (iii) for AAA-001 except that 3-chloro-4-hydroxy-5-trifluoromethylbenzoic acid was used instead of 3,5-dichloro-4-(cyclopentyloxy)benzoic acid: m/z 374 [M+H]$^+$ (ES$^+$); $^1$H NMR (400 MHz, DMSO-d$_6$) δ: 11.43 (1H, br s), 10.50 (1H, s), 8.33 (1H, d), 8.16 (1H, d), 7.97 (2H, m), 7.91 (2H, m), 3.84 (3H, s).

Step (iii): Methyl 4-(3-chloro-4-cyclobutoxy-5-(trifluoromethyl)benzamido)benzoate (5)

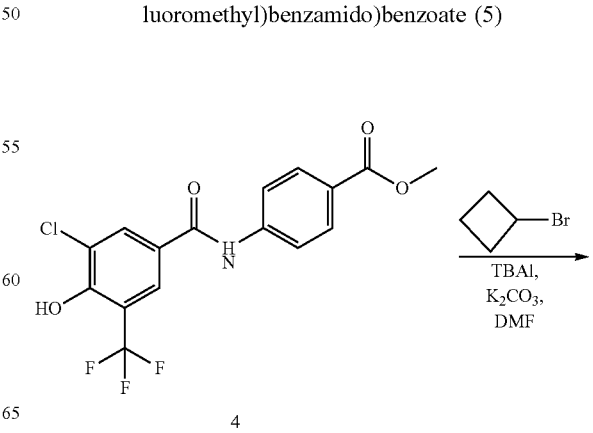

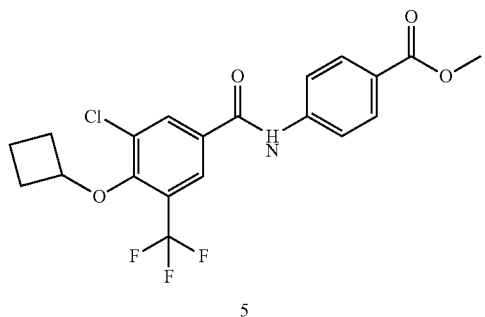

5

Methyl 4-(3-chloro-4-cyclobutoxy-5-(trifluoromethyl)benzamido)benzoate (5) (105 mg, 51%) was prepared in essentially the same manner as in steps (i) for AAA-001 except that cyclobutyl bromide and tetrabutylammonium iodide were used instead of cyclopentylbromide and that the reaction was carried out at 90° C.: m/z 428 [M+H]$^+$ (ES$^+$); $^1$H NMR (400 MHz, DMSO-d$_6$) δ: 10.72 (1H, s), 8.40 (1H, d), 8.20 (1H, d), 7.90 (2H, m), 7.97 (2H, m) 4.72 (1H, m), 3.84 (3H, s), 2.36 (2H, m), 2.27 (2H, m), 1.69 (1H, m), 1.44 (1H, m).

Step (iv): 4-(3-Chloro-4-cyclobutoxy-5-(trifluoromethyl)benzamido)benzoic acid (AAA-036)

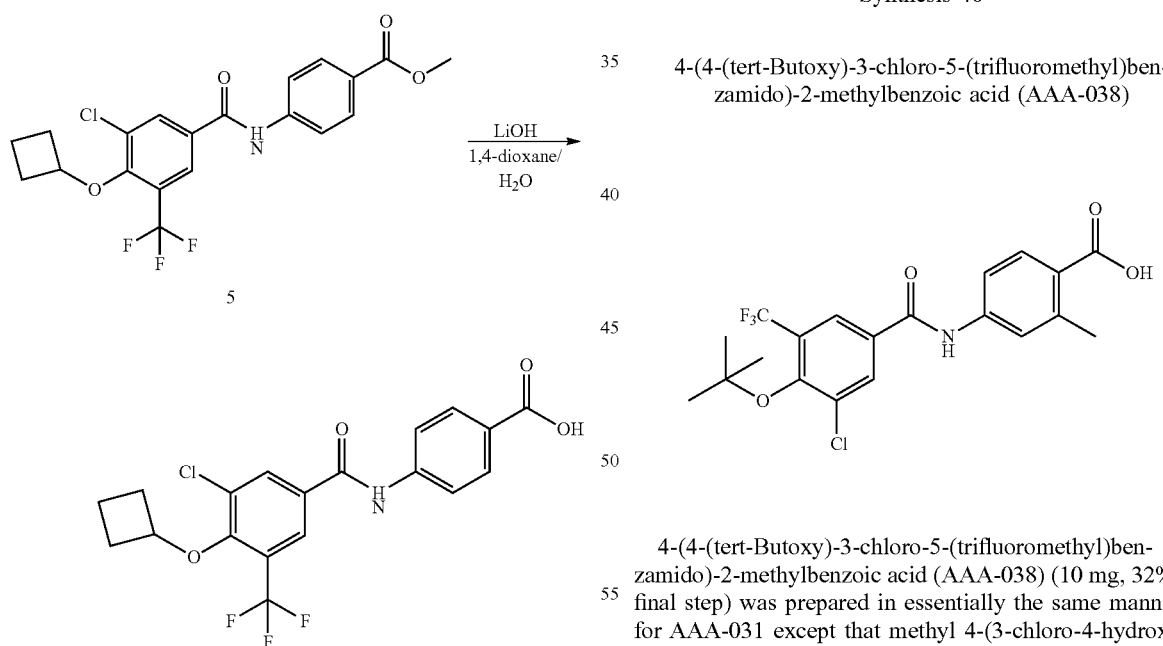

4-(3-Chloro-4-cyclobutoxy-5-(trifluoromethyl)benzamido)benzoic acid (96 mg, 91%) was prepared in essentially the same manner as in step (ii) for AAA-001 except that 1,4-dioxane was used instead of THF: m/z 412 [M−H]$^−$ (ES$^−$); $^1$H NMR (400 MHz, DMSO-d$_6$) δ: 12.81 (1H, br s), 10.70 (1H, s), 8.41 (1H, d), 8.20 (1H, d), 7.95 (2H, m), 7.88 (2H, m), 4.73 (1H, m), 2.36 (2H, m), 2.27 (2H, m), 1.69 (1H, m), 1.44 (1H, m).

Synthesis 39

4-(4-(tert-Butoxy)-3-chloro-5-(trifluoromethyl)benzamido)benzoic acid (AAA-037)

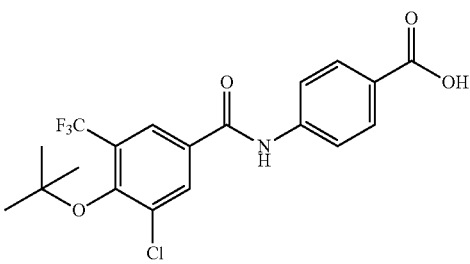 [SMILES: CC(C)(C)Oc1c(Cl)cc(C(=O)Nc2ccc(C(=O)O)cc2)cc1C(F)(F)F]

4-(4-(tert-Butoxy)-3-chloro-5-(trifluoromethyl)benzamido)benzoic acid (AAA-037) (27 mg, 39% for final step) was prepared in essentially the same manner as for AAA-031 except that methyl-4-(3-chloro-4-hydroxy-5-(trifluoromethyl)benzamido)benzoate (Synthesis 38 steps (i) and (ii)) was used instead of methyl 4-(3,5-dichloro-4-hydroxybenzamido)benzoate in step (i): m/z 416 [M+H]$^+$ (ES$^+$), 414 [M−H]$^−$ (ES$^−$); $^1$H-NMR (400 MHz, DMSO-d$_6$) δ: 12.77 (1H, s), 10.69 (1H, s), 8.40 (1H, d), 8.21 (1H, d), 7.95 (2H, m), 7.88 (2H, m), 1.48 (9H, s).

Synthesis 40

4-(4-(tert-Butoxy)-3-chloro-5-(trifluoromethyl)benzamido)-2-methylbenzoic acid (AAA-038)

4-(4-(tert-Butoxy)-3-chloro-5-(trifluoromethyl)benzamido)-2-methylbenzoic acid (AAA-038) (10 mg, 32% for final step) was prepared in essentially the same manner as for AAA-031 except that methyl 4-(3-chloro-4-hydroxy-5-(trifluoromethyl)benzamido)-2-methylbenzoate was used instead of methyl 4-(3,5-dichloro-4-hydroxybenzamido)benzoate in step (i). Methyl 4-(3-chloro-4-hydroxy-5-(trifluoromethyl)benzamido)-2-methylbenzoate was prepared essentially as in synthesis 38 steps (i) and (ii) except that and methyl 4-amino-2-methylbenzoate was used instead of methyl 4-aminobenzoate in step (ii): m/z 430 [M+H]$^+$ (ES$^+$), 428 [M−H]$^−$ (ES$^−$); $^1$H-NMR (400 MHz, d$_4$-MeOH) δ: 8.30 (1H, d), 8.20 (1H, d), 7.95 (1H, d), 7.68-7.65 (2H, m), 2.60 (3H, s), 1.54 (9H, s).

Synthesis 41

4-(3-Chloro-4-ethoxy-5-(trifluoromethyl)benzamido)-2-methylbenzoic acid (AAA-039)

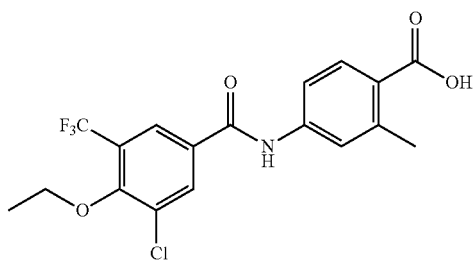

4-(3-Chloro-4-ethoxy-5-(trifluoromethyl)benzamido)-2-methylbenzoic acid (AAA-039) (36 mg, 53% for final step) was prepared in essentially the same manner as for AAA-019 except that 3-chloro-4-ethoxy-5-trifluoromethylbenzoic acid was used instead of 3,5-dichloro-4-ethoxybenzoic acid in step (i) and 1,4-dioxane (5 mL) was used instead of THF in step (ii): m/z 402 [M+H]$^+$ (ES$^+$), 400 [M−H]$^−$ (ES$^−$); $^1$H-NMR (400 MHz, DMSO-d$_6$) δ: 12.65 (1H, br s), 10.59 (1H, s), 8.42 (1H, d), 8.23 (1H, d), 7.88 (1H, d), 7.74-7.68 (2H, m), 4.20 (2H, q), 2.55 (3H, s), 1.42 (3H, t).

Synthesis 42

4-(3-Chloro-4-isopropoxy-5-(trifluoromethyl)benzamido)-2-methylbenzoic acid (AAA-040)

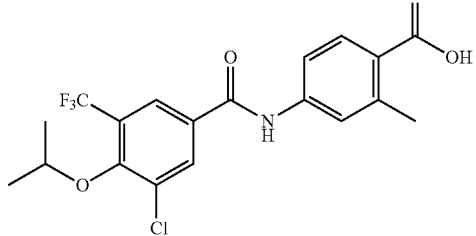

4-(3-Chloro-4-isopropoxy-5-(triuoromethyl)benzamido)-2-methylbenzoic acid (AAA-040) (36 mg, 65% for final step) was prepared in essentially the same manner as for AAA-019 except that 3-chloro-4-isopropoxy-5-trifluoromethylbenzoic acid was used instead of 3,5-dichloro-4-ethoxybenzoic acid in step (i) and 1,4-dioxane (5 mL) was used instead of THF in step (ii): m/z 416 [M+H]$^+$ (ES$^+$), 414 [M−H]$^−$ (ES$^−$); $^1$H-NMR (400 MHz, DMSO-d$_6$) δ: 12.57 (1H, br s), 10.56 (1H, s), 8.39 (1H, d), 8.22 (1H, d), 7.88 (1H, d), 7.73-7.67 (2H, m), 5.06 (2H, sep), 2.54 (3H, s), 1.29 (6H, d).

Synthesis 43

4-(3-Chloro-4-methoxy-5-(trifluoromethyl)benzamido)-2-methylbenzoic acid (AAA-041)

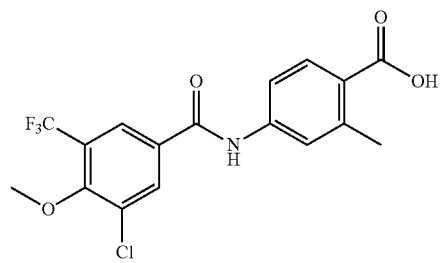 [SMILES: COc1c(Cl)cc(C(=O)Nc2ccc(C(=O)O)c(C)c2)cc1C(F)(F)F]

4-(3-Chloro-4-methoxy-5-(trifluoromethyl)benzamido)-2-methylbenzoic acid (AAA-041) (28 mg, 57% for final step) was prepared in essentially the same manner as for AAA-019 except that 3-chloro-4-methoxy-5-trifluoromethylbenzoic acid was used instead of 3,5-dichloro-4-ethoxybenzoic acid in step (i) and 1,4-dioxane (2.5 mL) was used instead of THF in step (ii): m/z 388 [M+H]$^+$ (ES$^+$), 386 [M−H]$^−$ (ES$^−$); $^1$H-NMR (400 MHz, DMSO-d$_6$) δ: 12.62 (1H, br s), 10.59 (1H, s), 8.43 (1H, d), 8.23 (1H, d), 7.88 (1H, d), 7.73-7.67 (2H, m), 3.97 (3H, s), 2.54 (3H, s).

Synthesis 44

4-(3-Bromo-4-ethoxy-5-(trifluoromethyl)benzamido)benzoic acid (AAA-042)

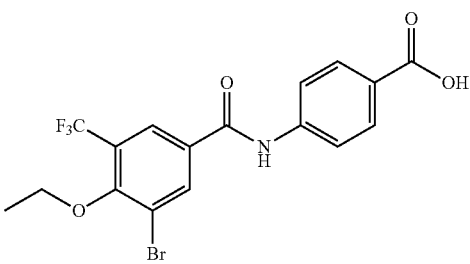

4-(3-Bromo-4-ethoxy-5-(trifluoromethyl)benzamido)benzoic acid (AAA-042) (35 mg, 60% for final step) was prepared in essentially the same manner as for AAA-019 except that 3-bromo-4-ethoxy-5-trifluoromethylbenzoic acid (prepared in 3 steps from 4-hydroxy-3-(trifluoromethyl)benzoic acid by sequential treatment with bromine in acetic acid, ethyl iodide and base and then lithium hydroxide) was used instead of 3,5-dichloro-4-ethoxybenzoic acid and methyl 4-aminobenzoate was used instead of methyl 4-amino-2-methylbenzoate in step (i) and 1,4-dioxane (2.5 mL) was used instead of THF in step (ii): m/z 434 [M+H]$^+$ (ES$^+$), 432 [M−H]$^−$ (ES$^−$); $^1$H-NMR (400 MHz, DMSO-d$_6$) δ: 12.81 (1H, br s), 10.71 (1H, s), 8.56 (1H, d), 8.26 (1H, d), 7.96 (2H, d), 7.88 (2H, d), 4.18 (2H, q), 1.43 (3H, t).

Synthesis 45

4-(3-Chloro-4-(cyclopentyloxy)-5-(trifluoromethyl)benzamido)benzoic acid (AAA-043)

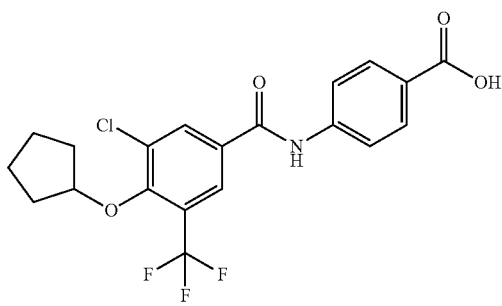 [SMILES: O=C(O)c1ccc(NC(=O)c2cc(Cl)c(OC3CCCC3)c(C(F)(F)F)c2)cc1]

4-(3-Chloro-4-(cyclopentyloxy)-5-(trifluoromethyl)benzamido)benzoic acid (AAA-043) (20 mg, 26% for final step) was prepared in essentially the same manner as for AAA-036 except that cyclopentyl iodide was used instead of cyclobutyl iodide in step (iii): m/z 426 [M–H]⁻ (ES⁻); $^1$H NMR (400 MHz, DMSO-$d_6$) δ: 12.71 (1H, br s), 10.69 (1H, s), 8.40 (1H, d), 8.22 (1H, d), 7.96 (2H, m), 7.88 (2H, m), 5.27 (1H, q), 1.86 (4H, m), 1.75 (2H, m), 1.59 (2H, m).

Synthesis 46

4-(3-Chloro-4,5-bis(cyclopentyloxy)benzamido)benzoic acid (AAA-044)

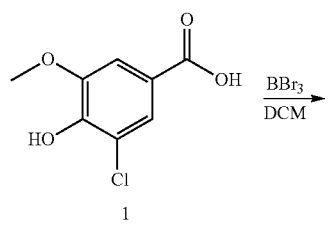

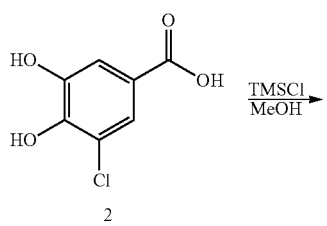

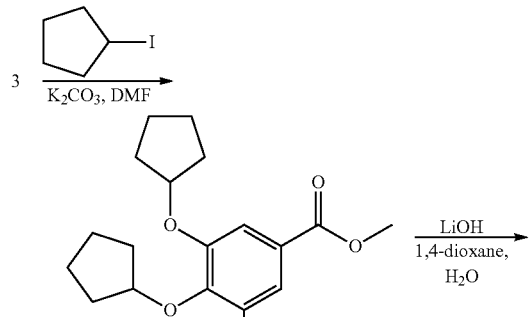

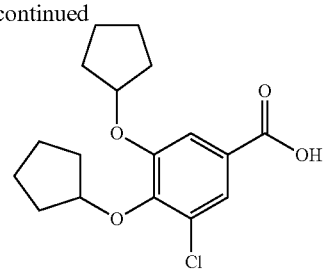

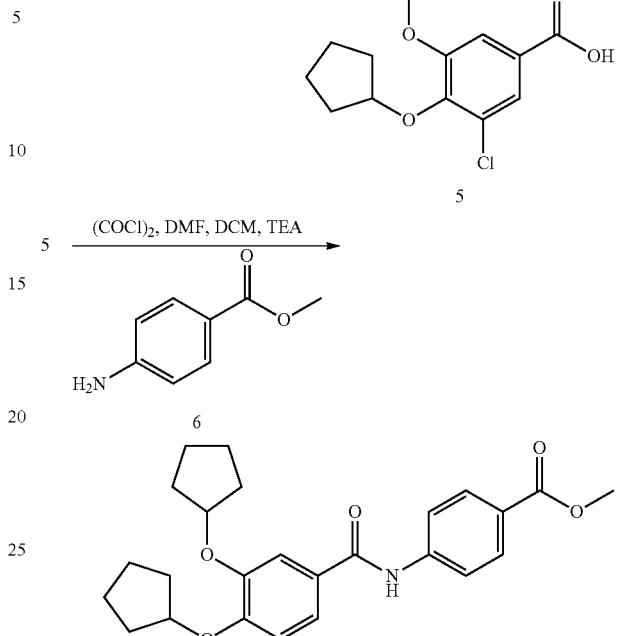

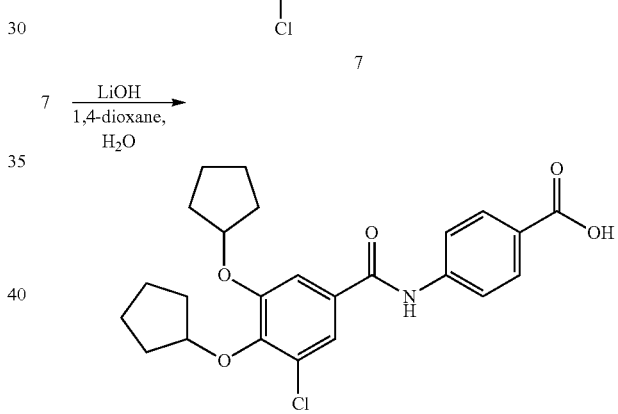

Step (i): 3-Chloro-4,5-dihydroxybenzoic acid (2)

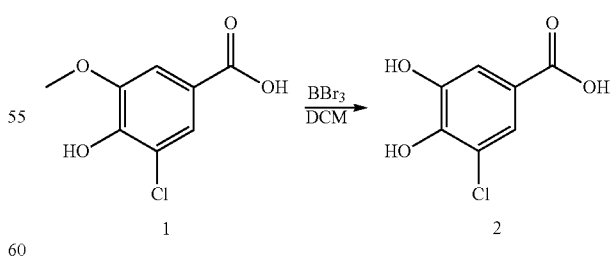

Tribromoborane (7.86 mL, 82 mmol) was added dropwise to a stirring mixture of 3-chloro-4-hydroxy-5-methoxybenzoic acid (1) (6.61 g, 32.6 mmol) in DCM (50 mL) under nitrogen at 0° C. The resulting orange mixture was stirred at the same temperature for 2 h then poured portionwise onto ice/brine (250 mL). The aqueous phase was extracted with EtOAc (2×150 mL) and the combined organic extracts were dried over MgSO$_4$ and filtered. The solvent was removed in vacuo to give 3-chloro-4,5-dihydroxybenzoic acid (2) (5.11 g, 79%): m/z 187 [M−H]$^-$ (ES$^-$); $^1$H NMR (400 MHz, DMSO-d$_6$) δ: 12.69 (1H, br s), 10.14 (2H, br s), 7.35 (1H, d), 7.32 (1H, d).

Step (ii): Methyl 3-chloro-4,5-dihydroxybenzoate (3)

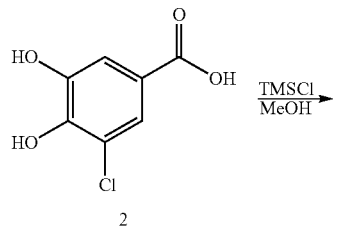

A solution of 3-chloro-4,5-dihydroxybenzoic acid (2) (3.16 g, 16.76 mmol) and chlorotrimethylsilane (6.36 mL, 50.3 mmol) in MeOH (50 mL) was stirred at 50° C., under nitrogen overnight. The solvent was removed in vacuo and the residue was partitioned between brine (75 mL) and EtOAc (75 mL). The organic layer was washed with brine (75 mL), dried over MgSO$_4$ and filtered. The solvent was removed in vacuo to give methyl 3-chloro-4,5-dihydroxybenzoate (3) (3.26 g, 13.68 mmol, 82% yield): m/z 201 [M−H]$^-$ (ES$^-$); $^1$H NMR (400 MHz, DMSO-d$_6$) δ: 10.17 (2H, br s), 7.38 (1H, d), 7.35 (1H, d), 3.78 (3H, s).

Step (iii): Methyl 3-chloro-4,5-bis(cyclopentyloxy)benzoate (4)

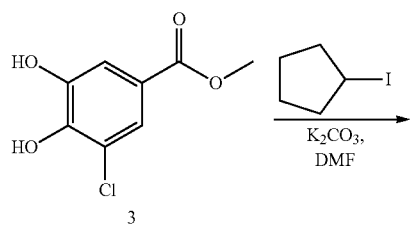

A mixture of methyl 3-chloro-4,5-dihydroxybenzoate (3) (300 mg, 1.48 mmol), iodocyclopentane (558 µL, 4.44 mmol) and potassium carbonate (614 mg, 4.44 mmol) in DMF (10 mL) was stirred at 70° C. for 46 h. The reaction mixture was cooled to room temperature and then partitioned between 1M HCl (75 mL) and EtOAc (100 mL). The phases were separated and the organic phase was washed with brine (2×75 mL) then dried over MgSO$_4$ and filtered. The solvent was removed in vacuo and the residue was purified by silica gel chromatography (40 g, 0-100% EtOAc in isohexane) to give methyl 3-chloro-4,5-bis(cyclopentyloxy)benzoate (4) (427 mg, 1.26 mmol, 85% yield): m/z 339 [M+H]$^+$ (ES$^+$); $^1$H NMR (400 MHz, CDCl$_3$) δ: 7.66 (1H, d), 7.45 (1H, d), 5.05-4.98 (1H, m), 4.87-4.83 (1H, m), 3.89 (3H, s), 1.95-1.55 (16H, m).

Step (iv): 3-Chloro-4,5-bis(cyclopentyloxy)benzoic acid (5)

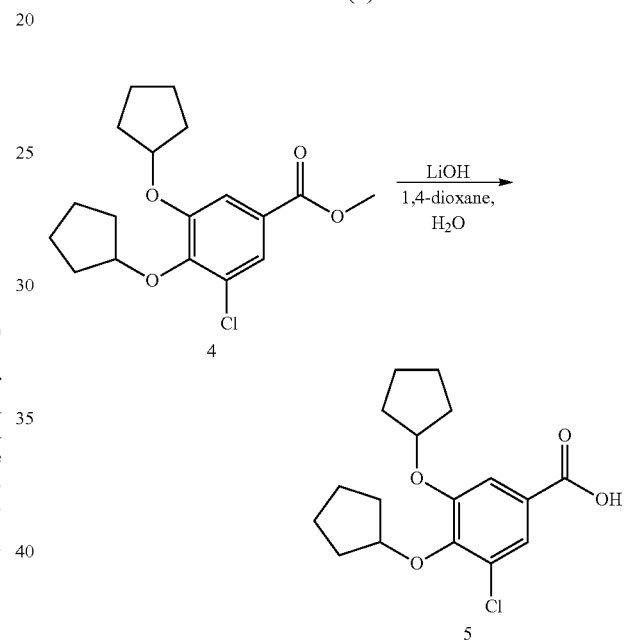

3-Chloro-4,5-bis(cyclopentyloxy)benzoic acid (5) (380 mg, 99%) was prepared from methyl 3-chloro-4,5-bis(cyclopentyloxy)benzoate (4) (400 mg, 1.18 mmol) using a procedure essentially the same as in Step (ii) for AAA-001, except that 1,4-dioxane (10 mL) was used instead of THF: m/z 323 [M−H]$^-$ (ES$^-$); $^1$H NMR (400 MHz, DMSO-d$_6$) δ: 13.07 (1H, br s), 7.52 (1H, d), 7.45 (1H, d), 4.97-4.91 (2H, m), 1.99-1.90 (2H, m), 1.70-1.57 (14H, m).

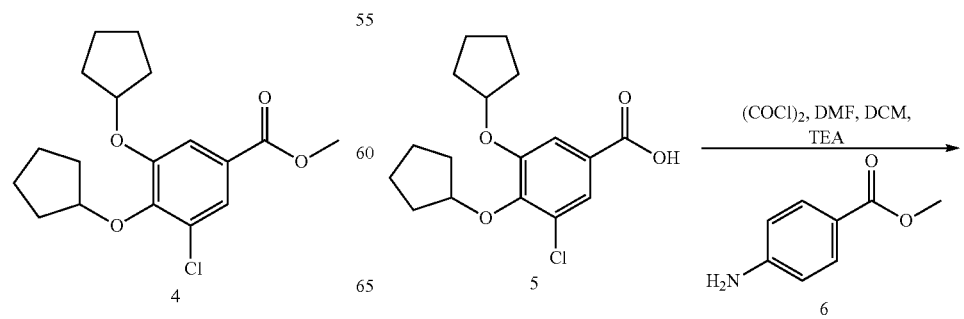

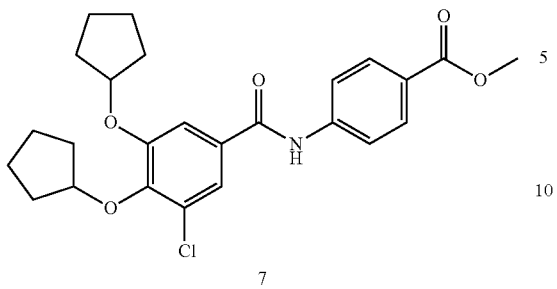

Step (v): Methyl 4-(3-chloro-4,5-bis(cyclopentyloxy)benzamido)benzoate (7)

Methyl 4-(3-chloro-4,5-bis(cyclopentyloxy)benzamido) benzoate (7) (155 mg, 49%) was prepared from 3-chloro-4,5-bis(cyclopentyloxy)benzoic acid (5) (200 mg, 0.616 mmol) using a procedure essentially the same as in Step (iii) for AAA-001: m/z 458 [M+H]$^+$ (ES$^+$), 456 [M−H]$^-$ (ES$^-$); $^1$H NMR (400 MHz, CDCl$_3$) δ: 8.06 (2H, d), 7.84 (1H, br s), 7.71 (2H, d), 7.38 (2H, d), 5.02 (1H, m), 4.88 (1H, m), 3.92 (3H, s), 1.95-1.63 (16H, m).

Step (vi): 4-(3-Chloro-4,5-bis(cyclopentyloxy)benzamido)benzoic acid (AAA-044)

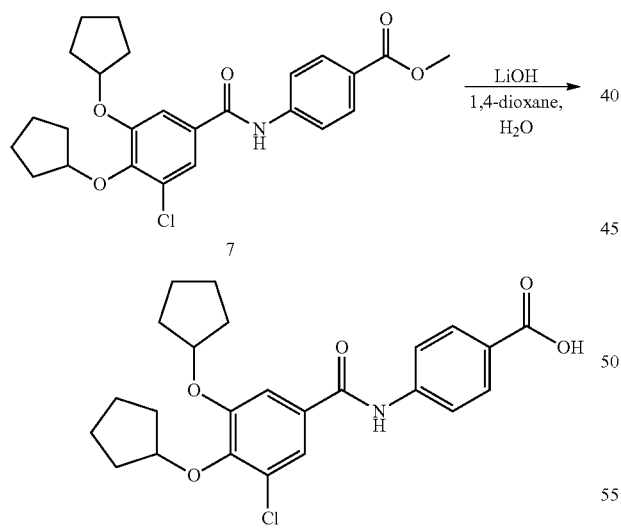

4-(3-Chloro-4,5-bis(cyclopentyloxy)benzamido)benzoic acid (AAA-044) (55 mg, 72%) was prepared from methyl 4-(3-chloro-4,5-bis(cyclopentyloxy)benzamido)benzoate (7) (75 mg, 0.16 mmol) using a procedure essentially the same as in Step (ii) for AAA-001, except that 1,4-dioxane (2.5 mL) was used instead of THF: m/z 442 [M−H]$^-$ (ES$^-$); $^1$H NMR (400 MHz, DMSO-d$_6$) δ: 12.74 (1H, br s), 10.45 (1H, s), 7.94 (2H, d), 7.88 (2H, d), 7.69 (1H, d), 7.52 (1H, d), 4.97 (2H, m), 1.99-1.93 (2H, m), 1.73-1.48 (14H, m).

Synthesis 47

4-(3,4-bis(benzyloxy)-5-chlorobenzamido)benzoic acid (AAA-045)

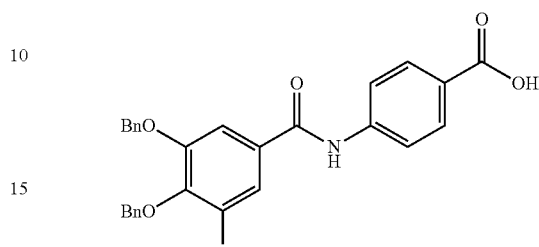

4-(3,4-bis(Benzyloxy)-5-chlorobenzamido)benzoic acid (AAA-045) (48 mg, 96% for final step) was prepared in essentially the same manner as for AAA-044 except that benzyl bromide was used instead of cyclopentyl iodide in step (iii) and stirring was carried out at 40° C. in step (v): m/z 486 [M−H]$^-$ (ES$^-$); $^1$H NMR (400 MHz, DMSO-d$_6$) δ: 12.76 (1H, br s), 10.51 (1H, s), 7.95 (2H, m), 7.89 (2H, m), 7.74 (2H, d), 7.52 (2H, d), 7.44-7.32 (8H, m), 5.31 (2H, s), 5.11 (2H, s).

Synthesis 48

4-(3-Chloro-4,5-bis(cyclopentyloxy)benzamido)-2-methylbenzoic acid (AAA-046)

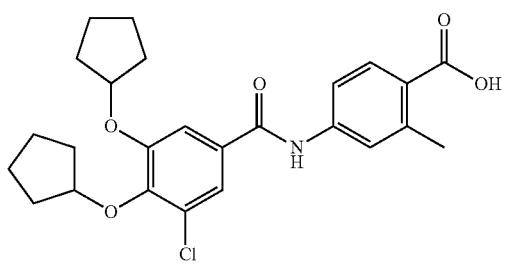 [SMILES: Cc1cc(NC(=O)c2cc(Cl)c(OC3CCCC3)c(OC3CCCC3)c2)ccc1C(=O)O]

4-(3-Chloro-4,5-bis(cyclopentyloxy)benzamido)-2-methylbenzoic acid (AAA-046) (65 mg, 85% for final step) was prepared in essentially the same manner as for AAA-044 except that methyl 4-amino-2-methylbenzoate (prepared from 4-amino-2-methylbenzoic acid by reaction with methanol and chlorotrimethylsilane) was used instead of methyl 4-aminobenzoate in Step (v): m/z 456 [M−H]$^-$ (ES$^-$); $^1$H NMR (400 MHz, DMSO-d$_6$) δ: 12.63 (1H, br s), 10.33 (1H, s), 7.86 (1H, d), 7.72-7.68 (3H, m), 7.52 (1H, d), 4.98 (2H, m), 2.54 (3H, s), 1.99-1.91 (2H, m), 1.78-1.58 (14H, m).

Synthesis 49
4-(3-Chloro-4,5-bis(cyclohexyloxy)benzamido)benzoic acid (AAA-047)
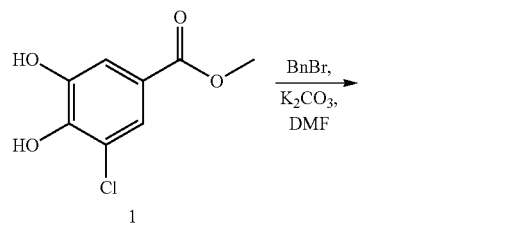
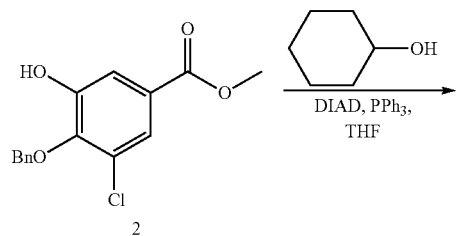
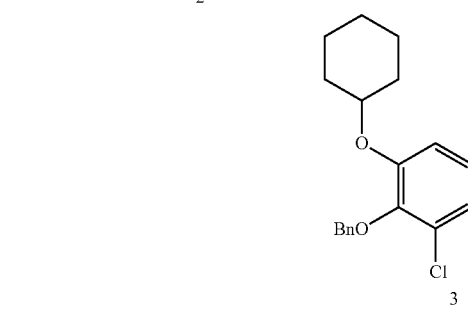
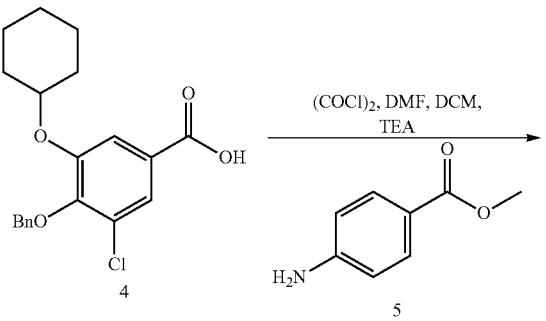
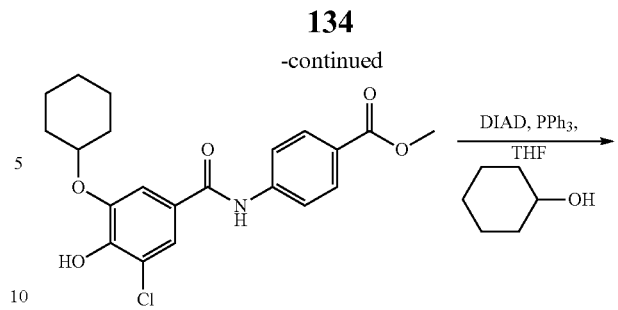
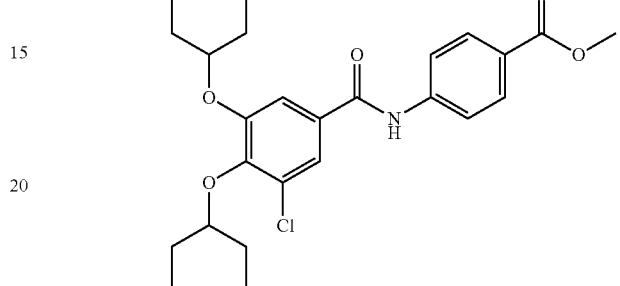
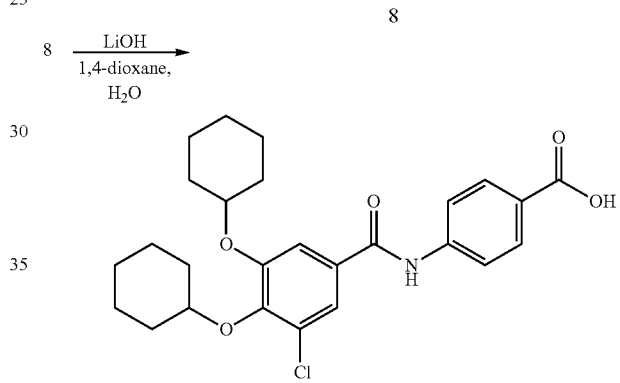
Step (i): Methyl 4-(benzyloxy)-3-chloro-5-hydroxybenzoate (2)
(Bromomethyl)benzene (1.41 mL, 11.9 mmol) was added dropwise to a stirring suspension of methyl 3-chloro-4,5- dihydroxybenzoate (1) (product step ii, Synthesis 46 (2.00 g, 9.87 mmol) and potassium carbonate (1.50 g, 10.9 mmol) in DMF (10 mL) at 5-10° C. The resulting mixture was stirred for 2 h at RT and then partitioned between 1M HCl (50 mL) and EtOAc (50 mL). The phases were separated and the organic solution was washed with water (2×40 mL), dried over MgSO$_4$ and filtered. The solvent was removed in vacuo and residue was purified by silica gel chromatography (80 g, 0-50% EtOAc in iso-hexanes) to give methyl 4-(benzyloxy)-3-chloro-5-hydroxybenzoate (2) (1.66 g, 54% yield): m/z 291 [M–H]$^-$ (ES$^-$); $^1$H NMR (400 MHz, DMSO-d$_6$) δ: 10.50 (1H, s), 7.49 (2H, m), 7.46 (1H, d), 7.40-7.33 (4H, m), 5.14 (2H, s), 3.82 (3H, s).

Step (ii): Methyl 4-(benzyloxy)-3-chloro-5-(cyclohexyloxy)benzoate (2)

Step (iii): 4-(Benzyloxy)-3-chloro-5-(cyclohexyloxy)benzoic acid (4)

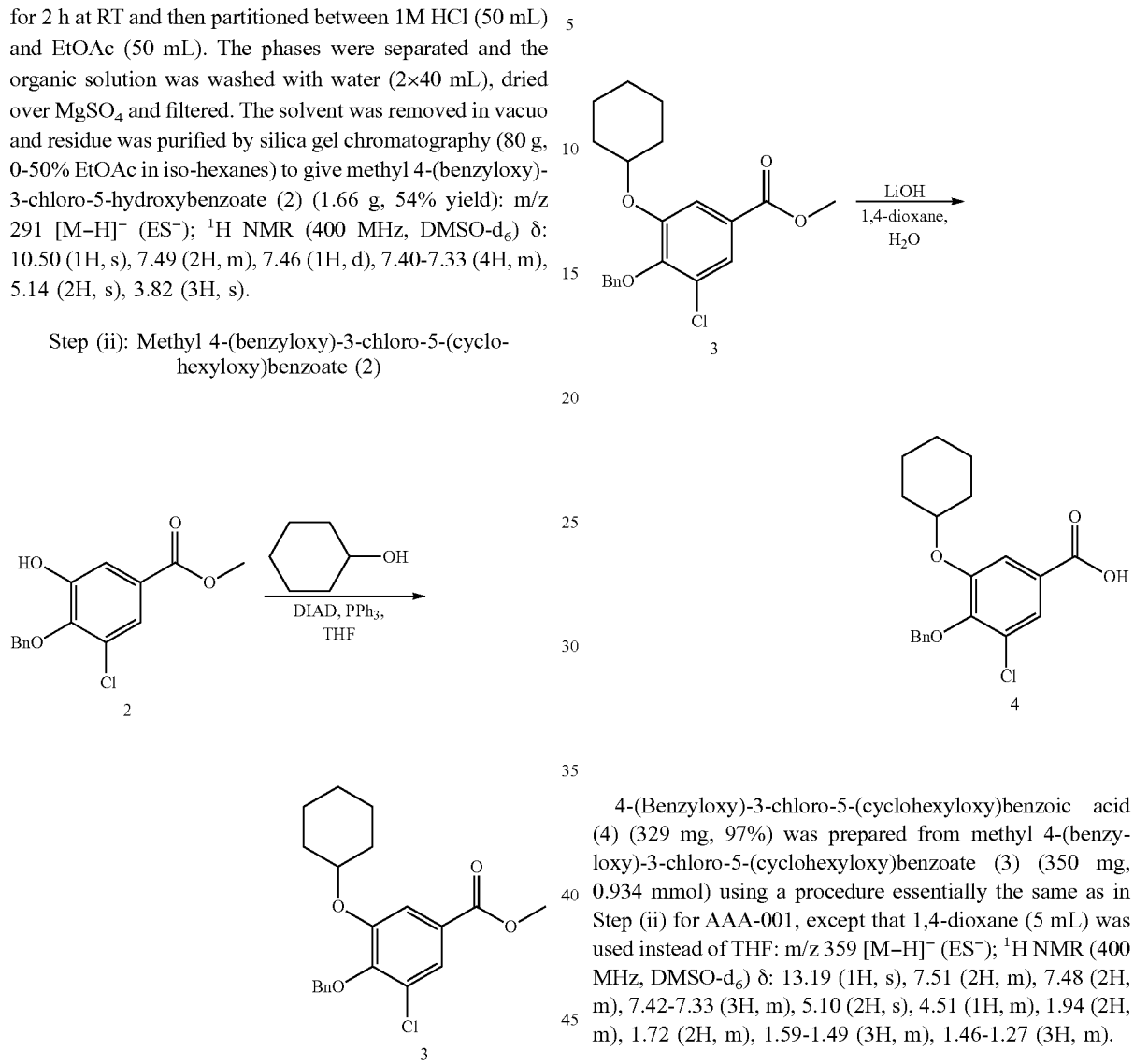

4-(Benzyloxy)-3-chloro-5-(cyclohexyloxy)benzoic acid (4) (329 mg, 97%) was prepared from methyl 4-(benzyloxy)-3-chloro-5-(cyclohexyloxy)benzoate (3) (350 mg, 0.934 mmol) using a procedure essentially the same as in Step (ii) for AAA-001, except that 1,4-dioxane (5 mL) was used instead of THF: m/z 359 [M–H]$^-$ (ES$^-$); $^1$H NMR (400 MHz, DMSO-d$_6$) δ: 13.19 (1H, s), 7.51 (2H, m), 7.48 (2H, m), 7.42-7.33 (3H, m), 5.10 (2H, s), 4.51 (1H, m), 1.94 (2H, m), 1.72 (2H, m), 1.59-1.49 (3H, m), 1.46-1.27 (3H, m).

Diisopropylazo dicarboxylate (807 µL, 4.10 mmol) was added dropwise to a stirring mixture of methyl 4-(benzyloxy)-3-chloro-5-hydroxybenzoate (2) (300 mg, 1.03 mmol), cyclohexanol (434 µL, 4.10 mmol) and triphenylphosphine (1.08 g, 4.10 mmol) in THF (5 mL) and the mixture was stirred at RT for 20 h. The reaction was quenched with MeOH (10 mL) and the solvent was removed in vacuo. The residue was purified by silica gel chromatography (80 g, 0-20% EtOAc in iso-hexane) to afford methyl 4-(benzyloxy)-3-chloro-5-(cyclohexyloxy)benzoate (2) (350 mg, 9%): $^1$H NMR (400 MHz, CDCl$_3$) δ: 7.66 (1H, d), 7.51 (3H, m), 7.38-7.33 (3H, m), 5.14 (2H, s), 4.38 (1H, m) 3.90 (3H, s) 2.01 (2H, m), 1.80 (2H, m), 1.62-1.50 (3H, m), 1.45-1.35 (3H, m).

Step (iv): Methyl 4-(4-(benzyloxy)-3-chloro-5-(cyclohexyloxy)benzamido)benzoate (6)

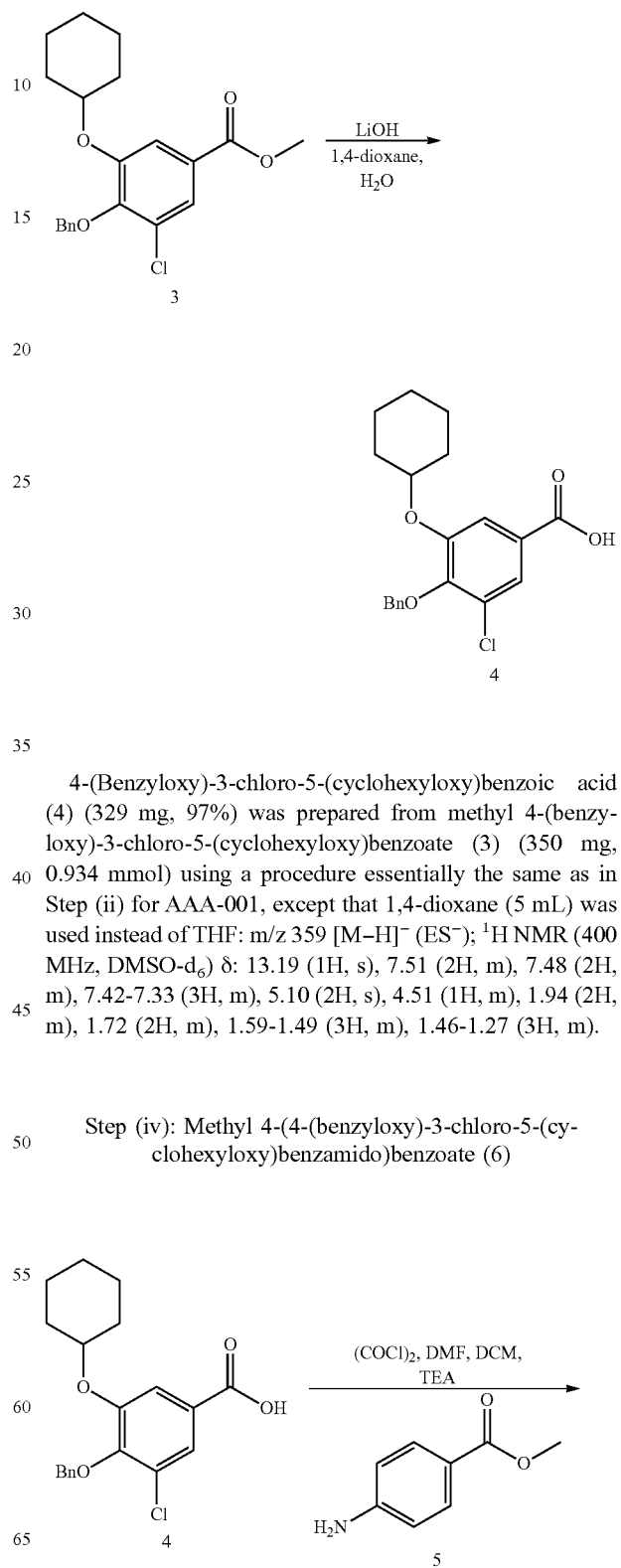

-continued

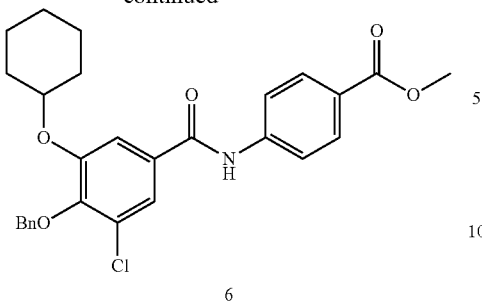

6

Methyl 4-(4-(benzyloxy)-3-chloro-5-(cyclohexyloxy)benzamido)benzoate (6) (323 mg, 70%) was prepared from 4-(benzyloxy)-3-chloro-5-(cyclohexyloxy)benzoic acid (4) (325 mg, 0.901 mmol) using a procedure essentially the same as in Step (iii) for AAA-001: m/z 494 [M+H]+ (ES+); 1H NMR (400-MHz, DMSO-d6) δ: 10.51 (1H, br s), 7.97 (2H, d), 7.91 (2H, d), 7.68 (1H, d), 7.58 (1H, d), 7.50 (2H, m), 7.42-7.36 (3H, m), 5.12 (2H, s), 4.57 (1H, m), 3.84 (3H, s), 1.98 (2H, m), 1.73 (2H, m), 1.62-1.51 (3H, m), 1.47-1.31 (3H, m).

Step (v): Methyl 4-(3-chloro-5-(cyclohexyloxy)-4-hydroxybenzamido)benzoate (7)

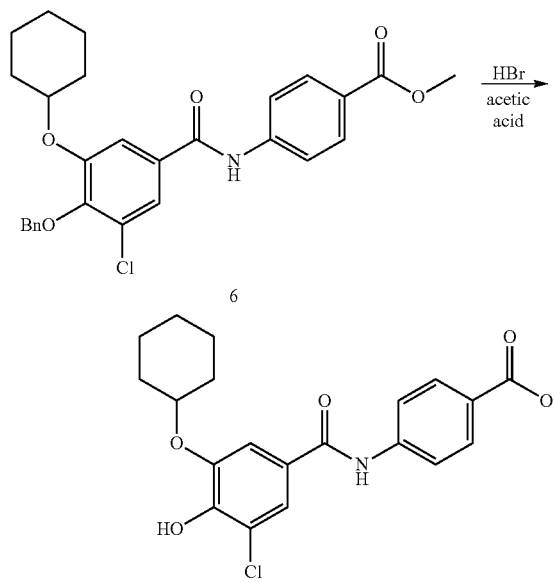

45% hydrogen bromide in acetic acid (26 µL, 0.20 mmol) was added to a stirring mixture of methyl 4-(4-(benzyloxy)-3-chloro-5-(cyclohexyloxy)benzamido)benzoate (6) (20 mg, 40 µmol) in TFA (3 mL) and the mixture was stirred at RT for 1 h. The mixture was partitioned between water (15 mL) and EtOAc (15 mL) and the phases were separated. The organic solution was washed with water (10 mL), dried over MgSO4 and the solvent was removed in vacuo to give methyl 4-(3-chloro-5-(cyclohexyloxy)-4-hydroxybenzamido)benzoate (7) (16 mg, 92%): m/z 402 [M−H]− (ES−); 1H NMR (400-MHz, DMSO-d6) δ: 10.37 (1H, s), 7.94 (4H, m), 7.68 (1H, d), 7.54 (1H, d), 4.40 (1H, m), 3.84 (3H, s), 1.94 (2H, m), 1.83-1.73 (2H, m), 1.57-1.45 (3H, m), 1.40-1.20 (3H, m).

Step (vi): Methyl 4-(3-chloro-4,5-bis(cyclohexyloxy)benzamido)benzoate (8)

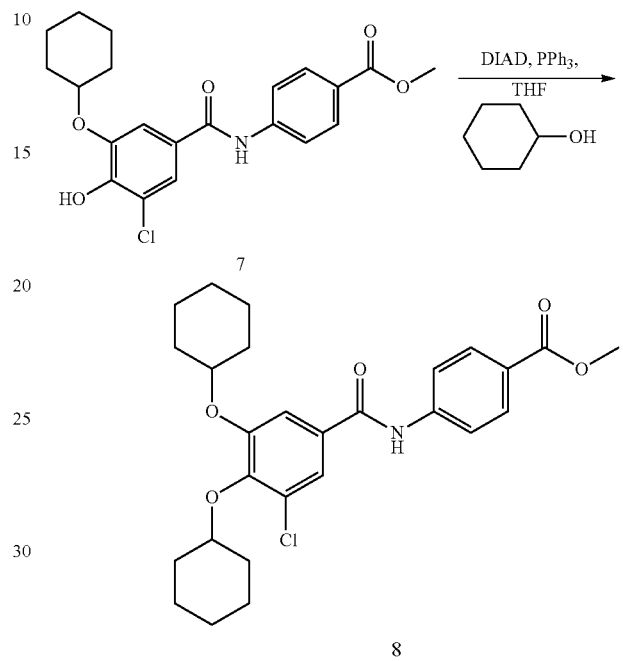

Diisopropylazo dicarboxylate (63 µL, 0.32 mmol) was added dropwise to a stirring mixture of methyl 4-(3-chloro-5-(cyclohexyloxy)-4-hydroxybenzamido)benzoate (7) (65 mg, 161 µmol), cyclohexanol (34 µL, 0.32 mmol) and triphenylphosphine (84 mg, 0.32 mmol) in THF (2 mL) and the resulting yellow mixture was stirred at RT for 20 h. The reaction was quenched with MeOH (5 mL) and the solvent was removed in vacuo. The residue was purified by silica gel chromatography (40 g, 0-15% EtOAc in iso-hexane) to give the desired methyl 4-(3-chloro-4,5-bis(cyclohexyloxy)benzamido)benzoate (8) (80 mg, 100%): m/z 486 [M+H]+ (ES+); 1H NMR (400-MHz, DMSO-d6) δ: 10.48 (1H, s), 7.97 (2H, d), 7.91 (2H, d), 7.67 (1H, d), 7.53 (1H, d), 4.53 (1H, m), 4.36 (1H, m), 3.84 (3H, m), 1.92 (4H, m), 1.80-1.70 (4H, m), 1.60-1.40 (6H, m), 1.30-1.05 (6H, m).

Step (vii): 4-(3-Chloro-4,5-bis(cyclohexyloxy)benzamido)benzoic acid (AAA-047)

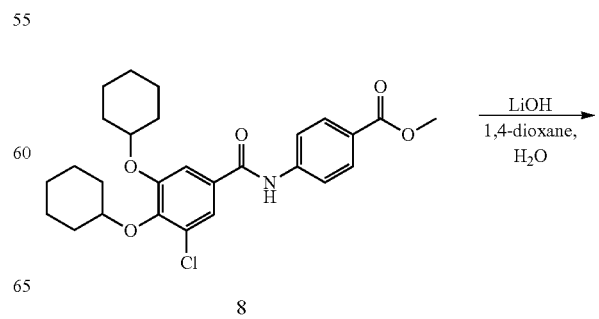

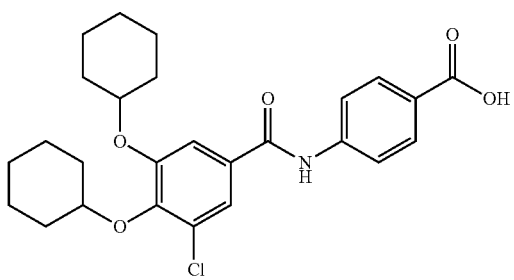

4-(3-Chloro-4,5-bis(cyclohexyloxy)benzamido)benzoic acid (AAA-047) (15 mg, 19%) was prepared from methyl 4-(3-chloro-4,5-bis(cyclohexyloxy)benzamido)benzoate (8) (80 mg, 0.17 mmol) using a procedure essentially the same as in Step (ii) for AAA-001, except that 1,4-dioxane (6 mL) was used instead of THF: m/z 470 [M−H]⁻ (ES⁻); ¹H NMR (400 MHz, DMSO-d₆) δ: 12.72 (1H, br s), 10.44 (1H, s), 7.94 (2H, d), 7.87 (2H, d), 7.67 (1H, d), 7.53 (1H, d), 4.53 (1H, m), 4.36 (1H, m), 1.98-1.82 (4H, m), 1.80-1.65 (4H, m), 1.58-1.20 (12H, m).

Synthesis 50

4-(3,4-Di-tert-butoxy-5-chlorobenzamido)benzoic acid (AAA-048)

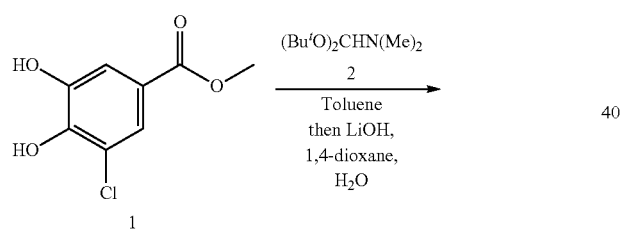

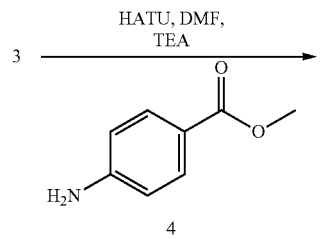

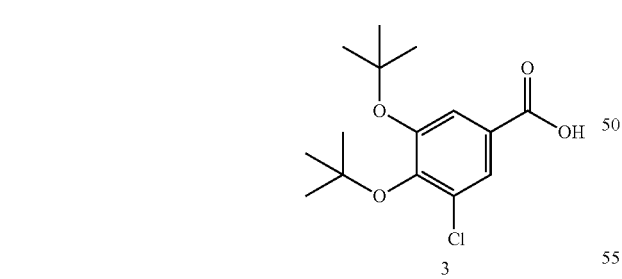

Step (i): 3,4-Di-tert-butoxy-5-chlorobenzoic acid (3)

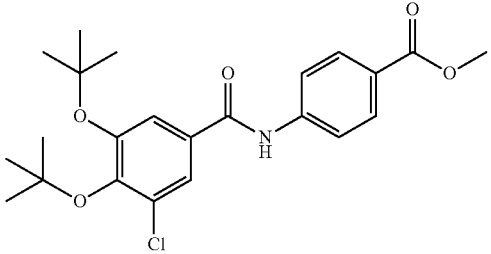

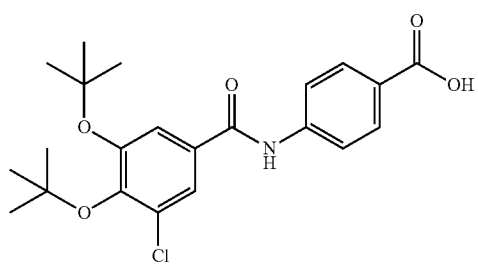

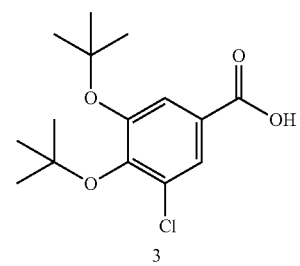

N,N-Dimethylformamide di-tert-butyl acetal (2) (5.92 mL, 24.7 mmol) was added to a solution of methyl 3-chloro-4,5-dihydroxybenzoate (1) (500 mg, 2.47 mmol) in toluene (10 mL) and the reaction mixture was stirred at RT under nitrogen for 21 h. The solvent was removed in vacuo and the residue was purified by silica gel chromatography (40 g, 0-20% EtOAc in iso-hexane) to give the bis-alkylated intermediate, which was dissolved in 1,4-dioxane/water (20 mL, 1:1) and treated with lithium hydroxide (591 mg, 24.7 mmol). The mixture was stirred 18 h at RT. The mixture was poured into 10% aqueous citric acid (100 mL) and the precipitate was collected by filtration. The solid was washed with water and dried to give 3,4-di-tert-butoxy-5-chlorobenzoic acid (2) (534 mg, 70%): m/z 299 [M−H]⁻ (ES⁻); ¹H NMR (400 MHz, DMSO-$d_6$) δ: 13.13 (1H, br s), 7.67 (1H, s), 7.53 (1H, s), 1.39 (9H, s), 1.32 (9H, s).

Step (ii): Methyl 4-(3,4-di-tert-butoxy-5-chlorobenzamido)benzoate (5)

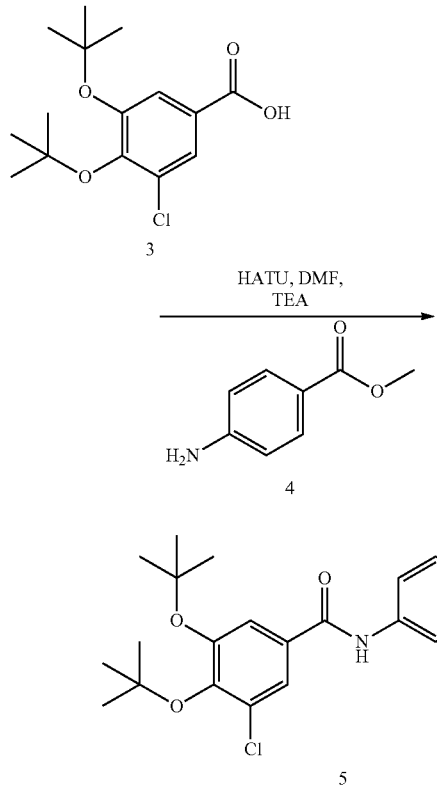

Methyl 4-(3,4-di-tert-butoxy-5-chlorobenzamido)benzoate (5) (185 mg, 50%) was prepared from 3,4-di-tert-butoxy-5-chlorobenzoic acid (3) (250 mg, 0.831 mmol) using a procedure essentially the same as in Step (i) for AAA-019 except that methyl 4-aminobenzoate was used instead of methyl 4-amino-2-methylenzoate and TEA (579 μL, 4.16 mmol) was used as base instead of DIPEA: m/z 432 [M−H]⁻ (ES⁻); ¹H NMR (400 MHz, DMSO-$d_6$) δ: 10.54 (1H, s), 7.96 (2H, d), 7.91 (2H, d), 7.86 (1H, d), 7.60 (1H, d), 3.84 (3H, s), 1.41 (9H, s), 1.32 (9H, s).

Step (iii): 4-(3,4-Di-tert-butoxy-5-chlorobenzamido)benzoic acid (AAA-048)

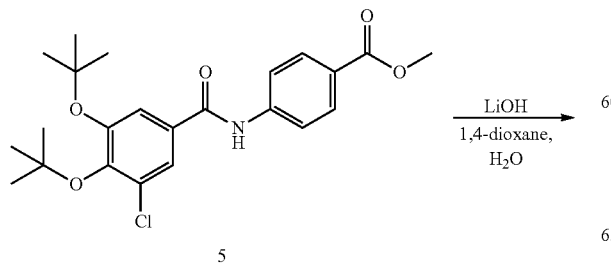

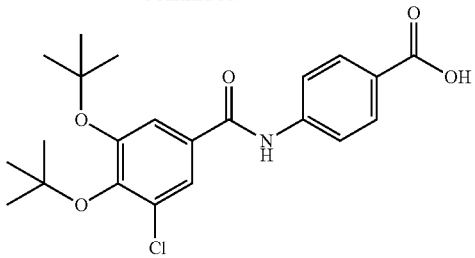 [SMILES: Cc1cc(NC(=O)c2cc(Cl)c(OC(C)(C)C)c(OC(C)(C)C)c2)ccc1C(=O)O]

4-(3,4-Di-tert-butoxy-5-chlorobenzamido)benzoic acid (AAA-048) (110 mg, 64%) was prepared from methyl 4-(3,4-di-tert-butoxy-5-chlorobenzamido)benzoate (5) (175 mg, 0.403 mmol) using a procedure essentially the same as in Step (ii) for AAA-001, except that 1,4-dioxane (6 mL) was used instead of THF: m/z 418 [M−H]⁻ (ES⁻); ¹H NMR (400 MHz, DMSO-$d_6$) δ: 12.78 (1H, br s). 10.49 (1H, s), 7.93 (2H, d), 7.87 (2H, d), 7.85 (1H, d), 7.59 (1H, d), 1.40 (9H, s), 1.34 (9H, s).

Synthesis 51

4-(3,4-Di-tert-butoxy-5-chlorobenzamido)-2-methylbenzoic acid (AAA-049)

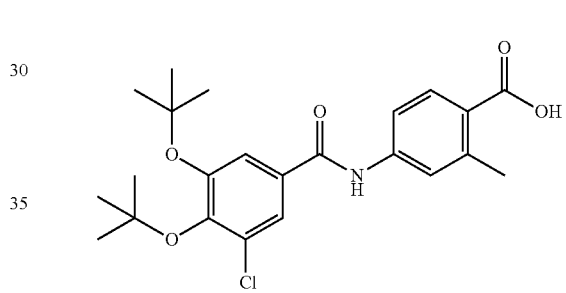

4-(3,4-Di-tert-butoxy-5-chlorobenzamido)-2-methylbenzoic acid (AAA-049) (86 mg, 49% for final step) was prepared in essentially the same manner as for AAA-048 except that methyl 4-amino-2-methylbenzoate was used instead of methyl 4-aminobenzoate in step (ii): m/z 432 [M−H]⁻ (ES⁻); ¹H NMR (400 MHz, DMSO-$d_6$) δ: 12.60 (1H, br s), 10.38 (1H, s), 7.86 (2H, m), 7.72 (1H, br d), 7.70 (1H, br s), 7.60 (1H, d), 2.45 (3H, s), 1.41 (9H, s), 1.32 (9H, s).

Synthesis 52

4-(3-Chloro-4,5-diisopropoxybenzamido)benzoic acid (AAA-050)

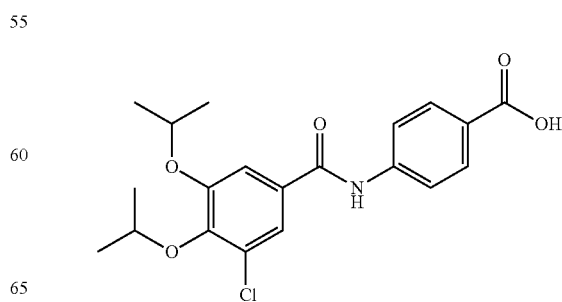

4-(3-Chloro-4,5-diisopropoxybenzamido)benzoic acid (AAA-050) (134 mg, 74% for final step) was prepared in essentially the same manner as AAA-044 except isopropyl bromide was used instead of cyclopentyl iodide and the reaction performed at 80° C. in step (iii): m/z 390 [M–H]⁻ (ES⁻); ¹H NMR (400 MHz, DMSO-$d_6$) δ: 12.78 (1H, br s), 10.46 (1H, s), 7.94 (2H, d), 7.87 (2H, d), 7.68 (1H, d), 7.54 (1H, d), 4.76 (1H, m), 4.59 (1H, m), 1.33 (6H, d), 1.28 (6H, d).

Synthesis 53

4-(3-Chloro-4,5-diisopropoxybenzamido)-2-methyl-benzoic acid (AAA-051)

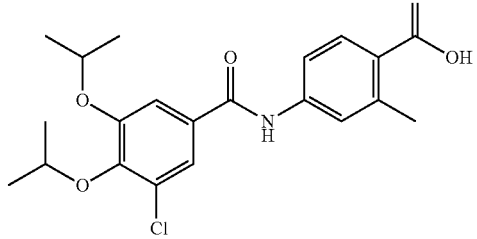

4-(3-Chloro-4,5-diisopropoxybenzamido)benzoic acid (AAA-051) (103 mg, 48% for final step) was prepared in essentially the same manner as AAA-044 except isopropyl bromide was used instead of cyclopentyl iodide and the reaction performed at 80° C. in step (iii) and that methyl 4-amino-2-methylbenzoate was used instead of methyl 4-aminobenzoate in step (v): m/z 404 [M–H]⁻ (ES⁻); ¹H NMR (400 MHz, DMSO-$d_6$) δ: 12.62 (1H, br s), 10.34 (1H, s), 7.87 (1H, d), 7.73 (1H, dd), 7.68 (2H, d), 7.54 (1H, d), 4.76 (1H, m), 4.59 (1H, m), 2.54 (3H, s), 1.33 (6H, d), 1.28 (6H, d).

Synthesis 54

4-(3,5-Dibromo-4-isopropoxybenzamido)-2-methyl-benzoic acid (AAA-052)

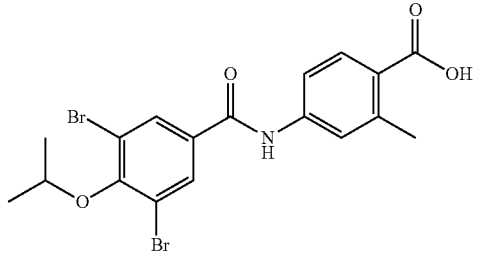 [SMILES: Cc1cc(NC(=O)c2cc(Br)c(OC(C)C)c(Br)c2)ccc1C(=O)O]

4-(3,5-Dibromo-4-isopropoxybenzamido)-2-methylbenzoic acid (AAA-052) (166 mg, 56% for final step) was prepared in essentially the same manner as for AAA-019 except that 3,5-dibromo-4-isopropoxybenzoic acid (prepared in 2 steps from 3,5-dibromo-4-hydroxybenzoic acid by sequential treatment with isopropyl bromide and base followed by lithium hydroxide) was used instead of 3,5-dichloro-4-ethoxybenzoic acid in step (i): m/z 470 [M–H]⁻ (ES⁻); ¹H NMR (400 MHz, DMSO-$d_6$) δ: 12.61 (1H, br s), 10.47 (1H, s), 8.25 (2H, s), 7.87 (1H, m), 7.71 (1H, m), 7.68 (1H, m), 4.75 (1H, m), 2.54 (3H, s), 1.35 (6H, d).

Synthesis 55

4-(3,5-Dibromo-4-ethoxybenzamido)-2-methylben-zoic acid (AAA-053)

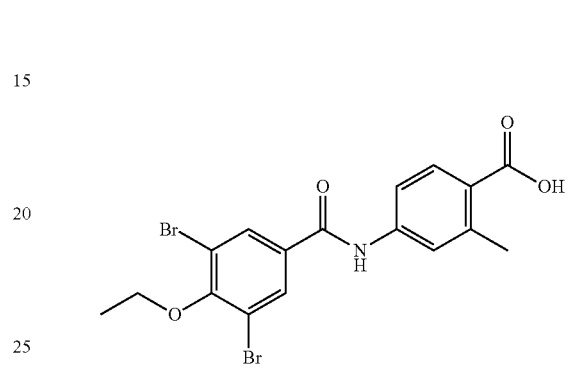

4-(3,5-Dibromo-4-ethoxybenzamido)-2-methylbenzoic acid (AAA-053) (57 mg, 64% for final step) was prepared in essentially the same manner as for AAA-019 except that 3,5-dibromo-4-ethoxybenzoic acid (prepared in 2 steps from 3,5-dibromo-4-hydroxybenzoic acid by sequential treatment with ethyl iodide and base followed by lithium hydroxide) was used instead of 3,5-dichloro-4-ethoxybenzoic acid in step (i): m/z 456 [M–H]⁻ (ES⁻); ¹H NMR (400 MHz, DMSO-$d_6$) δ: 12.64 (1H, br s), 10.48 (1H, s), 8.25 (2H, s), 7.87 (1H, m), 7.71 (1H, m), 7.67 (1H, m), 4.10 (2H, q), 2.54 (3H, s), 1.43 (3H, t).

Synthesis 56

4-(3,5-Dichloro-4-(cyclopentyloxy)benzamido)-2-methylbenzoic acid (AAA-054)

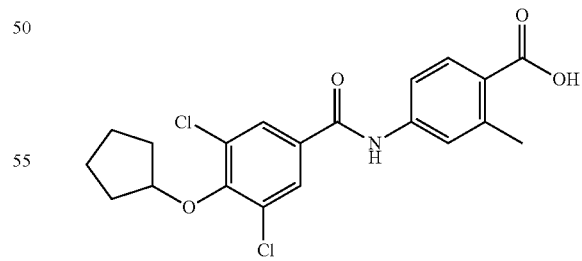

4-(3,5-Dichloro-4-(cyclopentyloxy)benzamido)-2-methylbenzoic acid (AAA-054) (137 mg, 46% for final step) was prepared in essentially the same manner as AAA-001 except that methyl 4-amino-2-methylbenzoate, HATU and DIPEA were used instead of methyl 4-aminobenzoate, oxalyl chloride, DIPEA and DMF in step (iii): m/z 406 [M–H]⁻ (ES⁻); ¹H NMR (400 MHz, DMSO-$d_6$) δ: 12.63 (1H, br s), 10.46

(1H, s), 8.07 (2H, s), 7.87 (1H, m), 7.72-7.68 (2H, m), 5.02 (1H, m), 2.54 (3H, s), 1.91-1.78 (6H, m), 1.63-1.60 (2H, m).

Synthesis 57

4-(3,5-Dichloro-4-methoxybenzamido)-2-methylbenzoic acid (AAA-055)

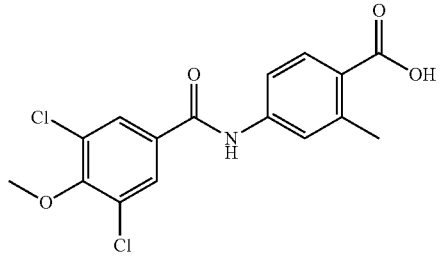 [SMILES: COc1c(Cl)cc(C(=O)Nc2ccc(C(=O)O)c(C)c2)cc1Cl]

4-(3,5-Dichloro-4-methoxybenzamido)-2-methylbenzoic acid (AAA-055) (53 mg, 18% for final step) was prepared in essentially the same manner as AAA-001 except that methyl iodide was used instead of cyclopentyl bromide in step (i) and methyl 4-amino-2-methylbenzoate, HATU and DIPEA were used instead of methyl 4-aminobenzoate, oxalyl chloride, DIPEA and DMF in step (iii): m/z 352 [M–H]⁻ (ES⁻), 354 [M+H]⁺ (ES⁺); ¹H NMR (400 MHz, DMSO-d₆) δ: 12.65 (1H, br s), 10.48 (1H, s), 8.09 (2H, s), 7.87 (1H, m), 7.73-7.68 (2H, m), 3.91 (3H, s), 2.89 (3H, s).

Synthesis 58

4-(4-tert-Butoxy-3,5-dichlorobenzamido)-2-methylbenzoic acid (AAA-056)

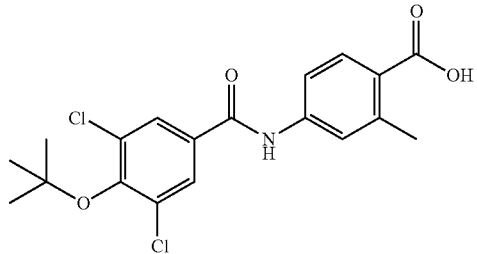 [SMILES: Cc1cc(NC(=O)c2cc(Cl)c(OC(C)(C)C)c(Cl)c2)ccc1C(=O)O]

4-(4-tert-Butoxy-3,5-dichlorobenzamido)-2-methylbenzoic acid (AAA-056) (73 mg, 24% for final step) was prepared in essentially the same manner as AAA-048 except that 5 eq. of N,N-dimethylformamide di-tert-butyl acetal was reacted with methyl 3,5-dichloro-4-hydroxybenzoate in step (i) and the product reacted with methyl 4-amino-2-methylbenzoate instead of methyl 4-aminobenzoate in step (ii): m/z 394 [M–H]⁻ (ES⁻), 396 [M+H]⁺ (ES⁺); ¹H NMR (400 MHz, DMSO-d₆) δ: 12.64 (1H, br s), 10.48 (1H, s), 8.07 (2H, s), 7.87 (1H, m), 7.72-7.68 (2H, m), 2.54 (3H, s), 1.50 (9H, s).

Synthesis 59

4-(3,5-Dichloro-4-ethoxybenzamido)-2-hydroxybenzoic acid (AAA-057)

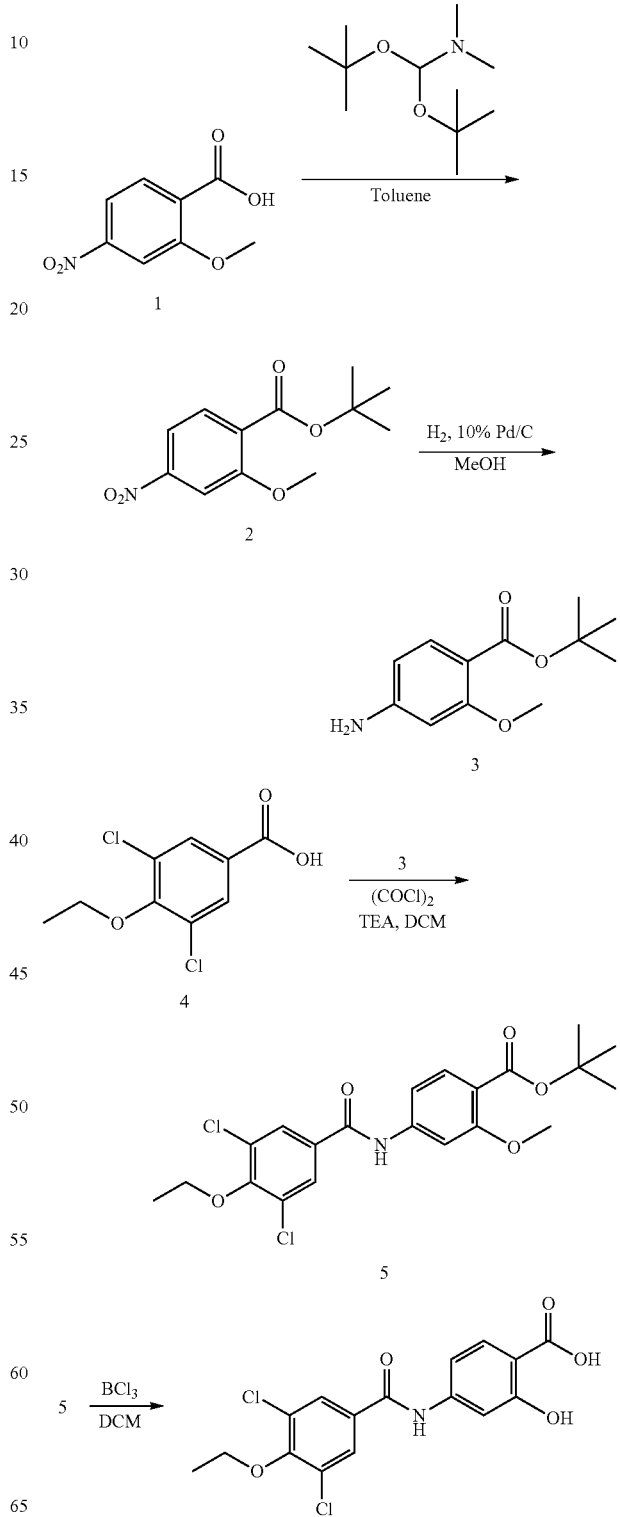

Step (i): tert-Butyl 2-methoxy-4-nitrobenzoate (2)

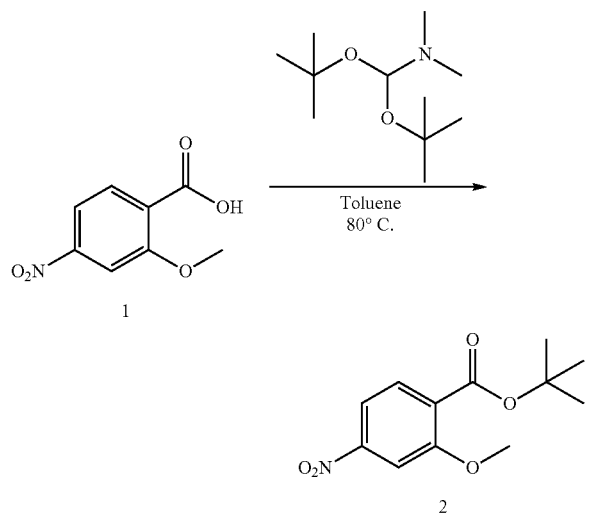

1,1-di-tert-Butoxy-N,N-dimethylmethanamine (608 µL, 2.54 mmol) was added dropwise to a solution of 2-methoxy-4-nitrobenzoic acid (1) (250 mg, 1.27 mmol) in toluene (7.5 mL) at 80° C. The reaction mixture was heated at 80° C. for 3 h, then a further quantity of 1,1-di-tert-butoxy-N,N-dimethylmethanamine (608 µL, 2.54 mmol) was added. The reaction mixture was heated at 80° C. for 16 h, then diluted with water (10 mL) and extracted with Et$_2$O (3×10 mL). The combined organic phases were washed with brine (30 mL), dried over MgSO$_4$, filtered and then concentrated in vacuo to afford tert-butyl 2-methoxy-4-nitrobenzoate (2) (271 mg, 78%) as a pale yellow solid. The material was used in the next step without further purification.

Step (ii): tert-Butyl 4-amino-2-methoxybenzoate (3)

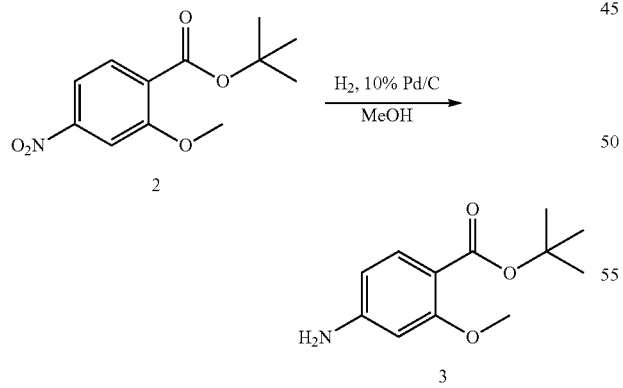

tert-Butyl 2-methoxy-4-nitrobenzoate (2) (271 mg, 1.07 mmol) was dissolved in MeOH (270 mL) and passed through a Thales 'H-cube' cartridge (10% Pd/C) at a flow rate of 1 mL/min at 25° C. under full H$_2$ mode. The solvent was removed in vacuo to afford tert-butyl 4-amino-2-methoxybenzoate (3) (234 mg, 92%) as a pale yellow solid: m/z 222 [M–H]$^-$ (ES$^-$); $^1$H-NMR (400 MHz, DMSO-d$_6$) δ: 7.41 (1H, d), 6.16 (1H, d), 6.09 (1H, dd), 5.82 (2H, br s), 3.68 (3H, s), 1.45 (9H, s).

Step (iii): tert-Butyl 4-(3,5-dichloro-4-ethoxybenzamido)-2-methoxybenzoate (5)

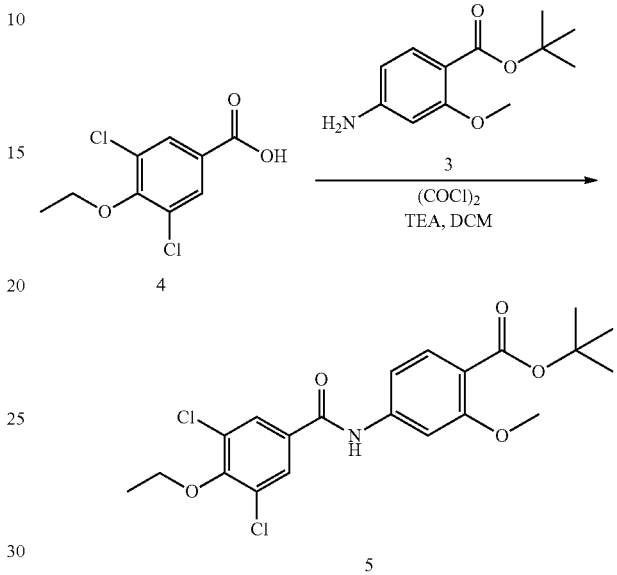

3,5-Dichloro-4-ethoxybenzoic acid (4) (75 mg, 0.32 mmol) in DCM (5 mL) was treated with oxalyl chloride (56 µL, 0.64 mmol) dropwise, followed by a drop of DMF. The reaction mixture was stirred at RT for 1 h, and then the solvent was removed in vacuo. The residue was dissolved in DCM (5 mL) and TEA (133 µL, 957 µmol) was added. The mixture was added to tert-butyl 4-amino-2-methoxybenzoate (3) (71 mg, 0.32 mmol) and stirred at RT for 16 h. The mixture was sequentially washed with sat. aq. NaHCO$_3$ (5 mL) and 1 M HCl (5 mL), and the organic phase was concentrated in vacuo. The residue was purified by silica gel chromatography (12 g, 0-100% EtOAc in isohexane) to afford tert-butyl 4-(3,5-dichloro-4-ethoxybenzamido)-2-methoxybenzoate (5) (59 mg, 42%) as a white solid: m/z 384 [M–$^t$Bu+2H]$^+$ (ES$^+$); $^1$H-NMR (400 MHz, DMSO-d$_6$) δ: 10.51 (1H, s), 8.09 (2H, s), 7.63 (1H, d), 7.60 (1H, d), 7.43 (1H, dd), 4.15 (2H, q), 3.81 (3H, s), 1.51 (9H, s), 1.41 (3H, t).

Step (iv): 4-(3,5-Dichloro-4-ethoxybenzamido)-2-hydroxybenzoic acid (AAA-057)

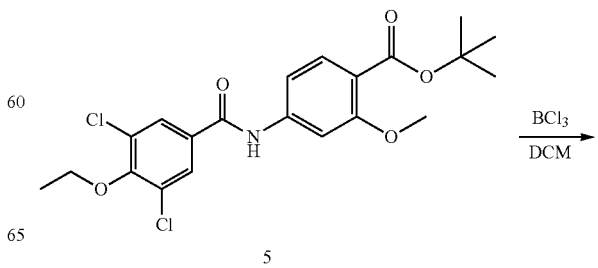

-continued

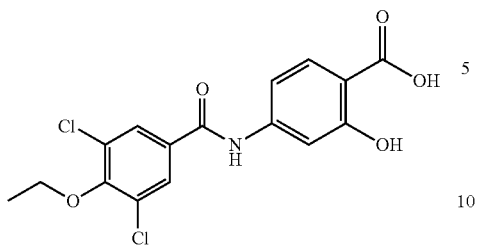

A solution of tert-butyl 4-(3,5-dichloro-4-ethoxybenzamido)-2-methoxybenzoate (5) (55 mg, 0.13 mmol) in DCM (5 mL) was cooled to 0° C. and treated dropwise with a solution of 1 M boron trichloride in DCM (349 µL, 349 µmol). The reaction mixture was stirred at 0° C. for 1 h and then at RT for 2 h. The reaction mixture was cooled to 0° C. and water (0.5 mL) and sat. aq. NaHCO$_3$ (2 mL) were added. The resulting white precipitate was collected by filtration and washed with water (2 mL). The solid was dried, then purified by capture and release on SAX, eluting with 5% AcOH in THF to afford 4-(3,5-dichloro-4-ethoxybenzamido)-2-hydroxybenzoic acid (AAA-057) (11 mg, 24%) as a white solid: m/z 370 [M+H]$^+$ (ES$^+$), 368 [M–H]$^-$ (ES$^-$); $^1$H-NMR (400 MHz, DMSO-d$_6$) δ: 10.51 (1H, s), 8.06 (2H, s), 7.76 (1H, d), 7.48 (1H, d), 7.28 (1H, dd), 4.14 (2H, q), 1.91 (1H, s), 1.40 (3H, t), 1.35 (1H, s).

Synthesis 60

4-(3,5-Bis(cyclopentyloxy)-4-ethoxybenzamido) benzoic acid (AAA-058)

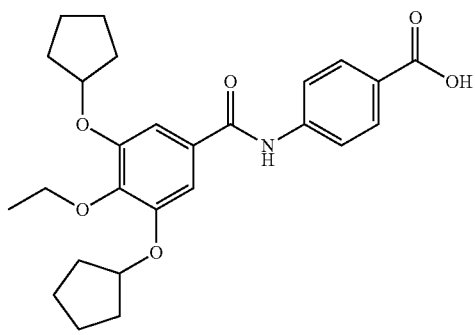 [SMILES: CCOc1c(OC2CCCC2)cc(C(=O)Nc2ccc(C(=O)O)cc2)cc1OC1CCCC1]

4-(3,5-Bis(cyclopentyloxy)-4-ethoxybenzamido)benzoic acid (AAA-058) (75 mg, 55% for final step) was prepared in essentially the same manner as in Steps (iii) and (iv) for AAA-001 except that 3,5-bis(cyclopentyloxy)-4-ethoxybenzoic acid (prepared in 3 steps from methyl 3,4,5-trihydroxybenzoate by sequential reaction with ethyl iodide and base, cyclopentyl bromide and base and then lithium hydroxide) was used instead of 3,5-dichloro-4-(cyclopentyloxy)benzoic acid in step (iii): m/z 454 [M+H]$^+$ (ES$^+$), 452 [M–H]$^-$ (ES$^-$); $^1$H NMR (400 MHz, CDCl$_3$) δ: 8.12 (2H, d), 7.83 (1H, s), 7.75 (2H, d), 7.04 (2H, s), 4.87 (2H, m), 4.06 (2H, q), 2.00-1.50 (16H, m), 1.35 (3H, t).

Synthesis 61

4-(3,4,5-Triisopropoxybenzamido)benzoic acid (AAA-059)

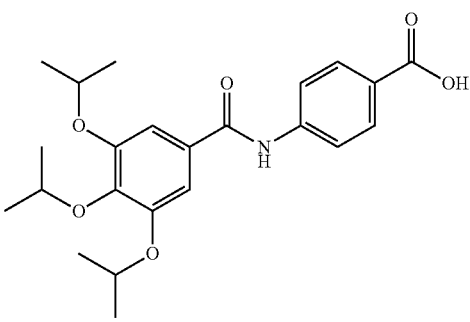 [SMILES: CC(C)Oc1cc(C(=O)Nc2ccc(C(=O)O)cc2)cc(OC(C)C)c1OC(C)C]

4-(3,4,5-Triisopropoxybenzamido)benzoic acid (AAA-059) (194 mg, 91% for final step) was prepared in essentially the same manner as in Steps (iii) and (iv) for AAA-001 except that 3,4,5-triisopropoxybenzoic acid (prepared in 2 steps from methyl 3,4,5-trihydroxybenzoate by sequential reaction with 2-bromopropane and base and then lithium hydroxide) was used instead of 3,5-dichloro-4-(cyclopentyloxy)benzoic acid in step (iii): m/z 416 [M+H]$^+$ (ES$^+$), 414 [M–H]$^-$ (ES$^-$); $^1$H NMR (400 MHz, CDCl$_3$) δ: 8.13 (2H, d), 7.87 (1H, s), 7.75 (2H, d), 7.08 (2H, s), 4.64 (2H, heptet), 4.46 (1H, heptet), 1.36 (12H, d), 1.32 (6H, d).

Synthesis 62

4-(3,4,5-Tri-tert-butoxybenzamido)benzoic acid (AAA-060)

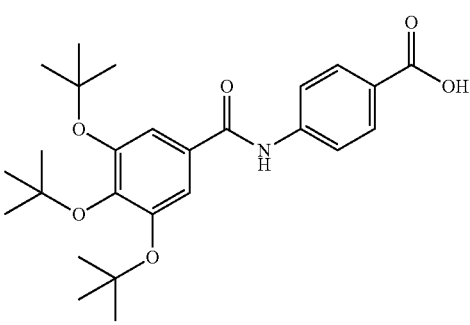 [SMILES: CC(C)(C)Oc1cc(C(=O)Nc2ccc(C(=O)O)cc2)cc(OC(C)(C)C)c1OC(C)(C)C]

4-(3,4,5-Tri-tert-butoxybenzamido)benzoic acid (AAA-060) (53 mg, 84% for final step) was prepared in essentially the same manner as in Steps (iii) and (iv) for AAA-001 except that 3,4,5-tri-tert-butoxybenzoic acid (prepared in 2 steps from methyl 3,4,5-trihydroxybenzoate by sequential reaction with 1,1-di-tert-butoxy-N,N-dimethylmethanamine and then lithium hydroxide) was used instead of 3,5-dichloro-4-(cyclopentyloxy)benzoic acid in step (iii): m/z 458 [M+H]$^+$ (ES$^+$), 456 [M–H]$^-$ (ES$^-$); $^1$H NMR (400 MHz, CDCl$_3$) δ: 8.12 (2H, d), 7.84 (1H, s), 7.75 (2H, d), 7.30 (2H, s), 1.38 (27H, s).

Synthesis 63

4-(4-Ethoxy-3,5-diisopropoxybenzamido)-2-methylbenzoic acid (AAA-061)

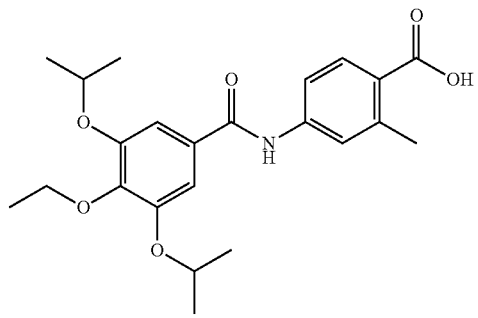 [SMILES: CCOc1c(OC(C)C)cc(C(=O)Nc2ccc(C(=O)O)c(C)c2)cc1OC(C)C]

4-(4-Ethoxy-3,5-diisopropoxybenzamido)-2-methylbenzoic acid (AAA-061) (30 mg, 31% for final step) was prepared in essentially the same manner as in steps (iii) and (iv) for AAA-001 except that 4-ethoxy-3,5-diisopropoxybenzoic acid was used instead of 3,5-dichloro-4-(cyclopentyloxy)benzoic acid and methyl 4-amino-2-methylbenzoate was used instead of methyl 4-aminobenzoate in step (iii): m/z 416 (M+H)$^+$ (ES$^+$); $^1$H NMR (400 MHz, DMSO) 12.60 (1H, bs), 10.19 (1H, s), 7.86 (1H, d), 7.70 (1H, dd), 7.66 (1H, d), 7.23 (2H, s), 4.67-4.61 (2H, m), 3.99 (2H, q), 2.53 (3H, s), 1.29 (12H, d), 1.25 (3H, t).

Synthesis 64

4-(3,5-Diisopropoxy-4-methoxybenzamido)benzoic acid (AAA-062)

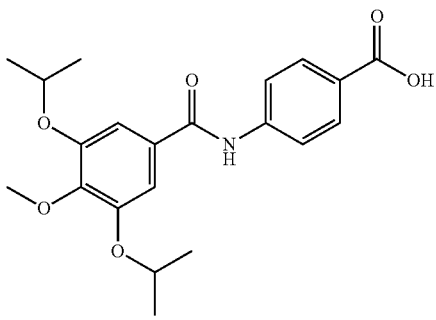 [SMILES: COc1c(OC(C)C)cc(C(=O)Nc2ccc(C(=O)O)cc2)cc1OC(C)C]

4-(3,5-Diisopropoxy-4-methoxybenzamido)benzoic acid (AAA-062) (223 mg, 77% for final step) was prepared in essentially the same manner as for AAA-019 except that 3,5-diisopropoxy-4-methoxybenzoic acid (prepared in 3 steps from methyl 3,4,5-trihydroxybenzoate by sequential treatment with methyl iodide and base, isopropyl bromide and base and then lithium hydroxide) was used instead of 3,5-dichloro-4-ethoxybenzoic acid and methyl 4-aminobenzoate was used instead of methyl 4-amino-2-methylbenzoate in step (i): m/z 388 [M+H]$^+$ (ES$^+$), 386 [M−H]$^-$ (ES$^-$). $^1$H-NMR (400 MHz, DMSO-d$_6$) δ: 12.77 (1H, br s), 10.32 (1H, s), 7.92 (2H, d), 7.87 (2H, d), 7.24 (2H, s), 7.88 (2H, d), 4.66 (2H, sep), 3.73 (3H, s), 1.30 (12H, d).

Synthesis 65

4-(3,5-Diisopropoxy-4-methoxybenzamido)-2-methylbenzoic acid (AAA-063)

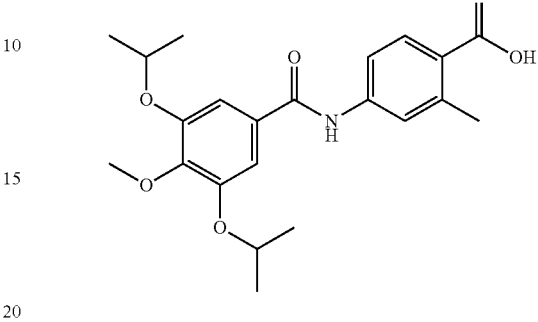

4-(3,5-Diisopropoxy-4-methoxybenzamido)-2-methylbenzoic acid (AAA-063) (207 mg, 69% for final step) was prepared in essentially the same manner as for AAA-019 except that 3,5-diisopropoxy-4-methoxybenzoic acid was used instead of 3,5-dichloro-4-ethoxybenzoic acid in step (i): m/z 402 [M+H]$^+$ (ES$^+$), 400 [M−H]$^-$ (ES$^-$). $^1$H-NMR (400 MHz, DMSO-d$_6$) δ: 12.62 (1H, br s), 10.21 (1H, s), 7.86 (1H, d), 7.73-7.66 (2H, m), 7.25 (2H, s), 4.66 (2H, sep), 3.74 (3H, s), 2.54 (3H, s), 1.30 (12H, d).

Synthesis 66

4-(3,5-Diisopropoxy-4-ethoxybenzamido)-2-fluorobenzoic acid (AAA-064)

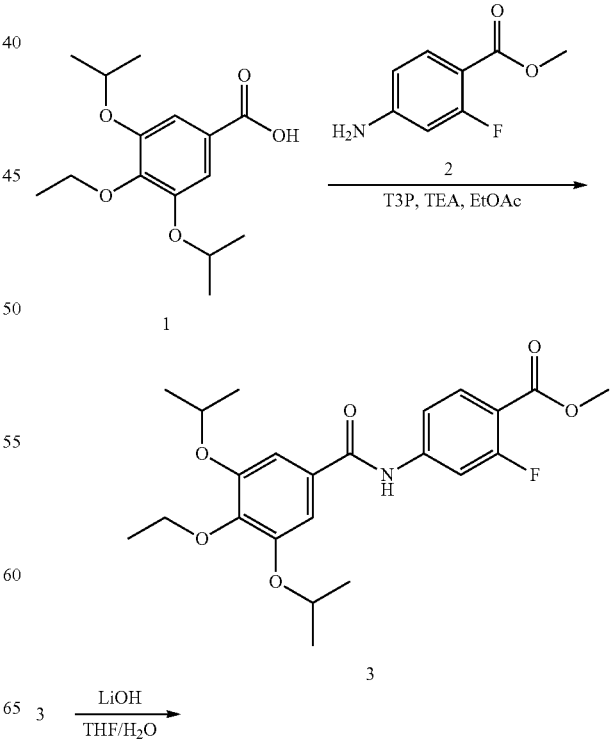

-continued

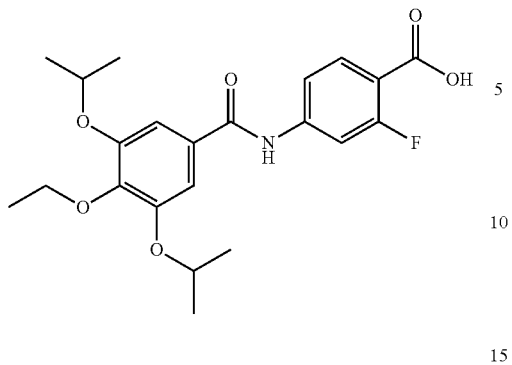

Step (i): Methyl 4-(3,5-diisopropoxy-4-ethoxybenzamido)-2-fluorobenzoate

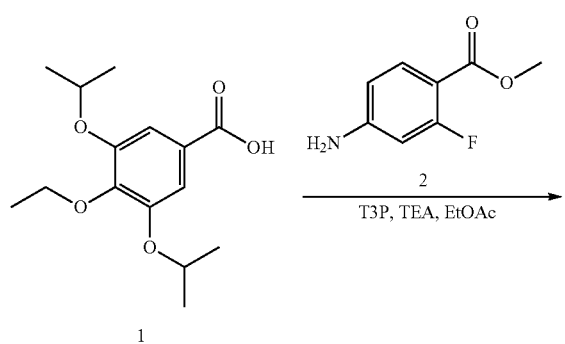

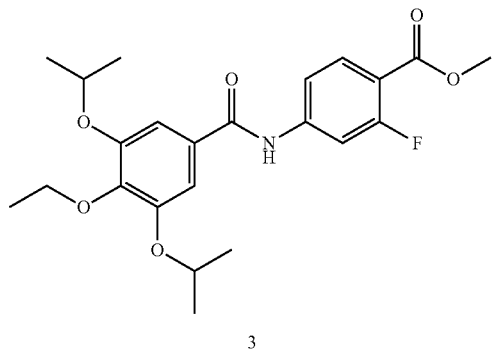

A mixture of 3,5-diisopropoxy-4-ethoxybenzoic acid (1) (300 mg, 1.06 mmol), methyl 4-amino-2-fluorobenzoate (2) (189 mg, 1.12 mmol) and TEA (149 µL, 1.06 mmol) in EtOAc (2.5 mL) was treated with T3P (50% wt. in EtOAc, 1.69 mL, 2.66 mmol). The reaction mixture was stirred at 60° C. for 1 h, and then allowed to cool to RT. The mixture was diluted with DCM (5 mL) and washed sequentially with 1M HCl (5 mL) and satd. NaHCO$_3$ (5 mL). The solvent was removed in vacuo and the residue was purified by silica gel chromatography (12 g, 0-30% EtOAc in isohexane) to afford methyl 4-(3,5-diisopropoxy-4-ethoxybenzamido)-2-fluorobenzoate (3) (326 mg, 56%): m/z 434 [M+H]$^+$ (ES$^+$), 432 [M−H]$^−$ (ES$^−$). $^1$H-NMR (400 MHz, DMSO-d$_6$) δ: 7.93 (1H, t), 7.82 (1H, br s), 7.73 (1H, dd), 7.27 (1H, dd), 7.04 (2H, s), 4.60 (2H, sep), 4.09 (2H, q), 3.91 (3H, s), 1.39-1.34 (15H, m).

Step (ii) 4-(3,5-Diisopropoxy-4-ethoxybenzamido)-2-fluorobenzoic acid (AAA-064)

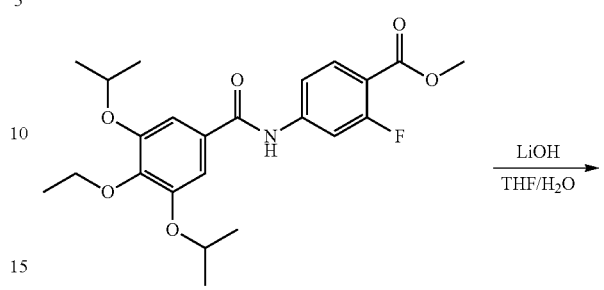

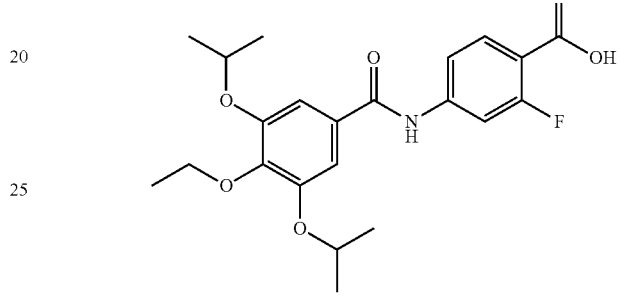

2 M Lithium hydroxide (554 µL, 1.11 mmol) was added to a solution of 4-(3,5-diisopropoxy-4-ethoxybenzamido)-2-fluorobenzoate (3) (320 mg, 0.740 mmol) in THF (5 mL) and the mixture was stirred at RT for 20 h. The mixture was partitioned between 1M HCl (5 mL) and DCM (10 mL) and the phases were separated. The organic solvent was removed in vacuo and the residue was purified by silica gel chromatography (40 g, 0-20% IPA in isohexane) to afford 4-(3,5-diisopropoxy-4-ethoxybenzamido)-2-fluorobenzoic acid (AAA-064) as a white solid (176 mg, 56%): m/z 420 [M+H]$^+$ (ES$^+$), 418 [M−H]$^−$ (ES$^−$). $^1$H-NMR (400 MHz, DMSO-d$_6$) δ: 13.03 (1H, br s), 10.45 (1H, s), 7.88 (1H, t), 7.81 (1H, dd), 7.61 (1H, dd), 7.22 (2H, s), 4.65 (2H, sep), 4.00 (2H, q), 1.29 (12H, d), 1.26 (3H, t).

Synthesis 67

6-(3-Chloro-4-methoxy-5-(trifluoromethyl)benzamido)nicotinic acid (AAA-065)

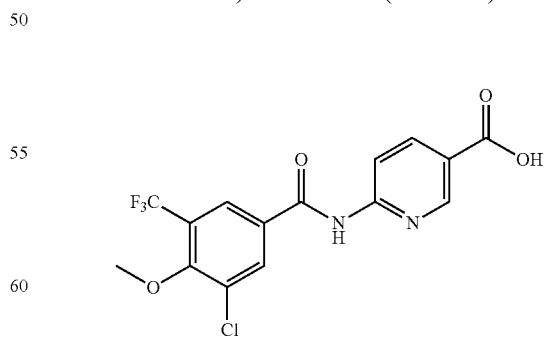

6-(3-Chloro-4-methoxy-5-(trifluoromethyl)benzamido)nicotinic acid (AAA-065) (65 mg, 48% for final step) was prepared in essentially the same manner as in steps (iii) and (iv) for AAA-001 except that 3-chloro-4-methoxy-5-(trifluoromethyl)benzoic acid was used instead of 3,5-dichloro-4-(cyclopentyloxy)benzoic acid, methyl 6-aminonicotinate was used instead of methyl 4-aminobenzoate and pyridine was used instead of TEA in step (iii) and 1,4-dioxane was used instead of THF in step (iv): m/z 375 [M+H]+ (ES+), 373 [M−H]− (ES−). $^1$H NMR (400 MHz, DMSO-d$_6$) δ: 13.24 (1H, br s), 11.54 (1H, s), 8.90 (1H, dd), 8.48 (1H, d), 8.39-8.24 (3H, m), 3.97 (3H, s).

Synthesis 68

4-(3-Chloro-4-methoxy-5-(trifluoromethyl)benzamido)-2-fluorobenzoic acid (AAA-066)

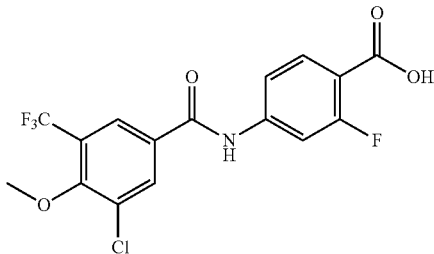 [SMILES: COc1c(Cl)cc(C(=O)Nc2ccc(C(=O)O)c(F)c2)cc1C(F)(F)F]

4-(3-Chloro-4-methoxy-5-(trifluoromethyl)benzamido)-2-fluorobenzoic acid (AAA-066) (30 mg, 42% for final step) was prepared in essentially the same manner as for AAA-019 except that 3-chloro-4-methoxy-5-(trifluoromethyl)benzoic acid was used instead of 3,5-dichloro-4-ethoxybenzoic acid, methyl 4-amino-2-fluorobenzoate was used instead of methyl 4-amino-2-methylbenzoate and TEA was used instead of DIPEA in step (i): m/z 392 [M+H]+ (ES+), 390 [M−H]− (ES−). $^1$H NMR (400 MHz, DMSO-d$_6$) δ: 13.11 (1H, br s), 10.85 (1H, s), 8.43 (1H, d), 8.22 (1H, d), 7.89 (1H, t), 7.79 (1H, dd), 7.61 (1H, dd), 3.98 (3H, s).

Synthesis 69

4-(3-Chloro-4-methoxy-5-(trifluoromethyl)benzamido)-3-fluorobenzoic acid (AAA-067)

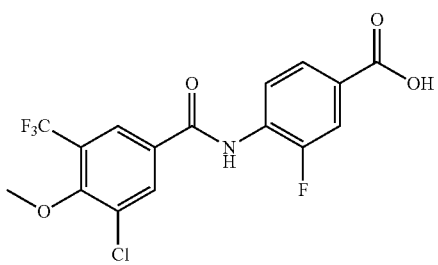 [SMILES: COc1c(Cl)cc(C(=O)Nc2ccc(C(=O)O)cc2F)cc1C(F)(F)F]

4-(3-Chloro-4-methoxy-5-(trifluoromethyl)benzamido)-3-fluorobenzoic acid (AAA-067) (11 mg, 31% for final step) was prepared in essentially the same manner as for AAA-019 except that 3-chloro-4-methoxy-5-(trifluoromethyl)benzoic acid was used instead of 3,5-dichloro-4-ethoxybenzoic acid, methyl 4-amino-3-fluorobenzoate was used instead of methyl 4-amino-2-methylbenzoate and TEA was used instead of DIPEA in step (i): m/z 392 [M+H]+ (ES+), 390 [M−H]− (ES−). $^1$H NMR (400 MHz, DMSO-d$_6$) δ: 13.35 (1H, br s), 10.62 (1H, s), 8.42 (1H, d), 8.24 (1H, d), 7.83-7.73 (3H, m), 3.98 (3H, s).

Synthesis 70

4-(3-Chloro-4-ethoxy-5-(trifluoromethyl)benzamido)-2-fluorobenzoic acid (AAA-068)

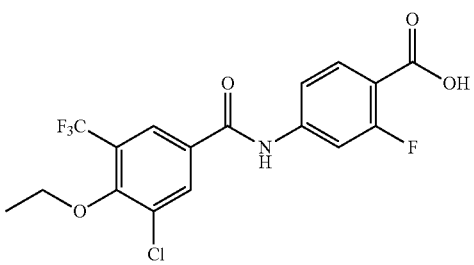 [SMILES: CCOc1c(Cl)cc(C(=O)Nc2ccc(C(=O)O)c(F)c2)cc1C(F)(F)F]

4-(3-Chloro-4-ethoxy-5-(trifluoromethyl)benzamido)-2-fluorobenzoic acid (AAA-068) (11 mg, 31% for final step) was prepared in essentially the same manner as for AAA-064 except that 3-chloro-4-ethoxy-5-(trifluoromethyl)benzoic acid was used instead of 3,5-diisopropoxy-4-ethoxybenzoic acid in step (i): m/z 404 [M−H]− (ES−). $^1$H NMR (400 MHz, DMSO-d$_6$) δ: 13.06 (1H, br s), 10.83 (1H, s), 8.41 (1H, d), 8.21 (1H, d), 7.90 (1H, t), 7.80 (1H, dd), 7.61 (1H, dd), 4.20 (2H, q), 1.41 (3H, t).

Synthesis 71

4-(3-Chloro-4-isopropoxy-5-(trifluoromethyl)benzamido)-2-fluorobenzoic acid (AAA-069)

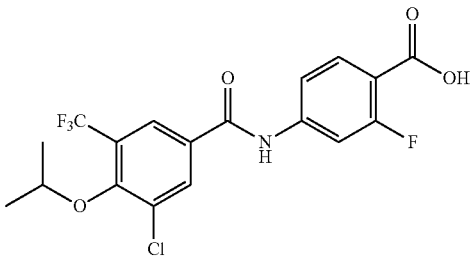 [SMILES: CC(C)Oc1c(Cl)cc(C(=O)Nc2ccc(C(=O)O)c(F)c2)cc1C(F)(F)F]

4-(3-Chloro-4-isopropoxy-5-(trifluoromethyl)benzamido)-2-fluorobenzoic acid (AAA-069) (155 mg, 67% for final step) was prepared in essentially the same manner as for AAA-064 except that 3-chloro-4-isopropoxy-5-(trifluoromethyl)benzoic acid was used instead of 3,5-diisopropoxy-4-ethoxybenzoic acid in step (i): m/z 418 [M−H]− (ES−). $^1$H NMR (400 MHz, DMSO-d$_6$) δ: 13.02 (1H, br s), 10.81 (1H, s), 8.38 (1H, d), 8.21 (1H, d), 7.90 (1H, t), 7.80 (1H, dd), 7.61 (1H, dd), 5.06 (1H, sep), 1.28 (6H, d).

Synthesis 72

4-(3-Chloro-4-methoxy-5-(trifluoromethyl)benzamido)-2-hydroxybenzoic acid (AAA-070)

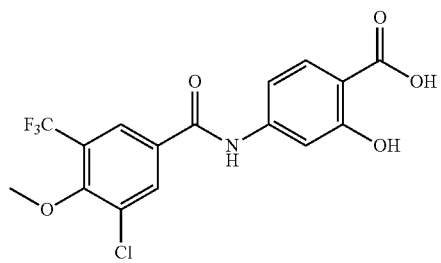 [SMILES: COc1c(Cl)cc(C(=O)Nc2ccc(C(=O)O)c(O)c2)cc1C(F)(F)F]

4-(3-Chloro-4-methoxy-5-(trifluoromethyl)benzamido)-2-hydroxybenzoic acid (AAA-070) (73 mg, 58% for final step) was prepared in essentially the same manner as for AAA-064 except that 3-chloro-4-methoxy-5-(trifluoromethyl)benzoic acid was used instead of 3,5-diisopropoxy-4-ethoxybenzoic acid and methyl 4-amino-2-hydroxybenzoate (prepared from methyl 4-amino-2-hydroxybenzoic acid by treatment with $H_2SO_4$ and MeOH) was used instead of methyl 4-amino-2-fluorobenzoate in step (i): m/z 388 [M−H]⁻ (ES⁻). ¹H NMR (400 MHz, DMSO-$d_6$) δ: 13.77 (1H, br s), 11.39 (1H, br s), 10.65 (1H, s), 8.43 (1H, d), 8.22 (1H, d), 7.80 (1H, d), 7.51 (1H, d), 7.31 (1H, dd), 3.99 (3H, s).

Synthesis 73

4-(3-Bromo-4-ethoxy-5-(trifluoromethyl)benzamido)-2-methylbenzoic acid (AAA-071)

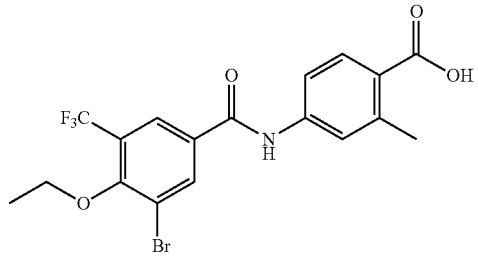 [SMILES: CCOc1c(Br)cc(C(=O)Nc2ccc(C(=O)O)c(C)c2)cc1C(F)(F)F]

4-(3-Bromo-4-ethoxy-5-(trifluoromethyl)benzamido)-2-methylbenzoic acid (AAA-071) (20 mg, 52% for final step) was prepared in essentially the same manner as for AAA-019 except that 3-bromo-4-ethoxy-5-trifluoromethylbenzoic acid was used instead of 3,5-dichloro-4-ethoxybenzoic acid in step (i): m/z 446 and 448 [M+H]⁺ (ES⁺), 444 and 446 [M−H]⁻ (ES⁻). ¹H-NMR (400 MHz, DMSO-$d_6$) δ: 12.66 (1H, br s), 10.60 (1H, s), 8.56 (1H, d), 8.26 (1H, d), 7.88 (1H, d), 7.73 (1H, dd), 7.68 (1H, d) 4.17 (2H, q), 2.55 (3H, s) 1.43 (3H, t).

Synthesis 74

4-(3-Bromo-4-ethoxy-5-(trifluoromethyl)benzamido)-2-fluorobenzoic acid (AAA-072)

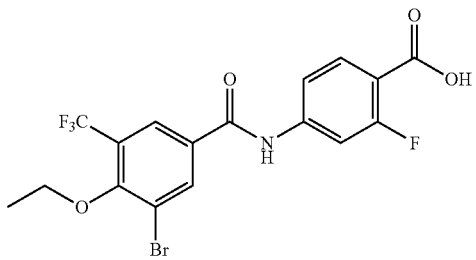 [SMILES: CCOc1c(Br)cc(C(=O)Nc2ccc(C(=O)O)c(F)c2)cc1C(F)(F)F]

4-(3-Bromo-4-ethoxy-5-(trifluoromethyl)benzamido)-2-fluorobenzoic acid (AAA-072) (95 mg, 64% for final step) was prepared in essentially the same manner as for AAA-019 except that 3-bromo-4-ethoxy-5-trifluoromethylbenzoic acid was used instead of 3,5-dichloro-4-ethoxybenzoic acid and methyl 4-amino-2-fluorobenzoate was used instead of methyl 4-amino-2-methylbenzoate in step (i): m/z 451 [M+H]⁺ (ES⁺), 449 [M−H]⁻ (ES⁻). ¹H-NMR (400 MHz, DMSO-$d_6$) δ: 13.08 (1H, br s), 10.85 (1H, s), 8.56 (1H, d), 8.26 (1H, d), 7.92 (1H, t), 7.82 (1H, dd), 7.63 (1H, dd), 4.18 (2H, q1.44 (3H, t).

Synthesis 75

4-(4-Ethoxy-3,5-difluorobenzamido)benzoic acid (AAA-073)

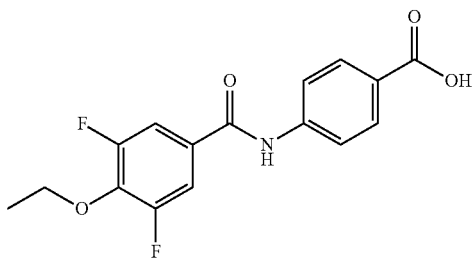 [SMILES: CCOc1c(F)cc(C(=O)Nc2ccc(C(=O)O)cc2)cc1F]

4-(4-Ethoxy-3,5-difluorobenzamido)benzoic acid (AAA-073) (74 mg, 80% for final step) was prepared in essentially the same manner as for AAA-019 except that 4-ethoxy-3,5-difluorobenzoic acid (prepared in 3 steps from 3,5-difluoro-4-methoxybenzoic acid by sequential treatment with $BBr_3$, ethyl iodide and base and then lithium hydroxide) was used instead of 3,5-dichloro-4-ethoxybenzoic acid, methyl 4-aminobenzoate was used instead of methyl 4-amino-2-methylbenzoate and TEA was used instead of DIPEA in step (i): m/z 322 [M+H]⁺ (ES⁺), 320 [M−H]⁻ (ES⁻). ¹H NMR (400 MHz, DMSO-$d_6$) δ: 12.82 (1H, br s), 10.53 (1H, s), 7.98-7.93 (2H, m), 7.92-7.87 (2H, m), 7.84-7.76 (2H, m), 4.30 (2H, q), 1.34 (3H, t).

Synthesis 76

4-(3-Chloro-5-fluoro-4-isopropoxybenzamido)-2-methylbenzoic acid (AAA-074)

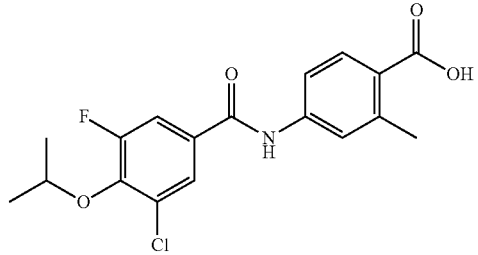 [SMILES: Cc1cc(NC(=O)c2cc(F)c(OC(C)C)c(Cl)c2)ccc1C(=O)O]

4-(3-Chloro-5-fluoro-4-isopropoxybenzamido)-2-methylbenzoic acid (AAA-074) (52 mg, 12% for final step) was prepared in essentially the same manner as for AAA-019 except that 4-(3-chloro-5-fluoro-4-isopropoxybenzoic acid (prepared in 3 steps from 3-chloro-5-fluoro-4-methoxybenzoic acid by sequential treatment with BBr$_3$, isopropyl bromide and base and then lithium hydroxide) was used instead of 3,5-dichloro-4-ethoxybenzoic acid and TEA was used instead of DIPEA in step (i): m/z 366 [M+H]$^+$ (ES$^+$), 364 [M−H]$^−$ (ES)$^−$. $^1$H NMR (400 MHz, DMSO-d$_6$) δ: 12.75 (1H, br s), 10.44 (1H, s), 7.99-7.96 (1H, m), 7.91-7.83 (2H, m), 7.69 (2H, m), 4.58 (1H, sep), 2.52 (3H, s), 1.33 (6H, d).

Synthesis 77

4-(3-Chloro-5-isopropoxy-4-methoxybenzamido)-2-methylbenzoic acid (AAA-075)

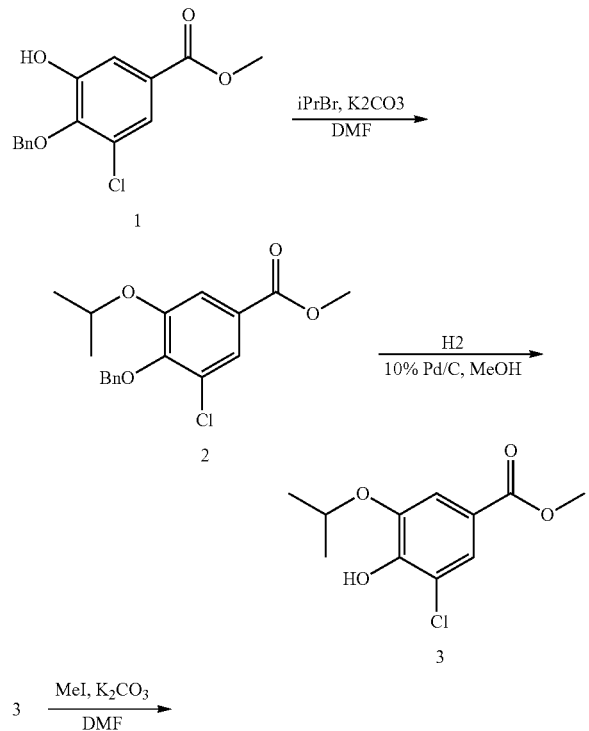

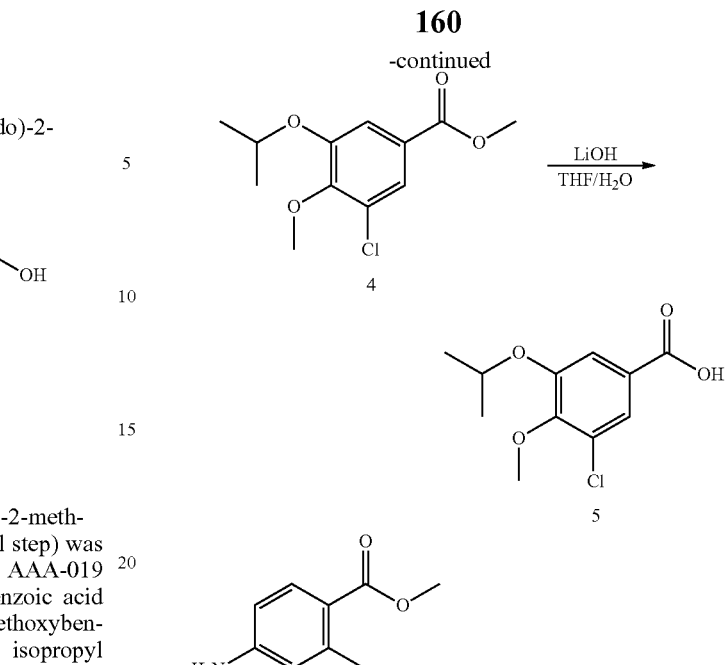

Step (i): Methyl 4-(benzyloxy)-3-chloro-5-isopropoxybenzoate (2)

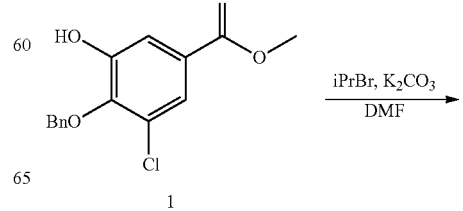

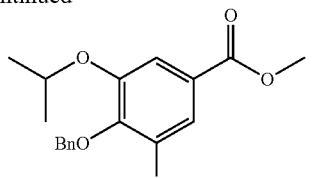

Methyl 4-(benzyloxy)-3-chloro-5-isopropoxybenzoate (2) (3.00 g, 94%) was prepared from methyl 4-(benzyloxy)-3-chloro-5-hydroxybenzoate (1) (Synthesis 49 (2.73 g, 9.33 mmol) using a procedure essentially the same as in step (i) for AAA-001 except that isopropyl bromide was used instead of cyclopentyl bromide: m/z 335 [M+H]$^+$ (ES$^+$). $^1$H NMR (400 MHz, CDCl$_3$) δ: 7.68 (1H, d), 7.56-7.47 (3H, m), 7.43-7.28 (3H, m), 5.12 (2H, s), 4.66 (1H, sep), 3.90 (3H, s), 1.38 (6H, d).

Step (ii): Methyl 3-chloro-4-hydroxy-5-isopropoxybenzoate (3)

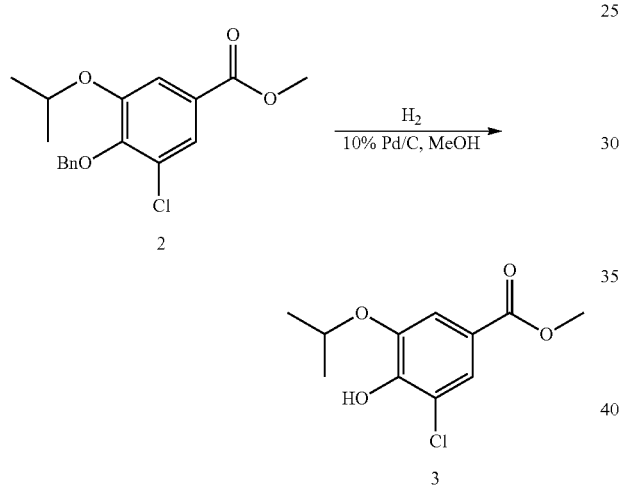

Methyl 4-(benzyloxy)-3-chloro-5-isopropoxybenzoate (2) (3.00 g, 8.96 mmol) was dissolved in a mixture of MeOH (100 mL), DCM (10 mL) and AcOH (0.1 mL) and the solution was passed through a Thales 'H-cube' cartridge (10% Pd/C) at a flow rate of 1 mL/min at 25° C. under H$_2$ (full H$_2$ mode). The solvents were removed in vacuo to afford methyl 3-chloro-4-hydroxy-5-isopropoxybenzoate (3) (2.03 g, 89%): m/z 245 [M+H]$^+$ (ES$^+$), 243 [M−H](ES$^−$).

Step (iii): Methyl 3-chloro-5-isopropoxy-4-methoxybenzoate (4)

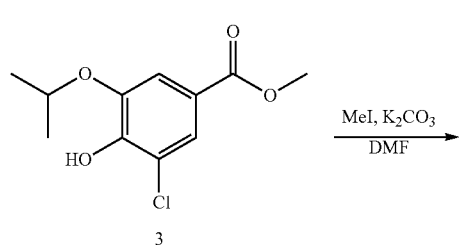

Methyl 3-chloro-5-isopropoxy-4-methoxybenzoate (4) (1.06 g, 95%) was prepared from methyl 3-chloro-4-hydroxy-5-isopropoxybenzoate (3) (1.00 g, 4.09 mmol) using a procedure essentially the same as in step (i) for AAA-001 except that methyl iodide was used instead of cyclopentyl bromide and the mixture was stirred at RT for 18 h.

Step (iv): 3-Chloro-5-isopropoxy-4-methoxybenzoic acid (5)

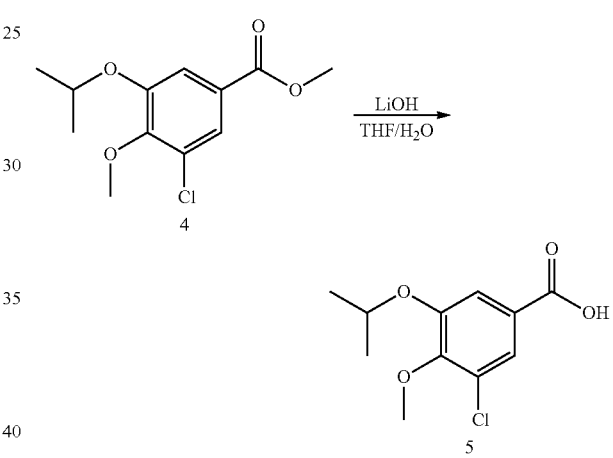

3-Chloro-5-isopropoxy-4-methoxybenzoic acid (5) (0.93 g, 89%) was prepared from methyl 3-chloro-5-isopropoxy-4-methoxybenzoate (4) (1.06 g, 4.10 mmol) using a procedure essentially the same as in step (ii) for AAA-001 except that MeOH instead of water was added dropwise until a solution formed: m/z 243 [M−H]$^−$ (ES$^−$).

Step (v): Methyl 4-(3-chloro-5-isopropoxy-4-methoxybenzamido)-2-methylbenzoate (7)

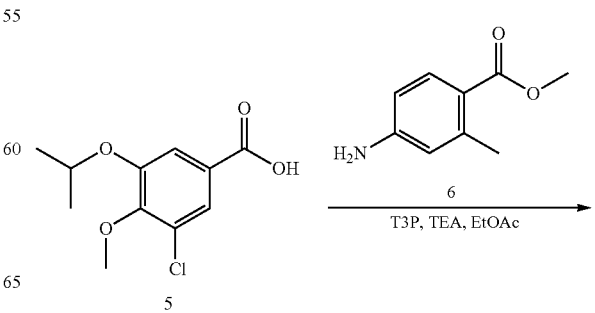

163

-continued

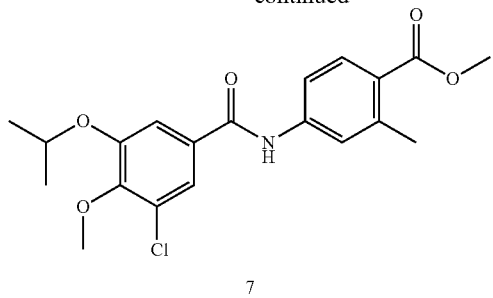

7

A mixture of 3-chloro-5-isopropoxy-4-methoxybenzoic acid (5) (250 mg, 1.02 mmol), methyl 4-amino-2-methylbenzoate (6) (177 mg, 1.07 mmol) and TEA (150 µL, 1.07 mmol) in EtOAc (2.5 mL) was treated with T3P (50% in EtOAc) (1.63 mL, 2.55 mmol) and the mixture was heated at 60° C. for 5 h. The mixture was diluted with DCM (5 mL) and washed with 1M HCl (5 mL) followed by satd. NaHCO₃ solution (5 mL). The organic solvents were removed in vacuo and the residue purified by silica gel chromatography (12 g, 0-100% EtOAc in isohexane to yield methyl 4-(3-chloro-5-isopropoxy-4-methoxybenzamido)-2-methylbenzoate (7) (167 mg, 40%): m/z 392 [M+H]⁺ (ES⁺), 390 [M−H]⁻ (ES⁻). ¹H NMR (400 MHz, CDCl₃) δ:7.98 (1H, d), 7.78 (1H, s), 7.59-7.50 (2H, m), 7.40 (2H, dd), 4.67 (1H, sep), 3.94 (3H, s), 3.89 (3H, s), 2.62 (3H, s), 1.40 (6H, d).

Step (vi): 4-(3-Chloro-5-isopropoxy-4-methoxybenzamido)-2-methylbenzoic acid (AAA-075)

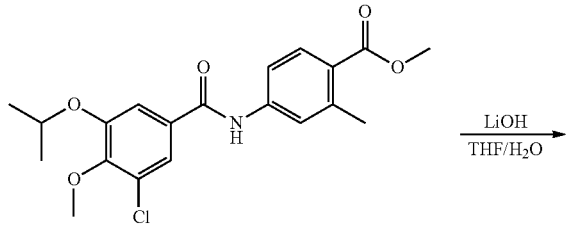

7

LiOH
THF/H₂O

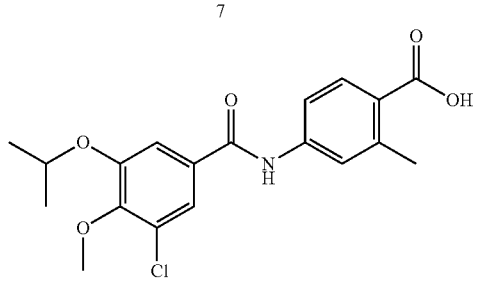

4-(3-Chloro-5-isopropoxy-4-methoxybenzamido)-2-methylbenzoic acid (AAA-075) (94 mg, 57%) was prepared from methyl 4-(3-chloro-5-isopropoxy-4-methoxybenzamido)-2-methylbenzoate (7) (167 mg, 4.10 mmol) using a procedure essentially the same as in step (ii) for AAA-001 except that MeOH was added dropwise until a solution formed and the mixture was stirred at 40° C. for 18 h: m/z 378 [M+H]⁺ (ES⁺), 376 [M−H]⁻ (ES⁻). ¹H NMR (400 MHz, DMSO-d₆) δ:12.63 (1H, br s), 10.34 (1H, s), 7.86 (1H, d), 7.75-7.63 (3H, m), 7.57 (1H, d), 4.77 (1H, sep), 3.83 (3H, s), 2.53 (3H, s), 1.34 (6H, d).

164

Synthesis 78

4-(3-Chloro-5-isopropoxy-4-methoxybenzamido)benzoic acid (AAA-076)

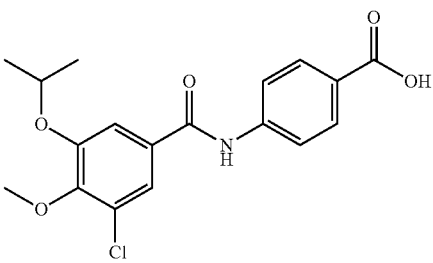 [SMILES: COc1c(Cl)cc(C(=O)Nc2ccc(C(=O)O)cc2)cc1OC(C)C]

4-(3-Chloro-5-isopropoxy-4-methoxybenzamido)benzoic acid (AAA-076) (47 mg, 56% for final step) was prepared in essentially the same manner as AAA-075 except that methyl 4-aminobenzoate was used instead of methyl 4-amino-2-methylbenzoate in step (v): m/z 364 [M+H]⁺ (ES⁺), 362 [M−H]⁻ (ES⁻). ¹H NMR (400 MHz, DMSO-d₆) δ:12.78 (1H, br s), 10.47 (1H, s), 7.94 (2H, d), 7.88 (2H, d), 7.69 (1H, d), 7.58 (1H, d), 4.78 (1H, sep), 3.83 (3H, s), 1.33 (6H, d).

Synthesis 79

4-(3-Chloro-5-isopropoxy-4-methoxybenzamido)-2-fluorobenzoic acid (AAA-077)

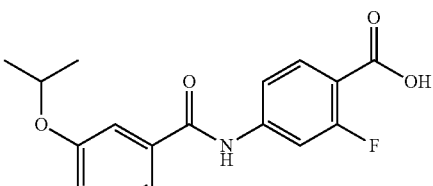

4-(3-Chloro-5-isopropoxy-4-methoxybenzamido)-2-fluorobenzoic acid (AAA-077) (116 mg, 76% for final step) was prepared in essentially the same manner as AAA-075 except that methyl 4-amino-2-fluorobenzoate was used instead of methyl 4-amino-2-methylbenzoate in step (v): m/z 380 [M−H]⁻ (ES⁻). ¹H NMR (400 MHz, DMSO-d₆) δ:13.03 (1H, br s), 10.60 (1H, s), 7.90 (1H, t), 7.82 (1H, dd), 7.69 (1H, d), 7.63 (1H, dd), 7.57 (1H, d), 4.78 (1H, sep), 3.85 (3H, s), 1.35 (6H, d).

Synthesis 80

4-(3-Chloro-4-ethoxy-5-isopropoxybenzamido)benzoic acid (AAA-078)

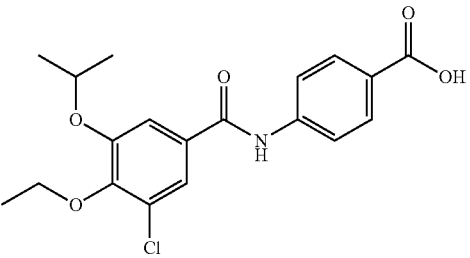 [SMILES: CCOc1c(Cl)cc(C(=O)Nc2ccc(C(=O)O)cc2)cc1OC(C)C]

4-(3-Chloro-4-ethoxy-5-isopropoxybenzamido)benzoic acid (AAA-078) (145 mg, 80% for final step) was prepared in essentially the same manner as AAA-075 except that ethyl iodide was used instead of methyl iodide in step(iii) and methyl 4-aminobenzoate was used instead of methyl 4-amino-2-methylbenzoate in step (v): m/z 378 [M+H]+ (ES+), 376 [M−H]− (ES−). $^1$H NMR (400 MHz, DMSO-d$_6$) δ: 12.77 (1H, br s), 10.46 (1H, s), 7.97-7.90 (2H, m), 7.90-7.84 (2H, m), 7.68 (1H, d), 7.55 (1H, d), 4.75 (1H, sep), 4.11 (2H, q), 1.35-1.28 (9H, m).

Synthesis 81

4-(3-Chloro-4-ethoxy-5-isopropoxybenzamido)-2-fluorobenzoic acid (AAA-079)

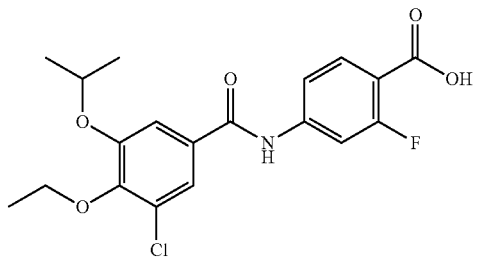 [SMILES: CCOc1c(Cl)cc(C(=O)Nc2ccc(C(=O)O)c(F)c2)cc1OC(C)C]

4-(3-Chloro-4-ethoxy-5-isopropoxybenzamido)-2-fluorobenzoic acid (AAA-079) (120 mg, 78% for final step) was prepared in essentially the same manner as AAA-075 except that ethyl iodide was used instead of methyl iodide in step(iii) and methyl 4-amino-2-fluorobenzoate was used instead of methyl 4-amino-2-methylbenzoate in step (v): m/z 394 [M−H]− (ES−). $^1$H NMR (400 MHz, DMSO-d$_6$) δ: 13.02 (1H, br s), 10.60 (1H, s), 7.90 (1H, t), 7.82 (1H, dd), 7.69 (1H, d), 7.63 (1H, dd), 7.55 (1H, d), 4.76 (1H, sep), 4.13 (2H, q), 1.38-1.27 (9H, m).

Synthesis 82

4-(3-Chloro-4-ethoxy-5-isopropoxybenzamido)-2-methylbenzoic acid (AAA-080)

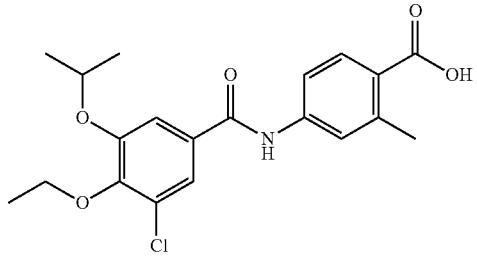 [SMILES: CCOc1c(Cl)cc(C(=O)Nc2ccc(C(=O)O)c(C)c2)cc1OC(C)C]

4-(3-Chloro-4-ethoxy-5-isopropoxybenzamido)-2-methylbenzoic acid (AAA-080) (155 mg, 74% for final step) was prepared in essentially the same manner as AAA-075 except that ethyl iodide was used instead of methyl iodide in step(iii): m/z 392 [M+H]+ (ES+), 390 [M−H]− (ES−). $^1$H NMR (400 MHz, DMSO-d$_6$) δ:12.64 (1H, br s), 10.34 (1H, s), 7.86 (1H, d), 7.74-7.63 (3H, m), 7.55 (1H, d), 4.75 (1H, sep), 4.10 (2H, q), 2.52 (3H, s), 1.37-1.26 (9H, m).

Synthesis 83

4-(3-Chloro-4-ethoxy-5-isopropoxybenzamido)-2-hydroxybenzoic acid (AAA-081)

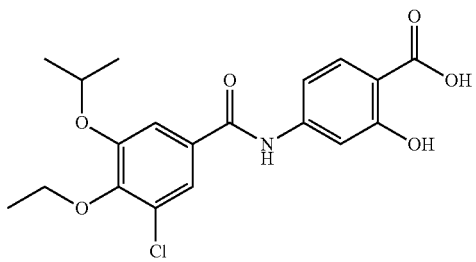 [SMILES: CCOc1c(Cl)cc(C(=O)Nc2ccc(C(=O)O)c(O)c2)cc1OC(C)C]

4-(3-Chloro-4-ethoxy-5-isopropoxybenzamido)-2-hydroxybenzoic acid (AAA-081) (29 mg, 37% for final step) was prepared in essentially the same manner as AAA-075 except that ethyl iodide was used instead of methyl iodide in step(iii) and methyl 4-amino-2-hydroxybenzoate was used instead of methyl 4-amino-2-methylbenzoate in step (v): m/z 394 [M+H]+ (ES+), 392 [M−H]− (ES−). $^1$H NMR (400 MHz, DMSO-d$_6$) δ: 13.78 (1H, br s), 11.40 (1H, br s), 10.40 (1H, s), 7.77 (1H, d), 7.67 (1H, d), 7.52 (2H, dd), 7.30 (1H, dd), 4.77 (1H, sep), 4.12 (2H, q), 1.37-1.28 (9H, m).

Synthesis 84

6-(3-Chloro-4-ethoxy-5-isopropoxybenzamido)pyridazine-3-carboxylic acid (AAA-082)

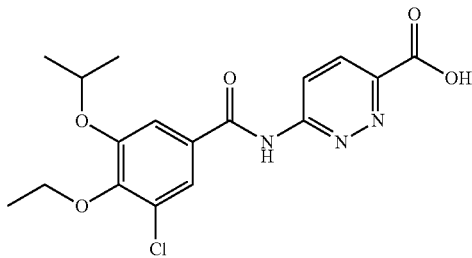 [SMILES: CCOc1c(Cl)cc(C(=O)Nc2ccc(C(=O)O)nn2)cc1OC(C)C]

6-(3-Chloro-4-ethoxy-5-isopropoxybenzamido)pyridazine-3-carboxylic acid (AAA-082) (25 mg, 43% for final step) was prepared in essentially the same manner as AAA-075 except that ethyl iodide was used instead of methyl iodide in step(iii) and methyl 6-aminopyridazine-3-carboxylate was used instead of methyl 4-amino-2-methylbenzoate in step (v): m/z 380 [M+H]+ (ES+), 378 [M−H]− (ES−). $^1$H NMR (400 MHz, DMSO-d$_6$) δ: 13.73 (1H, br s), 11.91 (1H, s), 8.55 (1H, d), 8.26 (1H, d), 7.79 (2H, dd), 4.85 (1H, sep), 4.14 (2H, q), 1.42-1.27 (9H, m).

Synthesis 85

4-(3-Chloro-4-isopropoxy-5-methoxybenzamido)benzoic acid (AAA-083)

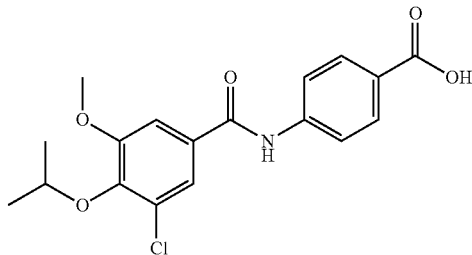 [SMILES: COc1cc(C(=O)Nc2ccc(C(=O)O)cc2)cc(Cl)c1OC(C)C]

4-(3-Chloro-4-isopropoxy-5-methoxybenzamido)benzoic acid (AAA-083) (116 mg, 55% for final step) was prepared in essentially the same manner as AAA-075 except that methyl iodide at RT was used instead of isopropyl bromide in step(i), isopropyl bromide at 60° C. was used instead of methyl iodide in step (iii) and methyl 4-aminobenzoate was used instead of methyl 4-amino-2-methylbenzoate in step (v): m/z 364 [M+H]$^+$ (ES$^+$), 362 [M–H]$^-$ (ES$^-$). $^1$H NMR (400 MHz, DMSO-d$_6$) δ: 12.76 (1H, br s), 10.50 (1H, s), 8.03-7.80 (4H, m), 7.70 (1H, d), 7.56 (1H, d), 4.59 (1H, sep), 3.92 (3H, s), 1.27 (6H, d).

Synthesis 86

4-(3-Chloro-4-ethoxy-5-methoxybenzamido)benzoic acid (AAA-084)

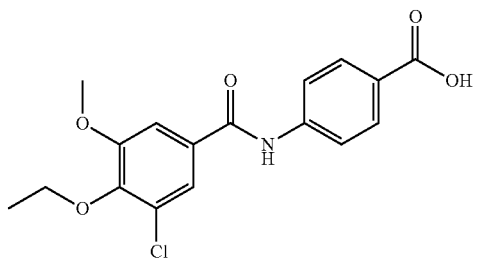 [SMILES: CCOc1c(Cl)cc(C(=O)Nc2ccc(C(=O)O)cc2)cc1OC]

4-(3-Chloro-4-ethoxy-5-methoxybenzamido)benzoic acid (AAA-084) (16 mg, 46% for final step) was prepared in essentially the same manner as AAA-019 except that 3-chloro-4-ethoxy-5-methoxybenzoic acid (prepared in 3 steps from methyl 4-hydroxy-3-methoxybenzoate by sequential treatment with sulfuryl chloride, ethyl iodide and base and then lithium hydroxide) was used instead of 3,5-dichloro-4-ethoxybenzoic acid and methyl 4-aminobenzoate was used instead of methyl 4-amino-2-methylbenzoate in step(i): m/z 350 [M+H]$^+$ (ES$^+$), 348 [M–H]$^-$ (ES$^-$). $^1$H NMR (400 MHz, DMSO-d$_6$) δ: 12.75 (1H, br s), 10.48 (1H, s), 7.91 (4H, dd), 7.70 (1H, d), 7.57 (1H, d), 4.09 (2H, q), 3.92 (3H, s), 1.31 (3H, t).

Synthesis 87

4-(3-Chloro-4-ethoxy-5-methoxybenzamido)-2-methylbenzoic acid (AAA-085)

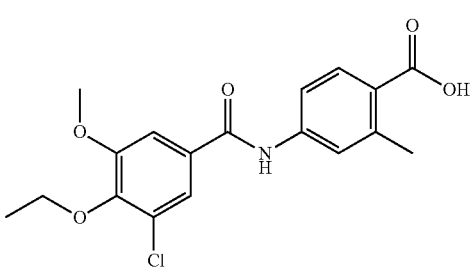 [SMILES: CCOc1c(Cl)cc(C(=O)Nc2ccc(C(=O)O)c(C)c2)cc1OC]

4-(3-Chloro-4-ethoxy-5-methoxybenzamido)-2-methylbenzoic acid (AAA-085) (97 mg, 52% for final step) was prepared in essentially the same manner as AAA-019 except that 3-chloro-4-ethoxy-5-methoxybenzoic acid (prepared in 3 steps from methyl 4-hydroxy-3-methoxybenzoate by sequential treatment with sulfuryl chloride, ethyl iodide and base and then lithium hydroxide) was used instead of 3,5-dichloro-4-ethoxybenzoic acid in step(i): m/z 364 [M+H]$^+$ (ES$^+$), 362 [M–H]$^-$ (ES$^-$). $^1$H NMR (400 MHz, DMSO-d$_6$) δ: 12.65 (1H, br s), 10.39 (1H, s), 7.88 (1H, d), 7.76-7.66 (3H, m), 7.58 (1H, d), 4.10 (2H, q), 3.93 (3H, s), 2.55 (3H, s), 1.32 (3H, t).

Synthesis 88

4-(3-Chloro-5-ethoxy-4-isopropoxybenzamido)benzoic acid (AAA-086)

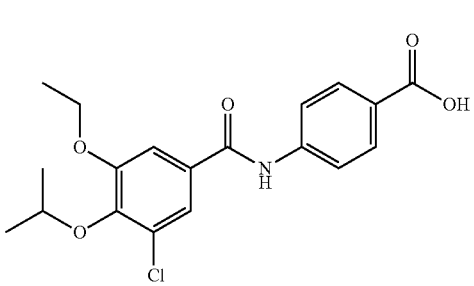 [SMILES: CCOc1cc(C(=O)Nc2ccc(C(=O)O)cc2)cc(Cl)c1OC(C)C]

4-(3-Chloro-5-ethoxy-4-isopropoxybenzamido)benzoic acid (AAA-086) (10 mg, 4% for final step) was prepared in essentially the same manner as AAA-075 except that ethyl iodide at RT was used instead of isopropyl bromide in step(i), isopropyl bromide at 60° C. was used instead of methyl iodide in step (iii) and methyl 4-aminobenzoate was used instead of methyl 4-amino-2-methylbenzoate in step (v): m/z 378 [M+H]$^+$ (ES$^+$), 376 [M–H]$^-$ (ES$^-$). $^1$H NMR (400 MHz, DMSO-d$_6$) δ: 12.70 (1H, br s), 10.39 (1H, s), 7.93-7.73 (4H, m), 7.61 (1H, d), 7.47 (1H, d), 4.51 (1H, sep), 4.09 (2H, q), 1.31 (3H, t), 1.20 (6H, d).

Synthesis 89

4-(3-Chloro-5-ethoxy-4-isopropoxybenzamido)-2-methylbenzoic acid (AAA-087)

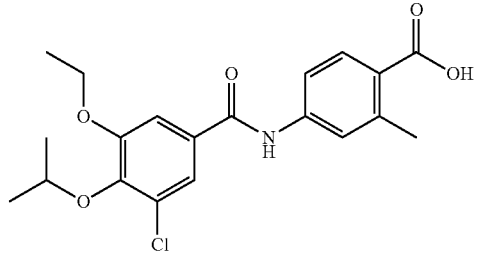 [SMILES: CCOc1cc(C(=O)Nc2ccc(C(=O)O)c(C)c2)cc(Cl)c1OC(C)C]

4-(3-Chloro-5-ethoxy-4-isopropoxybenzamido)-2-methylbenzoic acid (AAA-087) (129 mg, 56% for final step) was prepared in essentially the same manner as AAA-075 except that ethyl iodide at RT was used instead of isopropyl bromide in step(i) and isopropyl bromide at 60° C. was used instead of methyl iodide in step (iii): m/z 390 [M–H]⁻ (ES⁻). ¹H NMR (400 MHz, DMSO-d$_6$) δ: 12.68 (1H, s), 10.40 (1H, s), 7.92 (1H, d), 7.81-7.69 (3H, m), 7.59 (1H, d), 4.64 (1H, sep), 4.21 (2H, q), 2.58 (3H, s), 1.45 (3H, t), 1.33 (6H, d).

Synthesis 90

4-(3-Chloro-5-(cyclobutoxy)-4-ethoxybenzamido)benzoic acid (AAA-088)

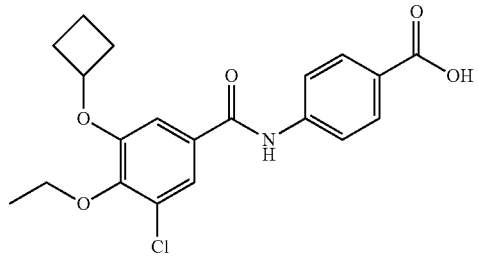 [SMILES: CCOc1c(Cl)cc(C(=O)Nc2ccc(C(=O)O)cc2)cc1OC1CCC1]

4-(3-Chloro-5-(cyclobutoxy)-4-ethoxybenzamido)benzoic acid (AAA-088) (112 mg, 41% for final step) was prepared in essentially the same manner as AAA-075 except that cyclobutyl bromide was used instead of isopropyl bromide in step (i), ethyl iodide was used instead of methyl iodide in step (iii) and methyl 4-aminobenzoate was used instead of methyl 4-amino-2-methylbenzoate in step (v): m/z 388 [M–H]⁻ (ES⁻). ¹H NMR (400 MHz, DMSO-d$_6$) δ: 12.75 (1H, br s), 10.46 (1H, s), 7.95-7.86 (4H, m), 7.71 (1H, d), 7.37 (1H, d), 4.85 (1H, quin), 4.14 (2H, q), 2.49-2.42 (2H, m), 2.19-2.01 (2H, m), 1.92-1.58 (2H, m), 1.33 (3H, t).

Synthesis 91

4-(3-Chloro-5-(cyclopropylmethoxy)-4-ethoxybenzamido)benzoic acid (AAA-089)

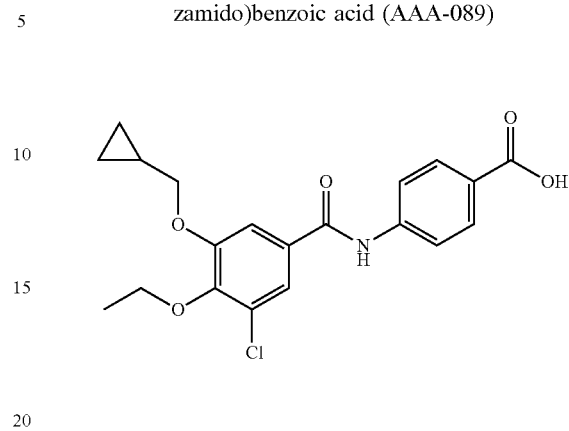

4-(3-Chloro-5-(cyclopropylmethoxy)-4-ethoxybenzamido)benzoic acid (AAA-089) (255 mg, 90% for final step) was prepared in essentially the same manner as AAA-075 except that bromomethylcyclopropane was used instead of isopropyl bromide in step (i), ethyl iodide was used instead of methyl iodide in step (iii) and methyl 4-aminobenzoate was used instead of methyl 4-amino-2-methylbenzoate in step (v): m/z 388 [M–H]⁻ (ES⁻). ¹H NMR (400 MHz, DMSO-d$_6$) δ: 12.76 (1H br s), 10.46 (1H, s), 7.92 (4H, dd), 7.70 (1H, d), 7.55 (1H, d), 4.17 (2H, q), 4.00 (2H, d), 1.34 (3H, t), 1.31-1.24 (1H, m), 0.66-0.55 (2H, m), 0.42-0.31 (2H, m).

Synthesis 92

4-(3-Chloro-5-(cyclopropylmethoxy)-4-ethoxybenzamido)-2-hydroxybenzoic acid (AAA-090)

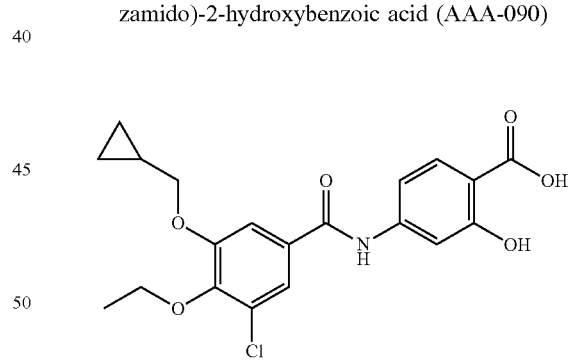

4-(3-Chloro-5-(cyclopropylmethoxy)-4-ethoxybenzamido)-2-hydroxybenzoic acid (AAA-090) (76 mg, 90% for final step) was prepared in essentially the same manner as AAA-075 except that bromomethylcyclopropane was used instead of isopropyl bromide in step (i), ethyl iodide was used instead of methyl iodide in step (iii) and methyl 4-amino-2-hydroxybenzoate was used instead of methyl 4-amino-2-methylbenzoate in step (v): m/z 406 [M+H]⁺ (ES⁺), 404 [M–H]⁻ (ES⁻). ¹H NMR (400 MHz, DMSO-d$_6$) δ: 13.72 (1H, br s), 11.40 (1H, br s), 10.39 (1H, s), 7.77 (1H, d), 7.68 (1H, d), 7.52 (2H, dd), 7.30 (1H, dd), 4.17 (2H, q), 4.00 (2H, d), 1.34 (3H, t), 1.31-1.24 (1H, m), 0.68-0.54 (2H, m), 0.44-0.31 (2H, m).

Synthesis 93

4-(3-Chloro-4,5-diisopropoxybenzamido)-2-hydroxybenzoic acid (AAA-091)

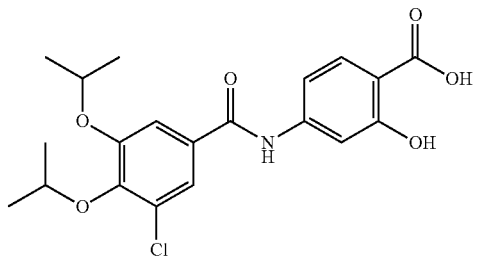 [SMILES: CC(C)Oc1cc(C(=O)Nc2ccc(C(=O)O)c(O)c2)cc(Cl)c1OC(C)C]

4-(3-Chloro-4,5-diisopropoxybenzamido)-2-hydroxybenzoic acid (AAA-091) (43 mg, 63% for final step) was prepared in essentially the same manner as in steps (v) and (vi) for AAA-075 except that 3-chloro-4,5-diisopropoxybenzoic acid (Synthesis 52) was used instead of 3-chloro-5-isopropoxy-4-methoxybenzoic acid and methyl 4-amino-2-hydroxybenzoate was used instead of methyl 4-amino-2-methylbenzoate in step (v): m/z 408 [M+H]$^+$ (ES$^+$), 406 [M−H]$^-$ (ES$^-$). $^1$H NMR (400 MHz, DMSO-d$_6$) δ: 13.75 (1H, br s), 11.40 (1H, br s), 10.39 (1H, s), 7.77 (1H, d), 7.67 (1H, d), 7.52 (2H, dd), 7.30 (1H, dd), 4.77 (1H, sep), 4.60 (1H, sep), 1.33 (6H, d), 1.28 (6H, d).

Synthesis 94

4-(3-Chloro-4,5-di(cyclobutyloxy)benzamido)benzoic acid (AAA-092)

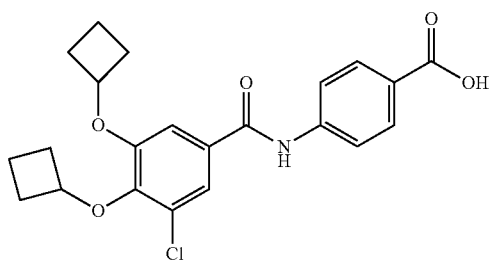 [SMILES: O=C(O)c1ccc(NC(=O)c2cc(Cl)c(OC3CCC3)c(OC3CCC3)c2)cc1]

4-(3-Chloro-4,5-di(cyclobutyloxy)benzamido)benzoic acid (AAA-092) (137 mg, 54% for final step) was prepared in essentially the same manner as in steps (v) and (vi) for AAA-075 except that 3-chloro-4,5-di(cyclobutyloxy)benzoic acid (prepared in 4 steps from 3-chloro-4-hydroxy-5-methoxybenzoic acid by sequential treatment with BBr$_3$, TMSCl and MeOH, cyclobutyl bromide and base and then lithium hydroxide) was used instead of 3-chloro-5-isopropoxy-4-methoxybenzoic acid and methyl 4-aminobenzoate was used instead of methyl 4-amino-2-methylbenzoate in step (v): m/z 414 [M−H]$^-$ (ES$^-$). $^1$H NMR (400 MHz, DMSO-d$_6$) δ: 12.76 (1H, br s), 10.46 (1H, s), 7.98-7.83 (4H, m), 7.70 (1H, d), 7.34 (1H, d), 4.83 (1H, quin), 4.71 (1H, quin), 2.49-2.42 (2H, m), 2.36-2.01 (6H, m), 1.92-1.61 (3H, m), 1.57-1.37 (1H, m).

Synthesis 95

4-(3-Chloro-4,5-di(cyclobutyloxy)benzamido)-2-methylbenzoic acid (AAA-093)

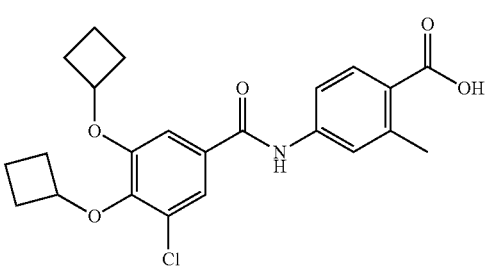 [SMILES: Cc1cc(NC(=O)c2cc(Cl)c(OC3CCC3)c(OC3CCC3)c2)ccc1C(=O)O]

4-(3-Chloro-4,5-di(cyclobutyloxy)benzamido)-2-methylbenzoic acid (AAA-093) (83 mg, 99% for final step) was prepared in essentially the same manner as in steps (v) and (vi) for AAA-075 except that 3-chloro-4,5-di(cyclobutyloxy)benzoic acid (Synthesis 94) was used instead of 3-chloro-5-isopropoxy-4-methoxybenzoic in step (v): m/z 428 [M−H]$^-$ (ES$^-$). $^1$H NMR (400 MHz, DMSO-d$_6$) δ: 12.62 (1H, br s), 10.35 (1H, s), 7.87 (1H, d), 7.73-7.66 (3H, m), 7.35 (1H, d), 4.84 (1H, quin), 4.72 (1H, quin), 2.55 (3H, s), 2.49-2.41 (2H, m), 2.22-2.06 (6H, m), 1.84-1.65 (3H, m), 1.54-1.42 (1H, m).

Synthesis 96

4-(3-Chloro-4,5-di(cyclobutyloxy)benzamido)-2-hydroxybenzoic acid (AAA-094)

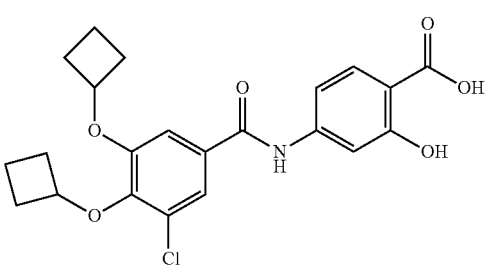 [SMILES: O=C(Nc1ccc(C(=O)O)c(O)c1)c1cc(Cl)c(OC2CCC2)c(OC2CCC2)c1]

4-(3-Chloro-4,5-di(cyclobutyloxy)benzamido)-2-hydroxybenzoic acid (AAA-094) (33 mg, 75% for final step) was prepared in essentially the same manner as in steps (v) and (vi) for AAA-075 except that 3-chloro-4,5-di(cyclobutyloxy)benzoic acid (Synthesis 94) was used instead of 3-chloro-5-isopropoxy-4-methoxybenzoic acid and methyl 4-amino-2-hydroxybenzoate was used instead of methyl 4-amino-2-methylbenzoate in step (v): m/z 432 [M+H]$^+$ (ES$^+$), 430 [M−H]$^-$ (ES$^-$). $^1$H NMR (400 MHz, DMSO-d$_6$) δ: 10.39 (1H, s), 7.76 (1H, d), 7.69 (1H, d), 7.49 (1H, d), 7.35-7.25 (2H, m), 4.88-4.80 (1H, m), 4.76-4.67 (1H, m), 2.48-2.43 (2H, m), 2.29-2.05 (6H, m), 1.87-1.81 (1H, m), 1.76-1.65 (2H, m), 1.53-1.44 (1H, m).

Synthesis 97

4-(3-Chloro-4,5-diisopropoxybenzamido)-2-fluorobenzoic acid (AAA-095)

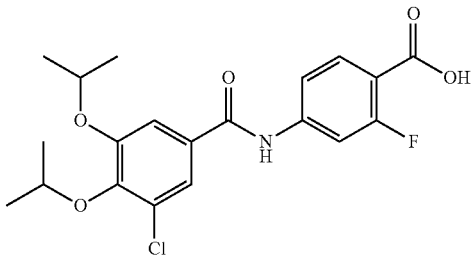

4-(3-Chloro-4,5-diisopropoxybenzamido)-2-fluorobenzoic acid (AAA-095) (207 mg, 93% for final step) was prepared in essentially the same manner as in steps (v) and (vi) for AAA-075 except that 3-chloro-4,5-diisopropoxybenzoic acid (Synthesis 52) was used instead of 3-chloro-5-isopropoxy-4-methoxybenzoic acid and methyl 4-amino-2-fluorobenzoate was used instead of methyl 4-amino-2-methylbenzoate in step (v): m/z 410 [M+H]$^+$ (ES$^+$), 408 [M−H](ES$^-$). $^1$H NMR (400 MHz, DMSO-d$_6$) δ: 13.05 (1H, br s), 10.61 (1H, s), 7.90 (1H, t), 7.82 (1H, dd), 7.69 (1H, d), 7.63 (1H, dd), 7.54 (1H, d), 4.77 (1H, sep), 4.61 (1H, sep), 1.34 (6H, d), 1.28 (6H, d).

Synthesis 98

4-(3-Chloro-5-(cyclobutoxy)-4-ethoxybenzamido)-2-methylbenzoic acid (AAA-096)

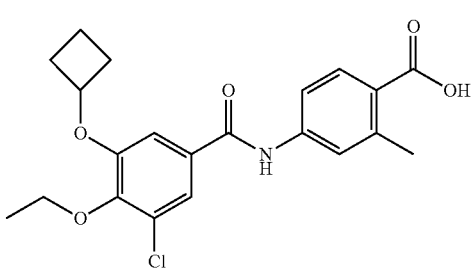 [SMILES: CCOc1c(Cl)cc(C(=O)Nc2ccc(C(=O)O)c(C)c2)cc1OC1CCC1]

4-(3-Chloro-5-(cyclobutoxy)-4-ethoxybenzamido)-2-methylbenzoic acid (AAA-096) (127 mg, 69% for final step) was prepared in essentially the same manner as AAA-075 except that cyclobutyl bromide was used instead of isopropyl bromide in step (i) and ethyl iodide was used instead of methyl iodide in step (iii): m/z 402 [M−H]$^-$ (ES$^-$). $^1$H NMR (400 MHz, DMSO-d$_6$) δ: 12.62 (1H, br s), 10.35 (1H, s), 7.87 (1H, d), 7.76-7.66 (3H, m), 7.38 (1H, d), 4.86 (1H, quin), 4.14 (2H, q), 2.53 (3H, s), 2.50-2.43 (2H, m), 2.19-2.03 (2H, m), 1.84 (1H, q), 1.69 (1H, dq), 1.34 (3H, t).

Synthesis 99

4-(3-Chloro-5-(cyclopropylmethoxy)-4-ethoxybenzamido)-2-methylbenzoic acid (AAA-097)

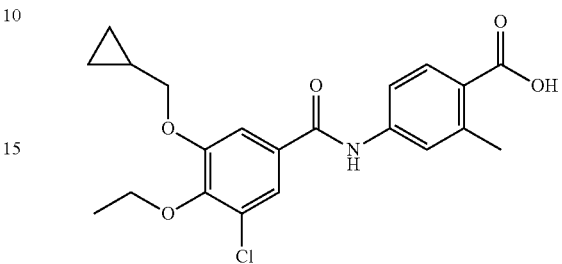

4-(3-Chloro-5-(cyclopropylmethoxy)-4-ethoxybenzamido)-2-methylbenzoic acid (AAA-097) (105 mg, 56% for final step) was prepared in essentially the same manner as AAA-075 except that bromomethylcyclopropane was used instead of isopropyl bromide in step (i) and ethyl iodide was used instead of methyl iodide in step (iii): m/z 402 [M−H]$^-$ (ES$^-$). $^1$H NMR (400 MHz, DMSO-d$_6$) δ: 12.65 (1H, br s), 10.35 (1H, s), 7.88 (1H, d), 7.75-7.65 (3H, m), 7.55 (1H, d), 4.17 (2H, q), 4.00 (2H, d), 2.54 (3H, s), 1.34 (3H, t), 1.31-1.25 (1H, m), 0.65-0.58 (2H, m), 0.43-0.35 (2H, m).

Synthesis 100

4-(3-Chloro-5-cyclobutoxy-4-methoxybenzamido)benzoic acid (AAA-098)

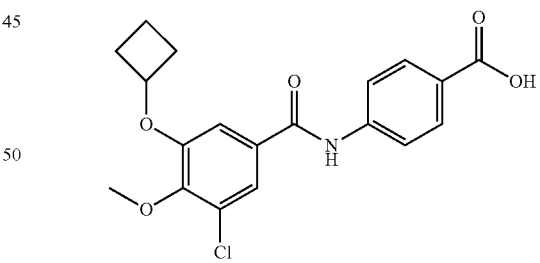

4-(3-Chloro-5-cyclobutoxy-4-methoxybenzamido)benzoic acid (AAA-098) (232 mg, 78% for final step) was prepared in essentially the same manner as AAA-075 except that cyclobutyl bromide was used instead of isopropyl bromide in step (i) and methyl 4-aminobenzoate was used instead of methyl 4-amino-2-methylbenzoate in step (v): m/z 374 [M−H]$^-$ (ES$^-$). $^1$H NMR (400 MHz, DMSO-d$_6$) δ: 12.79 (1H, br s), 10.49 (1H, s), 8.11-7.82 (4H, m), 7.73 (1H, d), 7.39 (1H, d), 4.87 (1H, quin), 3.87 (3H, s), 2.49-2.43 (2H, m), 2.30-1.97 (2H, m), 1.83 (1H, q), 1.69 (1H, dq).

Synthesis 101

4-(3-Chloro-5-cyclobutoxy-4-methoxybenzamido)-2-methylbenzoic acid (AAA-099)

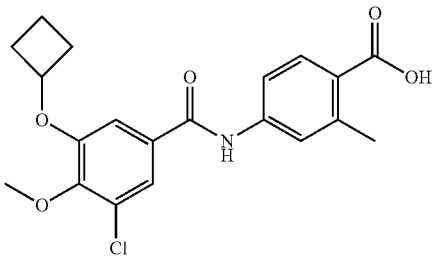 [SMILES: COc1c(Cl)cc(C(=O)Nc2ccc(C(=O)O)c(C)c2)cc1OC1CCC1]

4-(3-Chloro-5-cyclobutoxy-4-methoxybenzamido)-2-methylbenzoic acid (AAA-099) (170 mg, 75% for final step) was prepared in essentially the same manner as AAA-075 except that cyclobutyl bromide was used instead of isopropyl bromide in step (i): m/z 388 [M–H]$^-$ (ES$^-$). $^1$H NMR (400 MHz, DMSO-d$_6$) δ: 12.64 (1H, br s), 10.37 (1H, s), 7.88 (1H, d), 7.75-7.66 (3H, m), 7.39 (1H, d), 4.87 (1H, quin), 3.87 (3H, s), 2.53 (3H, s), 2.50-2.43 (2H, m), 2.19-2.05 (2H, m), 1.83 (1H, q), 1.76-1.62 (1H, m).

Synthesis 102

4-(3-Chloro-5-cyclobutoxy-4-methoxybenzamido)-2-fluorobenzoic acid (AAA-100)

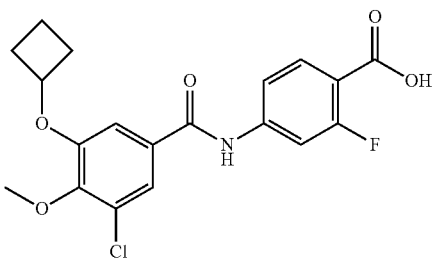 [SMILES: COc1c(Cl)cc(C(=O)Nc2ccc(C(=O)O)c(F)c2)cc1OC1CCC1]

4-(3-Chloro-5-cyclobutoxy-4-methoxybenzamido)-2-fluorobenzoic acid (AAA-100) (274 mg, 84% for final step) was prepared in essentially the same manner as AAA-075 except that cyclobutyl bromide was used instead of isopropyl bromide in step (i) and methyl 4-amino-2-fluorobenzoate was used instead of methyl 4-amino-2-methylbenzoate in step (v): m/z 392 [M–H]$^-$ (ES$^-$). $^1$H NMR (400 MHz, DMSO-d$_6$) δ: 13.06 (1H, br s), 10.62 (1H, s), 7.90 (1H, t), 7.82 (1H, dd), 7.73 (1H, d), 7.63 (1H, dd), 7.38 (1H, d), 4.87 (1H, quin), 3.87 (3H, s), 2.50-2.42 (2H, m), 2.20-2.05 (2H, m), 1.83 (1H, q), 1.69 (1H, dq).

Synthesis 103

4-(3-Chloro-4-methoxy-5-(pentan-3-yloxy)benzamido)benzoic acid (AAA-101)

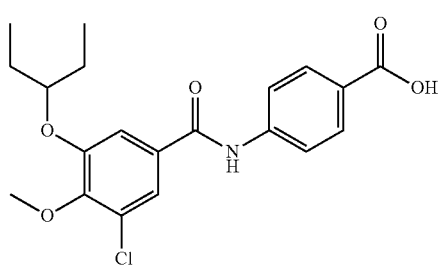 [SMILES: CCC(CC)Oc1cc(C(=O)Nc2ccc(C(=O)O)cc2)cc(Cl)c1OC]

4-(3-Chloro-4-methoxy-5-(pentan-3-yloxy)benzamido)benzoic acid (AAA-101) (232 mg, 97% for final step) was prepared in essentially the same manner as AAA-075 except that 3-bromopentane was used instead of isopropyl bromide in step (i) and methyl 4-aminobenzoate was used instead of methyl 4-amino-2-methylbenzoate in step (v): m/z 390 [M–H]$^-$ (ES$^-$). $^1$H NMR (400 MHz, DMSO-d$_6$) δ: 12.80 (1H, br s), 10.49 (1H, s), 8.01-7.84 (4H, m), 7.69 (1H, d), 7.55 (1H, d), 4.45 (1H, quin), 3.85 (3H, s), 1.79-1.61 (4H, m), 0.95 (6H, t).

Synthesis 104

4-(3-Chloro-4-methoxy-5-(pentan-3-yloxy)benzamido)-2-methylbenzoic acid (AAA-102)

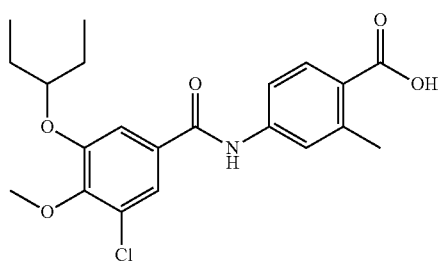 [SMILES: CCC(CC)Oc1cc(C(=O)Nc2ccc(C(=O)O)c(C)c2)cc(Cl)c1OC]

4-(3-Chloro-4-methoxy-5-(pentan-3-yloxy)benzamido)-2-methylbenzoic acid (AAA-102) (156 mg, 60% for final step) was prepared in essentially the same manner as AAA-075 except that 3-bromopentane was used instead of isopropyl bromide in step (i): m/z 404 [M–H]$^-$ (ES$^-$). $^1$H NMR (400 MHz, DMSO-d$_6$) δ: 12.63 (1H, br s), 10.36 (1H, s), 7.87 (1H, d), 7.75-7.65 (3H, m), 7.54 (1H, d), 4.43 (1H, quin), 3.85 (3H, s), 2.54 (3H, s), 1.76-1.62 (4H, m), 0.94 (6H, t).

Synthesis 105

4-(3-Chloro-4-methoxy-5-(pentan-3-yloxy)benzamido)-2-fluorobenzoic acid (AAA-103)

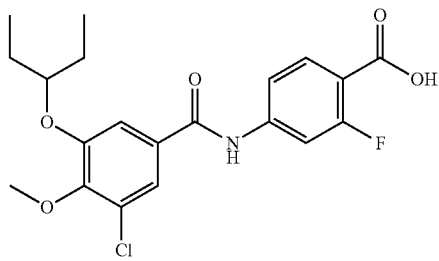 [SMILES: CCC(CC)Oc1cc(C(=O)Nc2ccc(C(=O)O)c(F)c2)cc(Cl)c1OC]

4-(3-Chloro-4-methoxy-5-(pentan-3-yloxy)benzamido)-2-fluorobenzoic acid (AAA-103) (253 mg, 90% for final step) was prepared in essentially the same manner as AAA-075 except that 3-bromopentane was used instead of isopropyl bromide in step (i) and methyl 4-amino-2-fluorobenzoate was used instead of methyl 4-amino-2-methylbenzoate in step (v): m/z 410 [M+H]$^+$ (ES$^+$), 408 [M–H]$^-$ (ES$^-$). $^1$H NMR (400 MHz, DMSO-d$_6$) δ: 13.03 (1H, br s), 10.61 (1H, s), 7.89 (1H, t), 7.81 (1H, dd), 7.68 (1H, d), 7.62 (1H, dd), 7.53 (1H, d), 4.44 (1H, quin), 3.85 (3H, s), 1.77-1.60 (4H, m), 0.94 (6H, t).

Synthesis 106

4-(3-Chloro-4-methoxy-5-(2-methoxyethoxy)benzamido)-2-fluorobenzoic acid (AAA-104)

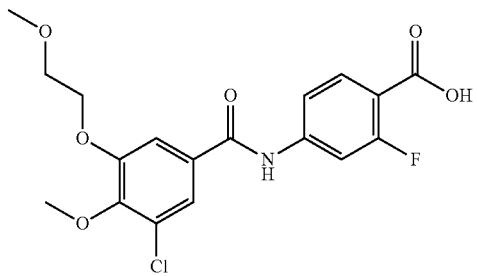 [SMILES: COCCOc1cc(C(=O)Nc2ccc(C(=O)O)c(F)c2)cc(Cl)c1OC]

4-(3-Chloro-4-methoxy-5-(2-methoxyethoxy)benzamido)-2-fluorobenzoic acid (AAA-104) (18 mg, 14% for final step) was prepared in essentially the same manner as AAA-075 except that 2-methoxyethyl bromide was used instead of isopropyl bromide in step (i) and methyl 4-amino-2-fluorobenzoate was used instead of methyl 4-amino-2-methylbenzoate in step (v): m/z 398 [M+H]$^+$ (ES$^+$), 396 [M–H]$^-$ (ES$^-$). $^1$H NMR (400 MHz, DMSO-d$_6$) δ: 12.97 (1H, br s), 10.62 (1H, s), 7.89 (1H, t), 7.81 (1H, dd), 7.70 (1H, d), 7.62 (1H, dd), 7.59 (1H, d), 4.33-4.23 (2H, m), 3.87 (3H, s), 3.78-3.69 (2H, m), 3.34 (3H, s).

Synthesis 107

4-(3-Chloro-4-methoxy-5-(neopentyloxy)benzamido)benzoic acid (AAA-105)

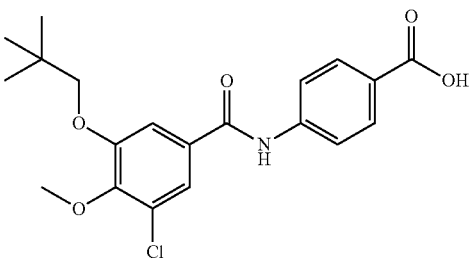 [SMILES: COc1c(Cl)cc(C(=O)Nc2ccc(C(=O)O)cc2)cc1OCC(C)(C)C]

4-(3-Chloro-4-methoxy-5-(neopentyloxy)benzamido) benzoic acid (AAA-105) (83 mg, 45% for final step) was prepared in essentially the same manner as AAA-075 except that neopentyl bromide, Cs$_2$CO$_3$ and NMP at (130° C., microwave, 20 min) were used instead of isopropyl bromide, K$_2$CO$_3$ and DMF in step (i) and methyl 4-aminobenzoate was used instead of methyl 4-amino-2-methylbenzoate in step (v): m/z 390 [M–H]$^-$ (ES$^-$). $^1$H NMR (400 MHz, DMSO-d$_6$) δ: 10.45 (1H, s), 7.90 (4H, m), 7.71 (1H, d), 7.58 (1H, d), 3.91 (3H, s), 3.81 (2H, s), 1.06 (9H, s).

Synthesis 108

4-(4-Bromo-3,5-diethoxybenzamido)benzoic acid (AAA-106)

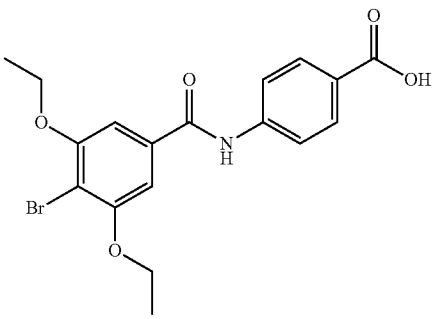 [SMILES: CCOc1cc(C(=O)Nc2ccc(C(=O)O)cc2)cc(OCC)c1Br]

4-(4-Bromo-3,5-diethoxybenzamido)benzoic acid (AAA-106) (300 mg, 62% for final step) was prepared in essentially the same manner as in steps (v) and (vi) for AAA-075 except that 4-bromo-3,5-diethoxybenzoic acid (prepared in 2 steps from 4-bromo-3,5-dihydroxybenzoic acid by sequential treatment with ethyl iodide and base and then lithium hydroxide) was used instead of 3-chloro-5-isopropoxy-4-methoxybenzoic acid and methyl 4-aminobenzoate was used instead of methyl 4-amino-2-methylbenzoate in step (v): m/z 408 [M+H]$^+$ (ES$^+$), 406 [M–H]$^-$ (ES$^-$). $^1$H NMR (400 MHz, DMSO-d$_6$) δ: 12.61 (1H, br s), 10.29 (1H, s), 7.80-7.71 (2H, m), 7.71-7.63 (2H, m), 7.05 (2H, s), 4.01 (4H, q), 1.20 (6H, t).

Synthesis 109

4-(4-Bromo-3,5-diisopropoxybenzamido)benzoic acid (AAA-107)

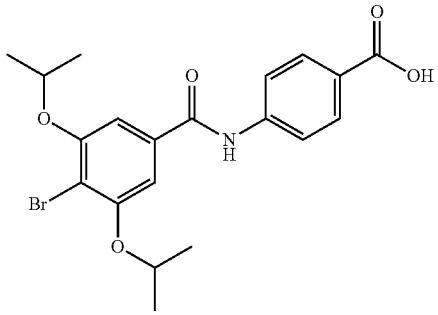 [SMILES: CC(C)Oc1cc(C(=O)Nc2ccc(C(=O)O)cc2)cc(OC(C)C)c1Br]

4-(4-Bromo-3,5-diisopropoxybenzamido)benzoic acid (AAA-107) (338 mg, 63% for final step) was prepared in essentially the same manner as in steps (v) and (vi) for AAA-075 except that 4-bromo-3,5-diisopropoxybenzoic acid (prepared in 2 steps from 4-bromo-3,5-dihydroxybenzoic acid by sequential treatment with isopropyl iodide and base and then lithium hydroxide) was used instead of 3-chloro-5-isopropoxy-4-methoxybenzoic acid and methyl 4-aminobenzoate was used instead of methyl 4-amino-2-methylbenzoate in step (v): m/z 436 [M+H]$^+$ (ES$^+$), 434 [M−H]$^-$ (ES$^-$). $^1$H NMR (400 MHz, DMSO-d$_6$) δ: 12.67 (1H, br s), 10.33 (1H, s), 7.83 (2H, d), 7.75 (2H, d), 7.12 (2H, s), 4.65 (2H, sep), 1.20 (12H, d).

Synthesis 110

4-(4-Bromo-3,5-diisopropoxybenzamido)-2-fluorobenzoic acid (AAA-108)

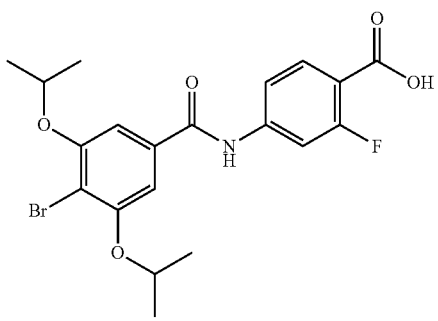 [SMILES: CC(C)Oc1cc(C(=O)Nc2ccc(C(=O)O)c(F)c2)cc(OC(C)C)c1Br]

4-(4-Bromo-3,5-diisopropoxybenzamido)-2-fluorobenzoic acid (AAA-108) (51 mg, 37% for final step) was prepared in essentially the same manner as in steps (v) and (vi) for AAA-075 except that 4-bromo-3,5-diisopropoxybenzoic acid (prepared in 2 steps from 4-bromo-3,5-dihydroxybenzoic acid by sequential treatment with isopropyl iodide and base and then lithium hydroxide) was used instead of 3-chloro-5-isopropoxy-4-methoxybenzoic acid and methyl 4-amino-2-fluorobenzoate was used instead of methyl 4-amino-2-methylbenzoate in step (v): m/z 452 and 454 [M−H]$^-$ (ES$^-$). $^1$H NMR (400 MHz, DMSO-d$_6$) δ: 13.05 (1H, br s), 10.59 (1H, s), 7.91 (1H, t), 7.82 (1H, dd), 7.62 (1H, dd), 7.24 (2H, s), 4.78 (2H, sep), 1.34 (12H, d).

Synthesis 111

4-(4-Bromo-3,5-diisopropoxybenzamido)-2-hydroxybenzoic acid (AAA-109)

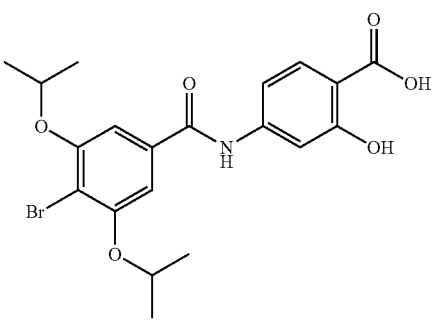 [SMILES: CC(C)Oc1cc(C(=O)Nc2ccc(C(=O)O)c(O)c2)cc(OC(C)C)c1Br]

4-(4-Bromo-3,5-diisopropoxybenzamido)-2-hydroxybenzoic acid (AAA-109) (68 mg, 55% for final step) was prepared in essentially the same manner as in steps (v) and (vi) for AAA-075 except that 4-bromo-3,5-diisopropoxybenzoic acid (prepared in 2 steps from 4-bromo-3,5-dihydroxybenzoic acid by sequential treatment with isopropyl iodide and base and then lithium hydroxide) was used instead of 3-chloro-5-isopropoxy-4-methoxybenzoic acid and methyl 4-amino-2-hydroxybenzoate was used instead of methyl 4-amino-2-methylbenzoate in step (v): m/z 452 [M+H]$^+$ (ES$^+$), 450 [M−H]$^-$ (ES$^-$). $^1$H NMR (400 MHz, DMSO-d$_6$) δ: $^1$H NMR (400 MHz, DMSO-d$_6$) δ: 13.75 (1H, br s), 11.40 (1H, br s), 10.38 (1H, s), 7.79 (1H, d), 7.51 (1H, d), 7.30 (1H, dd), 7.23 (2H, s), 4.78 (2H, sep), 1.34 (12H, d).

Synthesis 112

4-(4-Bromo-3,5-diethoxybenzamido)-2-methylbenzoic acid (AAA-110)

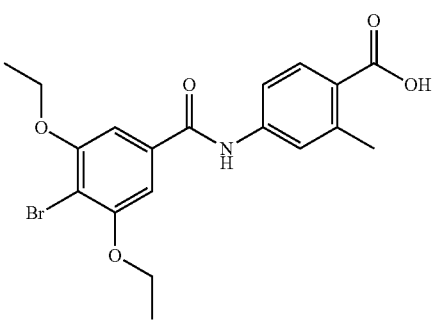 [SMILES: CCOc1cc(C(=O)Nc2ccc(C(=O)O)c(C)c2)cc(OCC)c1Br]

4-(4-Bromo-3,5-diethoxybenzamido)-2-methylbenzoic acid (AAA-110) (275 mg, 56% for final step) was prepared in essentially the same manner as in steps (v) and (vi) for AAA-075 except that 4-bromo-3,5-diethoxybenzoic acid (prepared in 2 steps from 4-bromo-3,5-dihydroxybenzoic acid by sequential treatment with ethyl iodide and base and then lithium hydroxide) was used instead of 3-chloro-5-isopropoxy-4-methoxybenzoic acid in step (v): m/z 422

[M+H]⁺ (ES⁺), 420 [M−H]⁻ (ES⁻). ¹H NMR (400 MHz, DMSO-d₆) δ: 12.45 (1H, br s), 10.18 (1H, s), 7.69 (1H, d), 7.56-7.50 (1H, m), 7.47 (1H, d), 7.06 (2H, s), 4.01 (4H, q), 2.35 (3H, s), 1.20 (6H, t).

Synthesis 113

4-(4-Bromo-3,5-diisopropoxybenzamido)-2-methyl-benzoic acid (AAA-111)

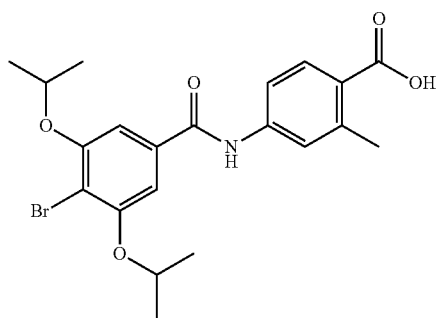 [SMILES: Cc1cc(NC(=O)c2cc(OC(C)C)c(Br)c(OC(C)C)c2)ccc1C(=O)O]

4-(4-Bromo-3,5-diisopropoxybenzamido)-2-methylbenzoic acid (AAA-111) (306 mg, 52% for final step) was prepared in essentially the same manner as in steps (v) and (vi) for AAA-075 except that 4-bromo-3,5-diisopropoxybenzoic acid (prepared in 2 steps from 4-bromo-3,5-dihydroxybenzoic acid by sequential treatment with isopropyl iodide and base and then lithium hydroxide) was used instead of 3-chloro-5-isopropoxy-4-methoxybenzoic acid in step (v): m/z 450 [M+H]⁺ (ES⁺), 448 [M−H]⁻ (ES⁻). ¹H NMR (400 MHz, DMSO-d₆) δ: 12.64 (1H, br s), 10.34 (1H, s), 7.88 (1H, d), 7.71 (1H, dd), 7.66 (1H, d), 7.24 (2H, s), 4.77 (2H, sep), 2.54 (3H, s), 1.32 (12H, d).

Synthesis 114

4-(4-Chloro-3,5-diisopropoxybenzamido)benzoic acid (AAA-112)

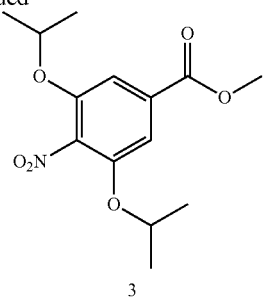

-continued

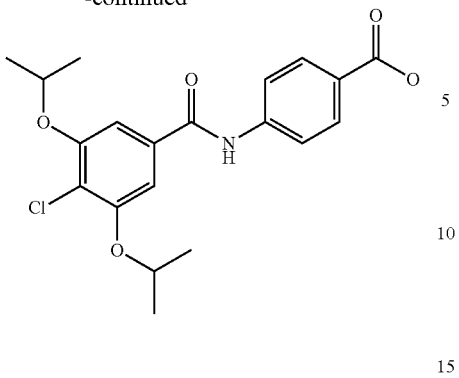

Step (i): Methyl 3,5-dihydroxy-4-nitrobenzoate (2)

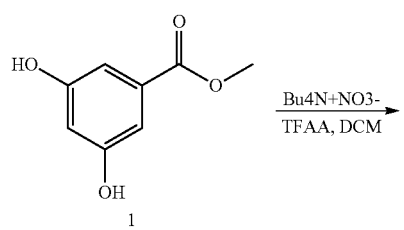

Tetrabutylammonium nitrate (10.9 g, 35.7 mmol) was dissolved in DCM (125 mL) and treated with TFAA (5.04 mL, 35.7 mmol). The resultant solution was added dropwise to an ice cooled solution of methyl 3,5-dihydroxybenzoate (1) (6.0 g, 36 mmol) in DCM (100 mL), keeping the temperature below 5° C. The resultant mixture was allowed to warm to RT and stirred for 18 h. The mixture was filtered through silica, washing through with 20% EtOAc in DCM (500 mL). The solvent was removed in vacuo and the residue was purified by silica gel chromatography (120 g, 0-5% EtOAc in DCM) to afford methyl 3,5-dihydroxy-4-nitrobenzoate (2) (0.36 g, 5% yield) as a bright orange solid: m/z 212 [M−H]⁻ (ES⁻).

Step (ii): Methyl 3,5-diisopropoxy-4-nitrobenzoate (3)

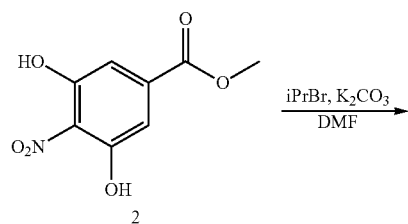

-continued

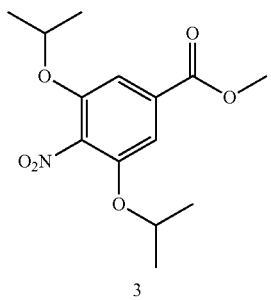

Methyl 3,5-diisopropoxy-4-nitrobenzoate (3) (610 mg, 97%) was prepared from methyl 3,5-dihydroxy-4-nitrobenzoate (2) (430 mg, 2.02 mmol) using a procedure essentially the same as in step (i) for AAA-001 except that isopropyl bromide was used instead of cyclopentyl bromide: $^1$H NMR (400 MHz, CDCl$_3$) δ: 7.25 (2H, s), 4.66 (2H, sep), 3.92 (3H, s), 1.32 (12H, d).

Step (iii): Methyl 4-amino-3,5-diisopropoxybenzoate (4)

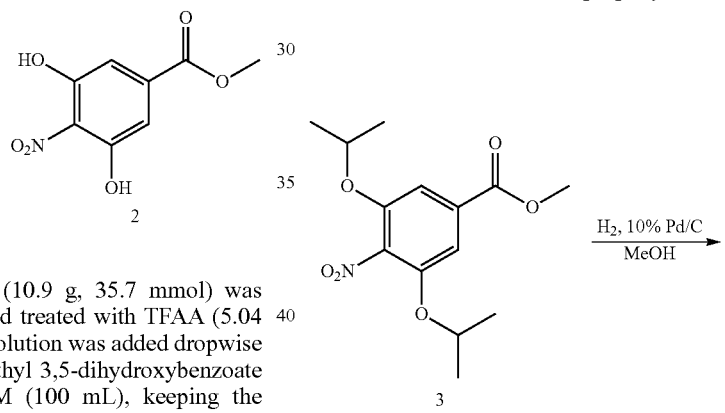

Methyl 3,5-diisopropoxy-4-nitrobenzoate (3) (594 mg, 2.00 mmol) was dissolved in a mixture of MeOH (40 mL) and formic acid (5 mL) and was passed through a Thales 'H-cube' cartridge (10% Pd/C) at a flow rate of 1 mL/min at 40° C. under H$_2$ (full H$_2$ mode). The solvents were removed in vacuo to yield methyl 4-amino-3,5-diisopropoxybenzoate (4) (398 mg, 72%) as a pale yellow oil: $^1$H NMR (400 MHz, CDCl$_3$) δ: 7.20 (2H, s), 4.59 (2H, sep), 4.23 (2H, br s), 3.83 (3H, s), 1.33 (12H, d).

Step (iv): Methyl 4-chloro-3,5-diisopropoxybenzoate (5)

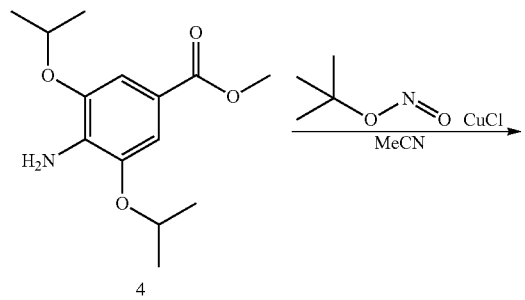

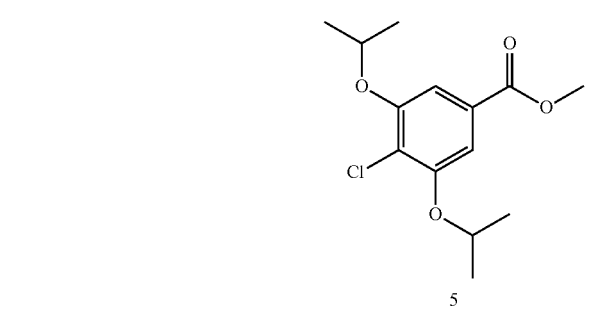

A suspension of copper (I) chloride (129 mg, 1.31 mmol) and tert-butyl nitrite (155 μL, 1.31 mmol) in anhydrous MeCN (2 mL) was stirred at 65° C. A solution of methyl 4-amino-3,5-diisopropoxybenzoate (4) (233 mg, 0.872 mmol) in anhydrous MeCN (1 mL) was added dropwise. Once the addition was complete the mixture was allowed to cool to RT and poured on to 20% HCl (5 mL). The mixture was partitioned between DCM (10 mL) and aq. ammonia (35%, 5 mL), the phases were separated and the organic solution was further washed with ammonia solution (17.5%, 10 mL), and brine (2×20 mL). The solvent was removed in vacuo and the residue was purified by silica gel chromatography (40 g, 0-100% EtOAc in isohexane) to afford methyl 4-chloro-3,5-diisopropoxybenzoate (93 mg, 36% yield) as a colourless oil: m/z 287 [M+H]$^+$ (ES$^+$).

Step (v): 4-Chloro-3,5-diisopropoxybenzoic acid (6)

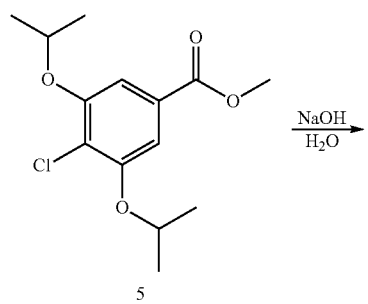

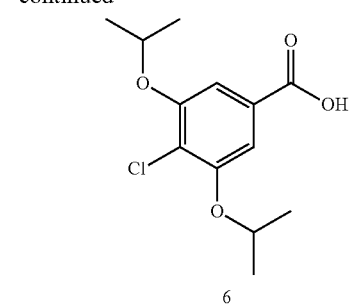

Methyl 4-chloro-3,5-diisopropoxybenzoate (5) (93 mg, 0.32 mmol) was suspended in 2M sodium hydroxide (1.6 mL, 3.2 mmol) and stirred at 100° C. for 3 h. After cooling to RT the mixture was acidified by the addition of 1 M HCl. The resulting precipitate was collected by filtration and dried in vacuo to afford 4-chloro-3,5-diisopropoxybenzoic acid (6) (60 mg, 66% yield) as a white solid. This material was used in the subsequent reaction step without purification.

Step (vi): Methyl 4-(4-chloro-3,5-diisopropoxybenzamido)benzoate (8)

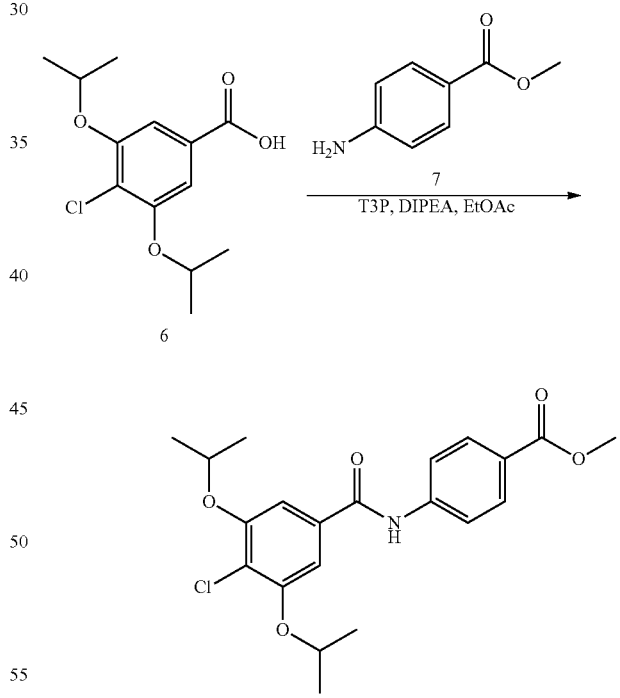

Methyl 4-(4-chloro-3,5-diisopropoxybenzamido)benzoate (8) (86 mg, 96%) was prepared from 4-chloro-3,5-diisopropoxybenzoic acid (6) (60 mg, 0.22 mmol) using a procedure essentially the same as in step (i) for AAA-064 except that DIPEA was used instead of TEA, and methyl 4-aminobenzoate was used instead of methyl 4-amino-2-fluorobenzoate: m/z 406 [M+H]$^+$ (ES$^+$), 404 [M−H]$^−$ (ES)$^−$.

Step (vii): 4-(4-Chloro-3,5-diisopropoxybenzamido) benzoic acid (AAA-112)

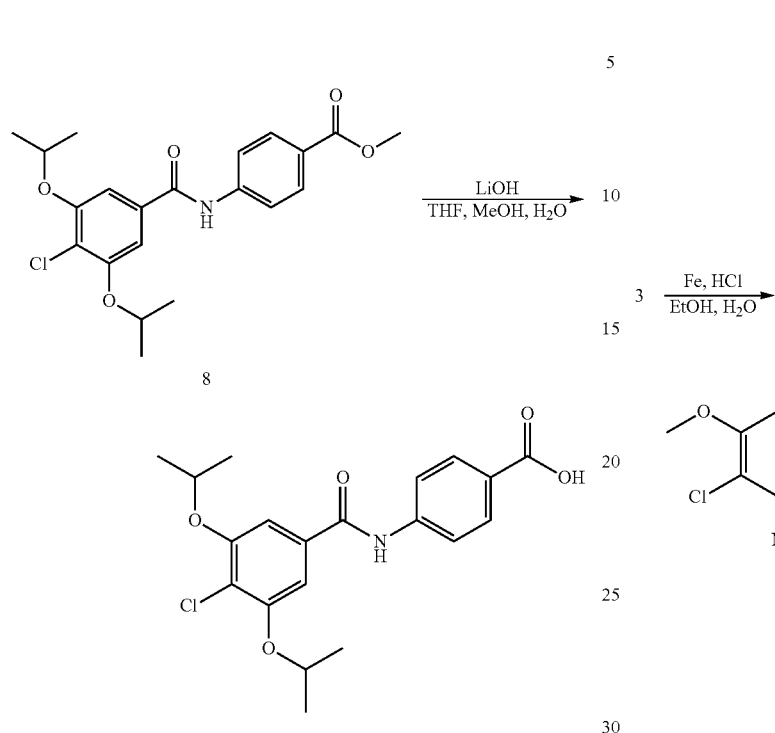

4-(4-Chloro-3,5-diisopropoxybenzamido)benzoic acid (AAA-112) (40 mg, 46%) was prepared from methyl 4-(4-chloro-3,5-diisopropoxybenzamido)benzoate (8) (86 mg, 0.21 mmol) using a procedure essentially the same as in step (ii) for AAA-001 except that MeOH was added dropwise to obtain a solution and the mixture was heated at 50° C. for 2 h then at RT for 15 h: m/z 390 [M–H]⁻ (ES⁻), ¹H NMR (400 MHz, DMSO-d₆) δ: 12.74 (1H, br s), 10.44 (1H, s), 8.01-7.84 (4H, m), 7.29 (2H, s), 4.78 (2H, sep), 1.33 (12H, d).

Synthesis 115

4-(3,4-Dichloro-5-isopropoxybenzamido)-2-methyl-benzoic acid (AAA-113)

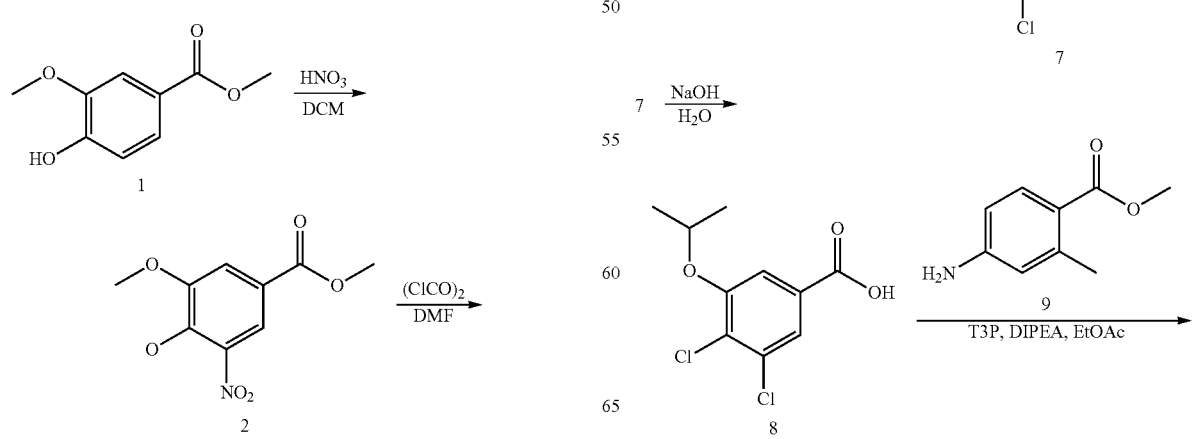

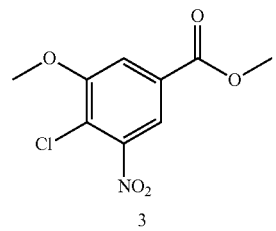

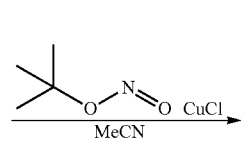

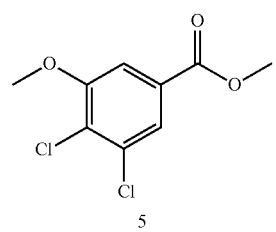

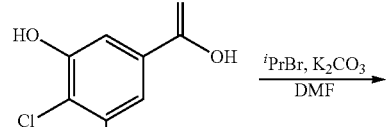

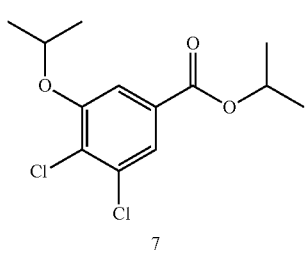

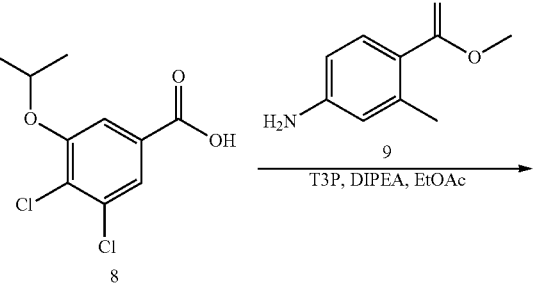

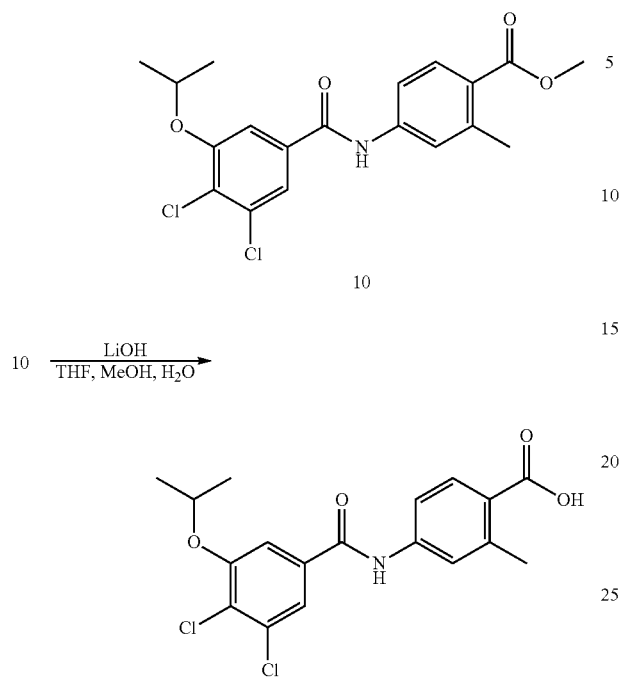

Step (i): Methyl 4-hydroxy-3-methoxy-5-nitrobenzoate (2)

A solution of methyl 4-hydroxy-3-methoxybenzoate (1) (10 g, 55 mmol) in DCM (100 mL) was cooled to −60° C. and fuming nitric acid (24.5 mL, 549 mmol) was added dropwise over 30 min. The reaction mixture was stirred at −60° C. for 2 h then added slowly to iced water (200 mL) with stirring. The precipitate was collected, washed with ice cold water and dried under suction to afford methyl 4-hydroxy-3-methoxy-5-nitrobenzoate (2) (4.4 g, 35% yield) as a bright yellow solid: $^1$H NMR (400 MHz, CDCl$_3$) δ: 11.08 (1H, d), 8.45 (1H, d), 7.77 (1H, d), 4.01 (3H, s), 3.95 (3H, s).

Step (ii): Methyl 4-chloro-3-methoxy-5-nitrobenzoate (3)

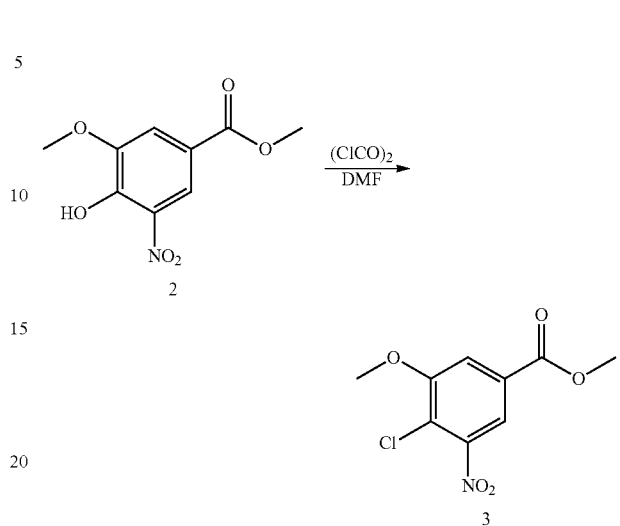

A solution of methyl 4-hydroxy-3-methoxy-5-nitrobenzoate (2) (4.4 g, 19 mmol) in DMF (30 mL) at 0° C. was treated with oxalyl chloride (5.09 mL, 58.1 mmol) dropwise. The mixture was then stirred at 80° C. for 3 h under a CaCl$_2$ drying tube. The mixture was allowed to cool to RT, poured in to iced water (100 mL) and stirred for 15 min. The precipitate was collected by filtration and washed with water and MeOH to afford methyl 4-chloro-3-methoxy-5-nitrobenzoate (3) (3.2 g, 65% yield) as a yellow solid: $^1$H NMR (400 MHz, CDCl$_3$) δ: 8.04 (1H, d), 7.77 (1H, d), 4.04 (3H, s), 3.97 (3H, s).

Step (iii): Methyl 3-amino-4-chloro-5-methoxybenzoate (4)

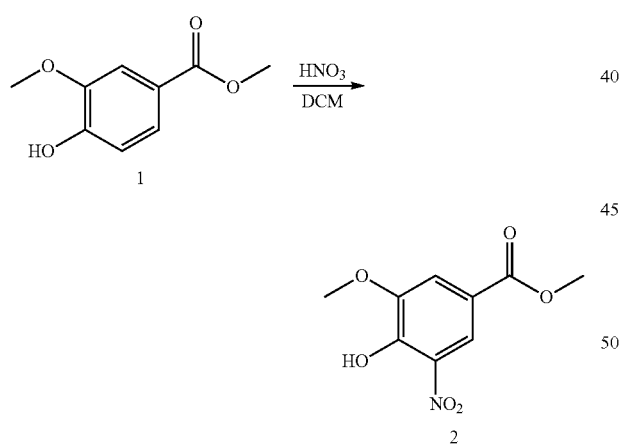

A suspension of methyl 4-chloro-3-methoxy-5-nitrobenzoate (3) (900 mg, 3.66 mmol) and iron powder (614 mg, 11.0 mmol) in a mixture of EtOH (15 mL) and water (15 mL) was heated to 70° C. and degassed with nitrogen for 20 min. Conc. HCl (44.5 µL, 1.47 mmol) was added and the reaction mixture was stirred at 70° C. for 3 h. Celite (1 g) was added and the suspension stirred for 10 min then filtered through a celite pad. The solvent was removed in vacuo and the residue was partitioned between EtOAc (15 mL) and water (15 mL). The phases were separated and the organic solution was washed with brine (2×15 mL). The solvent was removed in vacuo to afford methyl 3-amino-4-chloro-5-methoxybenzoate (0.82 g, 100% yield) as a yellow solid: $^1$H NMR (400 MHz, DMSO-d$_6$) δ: 7.10 (1H, d), 6.78 (1H, d), 5.68 (2H, s), 3.81 (6H, m).

Step (iv): Methyl 3,4-dichloro-5-methoxybenzoate (5)

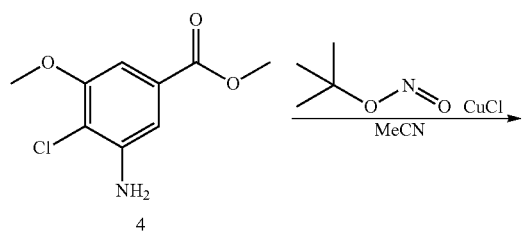

A suspension of copper (II) chloride (0.97 g, 7.2 mmol) and tert-butyl nitrite (1.07 mL, 9.04 mmol) in anhydrous MeCN (5 mL) was warmed to 65° C. A solution of methyl 3-amino-4-chloro-5-methoxybenzoate (4) (1.3 g, 6.0 mmol) in anhydrous MeCN (3 mL) was added dropwise. Once the addition was complete the mixture was allowed to cool to RT and poured on to 1M HCl (15 mL). The acidic mixture was neutralized with satd. NaHCO$_3$ solution and aq. ammonia (35%, 5 mL) was added. The product was extracted with DCM (25 mL) and then washed with aq. ammonia (17.5%, 20 mL) and brine (2×20 mL). The solvent was removed in vacuo and the residue was triturated with 10% EtOAc in isohexane to afford methyl 3,4-dichloro-5-methoxybenzoate (5) (1.17 g, 79% yield) as a brown solid: $^1$H NMR (400 MHz, DMSO-d$_6$) δ: 7.72 (1H, d), 7.57 (1H, d), 3.98 (3H, s), 3.89 (3H, s).

Step (v): 3,4-Dichloro-5-hydroxybenzoic acid (6)

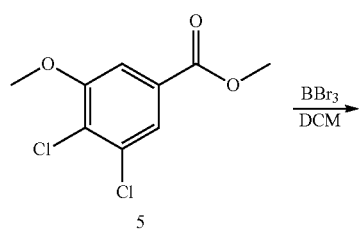

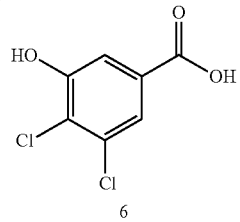

Methyl 3,4-dichloro-5-methoxybenzoate (5) (518 mg, 2.34 mmol) was suspended in DCM (10 mL) under a reflux condenser fitted with a CaCl$_2$ drying tube. BBr$_3$ (554 µL, 5.86 mmol) was added and the reaction mixture was stirred at RT for 15 h. The reaction mixture was cautiously poured in to iced water (20 mL) and the mixture stirred for 10 min. The product was extracted with EtOAc (50 mL), then the organic solution was washed with brine (2×50 mL) and dried over MgSO$_4$ and filtered. The solvent was removed in vacuo and the residue purified by silica gel chromatogrpahy (40 g, 0-100% EtOAc in isohexane) to afford 3,4-dichloro-5-hydroxybenzoic acid (6) (260 mg, 51% yield) as a white solid: m/z 205 [M−H]$^-$ (ES$^-$).

Step (vi): Isopropyl 3,4-dichloro-5-isopropoxybenzoate (7)

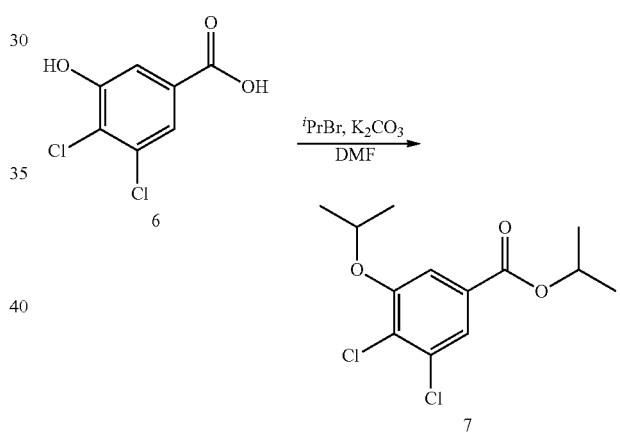

Isopropyl 3,4-dichloro-5-isopropoxybenzoate (7) (342 mg, 87%) was prepared from 3,4-dichloro-5-hydroxybenzoic acid (6) (260 mg, 1.26 mmol) using a procedure essentially the same as in step (i) for AAA-001 except that isopropyl bromide was used instead of cyclopentyl bromide.

Step (vii): 3,4-Dichloro-5-isopropoxybenzoic acid (8)

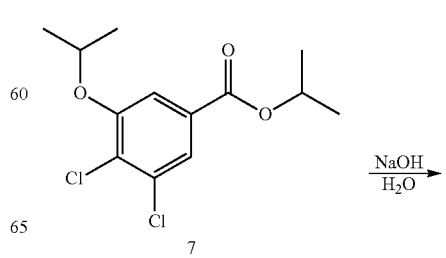

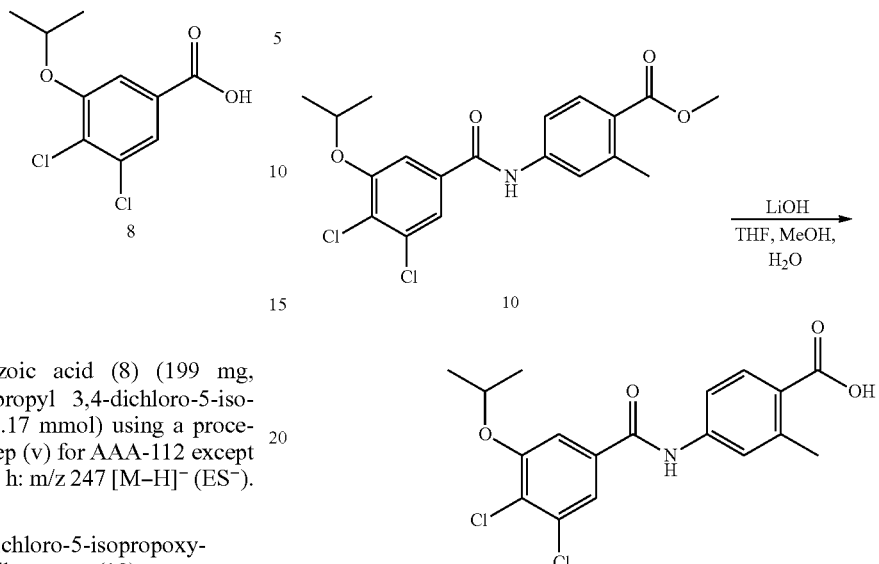

Step (ix): 4-(3,4-Dichloro-5-isopropoxybenzamido)-2-methylbenzoic acid (AAA-113)

3,4-Dichloro-5-isopropoxybenzoic acid (8) (199 mg, 63%) was prepared from isopropyl 3,4-dichloro-5-isopropoxybenzoate (7) (340 mg, 1.17 mmol) using a procedure essentially the same as in step (v) for AAA-112 except that the reaction was stirred for 15 h: m/z 247 [M−H]⁻ (ES⁻).

Step (viii): Methyl 4-(3,4-dichloro-5-isopropoxybenzamido)-2-methylbenzoate (10)

4-(3,4-Dichloro-5-isopropoxybenzamido)-2-methylbenzoic acid (AAA-113) (85 mg, 41%) was prepared from methyl 4-(3,4-dichloro-5-isopropoxybenzamido)-2-methylbenzoate (10) (210 mg, 0.530 mmol) using a procedure essentially the same as in step (ii) for AAA-001 except that MeOH was added dropwise to obtain a solution and the mixture was stirred at 40° C. for 20 h: m/z 380 [M−H]⁻ (ES⁻), $^1$H NMR (400 MHz, DMSO-$d_6$) δ: 12.66 (1H, br s), 10.48 (1H, s), 7.88 (1H, d), 7.81 (1H, d), 7.75-7.66 (2H, m), 7.64 (1H, d), 4.86 (1H, sep), 2.54 (3H, s), 1.35 (6H, d).

Synthesis 116

4-(4-Chloro-3-ethoxy-5-(pentan-3-yloxy)benzamido)benzoic acid (AAA-114)

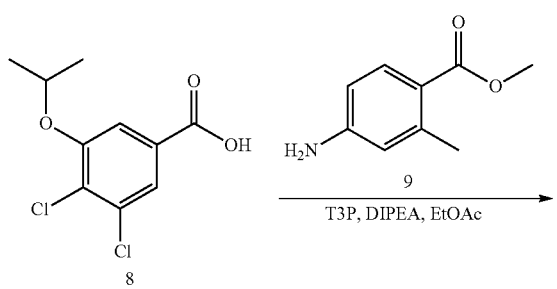

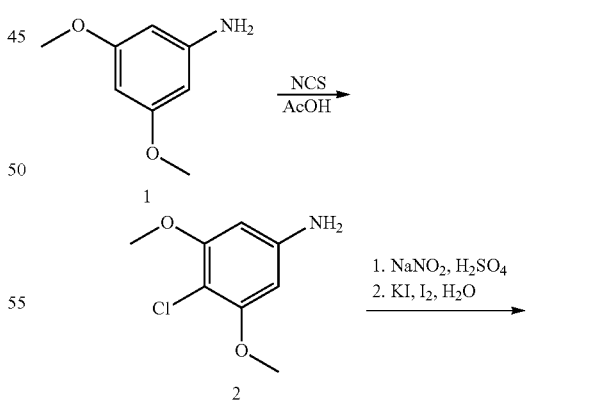

Methyl 4-(3,4-dichloro-5-isopropoxybenzamido)-2-methylbenzoate (10) (237 mg, 68%) was prepared from 3,4-dichloro-5-isopropoxybenzoic acid (8) (200 mg, 800 μmol) using a procedure essentially the same as in step (i) for AAA-064 except that DIPEA was used instead of TEA, and methyl 4-amino-2-methylbenzoate (9) was used instead of methyl 4-amino-2-fluorobenzoate: m/z 396 [M+H]⁺ (ES⁺), 394 [M−H]⁻ (ES⁻), $^1$H NMR (400 MHz, DMSO-$d_6$) δ: 10.51 (1H, s), 7.89 (1H, d), 7.81 (1H, d), 7.77-7.72 (2H, m), 7.64 (1H, d), 4.85 (1H, sep), 3.81 (3H, s), 2.54 (3H, s), 1.35 (6H, d).

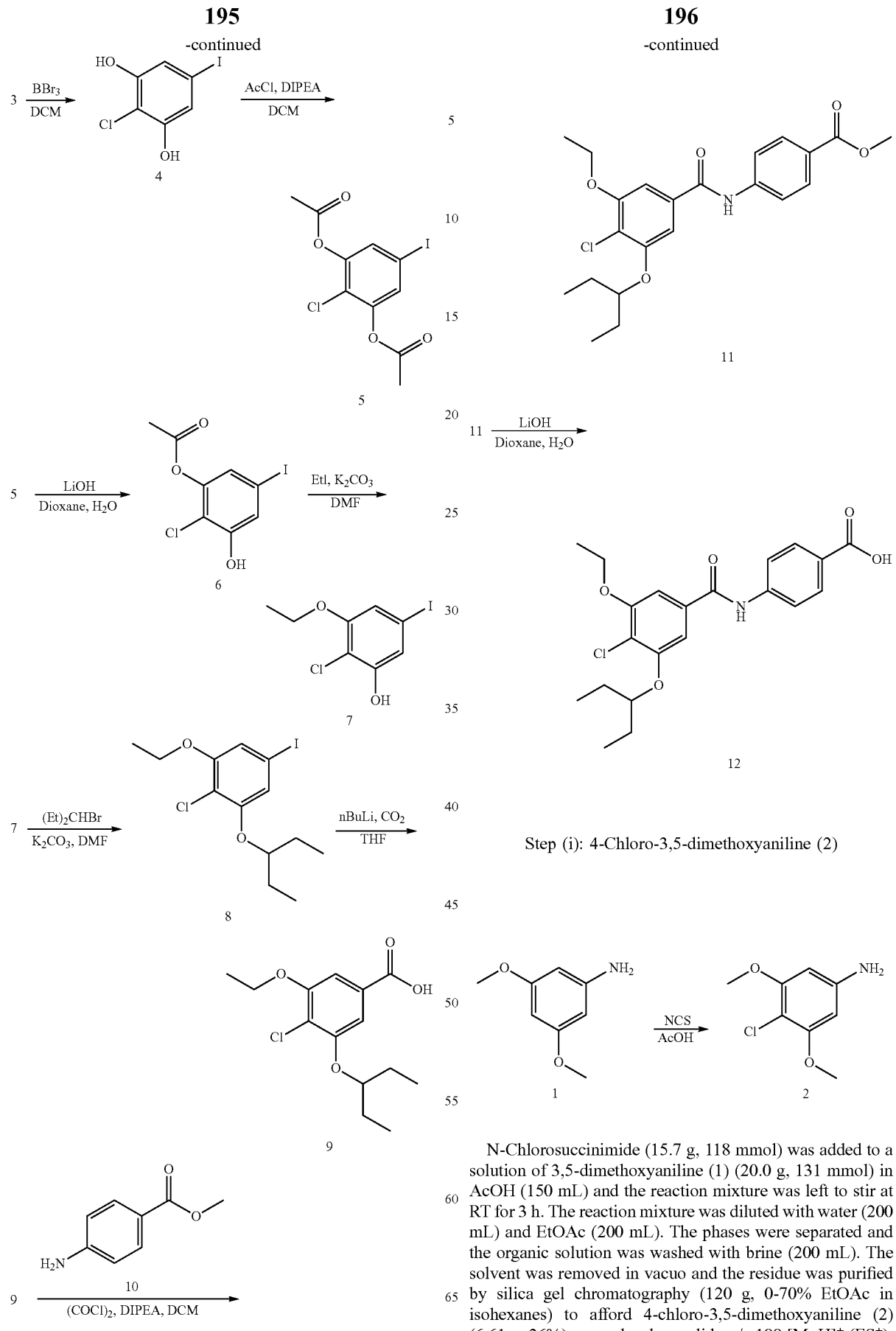

Step (i): 4-Chloro-3,5-dimethoxyaniline (2)

N-Chlorosuccinimide (15.7 g, 118 mmol) was added to a solution of 3,5-dimethoxyaniline (1) (20.0 g, 131 mmol) in AcOH (150 mL) and the reaction mixture was left to stir at RT for 3 h. The reaction mixture was diluted with water (200 mL) and EtOAc (200 mL). The phases were separated and the organic solution was washed with brine (200 mL). The solvent was removed in vacuo and the residue was purified by silica gel chromatography (120 g, 0-70% EtOAc in isohexanes) to afford 4-chloro-3,5-dimethoxyaniline (2) (6.61 g, 26%) as a colourless solid: m/z 188 [M+H]$^+$ (ES$^+$).

Step (ii): 2-Chloro-5-iodo-1,3-dimethoxybenzene (3)

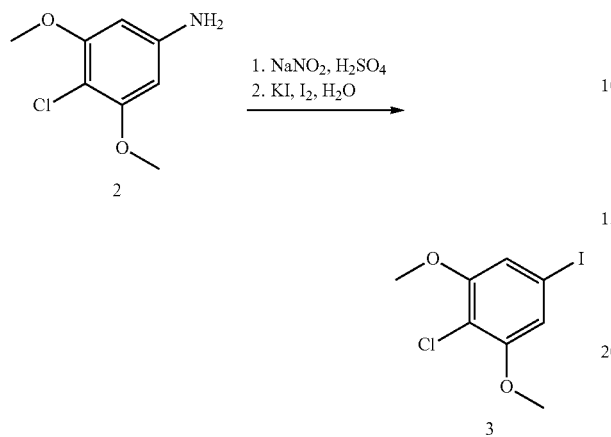

4-Chloro-3,5-dimethoxyaniline (2) (6.61 g, 35.2 mmol) was added to a mixture of sulfuric acid (9.39 mL, 176 mmol) and H$_2$O (100 mL) at 00° C. Sodium nitrite (3.16 g, 45.8 mmol) was added and the reaction mixture was stirred at 0° C. for 30 min. The mixture was added to a pre-warmed mixture of sodium iodide (21.1 g, 141 mmol), iodine (4.47 g, 17.6 mmol), sulphuric acid (8 mL) and H$_2$O (100 mL) at 80° C. and the resulting mixture was heated at reflux for 30 min. The mixture was allowed to cool to RT and then 40% sodium thiosulfate solution (200 mL) was added. The product was extracted with EtOAc (300 mL), the solvent was removed in vacuo and the residue was purified by silica gel chromatography (120 g, 0-50% EtOAc in isohexanes) to afford 2-chloro-5-iodo-1,3-dimethoxybenzene (3) (7.16 g, 67% yield).

Step (iii): 2-Chloro-5-iodobenzene-1,3-diol (4)

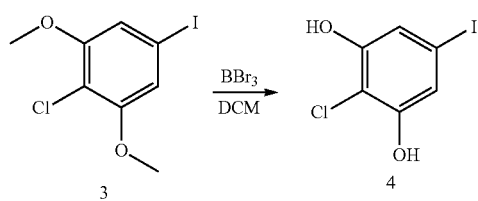

A solution of 2-chloro-5-iodo-1,3-dimethoxybenzene (3) (7.15 g, 23.9 mmol) in DCM (20 mL) was cooled to 0° C. Boron tribromide (11.3 mL, 120 mmol) was added dropwise over 30 min and the reaction mixture was allowed to slowly warm to RT and stirred for 20 h. The reaction mixture was cautiously added to iced water (30 mL) with stirring. The phases were separated and the organic solution was washed with brine (3×30 mL). The solvent was removed in vacuo to afford 2-chloro-5-iodobenzene-1,3-diol (4) (4.17 g, 64% yield) as a white solid: m/z 269 [M−H]$^-$ (ES$^-$).

Step (iv): 2-Chloro-5-iodo-1,3-phenylene diacetate (5)

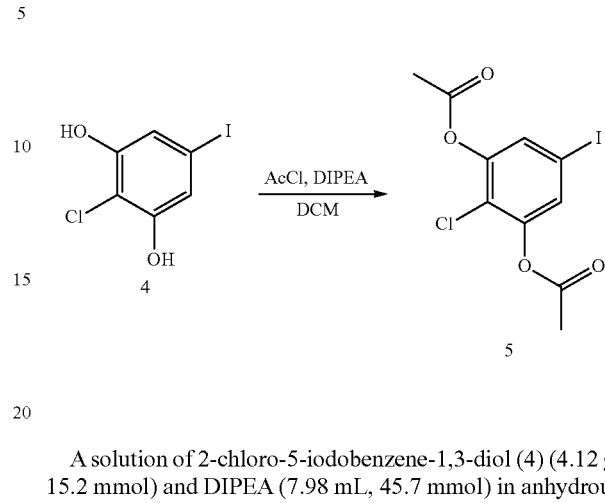

A solution of 2-chloro-5-iodobenzene-1,3-diol (4) (4.12 g, 15.2 mmol) and DIPEA (7.98 mL, 45.7 mmol) in anhydrous DCM (15 mL) was cooled to 0° C. before acetyl chloride (2.28 mL, 32.0 mmol) was added dropwise. The reaction mixture was allowed to slowly warm to RT and stirred for 20 h. The reaction mixture was diluted with DCM (15 mL), washed sequentially with water (20 mL), 1M HCl (20 mL) and brine (3×20 mL) and then dried over MgSO$_4$. The solvent was removed in vacuo to afford 2-chloro-5-iodo-1,3-phenylene diacetate (5) (5.16 g, 96% yield) as a white solid: m/z 372 [M+H$_2$O]$^+$ (ES$^+$).

Step (v): 2-Chloro-3-hydroxy-5-iodophenyl acetate (6)

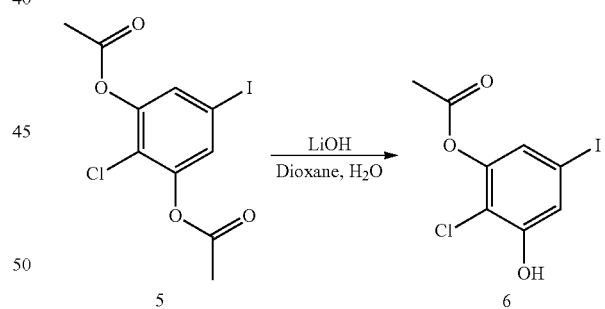

A mixture of 2-chloro-5-iodo-1,3-phenylene diacetate (5) (5.16 g, 14.5 mmol) and 1M lithium hydroxide (29.1 mL, 29.1 mmol) in H$_2$O (5 mL) and dioxane (20 mL) was stirred at 60° C. for 4 h then at RT for 20 h. The reaction mixture was acidified by the addition of 1M HCl and the product was extracted with EtOAc (150 mL). The organic solution was dried over MgSO$_4$ and the solvent was removed in vacuo. The resulting oil was slurried with 1:1 DCM: isohexanes and the solvents were removed in vacuo to yield 2-chloro-3-hydroxy-5-iodophenyl acetate (6) (4.88 g, 86%) as a brown solid: m/z 311 [M−H]$^-$ (ES$^-$).

Step (vi): 2-Chloro-3-ethoxy-5-iodophenol (7)

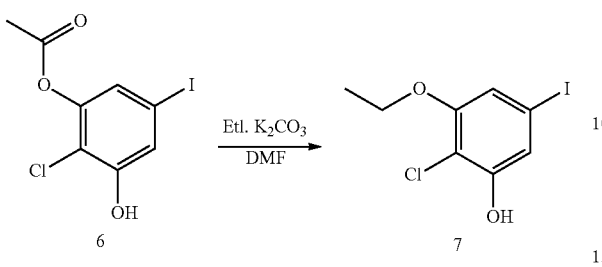

Iodoethane (0.78 mL, 9.6 mmol) and K$_2$CO$_3$ (1.3 g, 9.6 mmol) were added to a solution of 2-chloro-3-hydroxy-5-iodophenyl acetate (6) (2.0 g, 6.4 mmol) in DMF (5 mL) and the mixture was stirred at 60° C. for 1 h. The reaction mixture was cooled to RT, diluted with diethyl ether (100 mL) and washed with brine (3×100 mL). The solvent was removed in vacuo and the residue was dissolved in MeOH (20 mL). K$_2$CO$_3$ (1.0 g, 7.2 mmol) was added and the mixture was stirred at RT for 20 h. The solvent was removed in vacuo and the residue was partitioned between EtOAc (100 mL) and water (100 mL). The organic layer was washed with water (100 mL) and evaporated in vacuo. The residue was purified by silica gel chromatography (40 g, 0-30% EtOAc in isohexane) to afford 2-chloro-3-ethoxy-5-iodophenol (7) (1.1 g, 58% yield) as a colourless solid: m/z 297 [M−H]$^−$ (ES$^−$); $^1$H NMR (400 MHz, DMSO-d$_6$) δ: 10.45 (1H, s), 6.89 (2H, d), 4.04 (2H, br s), 1.32 (3H, br s).

Step (vii): 2-Chloro-1-ethoxy-5-iodo-3-(pentan-3-yloxy)benzene (8)

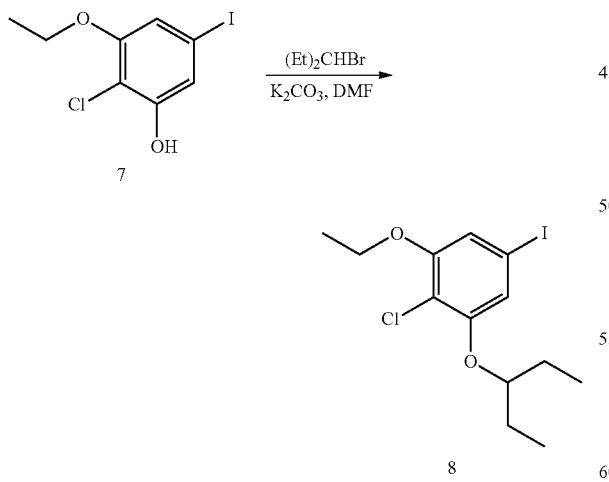

2-Chloro-1-ethoxy-5-iodo-3-(pentan-3-yloxy)benzene (8) (1.2 g, 79%) was prepared from 2-chloro-3-ethoxy-5-iodophenol (7) (1.1 g, 3.7 mmol) using a procedure essentially the same as in step (i) for AAA-001 except that 3-bromopentane was used instead of cyclopentyl bromide.

Step (viii): 4-Chloro-3-ethoxy-5-(pentan-3-yloxy)benzoic acid

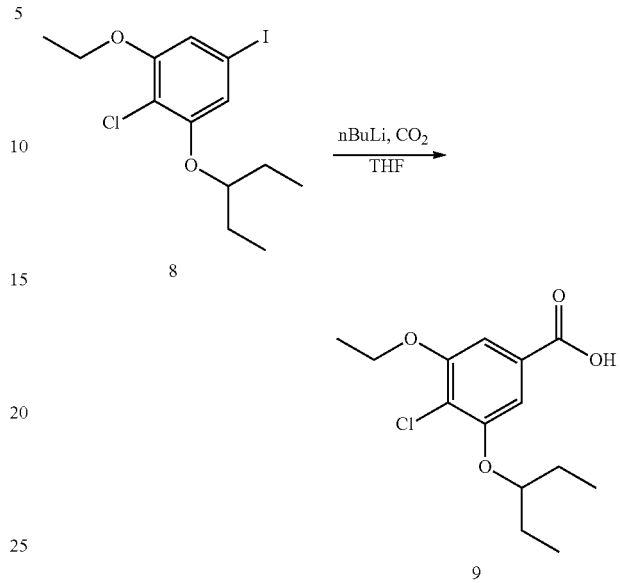

n-Butyllithium (1.3 mL, 3.3 mmol) was slowly added to a stirred solution of 2-chloro-1-ethoxy-5-iodo-3-(pentan-3-yloxy)benzene (8) (1.2 g, 3.3 mmol) in anhydrous THF at −78° C. After 5 min CO$_2$ gas was bubbled through the mixture via a CaCl$_2$ drying tube. The solution was allowed to warm to RT under a constant stream of CO$_2$ gas. 1M NaOH, followed by diethyl ether (50 mL) were added to the mixture and the phases were separated. The organic phase was retained. The aqueous phase was acidified by the addition of 1M HCl and then shaken with EtOAc (50 mL). The phases were separated and the organic phase was evaporated to give 100 mg of the desired acid. The organic solution retained from the initial separated mixture was diluted further with diethyl ether and shaken with 1M HCl and the phases were separated. The organic solution was dried over MgSO$_4$ and the solvent was removed in vacuo, the solid obtained was combined with the 100 mg obtained previously to give 4-chloro-3-ethoxy-5-(pentan-3-yloxy)benzoic acid (9) (0.76 g, 76%) as a white solid: m/z 285 [M−H]$^−$ (ES$^−$).

Step (ix): Methyl 4-(4-chloro-3-ethoxy-5-(pentan-3-yloxy)benzamido)benzoate (11)

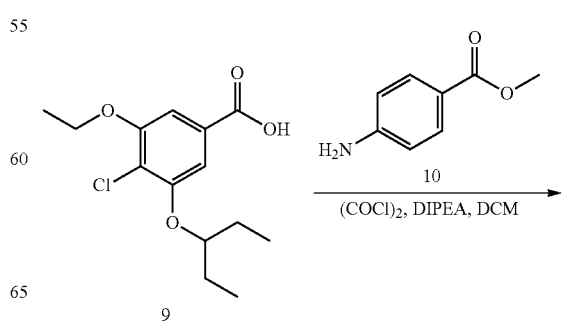

-continued

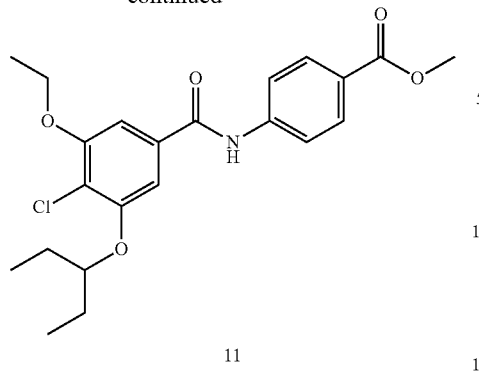

11

Methyl 4-(4-chloro-3-ethoxy-5-(pentan-3-yloxy)benzamido)benzoate (11) (76 mg, 51%) was prepared from 4-chloro-3-ethoxy-5-(pentan-3-yloxy)benzoic acid (9) (100 mg, 0.349 mmol) using a procedure essentially the same as in step (iii) for AAA-001: m/z 420 [M+H]$^+$ (ES$^+$), 418 [M−H]$^−$ (ES$^−$).

Step (x): 4-(4-Chloro-3-ethoxy-5-(pentan-3-yloxy)benzamido)benzoic acid (AAA-114)

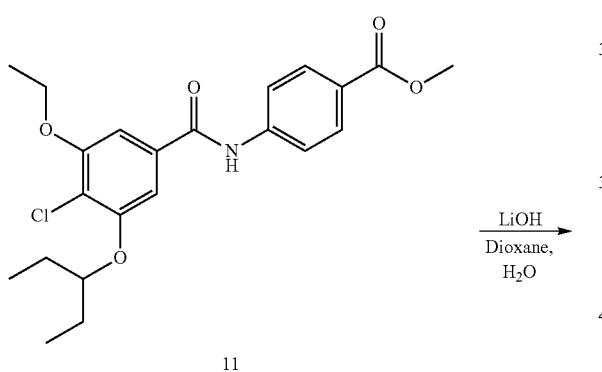

11

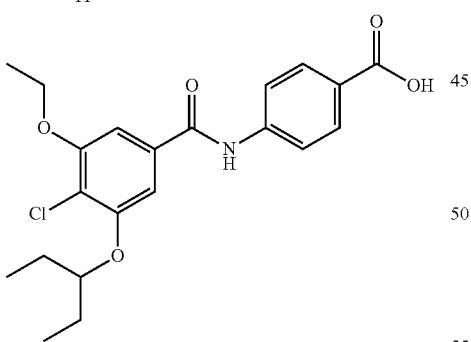

4-(4-Chloro-3-ethoxy-5-(pentan-3-yloxy)benzamido)benzoic acid (AAA-114) (50 mg, 65%) was prepared from methyl 4-(4-chloro-3-ethoxy-5-(pentan-3-yloxy)benzamido)benzoate (11) (76 mg, 0.18 mmol) using a procedure essentially the same as in step (ii) for AAA-001 except that dioxane (2 mL) was used instead of THF and the mixture was stirred at 50° C. for 2 h: m/z 406 [M+H]$^+$ (ES$^+$), 404 [M−H]$^−$ (ES$^−$); $^1$H NMR (400 MHz, DMSO-d$_6$) δ: 12.79 (1H, br s), 10.46 (1H, s), 7.99-7.93 (2H, m), 7.91-7.82 (2H, m), 7.27 (2H, dd), 4.46 (1H, quin), 4.20 (2H, q), 1.71-1.64 (4H, m), 1.39 (3H, t), 0.93 (6H, t).

Synthesis 117

4-(4-Chloro-3-ethoxy-5-(pentan-3-yloxy)benzamido)-2-methylbenzoic acid (AAA-115)

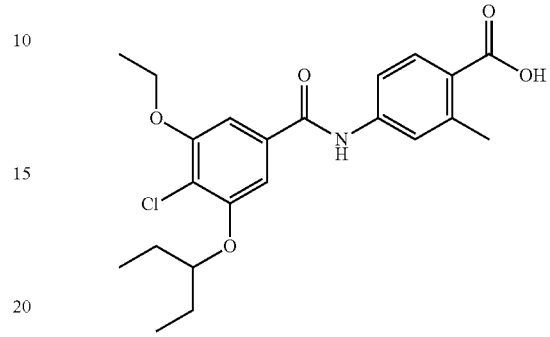

4-(4-Chloro-3-ethoxy-5-(pentan-3-yloxy)benzamido)-2-methylbenzoic acid (AAA-115) (57 mg, 78% for final step) was prepared in essentially the same manner as AAA-114 except that methyl 4-amino-2-methylbenzoate was used instead of methyl 4-aminobenzoate in step(ix): m/z 420 [M+H]$^+$ (ES$^+$), 418 [M−H]$^−$ (ES$^−$); $^1$H NMR (400 MHz, DMSO-d$_6$) δ: 12.62 (1H, br s), 10.35 (1H, s), 7.88 (1H, d), 7.72 (1H, dd), 7.66 (1H, d), 7.32-7.24 (2H, m), 4.45 (1H, quin), 4.20 (2H, q), 2.55 (3H, s), 1.73-1.61 (4H, m), 1.39 (3H, t), 0.93 (6H, t).

Synthesis 118

4-(4-Chloro-3-ethoxy-5-(pentan-3-yloxy)benzamido)-2-fluorobenzoic acid (AAA-116)

4-(4-Chloro-3-ethoxy-5-(pentan-3-yloxy)benzamido)-2-fluorobenzoic acid (AAA-116) (44 mg, 81% for final step) was prepared in essentially the same manner as AAA-114 except that methyl 4-amino-2-fluorobenzoate was used instead of methyl 4-aminobenzoate in step(ix): m/z 424 [M+H]$^+$ (ES$^+$), 422 [M−H]$^−$ (ES$^−$); $^1$H NMR (400 MHz, DMSO-d$_6$) δ: 13.05 (1H, br s), 10.60 (1H, s), 7.91 (1H, t), 7.82 (1H, dd), 7.61 (1H, dd), 7.26 (2H, dd), 4.46 (1H, quin), 4.20 (2H, q), 1.73-1.61 (4H, m), 1.39 (3H, t), 0.92 (6H, t).

Synthesis 119

4-(4-Chloro-3,5-diisopropoxybenzamido)-2-methylbenzoic acid (AAA-117)

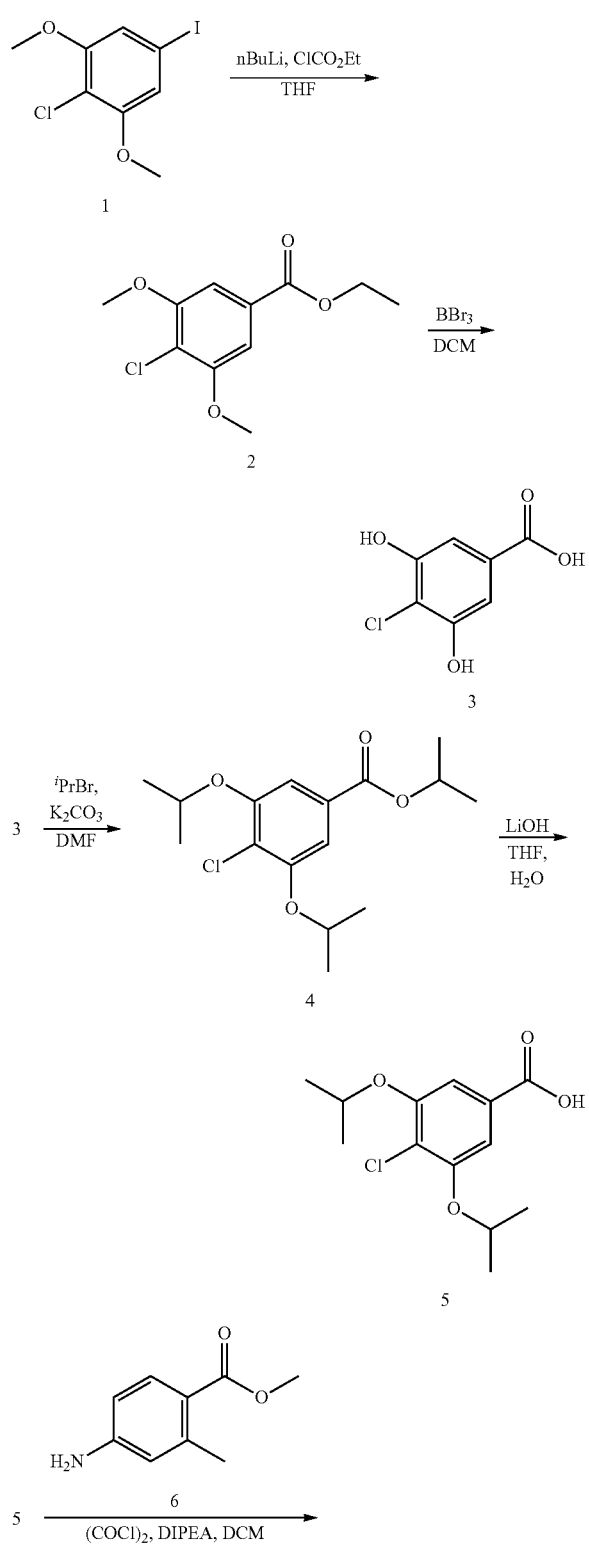

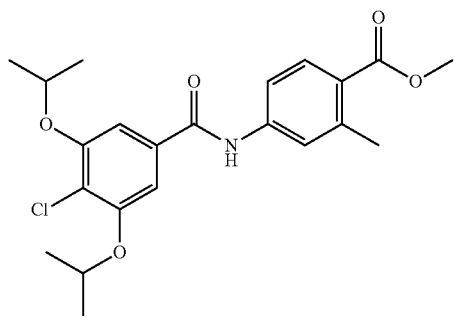

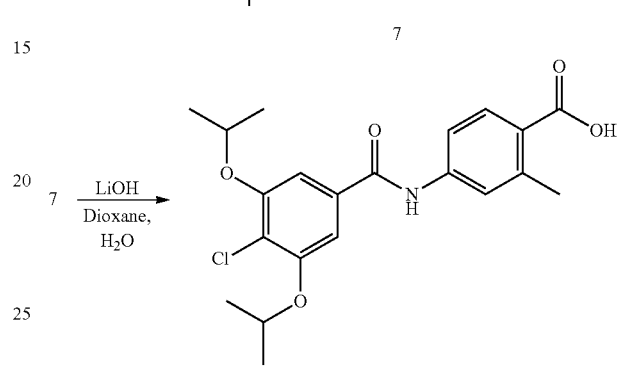

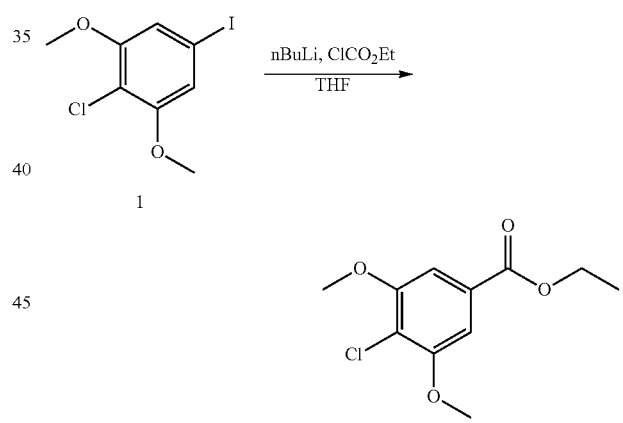

Step (i): Ethyl 4-chloro-3,5-dimethoxybenzoate (2)

A solution of 2-chloro-5-iodo-1,3-dimethoxybenzene (1) (3.4 g, 11 mmol) in anhydrous THF (100 mL) was cooled to −70° C. and treated with n-butyllithium (5.5 mL, 12 mmol). The reaction mixture was stirred at −70° C. for 45 min then ethyl chloroformate (1.6 mL, 17 mmol) was added dropwise and the reaction mixture was allowed to warm to RT and stirred for 20 h. The reaction mixture was poured on to ice (100 mL) and the product was extracted with EtOAc (2×100 mL). The organic solution was washed with brine (3×100 mL) and the solvent was removed in vacuo. The residue was purified by silica gel chromatography (120 g, 0-50% EtOAc in isohexane) to afford ethyl 4-chloro-3,5-dimethoxybenzoate (2) (0.12 g, 4%): $^1$H NMR (400 MHz, CDCl$_3$) δ: 7.30 (2H, s), 4.40 (2H, q), 3.96 (6H, s), 1.42 (3H, t).

Step (ii): 4-Chloro-3,5-dihydroxybenzoic acid (3)

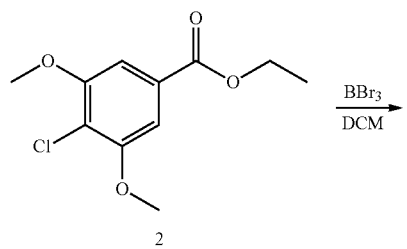

Tribromoborane (318 μL, 3.29 mmol) was added dropwise to a solution of ethyl 4-chloro-3,5-dimethoxybenzoate (2) (115 mg, 0.470 mmol) in DCM (1.5 mL) at 0° C. and the mixture was stirred at the same temperature for 4 h. The reaction mixture was allowed to warm to RT and then poured cautiously in to iced water (5 mL). The mixture was extracted with EtOAc (3×5 mL), and the combined organic extracts were washed with brine (2×5 mL), dried over MgSO$_4$ and evaporated in vacuo to give 4-chloro-3,5-dihydroxybenzoic acid (3) (72 mg, 78%) as a brown solid: m/z 187 [M–H]$^-$ (ES$^-$).

Step (iii): Isopropyl 4-chloro-3,5-diisopropoxybenzoate (4)

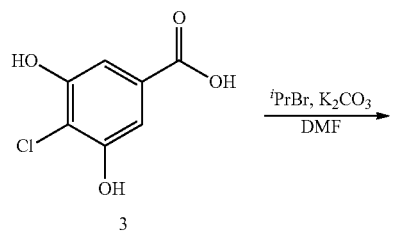

Isopropyl 4-chloro-3,5-diisopropoxybenzoate (4) (43 mg, 0.12 mmol) was prepared from 4-chloro-3,5-dihydroxybenzoic acid (3) (72 mg, 0.38 mmol) using a procedure essentially the same as in step (i) for AAA-001 except that isopropyl bromide (8 eq.) was used instead of cyclopentyl bromide and the mixture was stirred at 50° C. for 20 h: $^1$H NMR (400 MHz, CDCl$_3$) δ: 7.25 (2H, s), 5.23 (1H, sep), 4.63 (2H, sep), 1.38 (18H, m).

Step (iv): 4-Chloro-3,5-diisopropoxybenzoic acid (5)

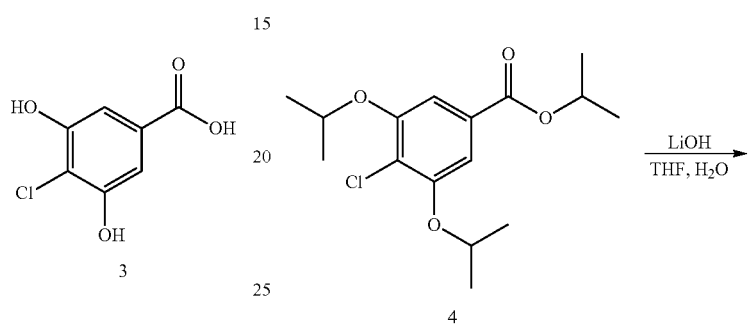

4-Chloro-3,5-diisopropoxybenzoic acid (5) (36 mg, 95%) was prepared from isopropyl 4-chloro-3,5-diisopropoxybenzoate (4) (43 mg, 0.14 mmol) using a procedure essentially the same as in step (ii) for AAA-001 except that the mixture was stirred at 40° C. for 20 h: m/z 271 [M–H]$^-$ (ES$^-$).

Step (v): Methyl 4-(4-chloro-3,5-diisopropoxybenzamido)-2-methylbenzoate (7)

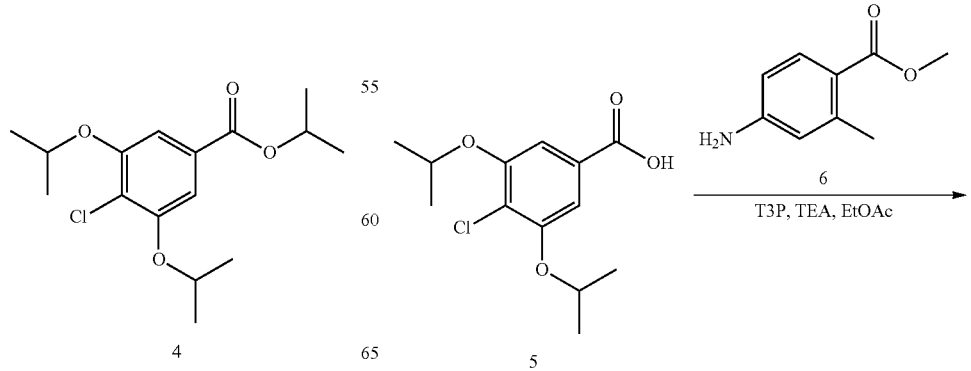

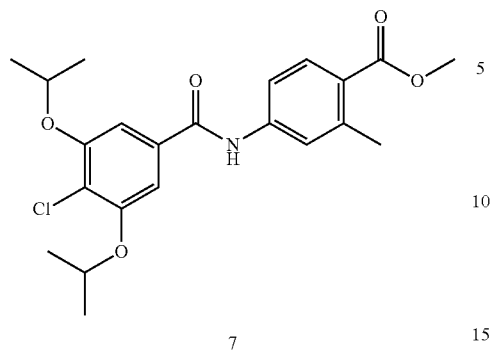

Methyl 4-(4-chloro-3,5-diisopropoxybenzamido)-2-methylbenzoate (7) (29 mg, 52%) was prepared from 4-chloro-3,5-diisopropoxybenzoic acid (5) (36 mg, 0.13 mmol) using a procedure essentially the same as in step (v) for AAA-075 except that the mixture was stirred at 60° C. for 90 min: m/z 420 [M+H]+ (ES+), 418 [M–H]− (ES−); 1H NMR (400 MHz, CDCl3) δ: 7.98 (1H, d), 7.88 (1H, br s), 7.61-7.52 (2H, m), 7.06 (2H, s), 4.71-4.59 (2H, m), 3.89 (3H, s), 2.64 (3H, s), 1.41 (12H, d).

Step (vi): 4-(4-Chloro-3,5-diisopropoxybenzamido)-2-methylbenzoic acid (AAA-117)

4-(4-Chloro-3,5-diisopropoxybenzamido)-2-methylbenzoic acid (AAA-117) (21 mg, 83%) was prepared from methyl 4-(4-chloro-3,5-diisopropoxybenzamido)-2-methylbenzoate (7) (25 mg, 60 μmol) using a procedure essentially the same as in step (ii) for AAA-001 except that the mixture was stirred at 40° C. for 20 h: m/z 404 [M–H]− (ES−); 1H NMR (400 MHz, DMSO-d6) δ: 12.61 (1H, br s), 10.33 (1H, s), 7.88 (1H, d), 7.71 (2H, dd), 7.26 (2H, d), 4.78 (2H, sep), 2.55 (3H, s), 1.33 (12H, d).

Synthesis 120

4-(4-Chloro-3-isopropoxy-5-methoxybenzamido) benzoic acid (AAA-118)

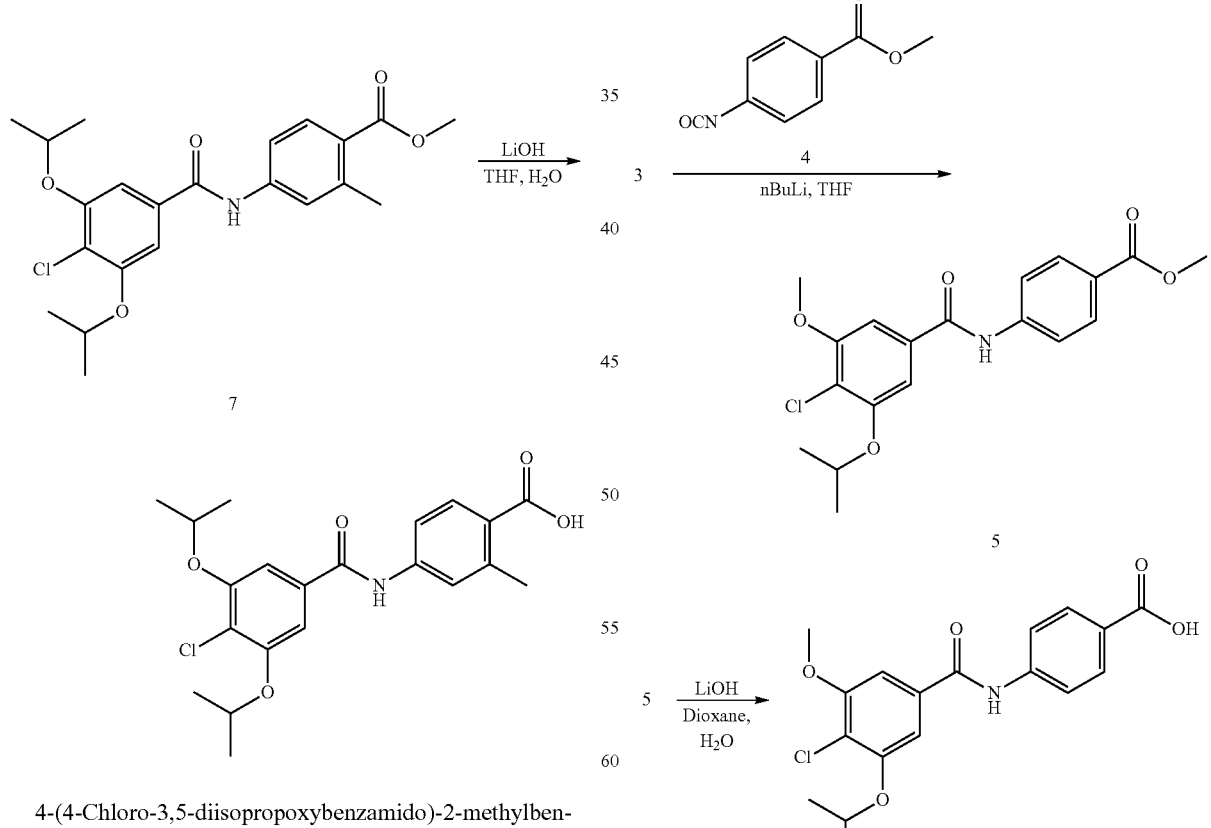

Step (i): 2-Chloro-5-iodo-3-methoxyphenol (2)

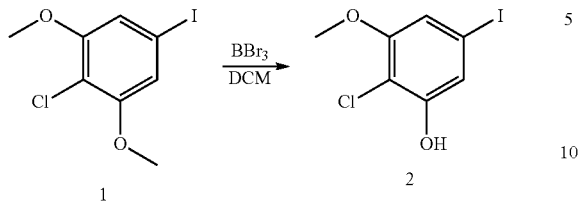

Tribromoborane (156 µL, 1.65 mmol) was added to a solution of 2-chloro-5-iodo-1,3-dimethoxybenzene (1) (380 mg, 1.27 mmol) in DCM (5 mL) and the mixture was stirred at RT for 1 h. The mixture was poured into iced water (20 mL) and made basic by the addition of 2M NaOH (50 mL). The aqueous mixture was washed with DCM (50 mL) and then acidified by the addition of 4M HCl. The product was then extracted into DCM (50 mL), the organic solution was dried over $MgSO_4$ and the solvent was removed in vacuo to give 2-chloro-5-iodo-3-methoxyphenol (2) (290 mg, 78%) as a colourless oil: m/z 283 [M−H]⁻ (ES⁻).

Step (ii): 2-Chloro-5-iodo-1-isopropoxy-3-methoxybenzene (3)

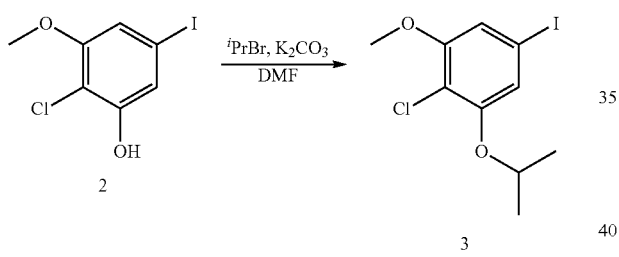

2-Chloro-5-iodo-1-isopropoxy-3-methoxybenzene (3) (270 mg, 77%) was prepared from 2-chloro-5-iodo-3-methoxyphenol (2) (290 mg, 1.02 mmol) using a procedure essentially the same as in step (i) for AAA-001 except that isopropyl bromide was used instead of cyclopentyl bromide.

Step (iii): Methyl 4-(4-chloro-3-isopropoxy-5-methoxybenzamido)benzoate 5

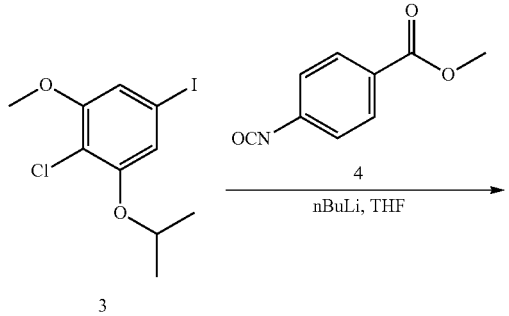

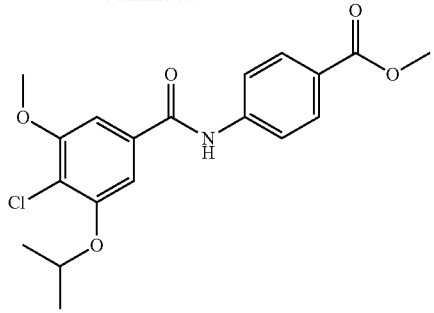

n-Butyllithium (364 µl, 0.909 mmol) was slowly added to a solution of 2-chloro-5-iodo-1-isopropoxy-3-methoxybenzene (3) (270 mg, 0.827 mmol) in anhydrous THF (5 mL) at −78° C. After stirring for 15 min at this temperature a solution of methyl 4-isocyanatobenzoate (176 mg, 0.992 mmol) in anhydrous THF (5 mL) was added dropwise. The solution was allowed to warm to RT and stirred for a further 20 h. The reaction mixture was partitioned between DCM (40 mL) and brine (100 mL). The phases were separated and the organic solution was dried over $MgSO_4$, filtered and the solvent was removed in vacuo. The residue was purified by silica gel chromatography (40 g, 0-40% EtOAc in isohexane) to afford methyl 4-(4-chloro-3-isopropoxy-5-methoxybenzamido)benzoate (5) (20 mg, 6%) as a colourless oil: m/z 376 [M−H]⁻ (ES⁻).

Step (iv): 4-(4-Chloro-3-isopropoxy-5-methoxybenzamido)benzoic acid (AAA-118)

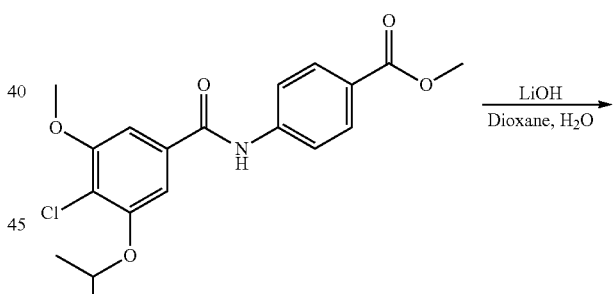

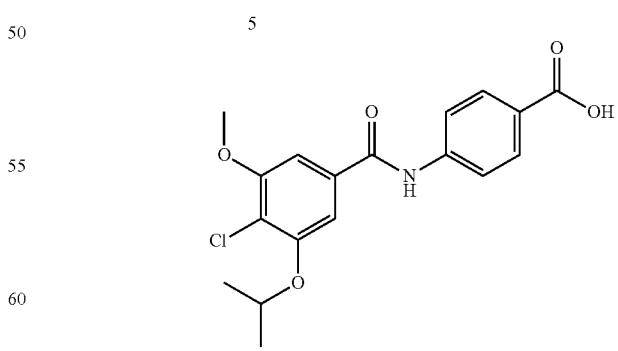

4-(4-Chloro-3-isopropoxy-5-methoxybenzamido)benzoic acid (AAA-118) (10 mg, 55%) was prepared from methyl 4-(4-chloro-3-isopropoxy-5-methoxybenzamido)benzoate (5) (20 mg, 48 µmol) using a procedure essentially the same as in step (ii) for AAA-001 except that dioxane (3 mL) was used instead of THF: m/z 362 [M–H]⁻ (ES⁻); ¹H NMR (400 MHz, DMSO-d₆) δ: 12.80 (1H, br s), 10.47 (1H, s), 7.99-7.92 (2H, m), 7.90-7.83 (2H, m), 7.31 (2H, dd), 4.79 (1H, sep), 3.94 (3H, s), 1.33 (6H, d).
Synthesis 121
4-(4-Fluoro-3,5-diisopropoxybenzamido)benzoic acid (AAA-119)
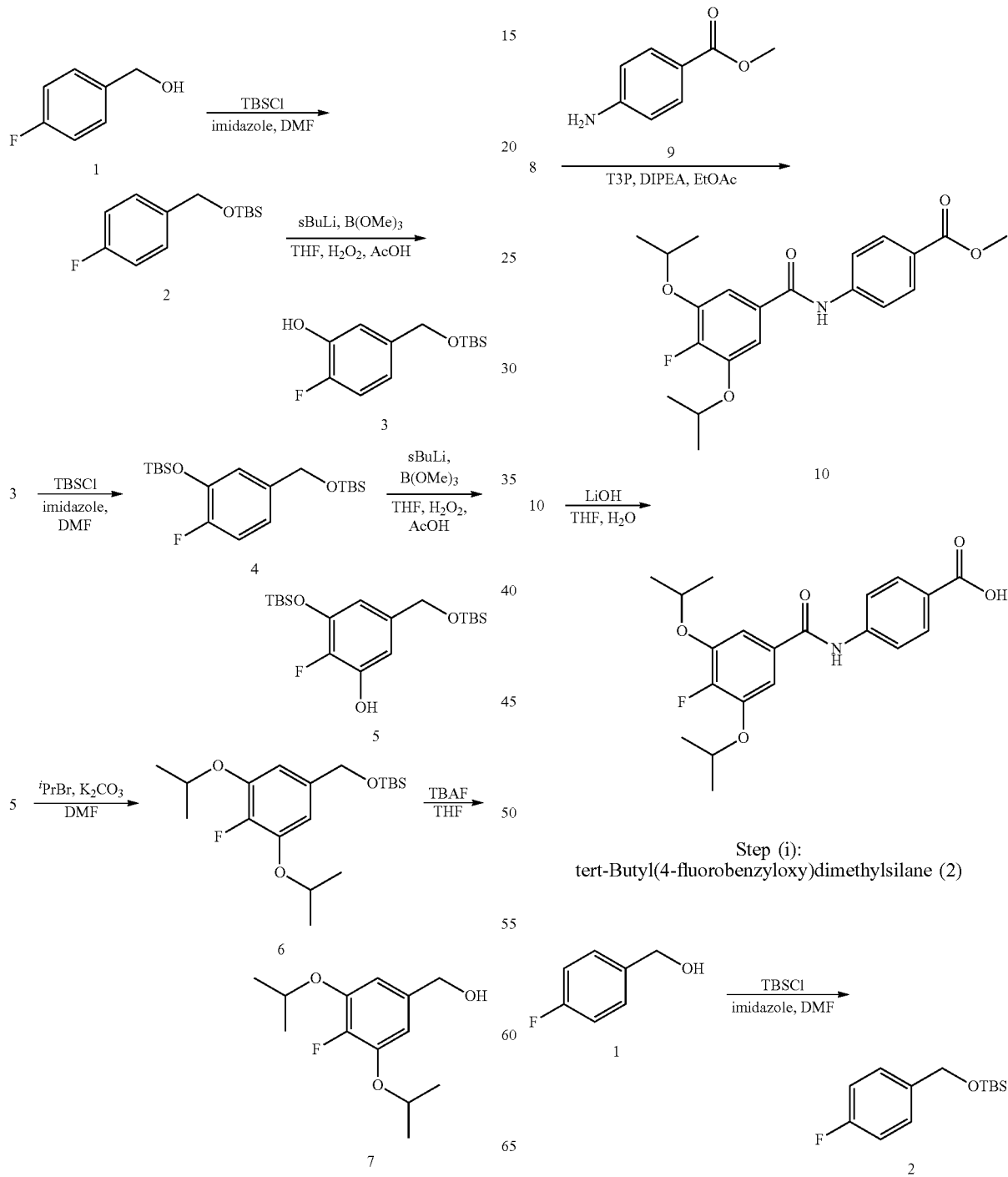
Step (i):
tert-Butyl(4-fluorobenzyloxy)dimethylsilane (2)

A solution of (4-fluorophenyl)methanol (1) (8.6 mL, 79 mmol) in anhydrous DMF (40 mL) was cooled to 0° C. before imidazole (5.9 g, 87 mmol) was added portionwise, followed by tert-butylchlorodimethylsilane (13 g, 87 mmol). The reaction mixture was allowed to warm to RT and stirred for 20 h. The reaction mixture was diluted with EtOAc (200 mL) and the organic solution was washed with satd NaHCO₃ (3×200 mL) and then brine (4×300 mL). The organic solution was dried over MgSO₄ and the solvent was removed in vacuo. The residue was purified by silica gel chromatography (120 g, 0-10% EtOAc in isohexane) to afford tert-butyl (4-fluorobenzyloxy)dimethylsilane (2) (15.4 g, 81%) as a clear oil: ¹H NMR (400 MHz, DMSO-d₆) δ: 7.38-7.28 (2H, m), 7.16 (2H, dd), 4.68 (2H, s), 0.89 (9H, s), 0.07 (6H, s).

Step (ii): 5-((tert-Butyldimethylsilyloxy)methyl)-2-fluorophenol (3)

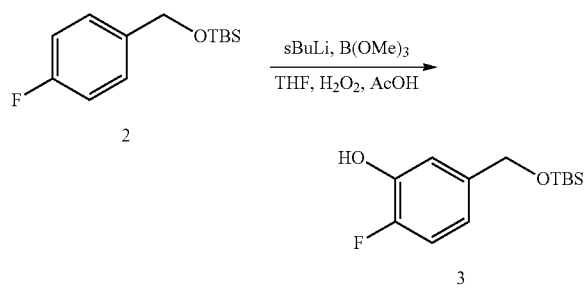

sec-Butyllithium (20.7 mL, 29.0 mmol) was added dropwise to a solution of tert-butyl(4-fluorobenzyloxy)dimethylsilane (2) (6.33 g, 26.3 mmol) in THF (30 mL) over 30 min, at −78° C. Trimethyl borate (2.99 mL, 26.3 mmol) was added dropwise over 30 min while the temperature was maintained at −78° C. The reaction mixture was allowed to warm to 0° C. and AcOH (2.26 mL, 39.5 mmol) was added dropwise, followed by hydrogen peroxide (2.48 mL, 29.0 mmol). The mixture was stirred at 0° C. for 30 min then allowed to warm to RT and stirred for 1 h. The reaction mixture was diluted with diethyl ether (100 mL) and washed with 2M NaOH (100 mL) and brine (100 mL). The organic solution was dried over MgSO₄, filtered and the solvent was removed in vacuo to give 5-((tert-butyldimethylsilyloxy)methyl)-2-fluorophenol (3) (4.0 g, 50%) as a colourless oil: m/z 255 [M−H]⁻ (ES⁻).

Step (iii): tert-Butyl(3-(tert-butyldimethylsilyloxy)-4-fluorobenzyloxy)dimethylsilane (4)

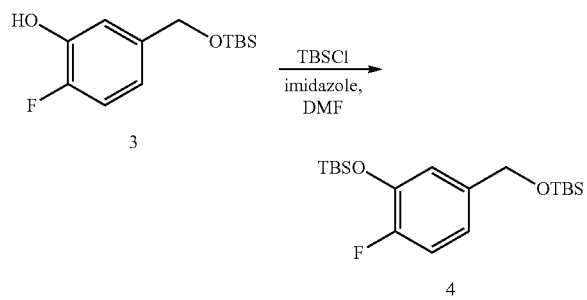

tert-Butyl(3-(tert-butyldimethylsilyloxy)-4-fluorobenzyloxy)dimethylsilane (4) (4.9 g, 81%) was prepared from 5-((tert-butyldimethylsilyloxy)methyl)-2-fluorophenol (3) (4.00 g, 15.6 mmol) using a procedure essentially the same as in step (i).

Step (iv): 3-(tert-Butyldimethylsilyloxy)-5-((tert-butyldimethylsilyloxy)methyl)-2-fluorophenol (5)

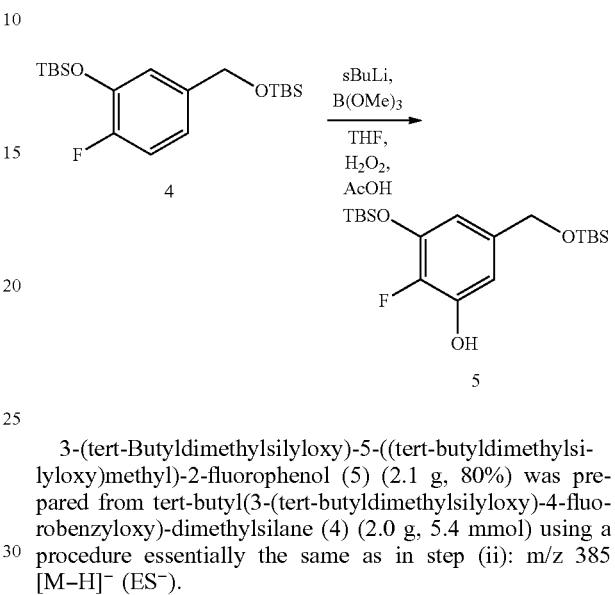

3-(tert-Butyldimethylsilyloxy)-5-((tert-butyldimethylsilyloxy)methyl)-2-fluorophenol (5) (2.1 g, 80%) was prepared from tert-butyl(3-(tert-butyldimethylsilyloxy)-4-fluorobenzyloxy)-dimethylsilane (4) (2.0 g, 5.4 mmol) using a procedure essentially the same as in step (ii): m/z 385 [M−H]⁻ (ES⁻).

Step (v): tert-Butyl(4-fluoro-3,5-diisopropoxybenzyloxy)dimethylsilane (6)

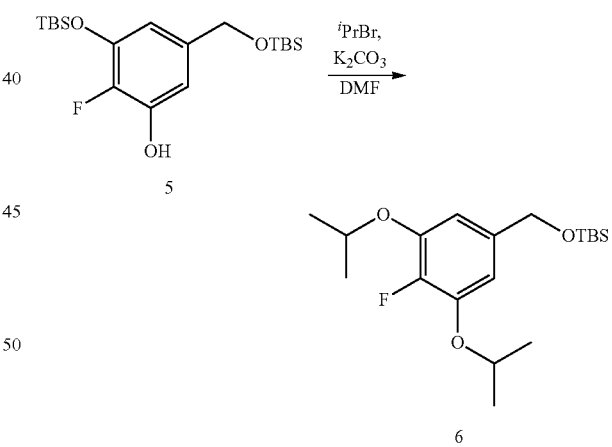

2-Bromopropane (0.90 mL, 9.5 mmol) and K₂CO₃ (1.49 g, 10.8 mmol) were added to a stirred solution of 3-(tert-butyldimethylsilyloxy)-5-((tert-butyldimethylsilyloxy) methyl)-2-fluorophenol (5) (2.08 g, 4.30 mmol) in DMF (3 mL) and the mixture was stirred at 60° C. for 2 h. The reaction mixture was allowed to cool to RT and diluted with diethyl ether (50 mL). The organic solution was washed with brine (3×50 mL), dried over MgSO₄, filtered and the solvent was removed in vacuo to afford tert-butyl(4-fluoro-3,5-diisopropoxybenzyloxy)dimethylsilane (6) (0.6 g, 31%). This material was used in the subsequent reaction step without purification.

Step (vi): (4-Fluoro-3,5-diisopropoxyphenyl)methanol (7)

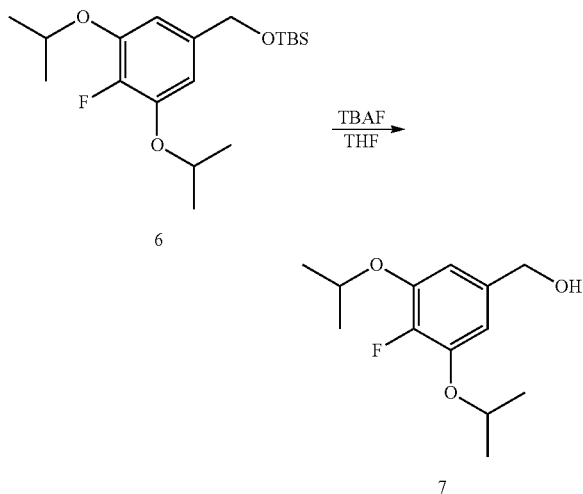

TBAF (1M in THF) (1.35 mL, 1.35 mmol) was added to a solution of tert-butyl(4-fluoro-3,5-diisopropoxybenzyloxy)dimethylsilane (6) (600 mg, 1.35 mmol) in THF at 0° C. and the mixture was stirred at this temperature for 1 h. The mixture was partitioned between NH$_4$Cl (satd. aq.) (50 mL) and EtOAc (100 mL). The phases were separated and the organic solution was washed with brine (50 mL), then dried over MgSO$_4$ and filtered. The solvent was removed in vacuo and the residue was purified by silica gel chromatography (40 g, 0-50% EtOAc in isohexane) to afford (4-fluoro-3,5-diisopropoxyphenyl)methanol (7) (382 mg, 100%) as a colourless oil.

Step (vii): 4-Fluoro-3,5-diisopropoxybenzoic acid (8)

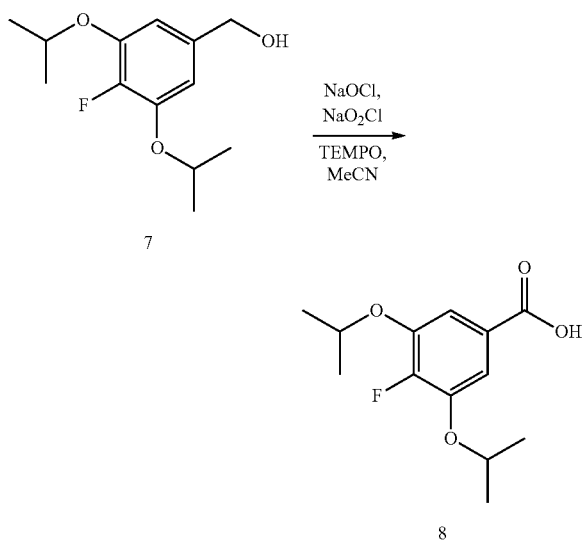

TEMPO (12 mg, 79 µmol) was added to (4-fluoro-3,5-diisopropoxyphenyl)methanol (7) (382 mg, 1.58 mmol) in a mixture of MeCN (10 mL) and sodium phosphate buffer at 35° C. Sodium chlorite (285 mg, 3.15 mmol) in water (5 mL) and sodium hypochlorite (97 µl, 1.6 mmol) were added cautiously (portionwise, 20% of one then the other every 10 min until the addition was complete). Once the reaction was complete the mixture was basified to pH 9 by the addition of NaOH (15 mL). Sodium sulfite (aq., 20 mL) was added and the aqueous mixture was washed with diethyl ether (50 mL). The aqueous layer was acidified by the addition of 4M HCl and the product was extracted into EtOAc (50 mL). The organic solution was dried over MgSO$_4$, filtered and the solvent was removed in vacuo. The residue was purified by silica gel chromatography (12 g, 0-40% EtOAc in isohexane) to afford 4-fluoro-3,5-diisopropoxybenzoic acid (8) (50 mg, 12%) as a white solid: m/z 255 [M–H]$^-$ (ES$^-$).

Step (viii): Methyl 4-(4-fluoro-3,5-diisopropoxybenzamido)benzoate (10)

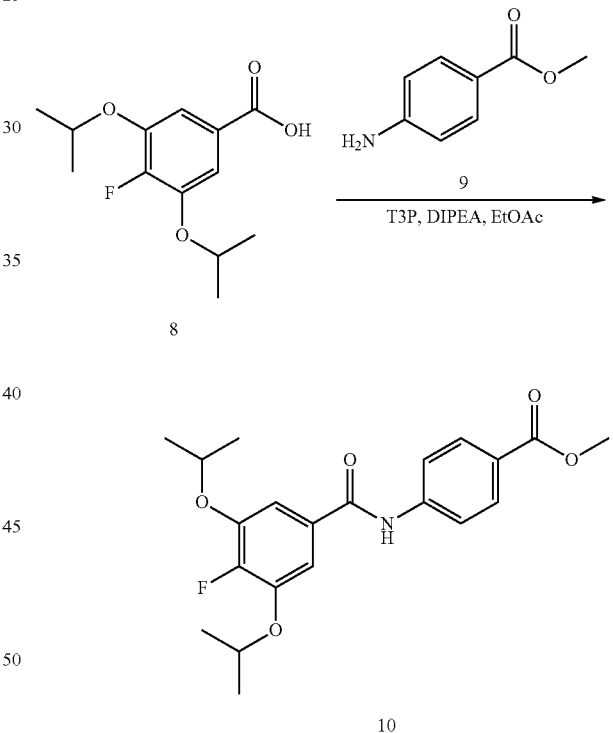

A mixture of 4-fluoro-3,5-diisopropoxybenzoic acid (8) (54 mg, 0.21 mmol), DIPEA (110 µL, 0.632 mmol) and T3P (50% solution in EtOAc) (310 µL, 0.527 mmol) in EtOAc (1 mL) was stirred at RT for 10 min before a solution of methyl 4-aminobenzoate (9) (35 mg, 0.23 mmol) in EtOAc (1 mL) was added dropwise and the mixture was stirred at 40° C. for 20 h. The reaction mixture was adsorbed on to silica and purified by silica gel chromatography (4 g, 0-100% EtOAc in isohexane), then (4 g, 0-10% MeOH in DCM) to afford methyl 4-(4-fluoro-3,5-diisopropoxybenzamido)benzoate (10) (32 mg, 51% purity). The material was taken on in the subsequent reaction step without further purification.

Step (ix): 4-(4-Fluoro-3,5-diisopropoxybenzamido) benzoic acid (AAA-119)

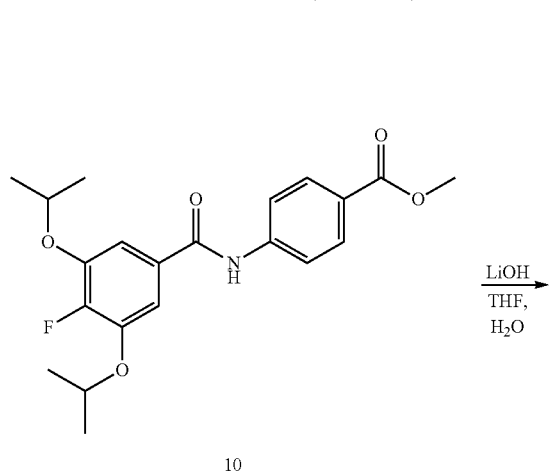

A suspension of methyl 4-(4-fluoro-3,5-diisopropoxybenzamido)benzoate (10) (32 mg, 51% purity, 82 μmol) in THF (1 mL) and 2M LiOH (0.16 mL, 0.33 mmol) was stirred at RT for 20 h, then at 45° C. for 2 h. The mixture was allowed to cool to RT and was acidified by the addition of 1M HCl. The mixture was partitioned between EtOAc (10 mL) and water (10 mL) and the phases were separated. The organic solution was washed with brine (3× mL), then dried over MgSO$_4$ and filtered. The solvent was removed in vacuo and the residue was purified by reverse phase HPLC to afford 4-(4-fluoro-3,5-diisopropoxybenzamido)benzoic acid (AAA-119) (8 mg, 38%) as a white solid: m/z 376 [M+H]$^+$ (ES$^+$), 374 [M−H]$^-$ (ES$^-$); $^1$H NMR (400 MHz, DMSO-d$_6$) δ: 10.37 (1H, s), 7.93 (2H, d), 7.83 (2H, d), 7.35 (2H, d), 4.73 (2H, sep), 1.32 (12H, d). NB acid proton not visible.

Synthesis 122

4-(3,4-Diisopropoxy-5-(trifluoromethyl)benzamido) benzoic acid (AAA-120)

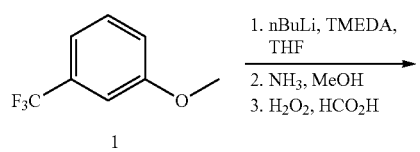

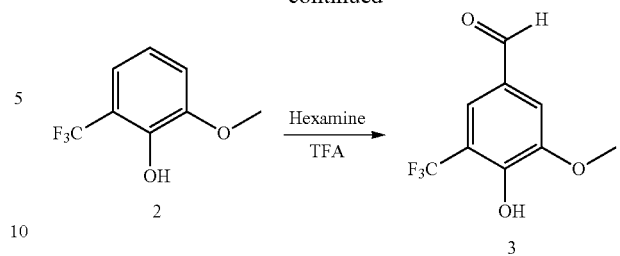

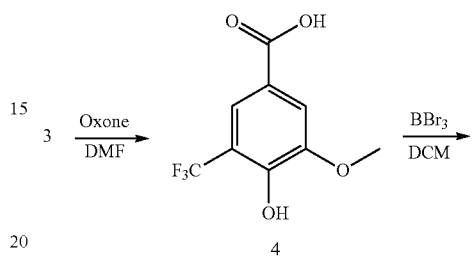

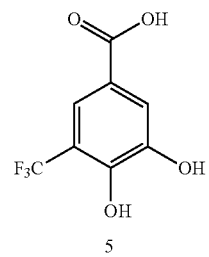

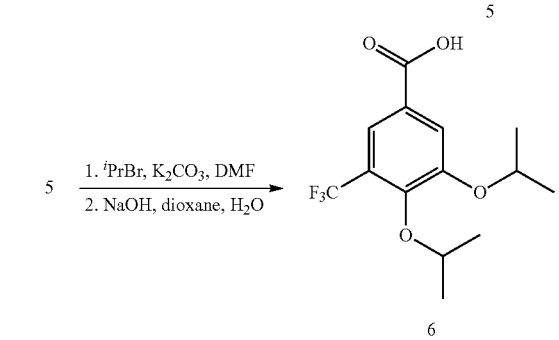

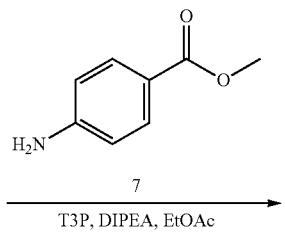

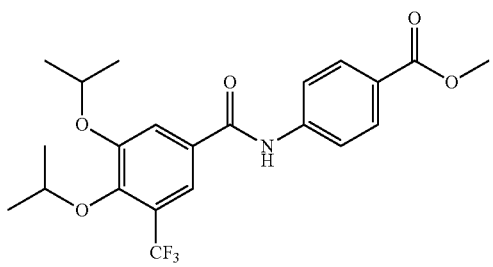

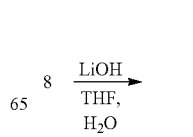

-continued

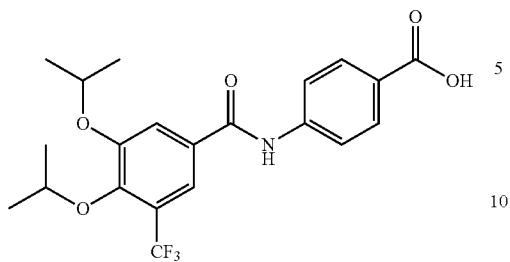

Step (i): 2-Methoxy-6-(trifluoromethyl)phenol (2)

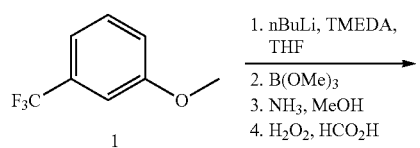

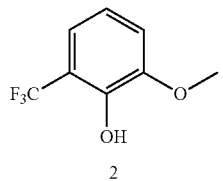

A solution of n-butyllithium (20.4 mL, 51.1 mmol) and TMEDA (9.00 mL, 59.6 mmol) in anhydrous THF (50 mL) was cooled to −78° C. 1-Methoxy-3-(trifluoromethyl)benzene (1) (10 g, 57 mmol) was added dropwise and the reaction mixture was stirred at −78° C. for 15 min then allowed to warm to RT and stirred for 10 min. The reaction mixture was cooled to −78° C. and trimethyl borate (16.1 mL, 142 mmol) was added slowly, dropwise, and the reaction mixture was stirred at −78° C. for 15 min then allowed to warm to RT and stirred for 20 h. 7N $NH_3$/MeOH (20 mL) was added and the solvent was removed in vacuo. The residue was dissolved in formic acid (20 mL) and cooled to 0° C. before hydrogen peroxide (6.00 mL, 68.5 mmol) was added and the solution was allowed to warm to RT and stirred for 2 h. The product was extracted with EtOAc (3×50 mL), and then the combined organics were shaken with NaOH (2×50 mL). The aq phase was acidified with 1M HCl and the product was extracted with DCM (2×30 mL). The organic solution was washed with brine (2×30 mL), dried over $MgSO_4$ and filtered. The solvent was removed in vacuo and the residue was purified by silica gel chromatography (120 g, 0-5% MeOH in DCM) to afford 2-methoxy-6-(trifluoromethyl)phenol (2) (4.95 g, 45%) as a colourless oil: m/z 191 [M−H]⁻ (ES⁻); ¹H NMR (400 MHz, $CDCl_3$) δ: 7.15-7.09 (1H, m), 7.04-6.98 (1H, m), 6.89 (1H, td), 6.14 (1H, br s), 3.91 (3H, s).

Step (ii): 4-Hydroxy-3-methoxy-5-(trifluoromethyl) benzaldehyde (3)

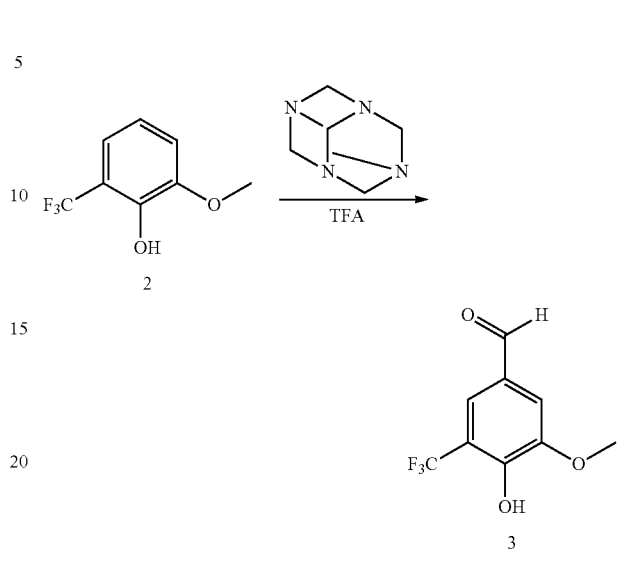

A mixture of 2-methoxy-6-(trifluoromethyl)phenol (2) (2.5 g, 13 mmol) and hexamethylenetetramine (1.8 g, 13 mmol) in TFA (40 mL) was stirred under reflux for 3 h. The solvent was removed in vacuo and the residue was dissolved in 1M HCl (20 mL). The product was extracted with DCM (3×20 mL), the combined organics were washed with brine (2×20 mL) and then the solvent was removed in vacuo. The residue was purified by silica gel chromatography (80 g, 0-100% EtOAc in isohexane) to afford 4-hydroxy-3-methoxy-5-(trifluoromethyl)benzaldehyde (3) (1.03 g, 34%) as a white solid: m/z 219 [M−H]⁻ (ES⁻).

Step (iii): 4-Hydroxy-3-methoxy-5-(trifluoromethyl) benzoic acid (4)

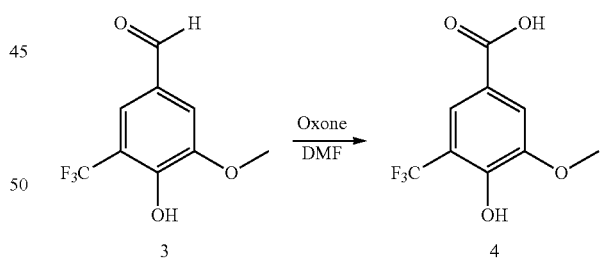

A suspension of 4-hydroxy-3-methoxy-5-(trifluoromethyl)benzaldehyde (1.03 g, 4.68 mmol) and Oxone™ (3.45 g, 5.61 mmol) in DMF (10 mL) was stirred at RT for 2 h. The reaction mixture was diluted with EtOAc (40 mL) and the solution was washed sequentially with 1M HCl (40 mL) and brine (4×40 mL). The solvent was removed in vacuo and the residue was purified by silica gel chromatography (80 g, 0-10% MeOH in DCM) to afford 4-hydroxy-3-methoxy-5-(trifluoromethyl)benzoic acid (4) (392 mg, 35%) as a white solid: m/z 235 [M−H]⁻ (ES⁻); ¹H NMR (400 MHz, DMSO-$d_6$) δ: 13.01 (1H, br s), 10.74 (1H, br s), 7.68 (2H, dd), 3.92 (3H, s).

Step (iv): 3,4-Dihydroxy-5-(trifluoromethyl)benzoic acid (5)

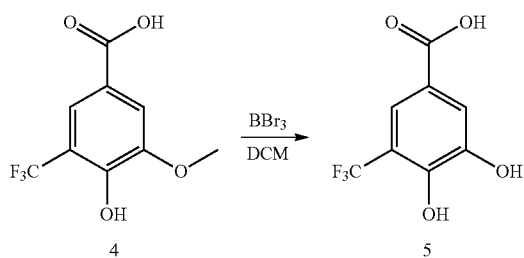 [SMILES: COc1cc(C(=O)O)cc(C(F)(F)F)c1O ; "BBr3" ; O=C(O)c1cc(O)c(O)c(C(F)(F)F)c1]

Boron tribromide (392 µL, 4.15 mmol) was added to a suspension of 4-hydroxy-3-methoxy-5-(trifluoromethyl)benzoic acid (4) (392 mg, 1.66 mmol) in DCM (10 mL) at 0° C. The reaction mixture was allowed to warm to RT and stirred for 70 h. The reaction mixture was cautiously added to stirring iced water (50 mL) and stirred for 10 min. The product was extracted with DCM (2×20 mL), and then the combined organic extracts were washed with brine (2×20 mL). The solvent was removed in vacuo and the residue was purified by silica chromatography (12 g, 0-10% MeOH in DCM) to afford 3,4-dihydroxy-5-(trifluoromethyl)benzoic acid (5) (257 mg, 68%) as a white solid: m/z 221 [M−H]− (ES−); $^1$H NMR (400 MHz, DMSO-d$_6$) δ: 12.83 (1H, br s), 10.45 (2H, br d), 7.56 (2H, dd).

Step (v): 3,4-Diisopropoxy-5-(trifluoromethyl)benzoic acid (6)

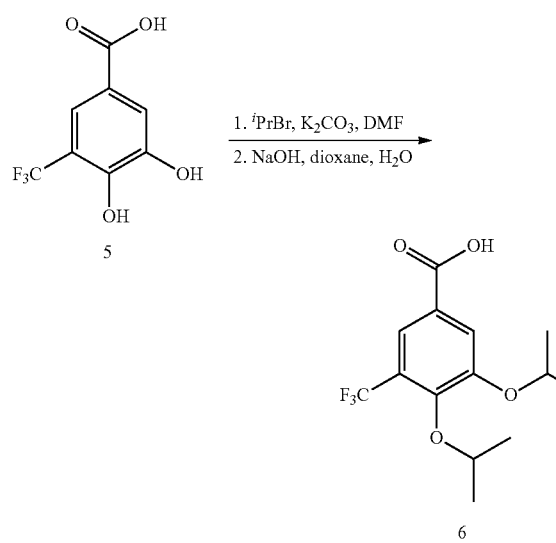

2-Bromopropane (380 µL, 4.05 mmol) was added to a suspension of 3,4-dihydroxy-5-(trifluoromethyl)benzoic acid (5) (257 mg, 1.16 mmol) and K$_2$CO$_3$ (560 mg, 4.05 mmol) in DMF (10 mL) and the reaction mixture was stirred at 80° C. for 20 h. The reaction mixture was diluted with EtOAc (30 mL) and washed sequentially with 1M HCl (30 mL) and brine (5×30 mL), and then the solvent was removed in vacuo. The residue was suspended in 2M sodium hydroxide (5.8 mL, 12 mmol) and the mixture was stirred at 80° C. for 4 h. Dioxane (10 mL) was added and the mixture continued to stir at 80° C. for a further 20 h. The solvents were removed in vacuo and the residue was partitioned between EtOAc (50 mL) and 1M HCl (50 mL). The phases were separated and the organic solution was washed with brine (3×40 mL), and then dried over MgSO$_4$, and filtered. The solvent was removed in vacuo and the residue was purified by silica chromatography (40 g, 0-15% MeOH in DCM) to afford 3,4-diisopropoxy-5-(trifluoromethyl)benzoic acid (6) (118 mg, 33%) as a yellow solid.

Step (vi): Methyl 4-(3,4-diisopropoxy-5-(trifluoromethyl)benzamido)benzoate (8)

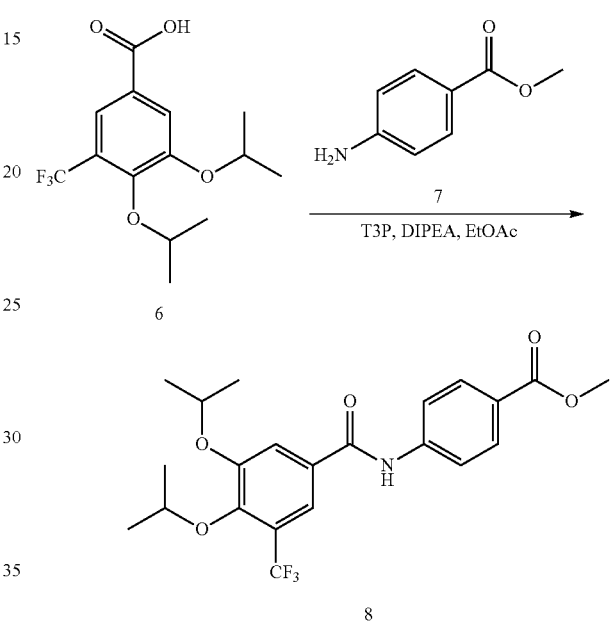

Methyl 4-(3,4-diisopropoxy-5-(trifluoromethyl)benzamido)benzoate (8) (11 mg, 19%) was prepared from 3,4-diisopropoxy-5-(trifluoromethyl)benzoic acid (6) (40 mg, 0.13 µmol) using a procedure essentially the same as in step (i) for AAA-064 except that methyl 4-aminobenzoate (7) was used instead of methyl 4-amino-2-fluorobenzoate: $^1$H NMR (400 MHz, DMSO-d$_6$) δ: 10.59 (1H, s), 8.02-7.88 (4H, m), 7.87-7.80 (2H, m), 5.12-5.01 (1H, m), 4.90-4.78 (1H, m), 3.85 (3H, s), 1.37 (6H, d), 1.24 (7H, d).

Step (vii): 4-(3,4-Diisopropoxy-5-(trifluoromethyl)benzamido)benzoic acid (AAA-120)

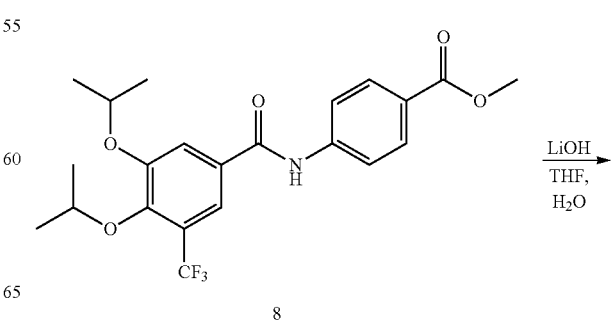

-continued

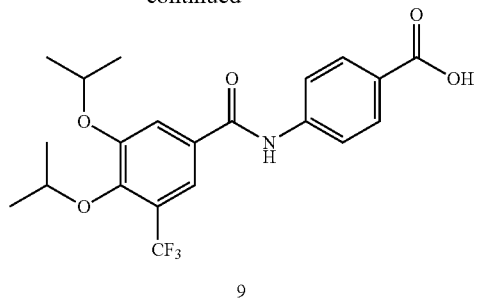

9

4-(3,4-Diisopropoxy-5-(trifluoromethyl)benzamido)benzoic acid (AAA-120) (8 mg, 71%) was prepared from methyl 4-(3,4-diisopropoxy-5-(trifluoromethyl)benzamido)benzoate (8) (11 mg, 25 μmol) using a procedure essentially the same as in step (ii) for AAA-001 except the mixture was stirred at 40° C. for 20 h: m/z 424 [M−H]$^-$ (ES$^-$); $^1$H NMR (400 MHz, DMSO-d$_6$) δ: 12.79 (1H, br s), 10.55 (1H, s), 7.95 (2H, d), 7.87-7.82 (4H, m), 5.07 (1H, m), 4.85 (1H, m), 1.37 (6H, d), 1.24 (6H, d).

Biological Methods
Studies of Retinoic Acid Receptors

The inventors' have shown that RARα agonists are likely to be useful in the treatment of AD. They prevent neuronal cell death in the presence of Aβ42; in culture, they up-regulate choline acetyltransferase (chAT), down-regulate amyloid precursor protein (APP), and increase the expression of disintegrin-metalloproteinases 10 (ADAM10). In vivo, the inventors' have shown that feeding RARα agonists to Tg2576 mice (which overexpresses the Swedish mutation of the human APP leading to amyloid β deposits and cognitive decline) results in a significant reduction in the levels of both A140 and Aβ42, as well as positive behavioural changes.

Materials and Methods:
Culture of Cortical Neurons and Survival Assays:

Neuronal cultures were prepared from embryonic E19 mouse embryos. Fetal brain cortices were dissected and freed from meninges. The cortices were placed in ice cold PBS containing 0.25% glucose and triturated with fire polished Pasteur pipettes. Cortical cells (1×10$^5$) were plated onto poly-L-lysine (10 μg/mL) coated glass coverslips in 24-well tissue culture plates. They were cultured in Neurobasal medium containing B27 supplement, 2 mM glutamine, 20 μg/mL penicillin stepromycin, and 0.25% glucose. They were maintained for 7 days before been treated. For each treatment, 3 coverslips were used and the experiment was repeated 3 times.

Treatments consisted of 10 μM Aβ42 in the presence of increasing dose of agonist: all-trans retinoic acid (atRA), BMS 194753 (RARα), AM 580 (RARα), CD 2019 (RARβ), or CD 437 (RARγ).

TABLE 1

RAR Agonists

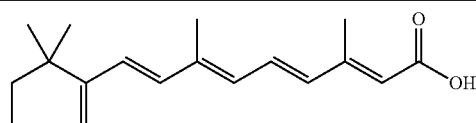

atRA

TABLE 1-continued

RAR Agonists

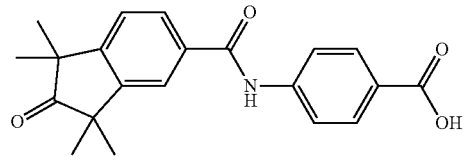

BMS194753

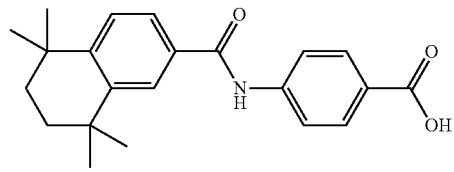

AM580

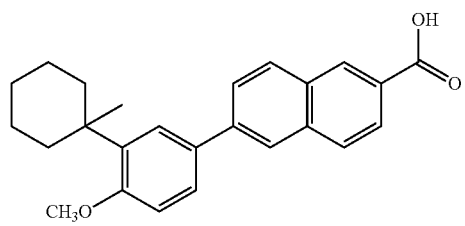

CD 2019

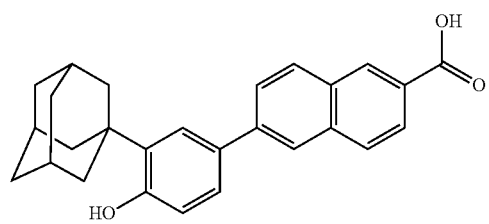

CD 437

After 3 days of culture, media was removed and Hoechst 33342 (10 μM) and propidium iodide (10 μM) in PBS was added to the wells for 15 minutes. Only neurons positive for Hoechst 33342 but negative for propidium iodide were counted as surviving neurons. In addition, cortical cultures were treated with agonist alone (0.1 μM) and assayed for chAT, APP, and ADAM10. The antibodies used were α chAT (1:200, Chemicon™), α APP (1:100, Chemicon™) and α ADAM10 (1:200, Chemicon™). Secondary antibody used was anti-rabbit Cy3 or Cy5 conjugated (Jackson™, used at 1:1000). The nuclear marker DAPI (1 μg/mL) was used to stain all cells. Cell counts were carried out in 31 mm$^2$ areas per coverslip by an investigator who did not know the treatments.

Animal Treatments:

Twenty seven 3 month old Tg2576 mice (Taconic™) were split into 3 groups of 9. One group was fed normal chow, the other groups were fed with 1 mg/Kg RARα agonist, either AM580 or BMS194753. Animals were analysed at 6 and 9 months of age.

Tissue Preparation:

Animals were perfused with PBS. The brain was dissected and one hemisegment was fixed in 4% PFA overnight, 20% sucrose for 3 days, embedded in OCT compound and stored frozen. The cortex was removed form the other hemisegment and the protein extracted.

Aβ Levels:

To measure Aβ40 and Aβ42 levels, a sandwich ELISA assay kit (Biosource™) was used according to the manufactures instructions. A 1:5000 of the guanidine-soluble extracts were made with TBS containing 5% BSA and 1×protease inhibitor (Calbiochem™) and centrifuged at 16000×g for 20 minutes at 4° C. Samples were diluted 1:10000 in sample diluent provided by the manufacturer. Samples were loaded in triplicate (100 mL) and the plate read at 420 nm, by an investigator who did not know the treatments.

Graphs and Statistics:

Graphs were plotted using Sigma Plot™. Data were expressed as mean+/−S.E.M and statistical analysis was carried out using student's t test.

Results:

RARα Signalling Prevents Neuronal Death in the Presence of Aβ42:

Cortical cultures were treated after 7 days with 10 μM Aβ42 and supplemented with 0.01-1 μM of agonist. After 3 days, the number of surviving cells was determined. In the presence of atRA, there was an increase in cell survival with increasing dose of atRA as compared to the control cultures (treated only with Aβ42). As atRA is a weak pan-agonist of all the RARs, it was decided to identify the specific receptor involved in this process using RAR specific agonists. Neuronal survival was notably better for each of two RARα selective agonists (AM 580 and BMS 194753) but notably worse for RARβ and RARγ selective agonists (CD 2019 and CD 437, respectively). The data are summarised in the following table. This suggests that it is RARα signalling that is required for neuronal survival in the presence of Aβ42.

TABLE 2

Effect of Increasing Dose of RAR Agonists on Survival of Cortical Neurons in the Presence of 10 μM Aβ42

| | | % Surviving Neurons | |
| --- | --- | --- | --- |
| Agonist | 0.01 μM agonist | 0.1 μM agonist | 1.0 μM agonist |
| atRA (pan-RAR) | 53 ± 4 | 69 ± 4 | 82 ± 4 |
| AM 580 (RARα) | 52 ± 7 | 70 ± 6 | 99 ± 9 |
| BMS 194753 (RARα) | 57 ± 7 | 69 ± 3 | 88 ± 4 |
| CD 2019 (RARβ) | 52 ± 3 | 58 ± 5 | 60 ± 5 |
| CD 437 (RARγ) | 53 ± 3 | 30 ± 11 | 26 ± 10 |
| Control 1 (no Aβ42) | | 100 ± 6 | |
| Control 2 (Aβ42; no agonist) | | 52 ± 7 | |

RARα Signalling Up-Regulates chAT Expression in Cultures of μ17 Cortical Neurons:

Cortical cultures were treated after 7 days with 0.1 μM of agonist, and analysed 3 days later. Only in the presence of RARα agonist was there a significant increase in choline acetyltransferase (chAT) expression (and so an increase in the number of chAT expressing neurons). The data are summarised in the following table.

TABLE 3

Effect of Agonists on chAT Expression in Cortical Neurons

| Agonist (0.01 μM) | Number of chAT Neurons |
| --- | --- |
| Control (no agonist) | 5 ± 1 |
| atRA | 16 ± 2 |

TABLE 3-continued

Effect of Agonists on chAT Expression in Cortical Neurons

| Agonist (0.01 μM) | Number of chAT Neurons |
| --- | --- |
| BMS 194753 (RARα) | 37 ± 3 |
| CD 2019 (RARβ) | 8 ± 1 |
| CD 437 (RARγ) | 2 ± 1 |

RARα Signalling Down-Regulates APP Expression in Cultures of E17 Cortical Neurons:

Cortical cultures were treated after 7 days with 0.1 μM of agonist, and analysed 3 days later. Only in the presence of the RARα agonist was there a significant decrease in amyloid precursor protein (APP) expression (and so a decrease in the number of APP expressing neurons). The data are summarised in the following table.

TABLE 4

Effect of Agonists on APP Expression in Cortical Neurons

| Agonist (0.01 μM) | Number of APP Neurons |
| --- | --- |
| Control (no agonist) | 27 ± 2 |
| atRA | 15 ± 2 |
| BMS 194753 (RARα) | 10 ± 2 |
| AM 580 (RARα) | 11 ± 2 |
| CD 2019 (RARβ) | 23 ± 2 |
| CD 437 (RARγ) | 22 ± 3 |

RARα Signalling Up-Regulates ADAM10 Expression in Cultures of E17 Cortical Neurons:

Cortical cultures were treated after 7 days with 0.1 μM of agonist, and analysed 3 days later. Only in the presence of the RARα agonist was there a significant increase in disintegrin-metalloproteinases 10 (ADAM10) expression (and so an increase in the number of ADAM10 expressing neurons). The data are summarised in the following table.

TABLE 5

Effect of Agonists on APP Expression in Cortical Neurons

| Agonist (0.01 μM) | Number of APP Neurons |
| --- | --- |
| Control (no agonist) | 2 ± 0.5 |
| atRA | 11 ± 1.5 |
| BMS 194753 (RARα) | 20 ± 2 |
| AM 580 (RARα) | 19 ± 3 |
| CD 2019 (RARβ) | 1 ± 0.5 |
| CD 437 (RARγ) | 2 ± 0.75 |

Oral Dosing of RARα Agonist Down-Regulates A340 and A342 Expression in the Tg2576 Mouse:

The above data taken together suggest that RARα signalling as opposed to RARβ and RARγ signalling regulates a number of genes involve in AD. In order to demonstrate the usefulness of a RARα agonists in vivo, a mouse model was employed which shows many aspects of AD. These are Tg2576 mice, which over-express the Swedish mutation of APP. These mice overproduce Aβ40 and Aβ42. Three month old mice were fed for 3 months with normal chow or chow supplemented with 1 mg/kg of agonist. At six months of age, there is a dramatic decrease in both Aβ40 and Aβ42 levels in the mice fed with the RARα agonist, as compared to the normal fed mice.

TABLE 6

Effect of Oral RARα Agonist on Aβ40 and Aβ42 in Tg2576 Mice

| Agonist | % of Aβ40 | % of Aβ42 |
|---|---|---|
| Control (no agonist) | 100 ± 2 | 100 ± 4 |
| AM 580 (RARα) | 4 ± 1 | 8 ± 1 |
| BMS 194753 (RARα) | 3 ± 0.5 | 7 ± 1 |

Behavioural Outcomes:

It is well known in the field that the Tg2576 mice become very aggressive with age and that this is one of the symptoms of AD. It was noted in the above studies, that while it was necessary to cage the control mice individually during the course of the experiment due to their aggression, the mice treated with RARα agonist displayed little or no aggression such that they could be caged together and displayed increased sexual activity. These data suggest that orally administered RARα agonist is of therapeutic value in the treatment of AD.

Transactivation Assays for RARα, RARβ, and RARγ Receptors

Transcriptional transactivation assays were performed with gal4 fusion receptor constructs, created using each of the RAR ligand binding domains, co-transfected with the pFR-luc (Stratagene™) reporter construct in COS-7 cells. Thus, transfected cells will constitutively express the gal4-RAR fusion protein which in turn may be transactivated by all trans retinoic acid (atRA) to induce the expression of the luciferase that is driven by a gal4UAS.

Briefly, on day 1, 96 well plates were seeded with 8000 cells per well then left to recover overnight. On day 2, the cells were co-transfected with 100 ng of reporter plasmid and 10 ng of the appropriate receptor plasmid per well using lipofectamine (Invitrogen™). On day 3, the lipofectamine containing media was replaced by a DMEM without phenol red, followed by the addition of test compound dissolved in 1 μL of DMSO to each well's 100 μL total volume. Finally, on day 4, the cells were lysed and their luciferase substrate was provided by the BrightGlo™ reagent (Promega™), the plates were then read on the MicroBeta TriLux™ (Perkin Elmer™).

On each plate, an 8 point dose-response curve of atRA was run in duplicate and dose-response curves of test compounds were also generated in duplicate.

$EC_{50}$ data both for test compounds and atRA was generated by fitting dose-response curves using GraphPad Prism™. Data for test compounds are quoted as a ratio of the test compound $EC_{50}$ to that of atRA obtained on the same plate. Where replicate data has been generated, the data are quoted as a ratio of the mean $EC_{50}$ from the separate experiments.

Bioloqical Data

A number of compounds of the invention were examined using the transactivation assay for RAR alpha, the transactivation assay for RAR beta, and the transactivation assay for RAR gamma, as described above.

For comparison purposes, data for several reference compounds, XXX-01, XXX-02, and XXX-03, were also obtained. A key structural feature of the compounds of the present invention is the presence of particular subsituents (i.e., —R¹, —R², and —R³) at the positions meta, para, and meta to the amide linkage (i.e., -J-). The comparison compounds described herein were selected because they are structurally similar to the compounds of the present invention, but lack one of these three substituents.

Comparison Compounds

| Code Number | Structure |
|---|---|
| XXX-01 | 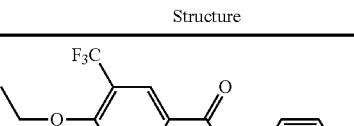 |
| XXX-02 | 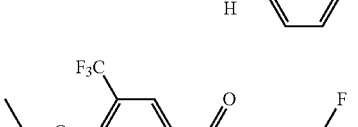 |
| XXX-03 | 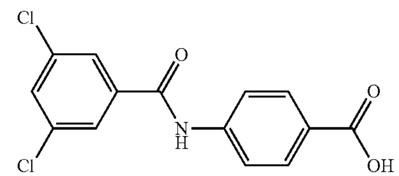 [SMILES: O=C(O)c1ccc(NC(=O)c2cc(Cl)cc(Cl)c2)cc1] |

The data are summarised in the following table.

| Code Number | RARα activity ratio | RARβ activity ratio | RARα/RARβ ratio (*) | RARγ activity ratio |
|---|---|---|---|---|
| atRA | 1 | 1 | 1 | 1 |
| XXX-01 | 327 | 2570 | 7.9 | inactive |
| XXX-02 | 2242 | — | — | — |
| XXX-03 | 90 | 642 | 7.1 | inactive |
| AAA-001 | 11 | 342 | 31.1 | 4700 |
| AAA-002 | 50 | 2900 | 58.0 | inactive |
| AAA-003 | 15 | 139 | 9.3 | 1200 |
| AAA-004 | 7 | 1420 | 202.9 | 820 |
| AAA-005 | 68 | 3570 | 52.5 | 3770 |
| AAA-006 | 14 | 1054 | 75.3 | 5840 |
| AAA-007 | 25 | 2010 | 80.4 | inactive |
| AAA-008 | 26 | 4560 | 175.4 | 56900 |
| AAA-009 | 29 | 2450 | 84.5 | 960 |
| AAA-010 | 102 | 2530 | 24.8 | inactive |
| AAA-011 | 34 | 2960 | 87.1 | 21800 |
| AAA-012 | 533 | 1300 | 2.4 | inactive |
| AAA-013 | 30 | 355 | 11.8 | inactive |
| AAA-014 | 58 | 1350 | 23.3 | inactive |
| AAA-015 | 20 | 540 | 27.0 | inactive |
| AAA-016 | 500 | — | — | — |
| AAA-017 | 140 | inactive | >500 | — |
| AAA-018 | 151 | 9660 | 64.0 | inactive |
| AAA-019 | 0.9 | 74 | 82.2 | 136 |
| AAA-020 | 108 | 214 | 2.0 | inactive |
| AAA-021 | 760 | — | — | — |
| AAA-022 | 448 | inactive | >50 | inactive |
| AAA-023 | 5 | 404 | 80.8 | 62370 |
| AAA-024 | 66 | 805 | 12.2 | 27200 |
| AAA-025 | 5 | 131 | 26.2 | inactive |
| AAA-026 | 180 | 4920 | 27.3 | inactive |
| AAA-027 | 260 | inactive | >5 | — |
| AAA-028 (PP-01) | 370 | 64000 | 173.0 | inactive |
| AAA-029 (PP-02) | 24 | 1920 | 80 | inactive |
| AAA-030 (PP-03) | 29 | 9525 | 328 | 5850 |
| AAA-031 | 7 | 2930 | 420 | 6250 |
| AAA-032 | 61 | 2700 | 44 | 16875 |
| AAA-033 | 13 | 19 | 1.5 | 148 |
| AAA-034 | 2 | 244 | 122 | 1250 |
| AAA-035 | 0.30 | 2620 | 8700 | 87000 |

| Code Number | RARα activity ratio | RARβ activity ratio | RARα/RARβ ratio (*) | RARγ activity ratio |
|---|---|---|---|---|
| AAA-036 | 7.0 | 215 | 31 | 2438 |
| AAA-037 | 0.25 | 324 | 1300 | >2600 |
| AAA-038 | 0.50 | 49 | 98 | 0.36 |
| AAA-039 | 3.0 | 177 | 59 | 2985 |
| AAA-040 | 1.1 | 60 | 55 | 194 |
| AAA-041 | 5.4 | 238 | 44 | 31340 |
| AAA-042 | 5.4 | 369 | 68 | 6000 |
| AAA-043 | 2 | 53 | 27 | 688 |
| AAA-044 | 1.7 | 55 | 32 | 571 |
| AAA-045 | 7.3 | 283 | 39 | 3651 |
| AAA-046 | 2.8 | 121 | 43 | 698 |
| AAA-047 | 11 | 22 | 2 | 270 |
| AAA-048 | 0.86 | 38 | 44 | 162 |
| AAA-049 | 0.64 | 8460 | 13200 | 82 |
| AAA-050 | 1.7 | 89 | 52 | 1386 |
| AAA-051 | 0.97 | 43 | 45 | 2859 |
| AAA-052 | 0.25 | 21 | 84 | 1923 |
| AAA-053 | 4.2 | 1410 | 336 | 414 |
| AAA-054 | 0.59 | 21 | 36 | 51 |
| AAA-055 | 18 | 1926 | 107 | 69000 |
| AAA-056 | 3.1 | >770 | >250 | 22 |
| AAA-057 | 33 | 1226 | 37 | 4920 |
| AAA-058 | 29 | 4200 | 145 | 550 |
| AAA-059 | 27 | 2600 | 96 | 225 |
| AAA-060 | 45 | 2267 | 50 | 30 |
| AAA-061 | 44 | 5200 | 118 | 1531 |
| AAA-062 | 85 | 714 | 8 | 5328 |
| AAA-063 | 76 | 1686 | 22 | 6429 |
| AAA-064 | 81 | >3500 | >40 | 1977 |
| AAA-065 | 15 | 140 | 9 | 3521 |
| AAA-066 | 32 | 7558 | 236 | |
| AAA-067 | 50 | 279 | 6 | 6047 |
| AAA-068 | 7 | 976 | 140 | 60833 |
| AAA-069 | 1.2 | 505 | 421 | 3380 |
| AAA-070 | 3.4 | 2386 | 701 | >62500 |
| AAA-071 | 5.2 | 160 | 31 | 13333 |
| AAA-072 | 9.4 | 2333 | 248 | 29474 |
| AAA-073 | 19 | 117 | 6 | 220 |
| AAA-074 | 154 | 32400 | 210 | 14500 |
| AAA-075 | 4.7 | 1134 | 241 | 2394 |
| AAA-076 | 5.3 | 1500 | 283 | 10833 |
| AAA-077 | 6.7 | 4082 | 609 | 117857 |
| AAA-078 | 0.7 | 103 | 147 | 8083 |
| AAA-079 | 1.1 | 536 | 487 | 6786 |
| AAA-080 | 1.6 | 318 | 200 | 17460 |
| AAA-081 | 9.0 | 1453 | 161 | >27000 |
| AAA-082 | 25 | 6885 | 275 | >56000 |
| AAA-083 | 9 | 90 | 10 | 4390 |
| AAA-084 | 26 | 6087 | 234 | >1400 |
| AAA-085 | 33 | 6923 | 210 | >8300 |
| AAA-086 | 2.1 | 7 | 3.1 | 1203 |
| AAA-087 | 7 | 2000 | 286 | 11725 |
| AAA-088 | 1.0 | 115 | 115 | 1706 |
| AAA-089 | 1.3 | 510 | 392 | 2647 |
| AAA-090 | 5.0 | 1250 | 250 | 367000 |
| AAA-091 | 1.6 | 216 | 135 | 75000 |
| AAA-092 | 2 | 53 | 27 | 1059 |
| AAA-093 | 2.0 | 92 | 46 | 10833 |
| AAA-094 | 0.23 | 656 | 2852 | 20000 |
| AAA-095 | 2.7 | 92 | 34 | 812 |
| AAA-096 | 3.2 | 215 | 67 | 7895 |
| AAA-097 | 2.6 | 151 | 58 | 100000 |
| AAA-098 | 12 | 433 | 36 | 2955 |
| AAA-099 | 11 | 655 | 59 | 89 |
| AAA-100 | 33 | 3273 | 99 | 11818 |
| AAA-101 | 1.7 | 39 | 23 | 375 |
| AAA-102 | 2.2 | 73 | 33 | 833 |
| AAA-103 | 2.6 | 57 | 21 | 583 |
| AAA-104 | 19 | 10164 | 535 | 5000 |
| AAA-105 | 0.66 | 8.4 | 13 | 941 |
| AAA-106 | 66 | 2245 | 34 | 2326 |
| AAA-107 | 4.8 | 647 | 135 | 2833 |
| AAA-108 | 5.1 | 1727 | 338 | 32500 |
| AAA-109 | 4 | 1583 | 396 | 792000 |
| AAA-110 | 16 | 1921 | 120 | >12000 |
| AAA-111 | 10 | 712 | 71 | 50000 |
| AAA-112 | 2 | 2464 | 1212 | 1268 |
| AAA-113 | 3.9 | 900 | 231 | 11093 |
| AAA-114 | 4.4 | 100 | 23 | 22759 |
| AAA-115 | 2.6 | 150 | 58 | 25172 |
| AAA-116 | 4.5 | 208 | 46 | 55172 |
| AAA-117 | 4 | 273 | 68 | 29730 |
| AAA-118 | 36 | 1700 | 47 | 933333 |
| AAA-119 | 26 | 5000 | 192 | >42000 |
| AAA-120 | 0.89 | 142 | 157 | 2162 |

(*) The ratio of the "RARα activity ratio" to the "RARβ activity ratio" is referred to as "RARα/RARβ ratio" and reflects the fold-selectivitity for RARα over RARβ.
(In the above table, "inactive" means that no agonist action was seen at the highest concentration tested.)

All of the above AAA compounds were found to be agonists of RARα. Most of the AAA compounds have a RARα activity ratio (with respect to atRA) of less than about 200. Many of the AAA compounds have a RARα activity ratio of less than about 70. Many of the AAA compounds have a RARα activity ratio of less than about 30. Many of the AAA compounds have a RARα activity ratio of less than about 10. Many of the AAA compounds have a RARα activity ratio of less than about 5.

In addition, all of the above AAA compounds were found to be selective for RARα as compared to RARβ. For most of the AAA compounds, the selectivity for RARα as compared to RARβ is by a factor or at least about 10 (e.g., the ratio of the RARα activity ratio to the RARβ activity ratio is at least about 10). For many of the AAA compounds, the selectivity for RARα as compared to RARβ is by a factor of at least about 20. For many of the AAA compounds, the selectivity for RARα as compared to RARβ is by a factor of at least about 50. For many of the AAA compounds, the selectivity for RARα as compared to RARβ is by a factor of at least about 100. For many of the AAA compounds, the selectivity for RARα as compared to RARβ is by a factor of at least about 200.

Indeed, many of the AAA compounds (e.g., AAA-001, AAA-004, AAA-006, AAA-007, AAA-008, AAA-009, AAA-015, AAA-019, AAA-023, AAA-025) provide at least a 3-fold increase in activity towards RARα (i.e., a RARα activity ratio of less than about 30), as compared to the three reference compounds, while simultaneously providing at least a 3-fold increase in RARα versus RARβ selectivity (i.e., a RARα/RARβ ratio greater than about 25) as compared to the three reference compounds.

In a comparison with compound XXX-01, compound AAA-025 provides a 65-fold increase in RARα activity (i.e., 5 versus 327) while simultaneously providing a 3-fold increase in RARα versus RARβ selectivity (i.e., 26.2 versus 7.9).

| Code Number | RARα activity ratio | RARβ activity ratio | RARα/RARβ ratio (*) |
|---|---|---|---|
| XXX-01 | 327 | 2570 | 7.9 |
| AAA-025 | 5 | 131 | 26.2 |

(*) The ratio of the "RARα activity ratio" to the "RARβ activity ratio" is referred to as "RARα/RARβ ratio" and reflects the fold-selectivitity for RARα over RARβ.

| Code Number | Structure |
|---|---|
| XXX-01 | (structure) |
| AAA-025 | (structure) |

Similarly, in a comparison with compound XXX-02, compound AAA-022 provides a 5-fold increase in RARα activity (i.e., 448 versus 2242) while simultaneously providing a very high selectivity for RARα as compared to RARβ selectivity (i.e., >50).

| Code Number | RARα activity ratio | RARβ activity ratio | RARα/RARβ ratio (*) |
|---|---|---|---|
| XXX-02 | 2242 | — | — |
| AAA-022 | 448 | inactive | >50 |

(*) The ratio of the "RARα activity ratio" to the "RARβ activity ratio" is referred to as "RARα/RARβ ratio" and reflects the fold-selectivitity for RARα over RARβ.

| Code Number | Structure |
|---|---|
| XXX-02 | (structure) |
| AAA-022 | (structure) |

Similarly, in a comparison with compound XXX-03, each of compounds AAA-001, AAA-003, AAA-004, AAA-005, AAA-010, AAA-011, AAA-019, AAA-029 (PP-02), and AAA-030 (PP-03) provides a comparable or improved activity towards RARα (i.e., from 0.9 to 102, versus 90), while simultaneously providing improved RARα versus RARβ selectivity (i.e., from 9.3 to 328, versus 7.1).

| Code Number | RARα activity ratio | Improvement | RARβ activity ratio | RARα/RARβ ratio (*) | Improvement |
|---|---|---|---|---|---|
| XXX-03 | 90 | — | 642 | 7.1 | — |
| AAA-001 | 11 | ~8.2-fold | 342 | 31.1 | ~4.4-fold |
| AAA-003 | 15 | ~6.0-fold | 139 | 9.3 | ~1.3-fold |
| AAA-004 | 7 | ~13-fold | 1420 | 203 | ~29-fold |
| AAA-005 | 68 | ~1.3-fold | 3570 | 52.5 | ~7.4-fold |
| AAA-010 | 102 | ~0.9-fold | 2530 | 24.8 | ~3.5-fold |
| AAA-011 | 34 | ~2.6-fold | 2960 | 87.1 | ~12-fold |
| AAA-019 | 0.9 | ~100-fold | 74 | 82.2 | ~12-fold |
| AAA-029 (PP-02) | 24 | ~3.8-fold | 1920 | 80.0 | ~11-fold |
| AAA-030 (PP-03) | 29 | ~3.1-fold | 9525 | 328 | ~46-fold |

(*) The ratio of the "RARα activity ratio" to the "RARβ activity ratio" is referred to as "RARα/RARβ ratio" and reflects the fold-selectivitity for RARα over RARβ.

It may be noted that some of the compounds (e.g., AAA-001, AAA-004, AAA-011, AAA-029, and AAA-030) provide both substantially improved activity towards RARα (i.e., from 7 to 34, versus 90), while simultaneously providing substantially improved RARα versus RARβ selectivity (i.e., from 31 to 328, versus 7.1).

| Code Number | Structure |
|---|---|
| XXX-03 | (structure) |
| AAA-001 | (structure) |
| AAA-003 | (structure) |
| AAA-004 | (structure) |
| AAA-005 | (structure) |
| AAA-010 | (structure) |

| Code Number | Structure |
|---|---|
| AAA-011 | 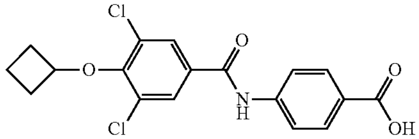 [SMILES: O=C(O)c1ccc(NC(=O)c2cc(Cl)c(OC3CCC3)c(Cl)c2)cc1] |
| AAA-019 | 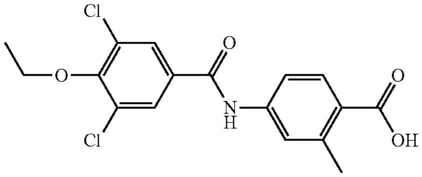 [SMILES: CCOc1c(Cl)cc(C(=O)Nc2ccc(C(=O)O)c(C)c2)cc1Cl] |
| AAA-029 (PP-02) | 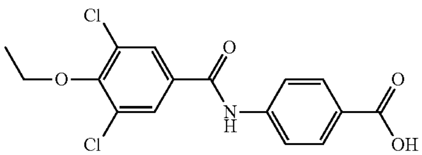 [SMILES: CCOc1c(Cl)cc(C(=O)Nc2ccc(C(=O)O)cc2)cc1Cl] |
| AAA-030 (PP-03) | 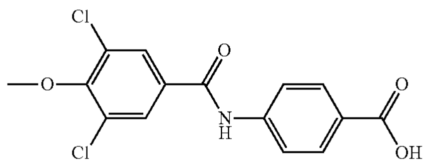 [SMILES: COc1c(Cl)cc(C(=O)Nc2ccc(C(=O)O)cc2)cc1Cl] |

And so, for example, one preferred group of compounds (e.g., compounds for use in therapy, use of compounds in the manufacture of a medicament, methods of treatment, etc.) are selected from compounds of the following formula, and pharmaceutically acceptable salts, hydrates, and solvates thereof:

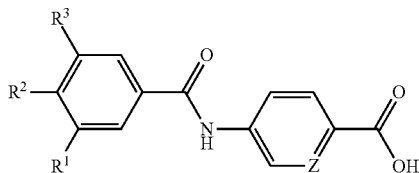

wherein:
—$R^1$ is independently —X or —$R^X$;
—$R^2$ is independently —O—$R^A$ or —O—$R^C$;
—$R^3$ is independently —X or —$R^X$;
wherein:
—Z= is —$CR^Z$=;
—$R^Z$ is independently —H or —$R^{ZZ}$;
—$R^{ZZ}$ is independently saturated aliphatic $C_{1-4}$alkyl, —OH, or —F;
wherein:
each —X is independently —Cl or —Br;
each —$R^X$ is independently saturated aliphatic $C_{1-6}$haloalkyl;
each —$R^A$ is independently saturated aliphatic $C_{1-6}$alkyl;
each —$R^C$ is independently saturated $C_{3-7}$cycloalkyl.

In a further embodiment of the above, —$R^{ZZ}$ is independently saturated aliphatic $C_{1-4}$alkyl.

Similarly, for example, one preferred group of compounds (e.g., compounds for use in therapy, use of compounds in the manufacture of a medicament, methods of treatment, etc.) are selected from compounds of the following formula, and pharmaceutically acceptable salts, hydrates, and solvates thereof:

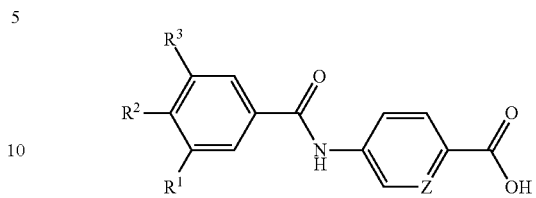

wherein:
—$R^1$ is independently —X;
—$R^2$ is independently —O—$R^A$ or —O—$R^C$;
—$R^3$ is independently —X;
wherein:
—Z= is —$CR^Z$=;
—$R^Z$ is independently —H or —$R^{ZZ}$;
—$R^{ZZ}$ is independently saturated aliphatic $C_{1-4}$alkyl, —OH, or —F;
wherein:
each —X is independently —Cl or —Br;
each —$R^A$ is independently saturated aliphatic $C_{1-6}$alkyl;
each —$R^C$ is independently saturated $C_{3-7}$cycloalkyl.

In a further embodiment of the above, —$R^{ZZ}$ is independently saturated aliphatic $C_{1-4}$alkyl.

Similarly, for example, one preferred group of compounds (e.g., compounds for use in therapy, use of compounds in the manufacture of a medicament, methods of treatment, etc.) are selected from compounds of the following formula, and pharmaceutically acceptable salts, hydrates, and solvates thereof:

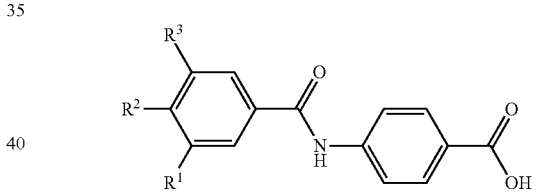

wherein: —$R^1$ is independently —X; —$R^2$ is independently —O—$R^A$ or —O—$R^C$; —$R^3$ is independently —X;
wherein:
each —X is independently —Cl or —Br;
each —$R^A$ is independently saturated aliphatic $C_{1-6}$alkyl;
each —$R^C$ is independently saturated $C_{3-7}$cycloalkyl.

It may be noted that some of the compounds (e.g., AAA-050, AAA-051, AAA-080) provide both substantially improved activity towards RARα (i.e., from 0.97 to 1.7, versus 90), while simultaneously providing substantially improved RARα versus RARβ selectivity (i.e., from 45 to 200, versus 7.1).

AAA-050

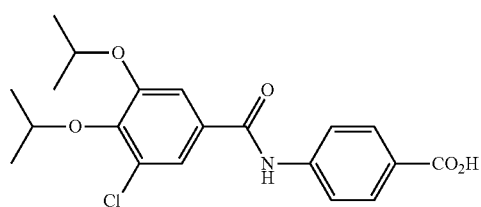

-continued

AAA-051

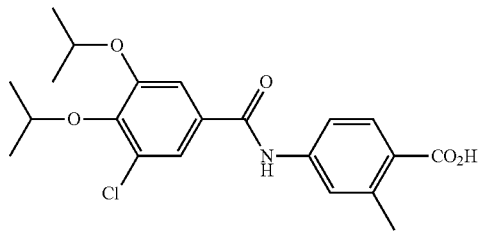

AAA-080

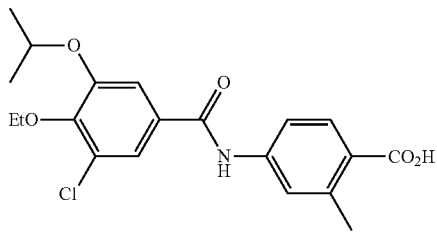

And so, for example, one preferred group of compounds (e.g., compounds for use in therapy, use of compounds in the manufacture of a medicament, methods of treatment, etc.) are selected from compounds of the following formula, and pharmaceutically acceptable salts, hydrates, and solvates thereof:

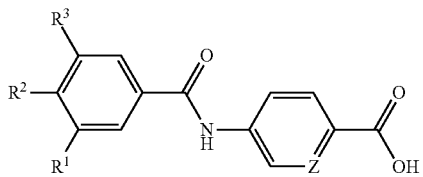

wherein:
—$R^1$ is independently —O—$R^A$ or —O—$R^C$;
—$R^2$ is independently —O—$R^A$ or —O—$R^C$;
—$R^3$ is independently —X;
or:
—$R^1$ is independently —X;
—$R^2$ is independently —O—$R^A$ or —O—$R^C$;
—$R^3$ is independently —O—$R^A$ or —O—$R^C$;
wherein:
—Z= is —$CR^Z$=;
—$R^Z$ is independently —H or —$R^{ZZ}$;
—$R^{ZZ}$ is independently saturated aliphatic $C_{1-4}$alkyl, —OH, or —F;
wherein:
each —X is independently —Cl or —Br;
each —$R^A$ is independently saturated aliphatic $C_{1-6}$alkyl; and
each —$R^C$ is independently saturated $C_{3-7}$cycloalkyl.

In a further embodiment of the above, —$R^{ZZ}$ is independently saturated aliphatic $C_{1-4}$alkyl.

Similarly, for example, one preferred group of compounds (e.g., compounds for use in therapy, use of compounds in the manufacture of a medicament, methods of treatment, etc.) are selected from compounds of the following formula, and pharmaceutically acceptable salts, hydrates, and solvates thereof:

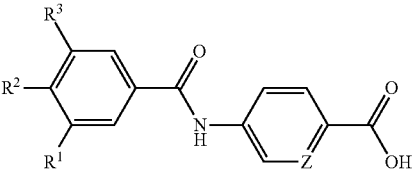

wherein:
—$R^1$ is independently —O—$R^A$;
—$R^2$ is independently —O—$R^A$;
—$R^3$ is independently —X;
or:
—$R^1$ is independently —X;
—$R^2$ is independently —O—$R^A$;
—$R^3$ is independently —O—$R^A$;
wherein:
—Z= is —CRZ=;
—$R^Z$ is independently —H or —$R^{ZZ}$;
—$R^{ZZ}$ is independently saturated aliphatic $C_{1-4}$alkyl, —OH, or —F;
wherein:
each —X is independently —Cl or —Br; and
each —$R^A$ is independently saturated aliphatic $C_{1-6}$alkyl.

In a further embodiment of the above, —$R^{ZZ}$ is independently saturated aliphatic $C_{1-4}$alkyl.

Similarly, for example, one preferred group of compounds (e.g., compounds for use in therapy, use of compounds in the manufacture of a medicament, methods of treatment, etc.) are selected from compounds of the following formula, and pharmaceutically acceptable salts, hydrates, and solvates thereof:

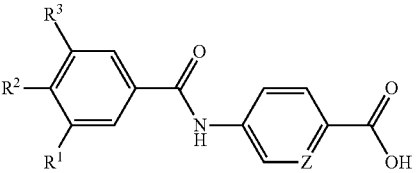

wherein:
—$R^1$ is independently —O—$R^A$;
—$R^2$ is independently —O—$R^A$;
—$R^3$ is independently —X;
or:
—$R^1$ is independently —X;
—$R^2$ is independently —O—$R^A$;
—$R^3$ is independently —O—$R^A$;
wherein:
—Z= is —$CR^Z$=;
—$R^Z$ is independently —H or —$R^{ZZ}$;
—$R^{ZZ}$ is independently -Me, —OH, or —F;
wherein:
each —X is independently —Cl; and
each —$R^A$ is independently saturated aliphatic $C_{1-4}$alkyl.

In a further embodiment of the above, —$R^{ZZ}$ is independently -Me.

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention.

REFERENCES

A number of patents and publications are cited herein in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

Albright et al., 1998, "Tricyclic Benzazepine Vasopressin Antagonists", U.S. Pat. No. 5,849,735 issued 15 Dec. 1998.

Annaert et al., 2000, "Neuronal models to study amyloid precursor protein expression and processing in vitro", Biochim. Biophys. Acta, Vol. 1502, pp. 53-62.

Bastien et al., 2004, "Nuclear retinoid receptors and the transcription of retinoid-target genes", Gene, Vol. 328, pp. 1-16.

Bejanin et al., 1994, "A unique gene organization for two cholinergic markers, choline acetyltransferase and a putative vesicular transporter of acetylcholine", J. Biol. Chem., Vol. 269, pp. 21944-21947.

Berrard et al., 1995, "Coregulation of two embedded gene products, choline acetyltransferase and the vesicular acetylcholine transporter", J. Neurochem., Vol. 65, pp. 939-942.

Bierer et al., 1995, "Neurochemical correlates of dementia severity in Alzheimer's disease: relative importance of the cholinergic deficits", J. Neurochem., Vol. 64, pp. 749-760.

Cervini, et al., 1994, "Regulation by CDF/LIF and retinoic acid of multiple ChAT mRNAs produced from distinct promoters", Neuroreport, Vol. 5, pp. 1346-1348.

Chandraratna, 1991, "Phenylethenyl compounds having retinoid-like activity", U.S. Pat. No. 4,992,468 granted 12 Feb. 1991.

Cocco et al., 2002, "Vitamin A deficiency produces spatial learning and memory impairment in rats", Neuroscience, Vol. 115, pp. 475-482.

Collerton et al., 1986, "Cholinergic function and intellectual decline in Alzheimer's disease", Neuroscience, Vol. 19, pp. 1-28.

Coppola et al., 2005, "Perhydroquinolylbenzamides as novel inhibitors of 11β-hydroxysteroid dehydrogenase type 1", J. Med. Chem., Vol. 48, pp. 6696-6712.

Corcoran, et al., 2004, "Disruption of the retinoid signalling pathway causes a deposition of amyloid beta in the adult rat brain", Eur. J. Neurosci., Vol. 20, pp. 896-902.

Coyle et al., 1983, "Alzheimer's disease: a disorder of cortical cholinergic innervation", Science, Vol. 219, pp. 1184-1190.

Dahl et al., 2000, "Substituted phenyl derivatives, their preparation and use", international (PCT) patent application publication number WO 02/24707 A1, published 4 May 2000.

DeKosky et al., 1992, "Cortical biopsy in Alzheimer's disease: diagnostic accuracy and neurochemical, neuropathological, and cognitive correlations", Intraventricular Bethanecol Study Group, Ann. Neurol., Vol. 32, pp. 625-632.

Ding et al., 2008, "Retinoic Acid Attenuates β-Amyloid Deposition and Rescues Memory Deficits in an Alzheimer's Disease Transgenic Mouse Model", J. Neuroscience, Vol. 28, No. 45, pp. 11622-11634.

Endres et al., 2005, "Shedding of the amyloid precursor protein-like protein APLP2 by disintegrin-metalloproteinases", FEBS J., Vol. 272, pp. 5808-5820.

Etchamendy et al., 2001, "Alleviation of a selective age-related relational memory deficit in mice by pharmacologically induced normalization of brain retinoid signalling", J. Neurosci., Vol. 21, pp. 6423-6429.

Fahrenholz et al., 2006, "α-Secretase Activation—An Approach to Alzheimer's Disease Therapy", Neurodeqenerative Dis., Vol. 3, pp. 255-261.

Fesus et al., 2000, "γ-RAR antagonist ligand or α-RAR agonist ligand as an apoptosis inhibitor", U.S. Pat. No. 6,063,797 granted 16 May 2000.

Fischer et al., 1989, "Degenerative Changes in Forebrain Cholinergic Nuclei Correlate with Cognitive Impairments in Aged Rats", Eur. J. Neurosci., Vol. 1, pp. 34-45.

Geula et al., 1998, "Relationship between plaques, tangles, and loss of cortical cholinergic fibers in Alzheimer disease", J. Neuropathol. Exp. Neurol., Vol. 57, pp. 63-75.

Goodman et al., 2003, "Evidence for defective retinoid transport and function in late onset Alzheimer's disease", Proc. Natl. Acad. Sci. USA, Vol. 100, pp. 2901-2905.

Hook, 2002, "Secretases Related to Alzheimer's Dementia", US patent application publication number US 2002/0072050 A1 published 13 Jun. 2002.

Kato et al., 1992, "Inhibitor of Denatured LDL Formation", European patent publication number 0 515 684 A1, in the name of Chugai Seiyaku Kabushiki Kaisha, published 2 Dec. 1992.

Kikuchi et al., 2003, "Heterocycle-containing carboxylic acid derivative and drug containing same", U.S. Pat. No. 6,541,474 granted 1 Apr. 2003.

Klaus, 1989, "Aromatic acid derivative", U.S. Pat. No. 4,808,631 granted 28 Febuary 1989.

Ladner et al., 1998, "Pharmacological drug treatment of Alzheimer disease: the cholinergic hypothesis revisited", J. Neuropathol. Exp. Neurol., Vol. 57, pp. 719-731.

Lammich et al., 1999, "Constitutive and regulated alpha-secretase cleavage of Alzheimer's amyloid precursor protein by a disintegrin metalloprotease", Proc. Natl. Acad. Sci. USA, Vol. 96, pp. 3922-3927.

Maden et al., 2002, "Method", international (PCT) patent application publication number WO 02/066068 A2, published 29 Aug. 2002.

Misner et al., 2001, "Vitamin A deprivation results in reversible loss of hippocampal long-term synaptic plasticity", Proc. Natl. Acad. Sci. USA, Vol. 98, pp. 11714-11719.

Mizukoshi et al., 1986, "Benzylpiperazine derivative", Japanese patent publication number 61-233678, in the name of Maruko Pharmaceutical Co., published 17 Oct. 1986.

Pan et al., 1993, "Altered levels and splicing of the amyloid precursor protein in the adult rat hippocampus after treatment with DMSO or retinoic acid", Brain Res. Mol. Brain Res., Vol. 18, pp. 259-266.

Perry et al., 1992, "Convergent cholinergic activities in aging and Alzheimer's disease", Neurobiol. Aging, Vol. 13, pp. 393-400.

Prinzen et al., 2005, "Genomic structure and functional characterization of the human ADAM10 promoter", FASEB J., Vol. 19, pp. 1522-1524.

Reichert et al., 1996, "Pharmaceutical or cosmetic composition containing a combination of a retinoid and a sterol", U.S. Pat. No. 5,587,367 granted 24 Dec. 1996.

Schmidt et al., 1975, "New Penicillins, Their Production and Their Pharmaceutical Use", United Kingdom patent publication number 1 409 689, in the name of Bayer Aktiengesellschaft, published 15 Oct. 1975.

Selkoe, 2001, "Alzheimer's disease: genes, proteins, and therapy", *Physiol. Rev.*, Vol. 81, pp. 741-766.

Shudo et al., 1996, "Method of treating bone disease with pyridine, carboxamide, and carboxylic derivatives", U.S. Pat. No. 5,525,618 granted 11 Jun. 1996.

Shudo, 1987, "Benzoic acid derivatives having a para substituent which is a substituted phenyl group connected by a linking radical; useful in neoplastic cell differentiation and diagnosis", U.S. Pat. No. 4,703,110 granted 27 Oct. 1987.

Shudo, 1990, "Flavone carboxylic acid derivatives", U.S. Pat. No. 4,925,979 granted 15 May 1990.

Snyder et al., 2002, "Nonpeptide agonists and antagonists of vasopressin receptors", international (PCT) patent application publication number WO 02/47679 A2, published 20 Jun. 2002.

Sugiyama et al., 2001, "Retinoid-Associated Receptor Regulators", European patent application publication number EP 1 092 711 A1 published 18 Apr. 2001.

Sugiyama et al., 2003, "Retinoied-related receptor function regulating agent", U.S. Pat. No. 6,545,009 granted 8 Apr. 2003.

Talesa, 2001, "Acetylcholinesterase in Alzheimer's disease", *Mech. Ageing Dev.*, Vol. 122, pp. 1961-1969.

Teng et al., 1997, "Substituted heteroarylamides having retinoid-like biological activity", U.S. Pat. No. 5,663,357.

Vinters, 1987, "Cerebral amyloid angiopathy: A critical review", *Stroke*, Vol. 18, pp. 311-324.

The invention claimed is:

1. A compound of the following formula, or a pharmaceutically acceptable salt thereof:

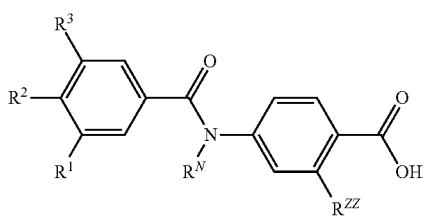

wherein:
—$R^{ZZ}$ is saturated aliphatic $C_{1-4}$alkyl;
—$R^{N}$ is independently —H or —$R^{NN}$;
—$R^{NN}$ is saturated aliphatic $C_{1-4}$alkyl;
—$R^{1}$ is independently —X, —$R^{X}$, —O—$R^{X}$, —O—$R^{A}$, —O—$R^{C}$, —O-L-$R^{C}$, —O—$R^{AR}$, or —O-L-$R^{AR}$;
—$R^{2}$ is independently —X, —$R^{X}$, —O—$R^{X}$, —O—$R^{A}$, —O—$R^{C}$, —O-L-$R^{C}$, —O—$R^{AR}$, or —O-L-$R^{AR}$;
—$R^{3}$ is independently —X, —$R^{X}$, —O—$R^{X}$, —O—$R^{A}$, —O—$R^{C}$, —O-L-$R^{C}$, —O—$R^{AR}$, or —O-L-$R^{AR}$;
with the proviso that —$R^{1}$, —$R^{2}$, and —$R^{3}$ are not all —O—$R^{A}$;
each —X is independently —F, —Cl, —Br, or —I;
each —$R^{X}$ is saturated aliphatic $C_{1-6}$haloalkyl;
each —$R^{A}$ is saturated aliphatic $C_{1-6}$alkyl;
each —$R^{C}$ is saturated $C_{3-7}$cycloalkyl;
each —$R^{AR}$ is phenyl or $C_{5-6}$heteroaryl; and
each -L- is saturated aliphatic $C_{1-3}$alkylene.

2. A compound according to claim 1, wherein:
—$R^{1}$ is independently —X, —$R^{X}$, —O—$R^{X}$, —O—$R^{A}$, —O—$R^{C}$, —O-L-$R^{C}$;
—$R^{2}$ is independently —X, —$R^{X}$, —O—$R^{X}$, —O—$R^{A}$, —O—$R^{C}$, —O-L-$R^{C}$;
—$R^{3}$ is independently —X, —$R^{X}$, —O—$R^{X}$, —O—$R^{A}$, —O—$R^{C}$, —O-L-$R^{C}$; and
with the proviso that —$R^{1}$, —$R^{2}$, and —$R^{3}$ are not all —O—$R^{A}$.

3. A compound according to claim 1, wherein:
—$R^{1}$ is independently —X, —$R^{X}$, —O—$R^{A}$, —O—$R^{C}$, —O-L-$R^{C}$;
—$R^{2}$ is independently —X, —$R^{X}$, —O—$R^{A}$, —O—$R^{C}$, —O-L-$R^{C}$;
—$R^{3}$ is independently —X, —$R^{X}$, —O—$R^{A}$, —O—$R^{C}$, —O-L-$R^{C}$; and
with the proviso that —$R^{1}$, —$R^{2}$, and —$R^{3}$ are not all —O—$R^{A}$.

4. A compound according to claim 1, wherein:
—$R^{1}$ is independently —O—$R^{A}$, —O—$R^{C}$, or —O-L-$R^{C}$;
—$R^{2}$ is independently —O—$R^{A}$, —O—$R^{C}$, or —O-L-$R^{C}$; and
—$R^{3}$ is independently —X or —$R^{X}$;
or:
—$R^{1}$ is independently —X or —$R^{X}$;
—$R^{2}$ is independently —O—$R^{A}$, —O—$R^{C}$, or —O-L-$R^{C}$; and
—$R^{3}$ is independently —O—$R^{A}$, —O—$R^{C}$, or —O-L-$R^{C}$;
or:
—$R^{1}$ is independently —O—$R^{A}$, —O—$R^{C}$, or —O-L-$R^{C}$;
—$R^{2}$ is independently —X or —$R^{X}$; and
—$R^{3}$ is independently —O—$R^{A}$, —O—$R^{C}$, or —O-L-$R^{C}$;
or:
—$R^{1}$ is independently —X or —$R^{X}$; and
—$R^{1}$ is independently —O—$R^{A}$, —O—$R^{C}$, or —O-L-$R^{C}$;
—$R^{3}$ is independently —X or —$R^{X}$.

5. A compound according to claim 1, wherein:
—$R^{1}$ is independently —O—$R^{A}$, —O—$R^{C}$, or —O-L-$R^{C}$;
—$R^{2}$ is independently —O—$R^{A}$, —O—$R^{C}$, or —O-L-$R^{C}$; and
—$R^{3}$ is independently —X or —$R^{X}$;
or:
—$R^{1}$ is independently —X or —$R^{X}$;
—$R^{2}$ is independently —O—$R^{A}$, —O—$R^{C}$, or —O-L-$R^{C}$; and
—$R^{3}$ is independently —O—$R^{A}$, —O—$R^{C}$, or —O-L-$R^{C}$;
or:
—$R^{1}$ is independently —O—$R^{A}$, —O—$R^{C}$, or —O-L-$R^{C}$;
—$R^{2}$ is independently —X or —$R^{X}$; and
—$R^{3}$ is independently —O—$R^{A}$, —O—$R^{C}$, or —O-L-$R^{C}$.

6. A compound according to claim 1, wherein:
—$R^{1}$ is independently —O—$R^{A}$, —O—$R^{C}$, or —O-L-$R^{C}$;
—$R^{2}$ is independently —O—$R^{A}$, —O—$R^{C}$, or —O-L-$R^{C}$; and
—$R^{3}$ is independently —X or —$R^{X}$;

or:
—R¹ is independently —X or —R^X;
—R² is independently —O—R^A, —O—R^C, or —O-L-R^C; and
—R³ is independently —O—R^A, —O—R^C, or —O-L-R^C.

7. A compound according to claim 1, wherein:
—R¹ is independently —O—R^A or —O—R^C;
—R² is independently —O—R^A or —O—R^C; and
—R³ is independently —X or —R^X;
or:
—R¹ is independently —X or —R^X;
—R² is independently —O—R^A or —O—R^C; and
—R³ is independently —O—R^A or —O—R^C.

8. A compound according to claim 1, wherein:
—R¹ is —O—R^A;
—R² is —O—R^A; and
—R³ is —X;
or:
—R¹ is —X;
—R² is —O—R^A; and
—R³ is —O—R^A.

9. A compound according to claim 1, wherein:
each —X is independently —F, —Cl, or —Br;
each —R^X is —CF₃;
each —R^A is saturated aliphatic $C_{1-4}$alkyl;
each —R^C is independently cyclopropyl, cyclobutyl, cyclopentyl, or cyclohexyl;
each —R^AR is independently phenyl, pyridinyl, pyrimidinyl, or pyridizinyl;
each -L- is independently —CH₂— or —CH₂CH₂—; and
—R^N is —H.

10. A compound according to claim 4, wherein:
each —X is independently —F, —Cl, or —Br;
each —R^X is —CF₃;
each —R^A is saturated aliphatic $C_{1-4}$alkyl;
each —R^C is independently cyclopropyl, cyclobutyl, cyclopentyl, or cyclohexyl;
each -L- is independently —CH₂— or —CH₂CH₂—; and
—R^N is —H.

11. A compound according to claim 6, wherein:
each —X is independently —F, —Cl, or —Br;
each —R^X is —CF₃;
each —R^A is saturated aliphatic $C_{1-4}$alkyl;
each —R^C is independently cyclopropyl, cyclobutyl, cyclopentyl, or cyclohexyl;
each -L- is independently —CH₂— or —CH₂CH₂—; and
—R^N is —H.

12. A compound according to claim 7, wherein:
each —X is independently —F, —Cl, or —Br;
each —R^X is —CF₃;
each —R^A is saturated aliphatic $C_{1-4}$alkyl;
each —R^C is independently cyclopropyl, cyclobutyl, cyclopentyl, or cyclohexyl; and
—R^N is —H.

13. A compound according to claim 8, wherein:
each —X is independently —F, —Cl, or —Br;
each —R^A is saturated aliphatic $C_{1-4}$alkyl; and
—R^N is —H.

14. A compound according to claim 9, wherein —R^ZZ is -Me.

15. A compound according to claim 10, wherein —R^ZZ is -Me.

16. A compound according to claim 11, wherein —R^ZZ is -Me.

17. A compound according to claim 12, wherein —R^ZZ is -Me.

18. A compound according to claim 13, wherein —R^ZZ is -Me.

19. A compound according to claim 1, which is a compound selected from the following compounds, or a pharmaceutically acceptable salt thereof:

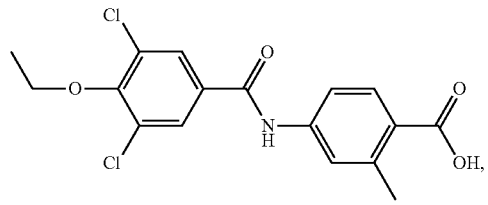
(AAA-019)

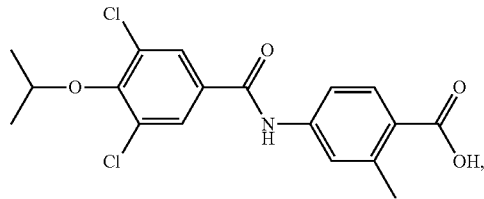
(AAA-032)

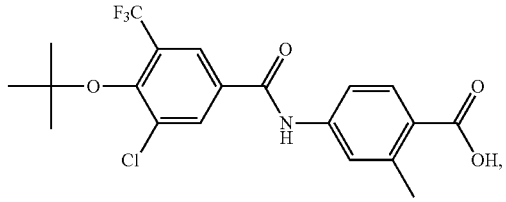
(AAA-038)

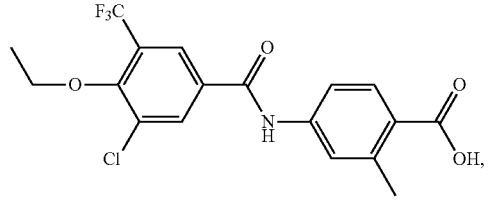
(AAA-039)

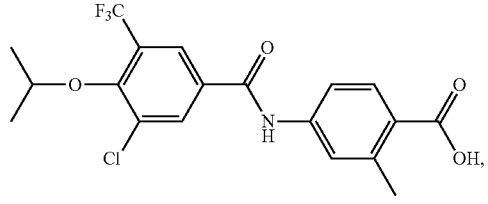
(AAA-040)

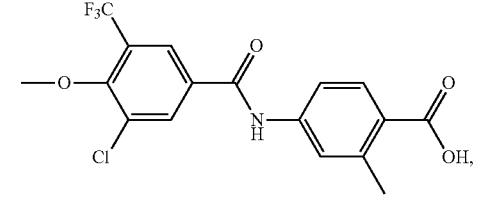
(AAA-041)

(AAA-046)
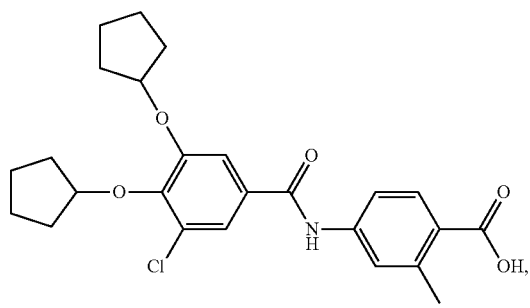
(AAA-049)
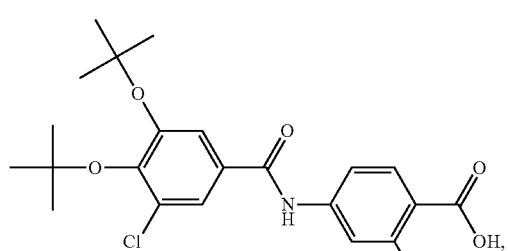
(AAA-051)
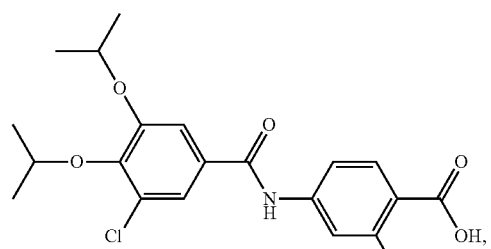
(AAA-052)
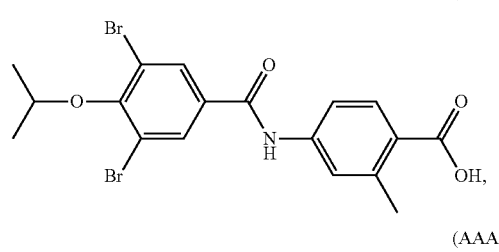
(AAA-053)
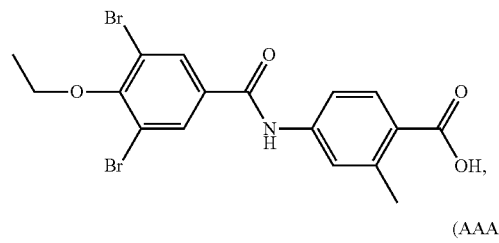
(AAA-054)
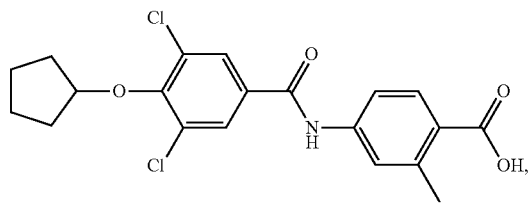
(AAA-055)
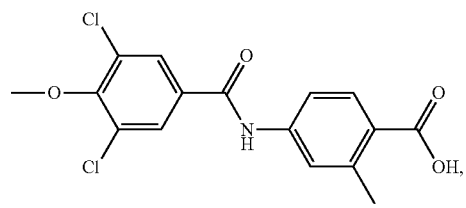
(AAA-056)
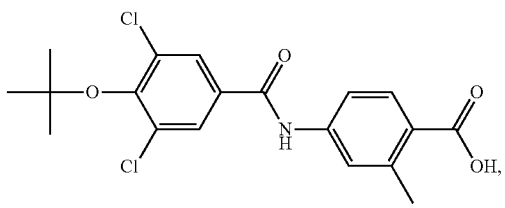
(AAA-071)
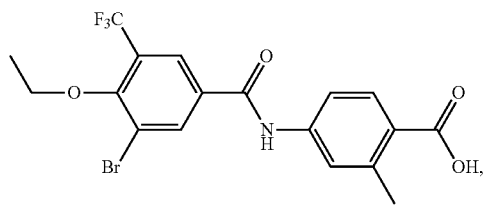
(AAA-074)
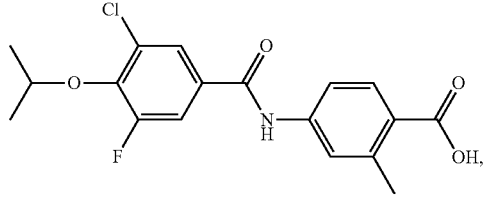
(AAA-075)
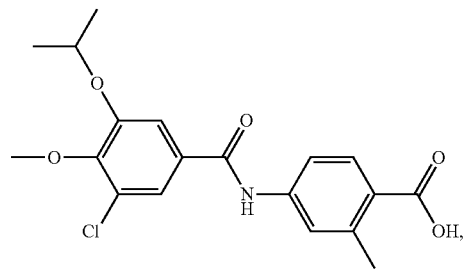
(AAA-080)
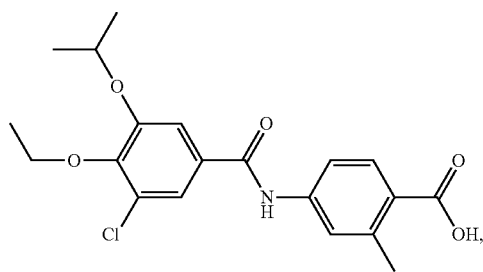

(AAA-085)
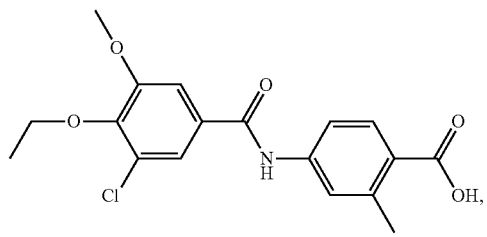
(AAA-087)
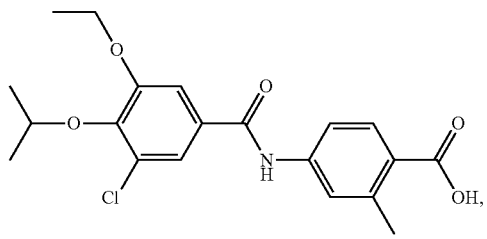
(AAA-093)
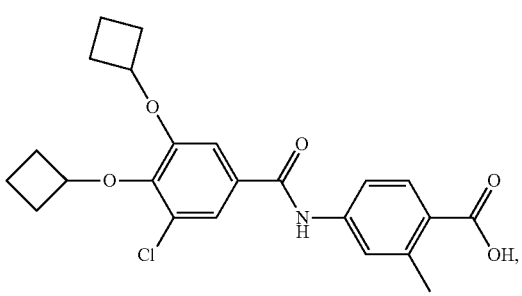
(AAA-096)
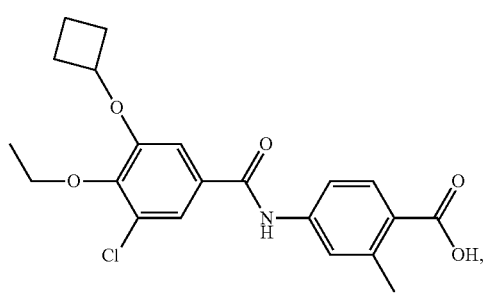
(AAA-097)
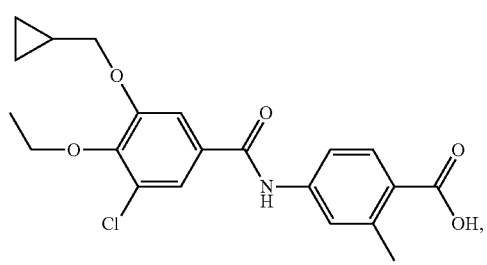
(AAA-099)
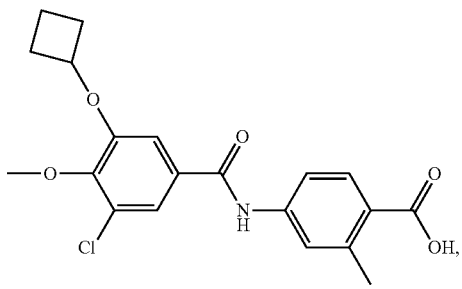
(AAA-102)
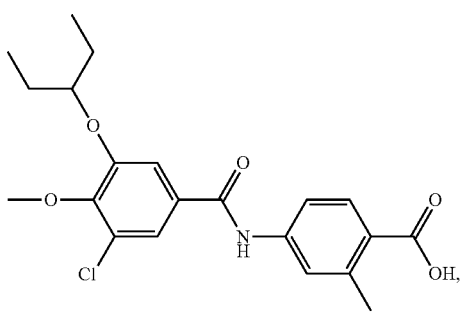
(AAA-110)
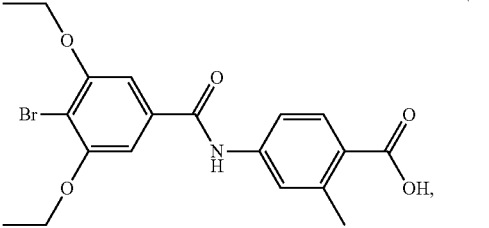
(AAA-111)
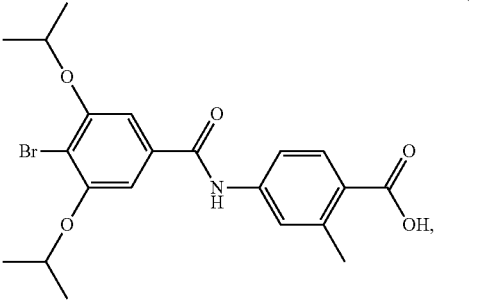
(AAA-113)
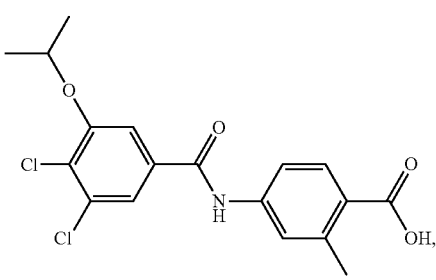

-continued
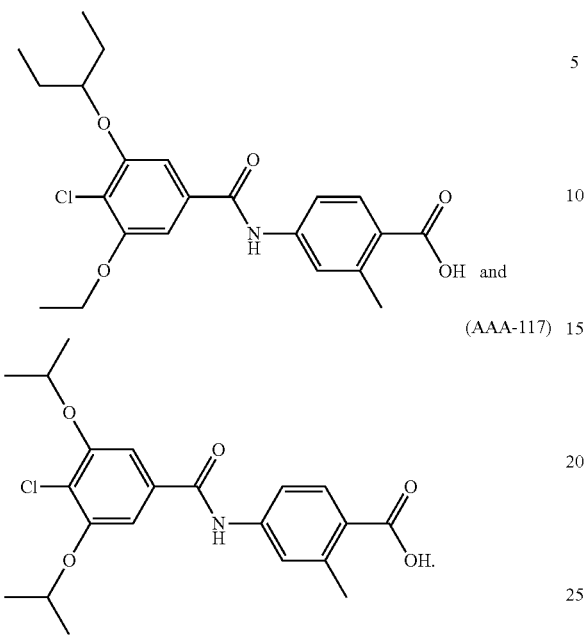
20. A composition comprising a compound according to claim 1 or a pharmaceutically acceptable salt thereof, and a pharmaceutically acceptable carrier, diluent, or excipient.
* * * * *